United States Patent
Honda et al.

(10) Patent No.: US 11,633,433 B2
(45) Date of Patent: Apr. 25, 2023

(54) ANTI-BACTERIAL COMPOSITION AGAINST TH1 CELL-INDUCING BACTERIA

(71) Applicant: KEIO UNIVERSITY, Tokyo (JP)

(72) Inventors: Kenya Honda, Tokyo (JP); Koji Atarashi, Tokyo (JP); Seiko Narushima, Tokyo (JP); Wataru Suda, Tokyo (JP); Masahira Hattori, Tokyo (JP); Munehiro Furuichi, Tokyo (JP); Takaaki Kawaguchi, Tokyo (JP); Keiko Mitobe, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 0 days.

(21) Appl. No.: 16/631,496

(22) PCT Filed: Jul. 18, 2018

(86) PCT No.: PCT/JP2018/026922
§ 371 (c)(1),
(2) Date: Jan. 16, 2020

(87) PCT Pub. No.: WO2019/017389
PCT Pub. Date: Jan. 24, 2019

(65) Prior Publication Data
US 2020/0171099 A1 Jun. 4, 2020

Related U.S. Application Data

(60) Provisional application No. 62/533,844, filed on Jul. 18, 2017.

(51) Int. Cl.
A61K 39/02 (2006.01)
A61K 35/74 (2015.01)
C12Q 1/02 (2006.01)

(52) U.S. Cl.
CPC .............. *A61K 35/74* (2013.01); *C12Q 1/02* (2013.01)

(58) Field of Classification Search
CPC ..................................................... A61K 35/74
See application file for complete search history.

(56) References Cited

U.S. PATENT DOCUMENTS

| | | | |
|---|---|---|---|
| 7,253,333 B2 * | 8/2007 | Tanaka | A01K 67/0339 800/10 |
| 2003/0103938 A1 * | 6/2003 | Jinquan | A61K 38/1709 424/85.2 |
| 2003/0108873 A1 * | 6/2003 | Dahlberg | C12N 15/10 435/6.18 |
| 2006/0094649 A1 * | 5/2006 | Keogh | C07K 14/71 424/185.1 |
| 2013/0336944 A1 | 12/2013 | Chambaud et al. | |
| 2016/0271188 A1 | 9/2016 | Berry et al. | |
| 2020/0405669 A1 * | 12/2020 | Scanlan | A61P 25/00 |
| 2020/0405775 A1 | 12/2020 | Caballero et al. | |

FOREIGN PATENT DOCUMENTS

| | | |
|---|---|---|
| JP | 2011-200211 A | 10/2011 |
| JP | 2014-501100 A | 1/2014 |
| WO | 2018/084172 A1 | 5/2018 |
| WO | 2019/118515 A2 | 6/2019 |

OTHER PUBLICATIONS

Ergin et al (J. Clin. Immunol. vol. 31, pp. 998-1009) (Year: 2011).*
Hill et al., "Intestinal Bacteria and the Regulation of Immune Cell Homeostasis", Annu. Rev. Immunol., 2010, vol. 28, pp. 623-667 (54 pages total).
"Uncultured bacterium clone SJTU_B_13_46 16S ribosomal RNA gene, partial sequence" & Li et al., "Symbiotic gut microbes modulate human metabolic phenotypes", Proceedings of the National Academy of Sciences, vol. 105, No. 6, Feb. 28, 2007, Database EMBL [Online], 1 page total.
Heimesaat et al., "Gram-Negative Bacteria Aggravate Murine Small Intestinal Th1-Type Immunopathology following Oral Infection with *Toxoplasma gondii*", The Journal of Immunology, 2006, vol. 177, pp. 8785-8795 (12 pages total).
Partial Supplementary European Search Report, dated May 21, 2021, issued by the European Patent Office in European Patent Application No. 18834915.3.
Communication, dated Jan. 30, 2020, issued by the International Bureau in International Application No. PCT/JP2018/026922.
C. Gourgue-Jeannot et al., "Dietary fructooligosaccharides alter the cultivable faecal population of rats but do not stimulate the growth of intestinal bifidobacteria", Can. J. Microbiol, 2006, pp. 924-933, vol. 52.
Shigeo Koyasu, Advanced medical technologies such as treatment achieved by exploring symbiotic strategy of pathogenic microorganism with host immune system, development of control method, intractable immune disorder, and infectious disease, Research representative selected in 2002, Apr. 16, 2009.
Yanfei Chen et al., "Dysbiosis of small intestinal microbiota in liver cirrhosis and its association with etiology", Scientific Reports 6:34055, 2016.

(Continued)

*Primary Examiner* — Albert M Navarro
*Assistant Examiner* — Mark Navarro
(74) *Attorney, Agent, or Firm* — Sughrue Mion, PLLC

(57) ABSTRACT

With the aim of proving an antibacterial composition against oral bacteria and the like capable of inducing Th1 cell proliferation or activation in an intestinal tract, the present inventors have found out that bacteria that suppress colonization and the like of the oral bacteria and the like in the intestinal tract are present in an intestinal microbiota. Moreover, the present inventors have succeeded in isolating intestinal bacteria that suppress intestinal colonization and the like of oral bacteria and the like.

4 Claims, 22 Drawing Sheets
Specification includes a Sequence Listing.

(56) References Cited

OTHER PUBLICATIONS

Dirk Gevers et al., "The treatment-naive microbiome in new-onset Crohn's disease", Cell Host Microbe, Mar. 12, 2014, pp. 382-392, vol. 15(3).
Catherine A. Lozupone at al., "Alterations in the Gut Microbiota Associated with HIV-1 Infection", Cell Host & Microbe, Sep. 11, 2013, pp. 329-339, vol. 14.
Ivan Vujkovic-Cvijin et al., "Dysbiosis of the Gut Microbiota Is Associated with HIV Disease Progression and Tryptophan Catabolism", Science Translational Medicine, Jul. 10, 2013, vol. 5, Issue 193 193ra91.
Nan Qin et al., "Alterations of the human gut microbiome in liver cirrhosis", Nature, Sep. 4, 2014, pp. 59-64, vol. 513.
Cynthia L. Sears et al., "Microbes, Microbiota and Colon Cancer", Cell Host Microbe, Mar. 12, 2014, pp. 317-328, vol. 15(3).
International Search Report for PCT/JP2018/026922 dated Oct. 16, 2018 [PCT/ISA/210].
Database EMBL [Online], "Bacterium NLAE-z1-H424 16S ribosomal RNA gene, partial sequence", Jul. 3, 2012, Database accession No. JX006636 (1 page total).
Database Geneseq [Online], "*Escherichia coli* 16S ribosomal RNA (majority) gene, Seq ID 9.", Aug. 13, 2015, Database accession No. BCB42203 (1 page total).
Extended European Search Report, dated Oct. 5, 2021, issued by the European Patent Office in European Application No. 18834915.3.

\* cited by examiner

Fig. 13

| KEGG | Uniprot | Gene category | Annotation |
|---|---|---|---|
| K00971 | | Fructose and mannose metabolism | Mannose-1-phosphate guanylyltransferase 1 |
| K11189 | | | Multiphosphoryl transfer protein |
| K02770 | | | PTS system fructose-specific EIIABC component |
| K15778 | | | Phosphomannomutase/phosphoglucomutase |
| K13058 | | | Mannosylfructose-phosphate synthase |
| K00008 | | | 3-oxoacyl-[acyl-carrier-protein] reductase FabG |
| K12995 | | | Mannosylmannosyltransferase |
| K00094 | | Galactose metabolism | Galactitol-1-phosphate 5-dehydrogenase |
| K02775 | | | Galactitol permease IIC component |
| K02774 | | | Galactitol-specific phosphotransferase enzyme IIB component |
| K16371 | | | D-tagatose-1,6-bisphosphate aldolase subunit GatZ |
| K00882 | | | Tagatose-6-phosphate kinase |
| K08302 | | | D-tagatose-1,6-bisphosphate aldolase subunit GatY |
| K02775 | | | Galactitol permease IIC component |
| K08256 | | Carbohydrate metabolism | GDP-mannose-dependent alpha-(1,2)-phosphatidylinositol mannosyltransferase |
| K08080 | | | L-xylulose/3-keto-L-gulonate kinase |
| K00874 | | | 2-dehydro-3-deoxygluconokinase |
| K00703 | | | Capsular glucan synthase |
| K18800 | A0A182AGT5 | | 3-octaprenyl-4-hydroxybenzoate carboxy-lyase partner protein |
| K03182 | | | 2-octaprenylphenol hydroxylase |
| K01572 | | | Phenolic acid decarboxylase subunit C |
| K01572 | | | Oxaloacetate decarboxylase beta chain |
| K01682 | A0A066RLJ2 | | Aconitate hydratase 2 |
| | | | Putative aldolase LsrF |
| K03625 | F0A1C7 | | Putative acetyltransferase |
| | | | Propanediol utilization protein PduA |
| | A0A0H4W3F2 | | Putative glycosyltransferase EpsF |

Fig. 15

| KEGG | UniProt | Gene category | Annotation |
|---|---|---|---|
| K02016 | | | Hemin-binding periplasmic protein HmuT precursor |
| K09691 | | | Teichoic acids export ATP-binding protein TagH |
| K09692 | | | Teichoic acid translocation permease protein TagG |
| K12340 | | | Outer membrane protein TolC precursor |
| K03297 | | | Multidrug transporter EmrE |
| K06189 | | | Magnesium and cobalt efflux protein CorC |
| K07797 | | | Inner membrane protein YibH |
| K07085 | | Membrane transportation | Aspartate/alanine antiporter |
| K02014 | | | Ferric enterobactin receptor precursor |
| K20973 | A0A0C7KHL0 | | Signal transduction histidine-protein kinase BarA |
| K15583 | | | Hemolysin transporter protein ShlB precursor |
| K15583 | | | Oligopeptide transport ATP-binding protein OppD |
| K01551 | | | Arsenical pump-driving ATPase |
| K04749 | | | Putative anti-sigma factor antagonist |
| K07150 | | | Putative membrane protein YdfK |
| K16087 | | | Putative hemoglobin and hemoglobin-haptoglobin-binding protein 2 precursor |

Fig. 17

| KEGG | Gene category | Annotation |
|---|---|---|
| K05884 | Amino acid metabolism | (2R)-3-sulfolactate dehydrogenase (NADP(+)) |
| K05995 | | Peptidase E |
| K01414 | | Oligopeptidase A |
| K03823 | | Phosphinothricin N-acetyltransferase |
| K00058 | | Putative 2-hydroxyacid dehydrogenase YoaD |

Fig. 19

| KEGG | Uniprot | Gene category | Annotation |
|---|---|---|---|
| K06218 | | | mRNA interferase RelE |
| K07462 | | | Single-stranded-DNA-specific exonuclease RecJ |
| K04763 | A0A0C7A6A2 | | Tyrosine recombinase XerD_6 |
| K03469 | | | Tyrosine recombinase XerD |
| K15835 | | Gene regulator | Glucitol operon repressor |
| P07774 | A0A0C7KER5 | | Formate hydrogenlyase transcriptional activator |
| K07774 | | | HTH-type transcriptional regulator TdfR |
| K03892 | | | HTH-type transcriptional regulator CatM |
| K13244 | | | Transcriptional regulatory protein tctD |
| K04757 | | | HTH-type transcriptional repressor AseR |
| | | | Cyclic di-GMP phosphodiesterase YahA |
| | | | Serine-protein kinase RsbW |

Fig. 21

| KEGG | Uniprot | Gene category | Annotation |
|---|---|---|---|
| K15125 | | | Filamentous hemagglutinin |
| K18974 | | | Dihydropteroate synthase |
| K01698 | | | Delta-aminolevulinic acid dehydratase |
| | A0A127MKS1 | | Aerobic respiration control protein ArcA |

ANTI-BACTERIAL COMPOSITION AGAINST TH1 CELL-INDUCING BACTERIA

CROSS REFERENCE TO RELATED APPLICATIONS

This application is a National Stage of International Application No. PCT/JP2018/026922 filed Jul. 18, 2018, claiming priority based on U.S. Patent Application No. 62/533,844 filed Jul. 18, 2017.

TECHNICAL FIELD

The present invention has been made as a result of the research based on the entrusted program in the unit-type research area "Innovation for Ideal Medical Treatment Based on the Understanding of Maintenance, Change and Breakdown Mechanisms of Homeostasis among Interacting Organ Systems" (the title of the research and development: "Discovering therapies for Intractable Diseases through the Identification and Characterization of the Gut Microbiota") in Advanced Research and Development Programs for Medical Innovation by Japan Agency for Medical Research and Development (AMED) in 2015.

The present invention relates to an antibacterial composition against a bacterium capable of inducing Th1 cell proliferation or activation in an intestinal tract (hereinafter also referred to as "Th1 cell-inducible bacterium"). In addition, the present invention relates to a pharmaceutical composition or method for treating, alleviating, or preventing a disease attributable to Th1 cells. Furthermore, the present invention relates to an intestinal bacterium having antibacterial activity against Th1 cell-inducible bacteria. In addition, the present invention relates to a composition for testing for a disease attributable to Th1 cells, the composition comprising a substance for specifically detecting the intestinal bacterium. Furthermore, the present invention relates to use of the intestinal bacterium for producing a pharmaceutical composition for treating, alleviating, or preventing a disease attributable to Th1 cells.

BACKGROUND ART

Diverse indigenous bacteria are present on mucosae of the digestive tract, oral cavity, and so forth, forming a flora as a whole. Indigenous floras play quite major roles in the host physiology and health maintenance. An indigenous floral imbalance is called dysbiosis, which has been gradually revealed to be a cause for various diseases. It is highly likely that a further progress in the elucidation of mucosal indigenous floras leads to novel disease controls and treatment developments against various diseases. Nevertheless, due to the complexity, the detailed mechanism has not been sufficiently revealed yet.

A human generates and swallows approximately 1.5 L of saliva every day. Normally, bacteria contained in saliva (oral bacteria) merely pass through the intestinal tract and do not colonize. However, oral bacteria may colonize in the intestinal tract under certain situations. There have been reports that the intestinal colonization of oral bacteria was observed from the early stage of the disease developments particularly in Crohn's disease, liver cirrhosis, and colorectal cancer. Moreover, it has been known that such colonized oral bacteria influence the disease status (NPLs 1 to 6).

CITATION LIST

Patent Literature

[PTL 1] International Publication No. WO2018/084172

Non Patent Literature

[NPL 1] Y. Chen et al., Scientific reports 6, 34055 (2016)
[NPL 2] D. Gevers et al., Cell host & microbe 15, 382-392 (2014)
[NPL 3] C. A. Lozupone et al., Cell host & microbe 14, 329-339 (2013)
[NPL 4] I. Vujkovic-Cvijin et al., Science translational medicine 5, 193ra191 (2013)
[NPL 5] N. Qin et al., Nature 513, 59-64 (2014)
[NPL 6] C. L. Sears, W. S. Garrett, Cell host & microbe 15, 317-328(2014)

SUMMARY OF INVENTION

Technical Problem

An object of the present invention is to provide a composition and so on for treating, alleviating, or preventing a disease such as Crohn's disease, which targets oral bacteria that induce Crohn's disease and the like by colonizing in the intestinal tract.

Solution to Problem

The present inventors conducted earnest studies to achieve the above-described object. As a result, the present inventors previously caused oral bacteria of patients with Crohn's disease and others to colonize in the intestinal tract and to induce Th1 cells, and thereby succeeded in isolation-culturing and identifying bacteria involved in the developments of the diseases (PTL 1).

More specifically, the present inventors found out that when salivas derived from some Crohn's disease patients were orally administered to germ-free mice, interferon-gamma (IFN-γ) producing CD4 positive T cells (Th1 cells) markedly increased in the colons as a result.

Then, the present inventors succeeded in isolation-culturing a Kp2H7 strain considered as belonging to *Klebsiella pneumoniae* from the intestine of the mice in which such an increase in Th1 cells had been observed. Moreover, the present inventors also clarified that the bacteria derived from the saliva of Crohn's disease patients are involved in the development of enteritis by colonizing in the intestinal tract and inducing the proliferation or activation of Th1 cells.

In addition, it was also found out that orally administering saliva of some ulcerative colitis patient to germ-free mice markedly induces Th1 cells in the colons as in the case of the above-described Crohn's disease patients. Moreover, as a result of identifying a bacterium that induces Th1 cells, it was also clarified that the Ka11E12 strain, which is a strain different from the Kp2H7 strain and belongs to *Klebsiella aeromobilis* closely related to *K. pneumoniae*, is involved in the induction of Th1 cells in the colons.

This time, the present inventors have found out that when the Kp2H7 strain or Ka11E12 strain is orally administered to SPF (specific-pathogen-free) mice, intestinal colonization of either of these bacterial strains is not observed unlike in the case of the germ-free mice. Moreover, it has also been clarified that administration of an antibiotic to SPF mice may allow these bacterial strains to colonize in the intestinal tracts of the mice.

Then, the present inventors assumed from these results that intestinal bacteria that inhibit intestinal colonization of Th1 cell-inducible bacteria (such as the Kp2H7 strain and the Ka11E12 strain) are present in the intestinal tract, and the administration of an antibiotic eliminates the intestinal bacteria from the intestinal tract, thereby enabling the intestinal colonization of the bacteria.

Based on the above, among human intestinal bacteria, the present inventors tried to identify bacteria that suppress the intestinal colonization of Th1 cell-inducible bacteria. As a result, the present inventors isolation-cultured 68, 37, and 42 intestinal bacterial strains from fecal samples derived from three healthy individuals (#K, #F, and #I), respectively, and succeeded in determining the sequence of 16S rDNA of each strain. Furthermore, the present inventors have found out that administration of these bacterial strains suppresses the intestinal colonization of Th1 cell-inducible bacteria. This finding has led to the completion of the present invention.

In summary, the present invention provides the following.

[1] An antibacterial composition against a bacterium capable of inducing Th1 cell proliferation or activation in an intestinal tract, comprising an intestinal bacterium as an active ingredient.

[2] The antibacterial composition according to [1], wherein the intestinal bacterium is at least one bacterium having a DNA composed of a base sequence specified at any of SEQ ID NOs: 1 to 147 or a base sequence having at least 90% identity with the base sequence.

[3] The antibacterial composition according to [1], wherein the intestinal bacterium is at least one bacterium having a DNA composed of a base sequence specified at any of SEQ ID NOs: 1 to 68 or a base sequence having at least 90% identity with the base sequence.

[4] The antibacterial composition according to [1], wherein the intestinal bacterium is at least one bacterium having a DNA composed of a base sequence specified at any of SEQ ID NOs: 69 to 105 or a base sequence having at least 90% identity with the base sequence.

[5] The antibacterial composition according to [1], wherein the intestinal bacterium is at least one bacterium having a DNA composed of a base sequence specified at any of SEQ ID NOs: 106 to 147 or a base sequence having at least 90% identity with the base sequence.

[6] The antibacterial composition according to any one of [1] to [5], which is a pharmaceutical composition.

[7] The antibacterial composition according to any one of [1] to [5], which is a pharmaceutical composition for treating, alleviating, or preventing a disease attributable to Th1 cells.

[8] A bacterium having an antibacterial activity against a bacterium capable of inducing Th1 cell proliferation or activation in an intestinal tract.

[9] At least one bacterium having a DNA composed of a base sequence specified at any of SEQ ID NOs: 1 to 147 or a base sequence having at least 90% identity with the base sequence.

[10] At least one bacterium having a DNA composed of a base sequence specified at any of SEQ ID NOs: 1 to 68 or a base sequence having at least 90% identity with the base sequence.

[11] At least one bacterium having a DNA composed of a base sequence specified at any of SEQ ID NOs: 69 to 105 or a base sequence having at least 90% identity with the base sequence.

[12] At least one bacterium having a DNA composed of a base sequence specified at any of SEQ ID NOs: 106 to 147 or a base sequence having at least 90% identity with the base sequence.

[13] The bacterium according to any one of [9] to [12], which is a bacterium having an antibacterial activity against a bacterium capable of inducing Th1 cell proliferation or activation in an intestinal tract.

[14] A composition for testing for a disease attributable to Th1 cells, the composition comprising an antibody that specifically recognizes the bacterium according to any one of [8] to [13].

[15] A composition for testing for a disease attributable to Th1 cells, the composition comprising a polynucleotide for detecting a nucleotide sequence specific to the bacterium according to any one of [8] to [13].

[16] A method comprising providing a subject with the bacterium according to any one of [8] to [13], to thereby treat, alleviate, or prevent a disease attributable to Th1 cells in the subject.

[17] Use of the bacterium according to any one of [8] to [13] for producing a pharmaceutical composition for treating, alleviating, or preventing a disease attributable to Th1 cells.

Note that, as explained in Examples to be described later, the base sequences specified in SEQ ID NOs: 1 to 68 are the 16 rDNA base sequences of the 68 bacterial strains isolated from the feces derived from healthy individual #K, the base sequence specified at any of SEQ ID NOs: 69 to 105 is the 16 rDNA base sequence of the corresponding one of the 37 bacterial strains isolated from the feces derived from healthy individual #F, and the base sequence specified at any of SEQ ID NOs: 106 to 147 is the 16 rDNA base sequence of the corresponding one of the 42 bacterial strains isolated from the feces derived from healthy individual #I.

Advantageous Effects of Invention

According to the present invention, suppression of the colonization and the like of Th1 cell-inducible bacteria in the intestinal tract makes it possible to suppress Th1 cell proliferation or activation, suppress intestinal immunity, and moreover treat, alleviate, or prevent a disease attributable to Th1 cells. In addition, the present invention makes it possible to test for a disease attributable to Th1 cells.

BRIEF DESCRIPTION OF DRAWINGS

In FIG. 1, "Amp" indicates an SPF mouse administered with ampicillin, and "Tyl" indicates an SPF mouse administered with tylosin. Note that the line completely overlapping the horizontal axis of the graph indicates a mouse (control) unfed with an antibiotic, and the two broken lines overlapping the horizontal axis of the graph after the 7th day following administration of the Kp2H7 strain indicate an SPF mouse administered with metronidazole and an SPF mouse administered with spectinomycin.

In FIG. 2, "VCM" indicates an SPF mouse administered with vancomycin, and "Tyl" indicates an SPF mouse administered with tylosin. Note that the line overlapping the horizontal axis of the graph indicates a mouse (control) unfed with an antibiotic, and the broken line overlapping the horizontal axis of the graph after the 7th day following administration of the Ka11E12 strain indicates an SPF mouse administered with metronidazole.

In FIG. 3, "ABPC" indicates an ampicillin administration period, and "MNZ" indicates a metronidazole administration period.

In FIG. 4, "FMT" indicates the administration date of the fecal samples, and "ABPC" indicates the ampicillin administration period.

In FIG. 5, "FMT" indicates the administration date of the fecal samples.

In FIG. 6, "FMT" indicates the administration date of the fecal samples.

In FIG. 7, "FMT" indicates the administration date of the fecal samples.

In FIG. 9, "K_47mix" indicates a germ-free mouse administered with a cocktail composed of 47 types of bacterial strains isolated from the feces of the healthy individual #K, "F_37mix" indicates a germ-free mouse administered with a cocktail composed of 37 types of bacterial strains isolated from the feces of the healthy individual #F, "I_42mix" indicates a germ-free mouse administered with a cocktail composed of 42 types of bacterial strains isolated from the feces of the healthy individual #I, and "fece I" indicates a germ-free mouse administered with a fecal sample derived from the healthy individual #I. In addition, "FMT" indicates the administration date of the bacterial cocktail or fecal sample. The notation in FIG. 9 is also the same in FIG. 10.

In FIG. 11, "K_68mix" indicates a germ-free mouse administered with a cocktail composed of 68 types of bacterial strains isolated from the feces of the healthy individual #K. The notation in FIG. 11 is also the same in FIG. 12.

FIG. 13 shows annotations of and information (KEGG or UniProt) on genes related to carbohydrate metabolism, among the genes related to the induction of the colonic Th1 cells.

FIG. 15 shows annotations of and information (KEGG or UniProt) on genes related to membrane transport, among the genes related to the induction of the colonic Th1 cells.

FIG. 17 shows annotations of and information (KEGG or UniProt) on genes related to amino acid metabolism, among the genes related to the induction of the colonic Th1 cells.

FIG. 19 shows annotations of and information (KEGG or UniProt) on genes related to gene regulation, among the genes related to the induction of the colonic Th1 cells.

FIG. 21 shows annotations of and information (KEGG or UniProt) on other genes than those in FIGS. 13-20, among the genes related to the induction of the colonic Th1 cells.

FIG. 22 shows the levels of colonic Th1 cells induced by the bacterial strains belonging to *Klebsiella*, and the levels of the other genes the bacterial strains comprise.

DESCRIPTION OF EMBODIMENTS

Figure 1:
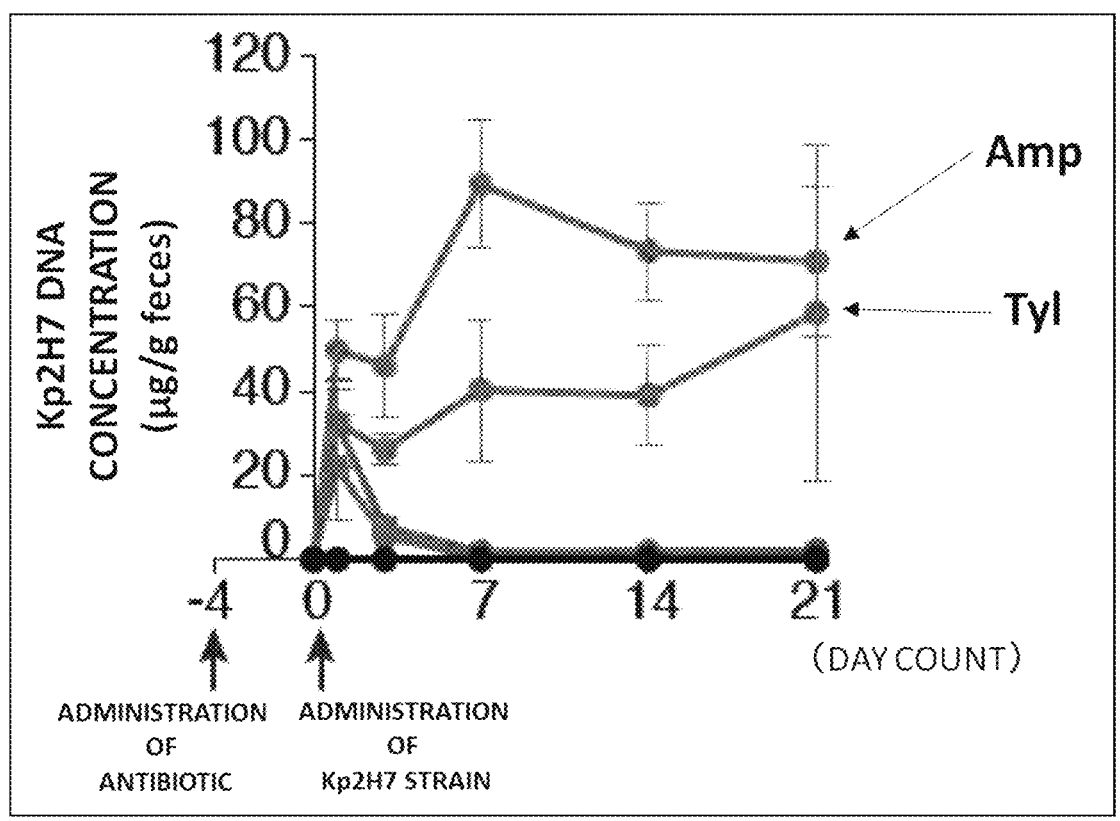
FIG. 1 is a graph illustrating the results of qPCR analysis of the change over time of the intestinal colonization level of a Kp2H7 strain in SPF mice administered with various antibiotics and then fed with the strain.

As explained in Examples to be described later, it has been clarified by the present inventors that intestinal bacteria suppress intestinal colonization and the like of bacteria capable of inducing Th1 cell proliferation or activation in an intestinal tract.

Therefore, the present invention provides an antibacterial composition against a bacterium capable of inducing Th1 cell proliferation or activation in an intestinal tract (Th1 cell-inducible bacterium), comprising an intestinal bacterium as an active ingredient.

First, description is provided for a bacterium capable of inducing Th1 cell proliferation or activation in an intestinal tract, which is the target of antibacterial activity of the composition.

(Bacteria That Induce Th1 Cells in Intestinal Tract)

In the present invention, the "bacterium capable of inducing Th1 cell proliferation or activation in an intestinal tract" isabacterium normally present in the human oral cavity and capable of inducing Th1 cell proliferation or activation upon intestinal colonization, and is a bacterium belonging to preferably *Klebsiella*, more preferably *Klebsiella pneumo-* niae or *Klebsiella* aeromobilis, and being capable of inducing Th1 cell proliferation or activation in an intestine. The "bacterium capable of inducing Th1 cell proliferation or activation in an intestinal tract" is preferably a bacterium easily colonizing in an intestinal environment where the diversity changes by antibacterial drug administration in comparison with a healthy state, and is also a bacterium easily colonizing in an intestinal environment where the diversity changes by colitis or the like in comparison with a healthy state.

Specific examples of the "bacterium capable of inducing Th1 cell proliferation or activation in an intestinal tract" include Kp2H7 strain, Ka11E12 strain, 34E1 strain, BAA-1705 strain, 700603 strain, and 40B3 strain belonging to *Klebsiella*, which have been revealed by the present inventors to cause significant induction of Th1 cells upon colonization in the intestinal tract, as described in PTL 1.

Note that the Kp2H7 strain, the Ka11E12 strain, the 34E1 strain, and the 40B3 strain are bacteria normally present in the human oral cavity (oral bacteria). Meanwhile, the BAA-1705 strain and the 700603 strain are also bacteria normally present in the human oral cavity, but the bacteria are detected in human urine (bacteria in urine).

In addition, the induction levels and genome sequences of colon Th1 cells were compared between these strains. As a result, as shown in FIGS. 13-22 to be described later, the present inventors have found 64 genes whose functions are already known that are related to induction of induction of Th1 cell proliferation or activation.

Thus, the "bacterium capable of inducing Th1 cell proliferation or activation in an intestinal tract" of the present invention preferably comprises genes encoding at least five proteins selected from the following protein group encoded by each of the 64 genes; more preferably, comprises genes encoding at least 10 proteins selected from the following protein group; further preferably comprises genes encoding at least 20 proteins selected from the following protein group; furthermore preferably, comprises genes encoding at least 30 proteins selected from the following protein group; and still furthermore preferably, comprises genes encoding at least 50 proteins selected from the following protein group.

Group of proteins:
Mannose-1-phosphate guanylyltransferase 1, Multiphosphoryl transfer protein,
PTS system fructose-specific EIIABC component, Phosphomannomutase/phosphoglucomutase, Mannosylfructose-phosphate synthase, 3-oxoacyl-[acyl-carrier-protein] reductase FabG, rhamnosyl/mannosyltransferase, Galactitol-1-phosphate 5-dehydrogenase,
Galactitol permease IIC component, Galactitol-specific phosphotransferase enzyme IIB component,
D-tagatose-1,6-bisphosphate aldolase subunit GatZ, Tagatose-6-phosphate kinase,
D-tagatose-1,6-bisphosphate aldolase subunit GatY, Galactitol permease IIC component, GDP-mannose-dependent alpha-(1-2)-phosphatidylinositol mannosyltransferase, L-xylulose/3-keto-L-gulonate kinase, 2-dehydro-3-deoxygluconokinase,
Capsular glucan synthase, 3-octaprenyl-4-hydroxybenzoate carboxy-lyase partner protein,
2-octaprenylphenol hydroxylase,
Phenolic acid decarboxylase subunit C, Oxaloacetate decarboxylase beta chain,
Aconitate hydratase 2,
Putative aldolase LsrF,
Putative acetyltransferase,
Propanediol utilization protein PduA,
Putative glycosyltransferase EpsF,
Hemin-binding periolasmic protein HmuT precursor,
Teichoic acids export ATP-binding protein TagH,
Teichoic acid translocation permease protein TagG,
Outer membrane protein TolC precursor,
Multidrug transporter EmrE,
Magnesium and cobalt efflux protein CorC,
Inner membrane protein YibH,
Aspartate/alanine antiporter,
Ferric enterobactin receptor precursor,
Signal transduction histidine-protein kinase BarA,
Hemolysin transporter protein Sh1B precursor,
Oligopeptide transport ATP-binding protein OppD,
Arsenical pump-driving ATPase,
Putative anti-sigma factor antagonist,
Putative membrane protein YdfK,
Putative hemoglobin and hemoglobin-haptoglobin-binding protein 2 precursor, (2R)-3-sulfolactate dehydrogenase (NADP(+)), Peptidase E,
Oligopeptidase A,
Phosphinothricin N-acetyltransferase,
Putative 2-hydroxyacid dehydrogenase YoaD, mRNA interferase RelE,
Single-stranded-DNA-specific exonuclease RecJ,
Tyrosine recombinase XerD_6,
Tyrosine recombinase XerD,
Glucitol operon repressor,
Formate hydrogenlyase transcriptional activator,
HTH-type transcriptional regulator TdfR,
HTH-type transcriptional regulator CatM,
Transcriptional regulatory protein tctD,
HTH-type transcriptional repressor AseR,
Cyclic di-GMP phosphodiesterase YahA,
Serine-protein kinase RsbW,
Filamentous hemagglutinin,
Dihydropteroate synthase,
Delta-aminolevulinic acid dehydratase, and
Aerobic respiration control protein ArcA.

Note that, in FIGS. 13-22, 2242, 2552, KP-1, 700721, 13882, 40B3, 34E1, 1705, 11E12, 700603, and 2H7 indicate the 2242 strain, the BAA-2552 strain, the KP-1 strain, the 700721 strain, the 13882 strain, the 40B3 strain, the 34E1 strain, the BAA-1705 strain, the Ka11E12 strain, the 700603 strain, and the Kp2H7 strain to be described later, respectively. In addition, weak, medium, and strong indicate the degree of action that induces the Th1 cell proliferation or activation in the intestinal tract of each strain.

Figure 14:
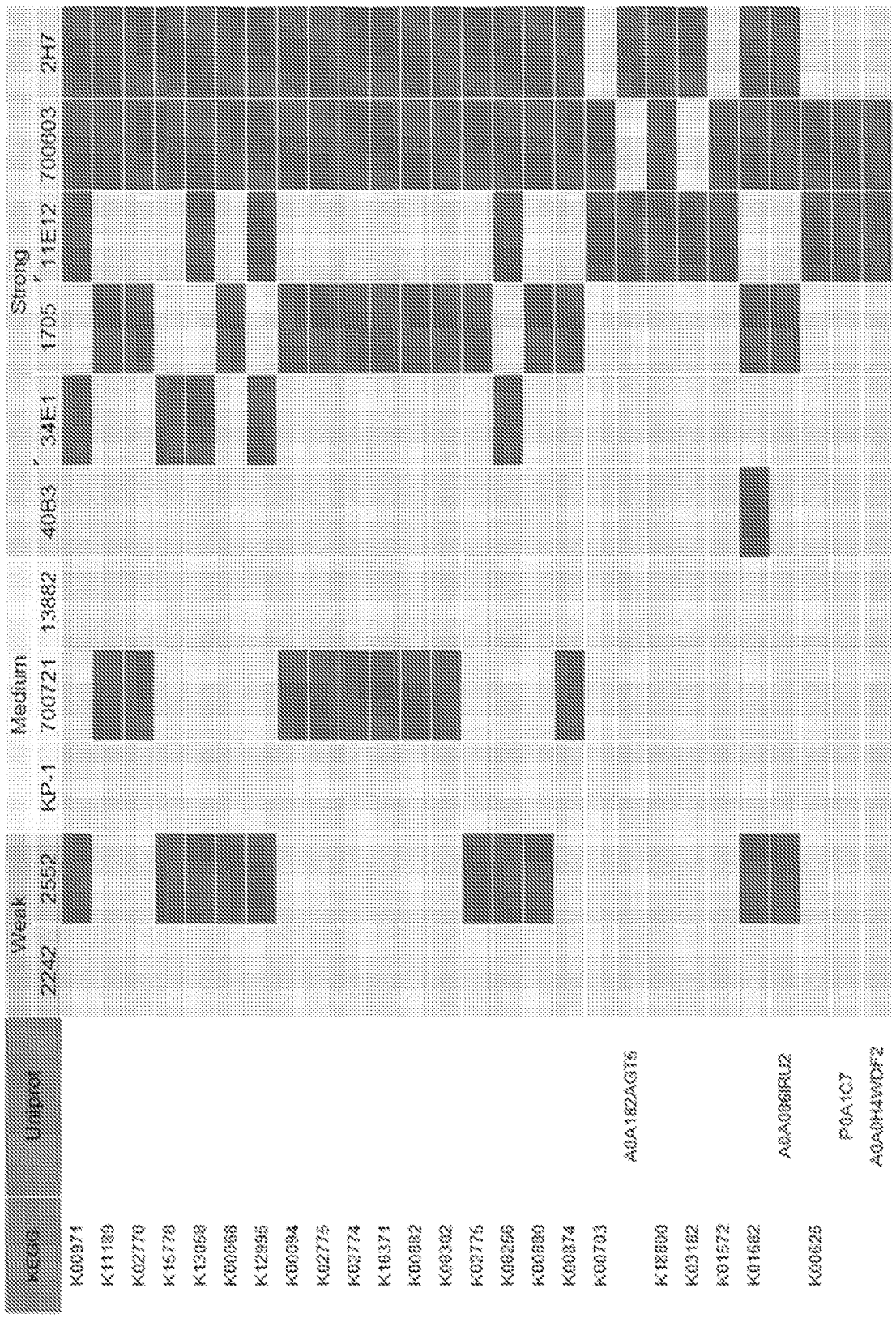
FIG. 14 shows the levels of colonic Th1 cells induced by the bacterial strains belonging to *Klebsiella*, and the levels of the genes related to the carbohydrate metabolism the bacterial strains comprise.

FIG. 13 shows annotations of and information (KEGG or UniProt) on genes related to carbohydrate metabolism, among the genes related to the induction of the colonic Th1 cells. FIG. 14 shows the levels of colonic Th1 cells induced by the bacterial strains belonging to *Klebsiella*, and the levels of the genes related to the carbohydrate metabolism the bacterial strains comprise.

Figure 16:
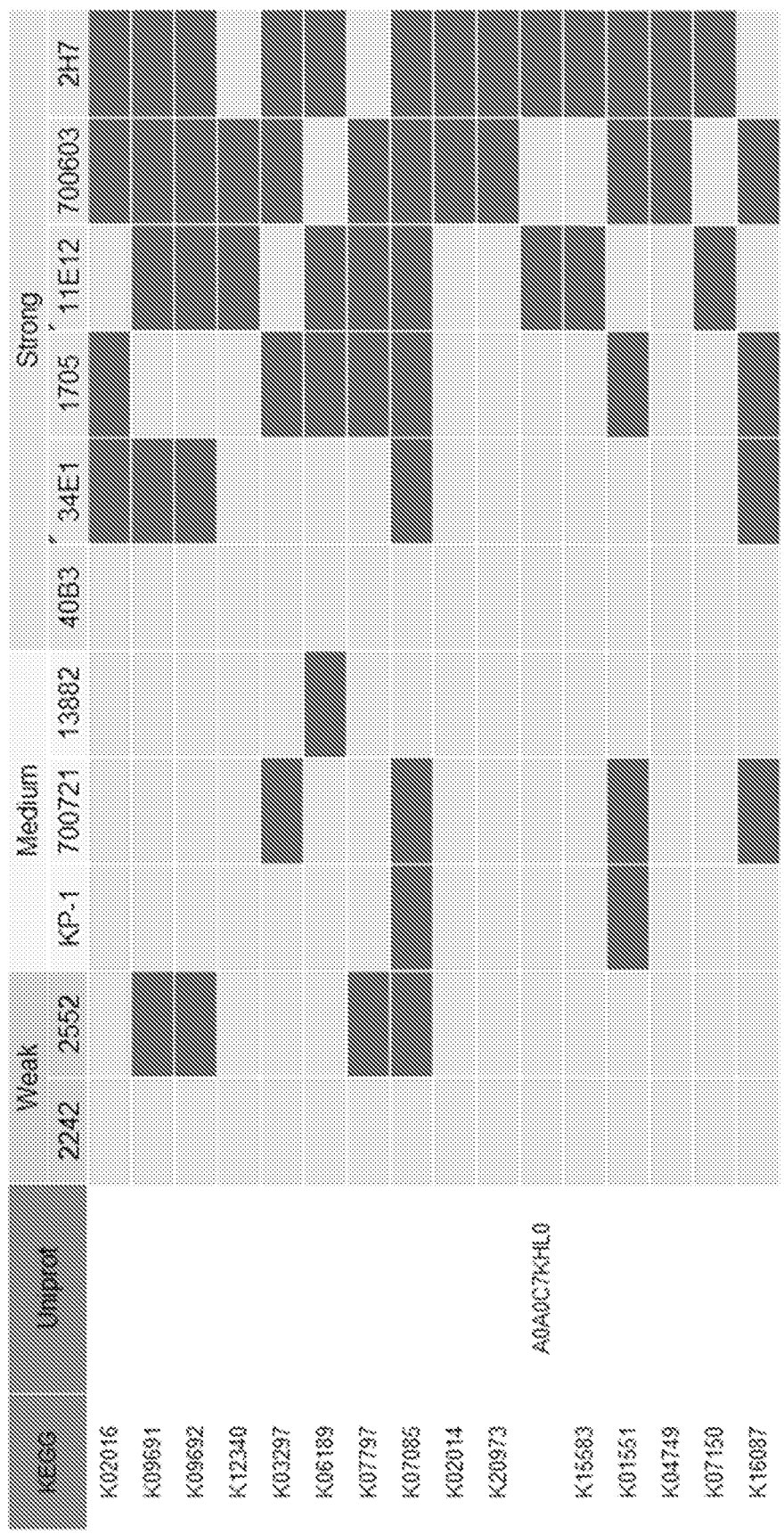
FIG. 16 shows the levels of colonic Th1 cells induced by the bacterial strains belonging to *Klebsiella*, and the levels of the genes related to the membrane transport the bacterial strains comprise.

FIG. 15 shows annotations of and information (KEGG or UniProt) on genes related to membrane transport, among the genes related to the induction of the colonic Th1 cells. FIG. 16 shows the levels of colonic Th1 cells induced by the bacterial strains belonging to *Klebsiella*, and the levels of the genes related to the membrane transport the bacterial strains comprise.

Figure 18:
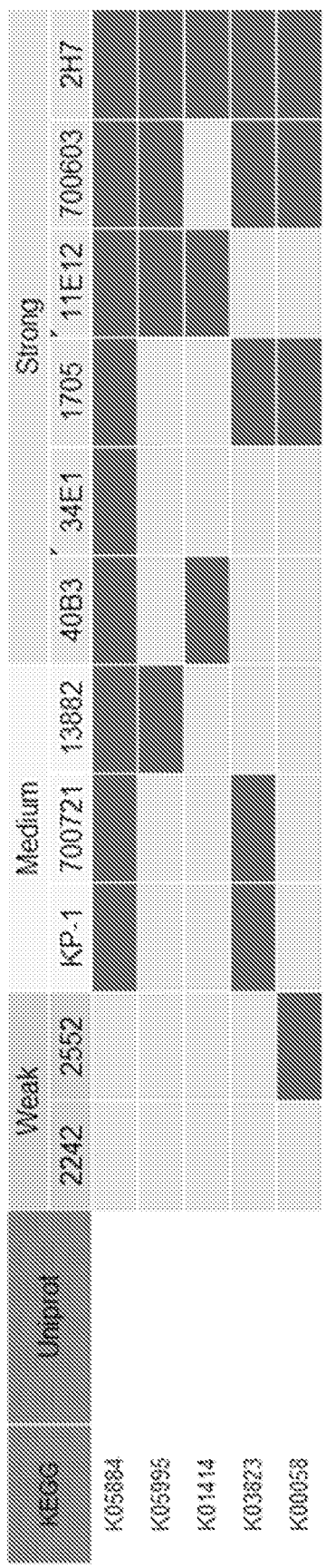
FIG. 18 shows the levels of colonic Th1 cells induced by the bacterial strains belonging to *Klebsiella*, and the levels of the genes related to the amino acid metabolism the bacterial strains comprise.

FIG. 17 shows annotations of and information (KEGG or UniProt) on genes related to amino acid metabolism, among the genes related to the induction of the colonic Th1 cells. FIG. 18 shows the levels of colonic Th1 cells induced by the bacterial strains belonging to *Klebsiella*, and the levels of the genes related to the amino acid metabolism the bacterial strains comprise.

Figure 20:
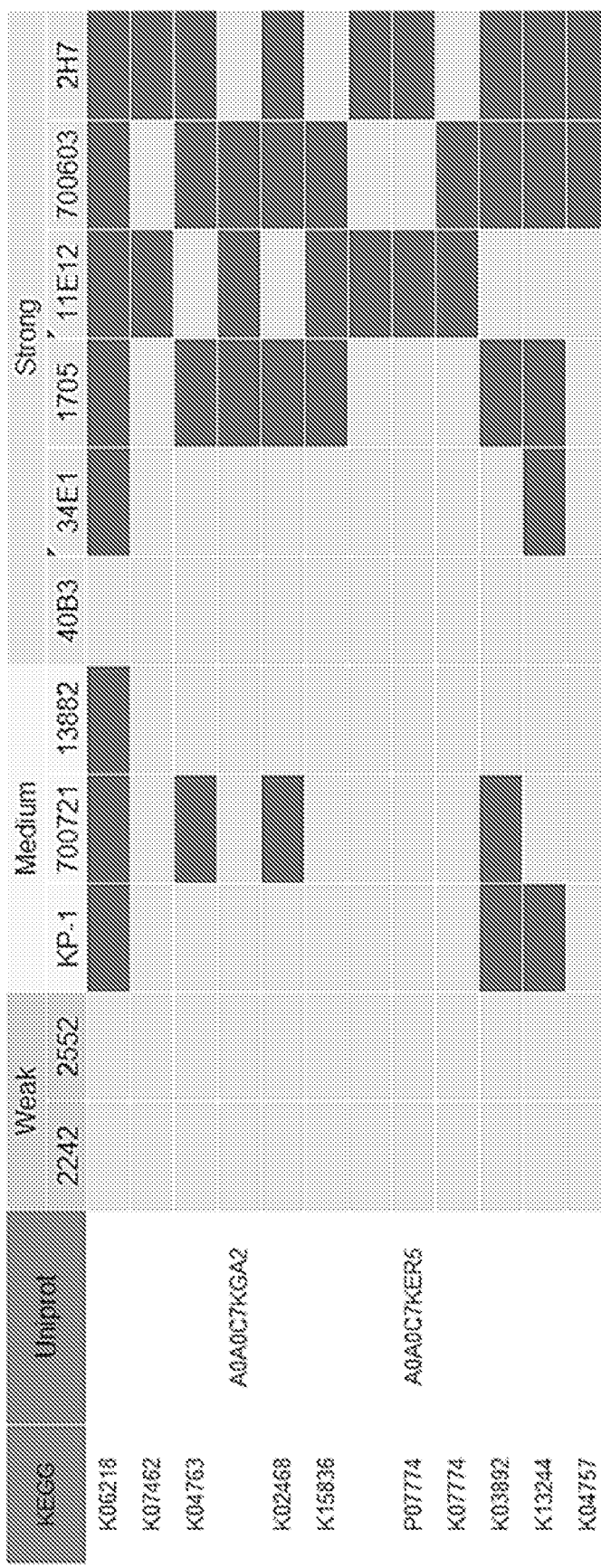
FIG. 20 shows the levels of colonic Th1 cells induced by the bacterial strains belonging to *Klebsiella*, and the levels of the genes related to the gene regulation the bacterial strains comprise.

FIG. 19 shows annotations of and information (KEGG or UniProt) on genes related to gene regulation, among the genes related to the induction of the colonic Th1 cells. FIG. 20 shows the levels of colonic Th1 cells induced by the bacterial strains belonging to *Klebsiella*, and the levels of the genes related to the gene regulation the bacterial strains comprise.

Figure 22:
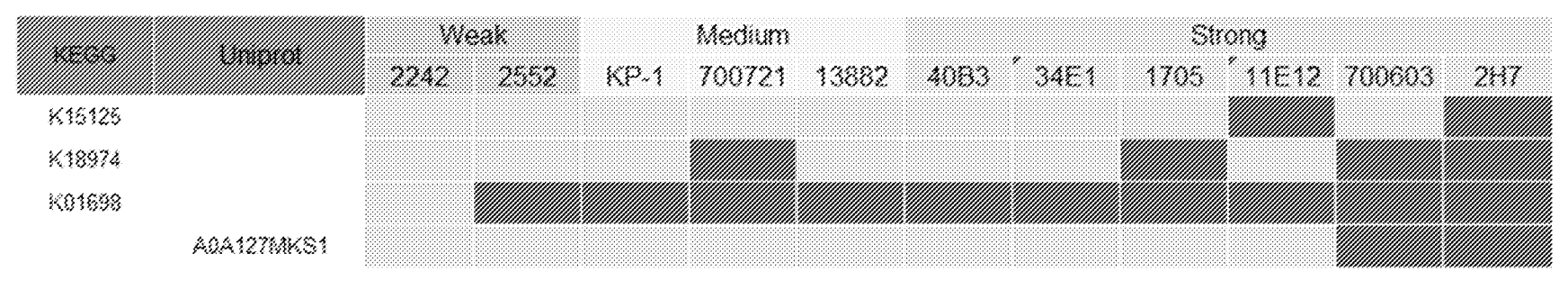

FIG. 21 shows annotations of and information (KEGG or UniProt) on other genes than those in FIGS. 13-20, among the genes related to the induction of the colonic Th1 cells. FIG. 22 shows the levels of colonic Th1 cells induced by the bacterial strains belonging to *Klebsiella*, and the levels of the other genes the bacterial strains comprise.

Meanwhile, although these proteins are specified by particular amino acid sequences (amino acid sequences specified under KEGG or UniProt ID) in FIGS. 13-22, the proteins according to the present invention include not only a bacterium which belongs to *Klebsiella*, forms no capsule, and induces Th1 cell proliferation or activation in an intestinal tract; more preferably, a bacterium which belongs to *Klebsiella pneumoniae*, forms no capsule, produces outer membrane vesicles (OMV) or OMV-like structures, and induces Th1 cell proliferation or activation in an intestinal tract.

Furthermore, the "bacterium capable of inducing Th1 cell proliferation or activation in an intestinal tract" is preferably a bacterium which belongs to *Klebsiella* and has a flagellum, or preferably a bacterium which belongs to *Klebsiella* and has a stimulatory action on TLR5.

As described above, examples of the "bacterium capable of inducing Th1 cell proliferation or activation in an intestinal tract" of the present invention typically include the Kp2H7 strain, the Ka11E12 strain, the 34E1 strain, the BAA-1705 strain, the 700603 strain, and the 40B3 strain belonging to *Klebsiella*. Of these, the Kp2H7 strain or the Ka11E12 strain is more preferable, and the Kp2H7 strain is particularly preferable. Note that, regarding details of these bacteria, see Table 1.

TABLE 1

| Bacterial Name | Supplier | Information from Supplier | Registry number |
| --- | --- | --- | --- |
| KCTC2242 | KCTC | http://kctc.kribb.re.kr/English/_SearchView.aspx?sn=2242 | NCBI Taxonomy ID: 1049565 |
| BAA-2552 | ATCC | https://www.atcc.org/Products/All/BAA-2552.aspx | NCBI Taxonomy ID: 507522 |
| KP-1 | — | — | NCBI Taxonomy ID: 1365186 |
| 700721 | ATCC | https://www.atcc.org/Products/All/700721.aspx | NCBI Taxonomy ID: 272620 |
| 13882 | JCM | https://www.atcc.org/Products/All/13882.aspx | NCBI Taxonomy ID: 1913574 |
| 40B3 | — | — | SAMD00083913 |
| 34E1 | — | — | SAMD00083911 |
| BAA-1705 | ATCC | https://www.atcc.org/Products/All/BAA-1705.aspx | NCBI Taxonomy ID: 1276652 |
| Ka11E12 | — | — | SAMD00083912 |
| 700603 | ATCC | https://www.atcc.org/Products/All/700603.aspx | NCBI Taxonomy ID: 1276653 |
| Kp2H7 | — | — | SAMD00083910 | the proteins specified by these typical amino acid sequences, but also functionally active derivatives thereof, functionally active fragments thereof, homologs thereof, and mutants encoded by nucleic acids capable of hybridizing to nucleic acids encoding the proteins under high stringency conditions or low stringency conditions. In addition, such derivatives, fragments, homologs, or mutants include proteins having a homology of at least 60% (preferably 70%, more preferably further preferably 90%, furthermore preferably 95%, particularly preferably 99%) with the particular amino acid sequences.

Note that the homology or identity of sequences (amino acid sequences or nucleotide (base) sequences) can be determined using a program (Altschul et al. J. Mol. Biol., 215:403-410, 1990) for BLAST (Basic Local Alignment Search). The program is based on the algorithm BLAST by Karlin and Altschul (Proc. Natl. Acad. Sci. USA, 87:2264-2268, 1990, Proc. Natl. Acad. Sci. USA, 90:5873-5877, 1993). When analyzing homology or identity between sequences by BLAST, determination is possible using, for example, BLAST from the National Center for Biotechnology Information (NCBI) (for example, using default, i.e., initially set parameters).

As shown in FIGS. 13 and 14, the proteins according to the present invention include proteins involved in a metabolism of mannose, fructose, or galactose. Thus, the "bacterium capable of inducing Th1 cell proliferation or activation in an intestinal tract" preferably expresses a gene involved in a metabolism of mannose, fructose, or galactose.

Further, the "bacterium capable of inducing Th1 cell proliferation or activation in an intestinal tract" is preferably The bacteria belonging to *Klebsiella*, the bacteria belonging to *Klebsiella* aeromobilis, the bacteria belonging to *Klebsiella pneumoniae*, the Kp2H7 strain, the Ka11E12 strain, the 34E1 strain, the BAA-1705 strain, the 700603 strain, and the 40B3 strain can be identified, for example, by determining the nucleotide sequence encoding 16S rRNA (such as the base sequence of 16S rDNA). In addition, these bacteria can also be identified based on a nucleotide sequence specific thereto, and so forth. Note that the nucleotide sequence specific to the Kp2H7 strain or the Ka11E12 strain is not particularly limited. Nevertheless, preferable examples of the nucleotide sequence include nucleotide sequences which the Kp2H7 strain or the Ka11E12 strain has, but which are not found in a BAA-2552 strain and a 700721 strain belonging to the same *Klebsiella* as those strains (more preferably, nucleotide sequences not found in the BAA-2552 strain, a KCTC2242 strain, the KP-1 strain, the 700721 strain, and a 13882 strain).

Note that the 700721 strain, 13882 strain, KP-1 strain, BAA-2552 strain, and KCTC2242 strain are *K. pneumoniae* strains, and have a weak or medium action of inducing the Th1 cell proliferation or activation in the intestinal tract (see FIGS. 13-22 and Table 1 and PTL 1 for these bacteria).

Moreover, the examples of the "bacterium capable of inducing Th1 cell proliferation or activation in an intestinal tract" of the present invention include bacteria comprising a DNA containing a nucleotide sequence having an identity of 90% or more (91% or more, 92% or more, 93% or more, 94% or more, 95% or more, 96% or more, 97% or more, 98% or more, 99% or more) with the nucleotide sequence encoding 16S rRNA of the Kp2H7 strain, the Ka11E12 strain, the 34E1 strain, the BAA-1705 strain, the 700603 strain, or the 40B3 strain. The examples further includes bacteria comprising a DNA containing a nucleotide sequence having a homology or an identity of 70% or more (preferably 80% or more, more preferably 85% or more, further preferably 90% or more, furthermore preferably 95% or more (96% or more, 97% or more, 98% or more, 99% or more) with the nucleotide sequence specific to the Kp2H7 strain, the Ka11E12 strain, the 34E1 strain, the BAA-1705 strain, the 700603 strain, or the 40B3 strain.

In the present invention, the term "Th1 cell" means a subtype of CD4 positive helper T cells (Th cells), and the cell enhances cell-mediated immunity. Moreover, the "activity of Th1 cells" and related terms mean to include: production of Th1 cytokines (such as IFN-γ) by the cells; activation of cells such as macrophages and cytotoxic T cells (CTL) with the cytokines; and enhancement of cell-mediated immunity through the activation. Further, "inducing Th1 cell proliferation or activation" and similar phrases mean to include differentiation induction from naive T cells to Th1 cells, leading to Th1 cell proliferation or activation.

The action of inducing Th1 cell proliferation or activation in an intestine can be evaluated by quantitatively detecting a marker (for example, CD4 and IFN-γ) specific to Th1 cells. Such quantitative detection can be conducted by known methods, for example, detection methods using an antibody (immunological methods) such as flow cytometry, imaging cytometry, ELISA methods, radioimmunoassay, immunohistochemical staining, immunoprecipitation, immunoblotting, and antibody array analyses.

Whether certain bacterium or the like has an action of inducing Th1 cell proliferation or activation in an intestine or not can be determined as follows. For example, if the percentage of IFN-γ$^+$ cells detected in an intestine by flow cytometry is 10% or more among CD4$^+$TCRβ$^+$T cells, it can be determined that the bacterium or the like has an action of inducing Th1 cell proliferation or activation in an intestine (It is preferable to determine that the bacterium or the like has an action of inducing Th1 cell proliferation or activation in an intestine if the percentage is 25% or more. It is more preferably to determine that the bacterium, substance, or the like has an action of inducing Th1 cell proliferation or activation in an intestine if the percentage is 30% or more).

Next, description is provided for intestinal bacteria contained as an active ingredient of the antibacterial composition of the present invention.

(Intestinal Bacterium)

In the present invention, the intestinal bacteria contained as an active ingredient of the antibacterial composition have an antibacterial activity against bacteria capable of inducing Th1 cell proliferation or activation in an intestinal tract.

In the present invention, the "antibacterial activity" means an activity that suppresses bacterial activity, and more specifically an activity that suppresses bacterial growth or colonization or kills bacteria.

The "Intestinal bacteria" means bacteria present in the intestinal tract of an animal. In addition, examples of animals in which such bacteria are present include humans and non-human animals (such as mice, rats, monkeys, pigs, cattle, horses, sheep, goats, chickens, ducks, ostriches, domesticated ducks, dogs, cats, rabbits, and hamsters). Among these animals, humans are preferable.

In the present invention, "intestinal bacteria" may be one strain of bacteria or a mixture of bacterial strains composed of two or more strains. In addition, in the case of two or more bacterial strains, it is desirable that at least one of the bacterial strains has antibacterial activity against Th1 cell-inducible bacteria. In addition, in that case, even in the case of a bacterial strain not having the above-described antibacterial activity, the two or more bacterial strains may include a bacterial strain having an action of enhancing the antibacterial activity of a bacterial strain, a bacterial strain having an action of maintaining the growth of a bacterial strain having the antibacterial activity, or a bacterial strain having an action of suppressing the inhibitory activity of a bacteria that inhibit the antibacterial activity.

In the present invention, examples of "intestinal bacteria" include at least one bacterium having a DNA composed of a base sequence specified at any of SEQ ID NOs: 1 to 147 or a base sequence having at least 70% identity with the base sequence, at least one bacterium having a DNA composed of a base sequence specified at any of SEQ ID NOs: 1 to 68 or a base sequence having at least 70% identity with the base sequence, at least one bacterium having a DNA composed of a base sequence specified at any of SEQ ID NOs: 69 to 105 or a base sequence having at least 70% identity with the base sequence, or at least one bacterium having a DNA composed of a base sequence specified at any of SEQ ID NOs: 106 to 147 or a base sequence having at least 70% identity with the base sequence.

Note that, regarding "at least 70% identity" in the intestinal bacterium of the present invention, the identity with each base sequence is preferably 80% or more, more preferably 85% or more, further preferably 90% or more (for example, 91% or more, 92% or more, 93% or more, 94% or more), more preferably 95%; or more (for example, 96% or more, 97% or more, 98% or more), and particularly preferably 99% or more.

In the present invention, the "intestinal bacterium" having a DNA composed of a base sequence specified at any of SEQ ID NOs: 1 to 147 or a base sequence having at least 70% identity with the base sequence is preferably at least bacteria in the intestinal bacterium group, more preferably at least 30 bacteria in the intestinal bacterium group, further preferably at least 75 bacteria in the intestinal bacterium group, more preferably at least 120 bacteria in the intestinal bacterium group, further preferably at least 135 bacteria in the intestinal bacterium group, more preferably at least 140 bacteria in the intestinal bacterium group, further preferably 147 intestinal bacteria each of which has a DNA composed of a base sequence specified at any of SEQ ID NOs: 1 to 147 or a base sequence having at least 70% identity with the base sequence, and particularly preferably 147 bacteria each of which has a DNA composed of a base sequence specified at any of SEQ ID NOs: 1 to 147.

In the present invention, the "intestinal bacterium" having a DNA composed of a base sequence specified at any of SEQ ID NOs: 1 to 68 or a base sequence having at least 90% identity with the base sequence is preferably at least 7 bacteria in the intestinal bacterium group, more preferably at least 15 bacteria in the intestinal bacterium group, further preferably at least 35 bacteria in the intestinal bacterium group, more preferably at least 60 bacteria in the intestinal bacterium group, further preferably at least 65 bacteria in the intestinal bacterium group, more preferably 68 intestinal bacteria each of which has a DNA composed of a base sequence specified at any of SEQ ID NOs: 1 to 68 or a base sequence having at least 70% identity with the base sequence, and particularly preferably 68 bacteria each of which has a DNA composed of a base sequence specified at any of SEQ ID NOs: 1 to 68. In addition, the "intestinal bacterium" having a DNA composed of a base sequence specified at any of SEQ ID NOs: 1 to 68 or a base sequence having at least 70% identity with the base sequence is desirably resistant to ampicillin. In addition, as shown in the Examples to be described later, 46 bacteria each having a DNA composed of a base sequence specified at any of SEQ ID NOs: 1 to 46 or a base sequence having at least 70% identity with the base sequence are also used suitably in the present invention.

In the present invention, the "intestinal bacterium" having a DNA composed of a base sequence specified at any of SEQ ID NOs: 69 to 105 or a base sequence having at least 70% identity with the base sequence is preferably at least 4 bacteria in the intestinal bacterium group, more preferably at least 8 bacteria in the intestinal bacterium group, further preferably at least 19 bacteria in the intestinal bacterium group, more preferably at least 30 bacteria in the intestinal bacterium group, further preferably at least 33 bacteria in the intestinal bacterium group, more preferably at least 35 bacteria in the intestinal bacterium group, further preferably 37 intestinal bacteria each of which has a DNA composed of a base sequence specified at any of SEQ ID NOs: 69 to 105 or a base sequence having at least 70% identity with the base sequence, and particularly preferably 37 bacteria each of which has a DNA composed of a base sequence specified at any of SEQ ID NOs: 69 to 105. In addition, the "intestinal bacterium" having a DNA composed of a base sequence specified at any of SEQ ID NOs: 69 to 105 or a base sequence having at Least 70% identity with the base sequence is desirably susceptible to ampicillin.

In the present invention, the "intestinal bacterium" having a DNA composed of a base sequence specified at any of SEQ ID NOs: 106 to 147 or a base sequence having at least 70% identity with the base sequence is preferably at least 4 bacteria in the intestinal bacterium group, more preferably at least 9 bacteria in the intestinal bacterium group, further preferably at least 22 bacteria in the intestinal bacterium group, more preferably at least 34 bacteria in the intestinal bacterium group, further preferably at least 39 bacteria in the intestinal bacterium group, more preferably at least 41 bacteria in the intestinal bacterium group, further preferably 42 intestinal bacteria each of which has a DNA composed of a base sequence specified at any of SEQ ID NOs: 106 to 147 or a base sequence having at least 70% identity with the base sequence, and particularly preferably 42 bacteria each of which has a DNA composed of a base sequence specified at any of SEQ ID NOs: 106 to 147. In addition, the "intestinal bacterium" having a DNA composed of a base sequence specified at any of SEQ ID NOs: 106 to 147 or a base sequence having at least 70% identity with the base sequence is desirably susceptible to ampicillin.

In addition, as shown in Examples to be described later, an aspect of the "intestinal bacterium" in the present invention is an intestinal bacterium which is resistant to at least one compound selected from the group consisting of spectinomycin, and/or susceptible to at least one compound selected from the group consisting of ampicillin, tylosin, and chloroform. In addition, another aspect is an intestinal bacterium which is resistant to metronidazole and/or susceptible to at least one compound selected from the group consisting of vancomycin and tylosin.

<Antibacterial Composition and Pharmaceutical Composition>

The composition of the present invention only needs to contain the above-described intestinal bacteria, and the bacteria may be living cells or dead cells. Alternatively, the composition can be used in combination. As a result of the combinational use, when the composition is provided or absorbed (when the composition is used in combination), the above-described intestinal bacteria may exist separately in two or more compositions.

The composition of the present invention may be in the form of a pharmaceutical composition, a food or drink (including an animal feed), or a reagent used for a research purpose (for example, in vitro or in vivo experiment).

The composition of the present invention suppresses the immunity and the Th1 cell induction in an intestine by the bacterium capable of inducing Th1 cell proliferation or activation in an intestinal tract. Accordingly, the composition of the present invention is suitably used as a pharmaceutical composition, food, or drink for treating, preventing, or alleviating the disease attributable to Th1 cells.

The composition of the present invention can be formulated by known formulation methods. The composition can be used for administration orally, parenterally (for example, intestinally, intramuscularly, intravenously, intratracheally, intranasally, transdermally, intradermally, subcutaneously, intraocularly, intravaginally, intraperitoneally, rectally or by inhalation), or through multiple routes consisting of a combination of these, in the form of, for example, a capsule, a tablet, a pill, a liquid, a powder, a granule, a fine granule, a film coating agent, a pellet, a troche, a sublingual tablet, a masticatory, a buccal, a paste, a syrup, a suspension, an elixir, an emulsion, an endermic liniment, an ointment, a plaster, a poultice, a percutaneous absorption preparation, a lotion, an inhalation, an aerosol, an injection, a suppository, or the like.

When formulated, these can be combined as appropriate with a pharmacologically acceptable carrier or a carrier acceptable as a food or drink, concretely, sterile water, a saline, a buffer solution, a medium, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a disintegrant, a buffer, a coating agent, a lubricant, a colorant, a sweetener, a viscous agent, a corrigent, a solubilizer, or other additives.

Meanwhile, in these formulations, from the viewpoints such as more efficiently suppressing the immunity and the Th1 cell proliferation or activation in an intestine, particularly in formulating a pharmaceutical preparation for oral administration, the composition of the present invention may be combined with a composition which enables an efficient delivery to an intestine. Such a composition enabling the delivery to an intestine is not particularly limited, and known compositions can be employed as appropriate. Examples thereof include pH sensitive compositions, compositions for suppressing the release into the intestinal tract (such as cellulose-based polymers, acrylic acid polymers and copolymers, vinyl acid polymers and copolymers), bioadhesive compositions which specifically adhere to mucosas of the intestinal tract (for example, a polymer described in the specification of U.S. Pat. No. 6,368,586), protease inhibitor-containing compositions, and compositions specifically degraded by enzymes in the intestine).

In addition, in the case where the antibacterial composition of the present invention is used as a pharmaceutical composition, the composition may further comprise a known substance (for example, an anti-inflammatory agent, an immunosuppressant) used for treating, preventing, or alleviating a disease attributable to Th1 cells, or may be used in combination with such a substance.

In the case where the composition of the present invention is used as a food or drink, the food or drink may be, for example, a health food, a functional food, a food for specified health use, a food with nutrient function claims, a function-labeled food, a nutritional supplementary food, a medical food for the ill, or an animal feed. Concrete examples of the food or drink include liquid foods such as fermented drinks, oil-containing products, soups, dairy drinks, refreshing drinks, tea drinks, alcoholic drinks, energy drinks, and jelly drinks, carbohydrate-containing foods, livestock-processed foods, processed seafoods; vegetable-processed foods, semi-solid foods, fermented foods, confectionaries, retort pouch foods, microwave foods, and the like. The examples further include health foods or drinks prepared in the form of powder, granule, tablet, capsule, liquid, paste, or jelly. Note that, in the present invention, the food or drink can be produced by production techniques known in this technical field. To the food or drink, an active ingredient (for example, a nutrient or the like) for alleviating or preventing a disease attributable to Th1 disease may be added. Moreover, in combination with another ingredient or another functional food which exhibit a function other than the alleviation or the like, a multi-functional food or drink can be prepared.

A product (drug, food, drink, reagent) of the composition of the present invention or a manual thereof may be provided with an indication stating that the product is used for suppressing Th1 cell proliferation or activation, or treating, alleviating, or preventing a disease attributable to Th1 cells. Meanwhile, in the case of the food or drink, the product of the composition or the like of the present invention may be provided with an indication of the health function as a health functional food (a food for specified health use, a food with nutrient function claims, a function-labeled food) to be distinguished from general foods by the appearance, target persons, and so forth. Herein, "a product or a manual provided with an indication" means that the indication is attached to the main body, container, package, or the like of the product, or that the indication is provided in the manual, package insert, advertisement, other printed materials, or the like disclosing information on the product. Further, the composition of the present invention may be in the form of a kit.

In addition, as described above, a pharmaceutical composition can be produced by a known formulation technique using the intestinal bacterium and the like of the present invention. Therefore, the present invention also provides use of the intestinal bacterium and the like of the present invention for producing a pharmaceutical composition for treating, alleviating, or preventing a disease attributable to Th1 cells.

<Bacteria Having Antibacterial Activity against Bacteria That Induce Th1 Cells in Intestinal Tract>

Regarding the present invention, as shown in FIG. 1, intestinal colonization of the Kp2H7 strain was not observed when the Kp2H7 strain was orally administered to SPF mice. However, it has been clarified that administration of ampicillin or tylosin to SPF mice allows the Kp2H7 strain to colonize in the mouse intestine. On the other hand, is has also been found by the present inventors that administration of metronidazole or spectinomycin to SPF mice does not cause intestinal colonization of the Kp2H7 strain.

Figure 2:
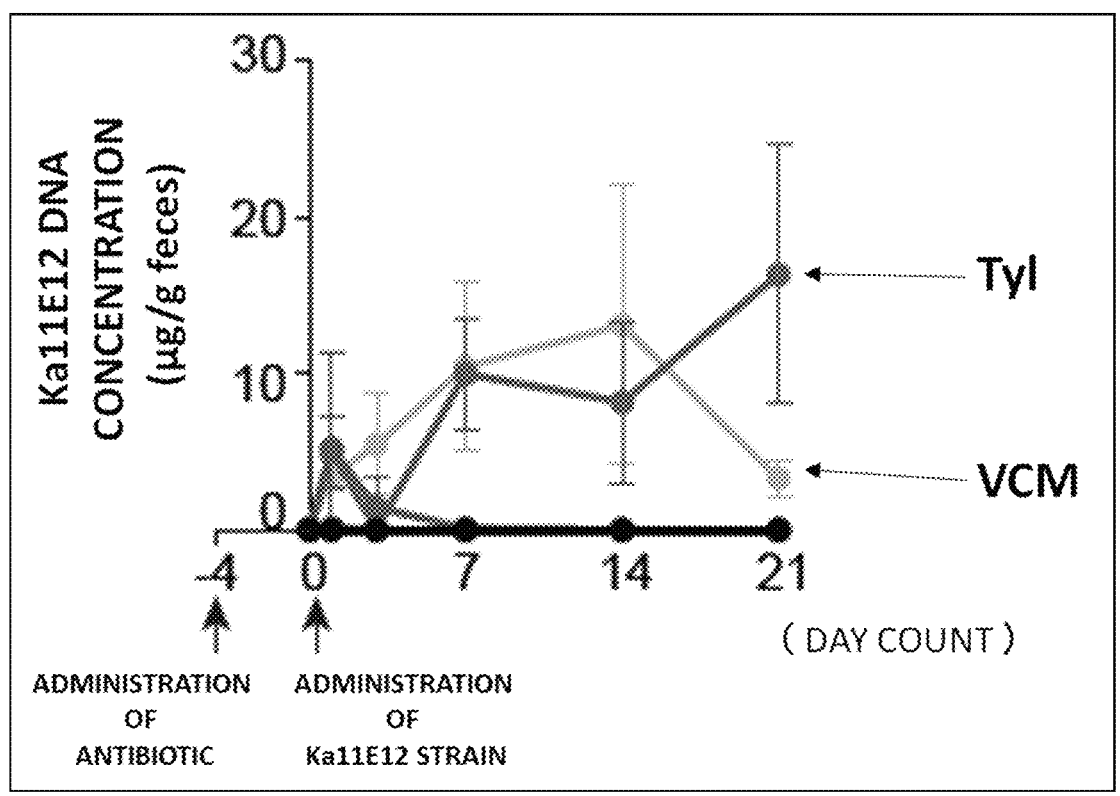
FIG. 2 is a graph illustrating the results of qPCR analysis of the change over time of the intestinal colonization level of a Ka11E12 strain in SPF mice administered with various antibiotics and then fed with the strain.
Figure 3:
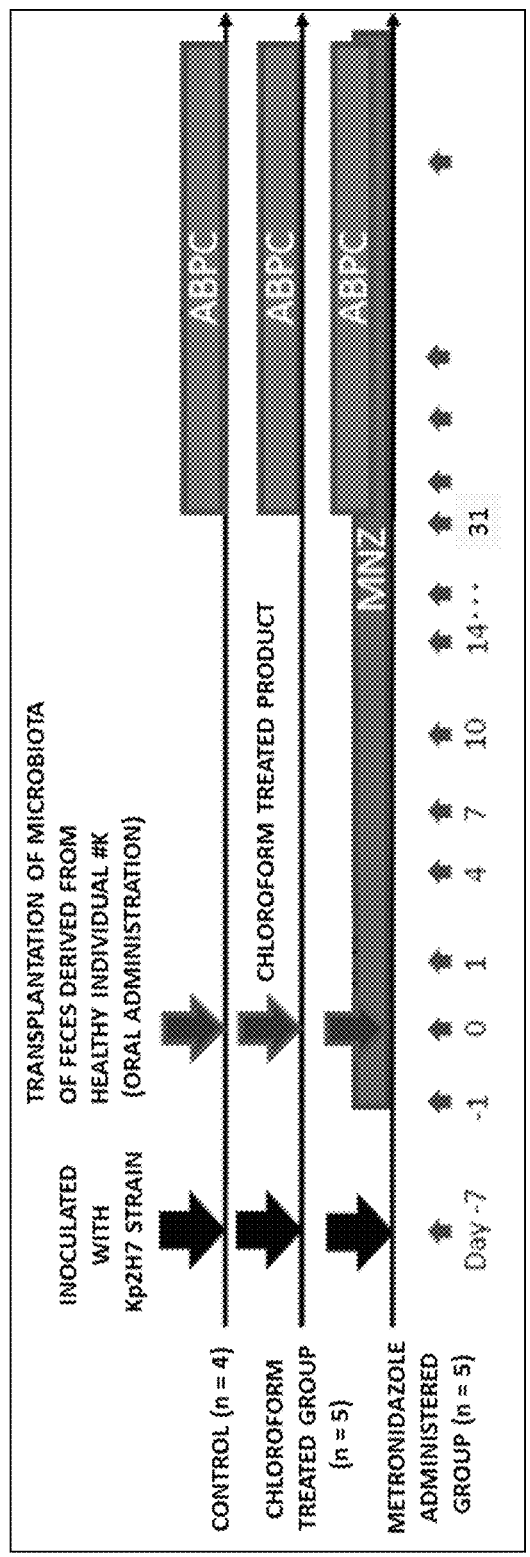
FIG. 3 is a diagram illustrating an overview of an experiment of administering fecal samples derived from a healthy individual (#K) to germ-free mice inoculated with the Kp2H7 strain.

In addition, germ-free mice were orally administered with the Kp2H7 strain, and were further provided with human (healthy individual) fecal samples. As a result, as shown in FIGS. 2 and 3, intestinal colonization of the Kp2H7 strain was not observed as in the above-described SPF mice. However, it has been revealed that the Kp2H7 strain is allowed to colonize in the mouse intestine when provided with a sample obtained by treating human feces with chloroform having a final concentration of 3%. On the other hand, it has also been found by the present inventors that administration of metronidazole to germ-free mice does not cause intestinal colonization of the Kp2H7 strain as in the above-described SPF mice. That is, the present inventors have also revealed for the first time that, in intestinal bacteria, there are bacteria that suppress colonization and the like of bacteria that induce Th1 cells in the intestinal tract.

Therefore, the present invention provides a bacterium having antibacterial activity against bacteria that induce Th1 cell proliferation or activation in the intestinal tract. Such a bacterium only needs to have the antibacterial activity, and examples thereof include the intestinal bacteria described above.

In addition, whether bacteria have the above-described antibacterial activity can be evaluated using the method or screening method described in Examples to be described later.

<Methods for Treating Disease Attributable to Th1 Cells, and the Like>

The present invention also provides a method for suppressing the proliferation or activation of Th1 cells in a subject, a method for suppressing immunity in the subject, or a method for treating, alleviating, or preventing a disease attributable to Th1 cells in the subject, the method comprising providing the subject with the above-described antibacterial composition or pharmaceutical composition, or the above-described intestinal bacterium or the above-mentioned bacterium having antibacterial activity, the bacteria serving as active ingredients of the compositions (hereinafter also collectively referred to as "the pharmaceutical and other compositions of the present invention or the active ingredients thereof").

In the present invention, the term "disease attributable to Th1 cells" means a disease induced by the Th1 cell proliferation or activation. Examples of the disease include inflammatory bowel diseases (chronic inflammatory bowel diseases such as Crohn's disease, ulcerative colitis, and inflammatory bowel diseases, and the like), diabetes mellitus type 1, autoimmune diseases such as rheumatoid arthritis, experimental autoimmune encephalomyelitis (EAE), multiple sclerosis, and systemic lupus erythematosus, and chronic inflammatory diseases. In addition, the "immunity" to be suppressed in the present invention includes not only mucosal immunity (such as intestinal immunity) but also general immunity. Moreover, the "immunity" includes not only cell-mediated immunity but also humoral immunity.

The pharmaceutical and other compositions of the present invention or the active ingredients thereof can be used for animals including human as the subject. The animals other than human are not particularly limited, and various domestic animals, poultry, pet animals, experimental animals, and the like can be the subject.

Moreover, the subject to be provided with the intestinal bacterium and the like of the present invention includes animals comprising the Th1 cell-inducible bacterium, regardless of the development of the disease attributable to Th1 cells. In addition, from the viewpoint of the prevention, animals which do not comprise or may comprise the bacterium may be provided with the pharmaceutical and other compositions of the present invention or the active ingredients thereof.

The method for providing the pharmaceutical and other compositions of the present invention or the active ingredients thereof is not particularly limited. They may be orally administered, or may be parenterally administered (for example, administered into an intestine). In the case of oral administration, from the viewpoint of further enhancing the effects of the pharmaceutical and other compositions of the present invention or the active ingredients thereof, the subject to be provided with the pharmaceutical and other compositions of the present invention or the active ingredients thereof is preferably provided with a proton-pump inhibitor (PPI) or the like in advance to reduce the production of gastric acid.

Moreover, when the pharmaceutical and other compositions of the present invention or the active ingredients thereof are provided, the amount provided can be selected as appropriate by those skilled in the art, depending on the age, body weight, disease symptom, and health state of the subject, the type of the composition (such as drug, food, drink), the providing method, and so forth.

<Composition for Testing for Disease attributable to Th1 Cells>

As described above, the present invention has revealed the presence of intestinal bacteria that can suppress the colonization and the like of the Th1 cell-inducible bacteria in the intestinal tract. Hence, a disease attributable to Th1 cells can be tested by detecting the presence of the intestinal bacterium.

Thus, the present invention provides the following compositions for testing for a disease attributable to Th1 cells.

A composition for testing for a disease attributable to Th1 cells, the composition comprising an antibody capable of specifically recognizing the intestinal bacterium and the like of the present invention.

A composition for testing for a disease attributable to Th1 cells, the composition comprising a polynucleotide for detecting a nucleotide sequence specific to the intestinal bacterium and the like of the present invention.

In the present invention, the "antibody capable of specifically recognizing the intestinal bacterium and the like of the present invention" may be a polyclonal antibody, a monoclonal antibody, or a functional fragment of an antibody (for example, Fab, Fab', F(ab')2, a variable region fragment (Fv), a disulfide-stabilized Fv, a single-chain Fv (scFv), sc(Fv)2, a diabody, a polyspecific antibody, or polymers thereof), as long as it is possible to specifically recognize the bacterium. If the antibody of the present invention is a polyclonal antibody, the polyclonal antibody can be obtained as follows. Concretely, a host animal is immunized with an antigen (such as a polypeptide, a polynucleotide, a carbohydrate, or a lipid derived from the intestinal bacterium and the like of the present invention). Then, an antiserum from the animal is purified by conventional means (for example, salting-out, centrifugation, dialysis, column chromatography, or the like). Thus, the polyclonal antibody can be obtained. Meanwhile, a monoclonal antibody can be prepared by a hybridoma method or a recombinant DNA method.

Moreover, as the antibody used in the test of the present invention, an antibody bound to a labeling substance can be used. Detecting the labeling substance enables direct measurement of the amount of the antibody bound to the intestinal bacterium and the like of the present invention or a substance derived from the bacterium. The labeling substance is not particularly limited, as long as the labeling substance can bind to the antibody and can be detected by a chemical or optical method. Examples of the labeling substance include fluorescent dyes (such as GFP), enzymes (such as HRP), and radioactive substances.

The testing composition of the present invention may comprise other ingredients acceptable as a composition than the antibody ingredient. Examples of such other ingredients includes carriers, excipients, disintegrants, buffers, emulsifiers, suspensions, stabilizers, preservatives, antiseptics, physiological salts, labeling substances, and secondary antibodies. Further, besides the testing composition, a substrate necessary for detection of the labeling substance, a positive control or a negative control, a buffer solution used to dilute or wash a sample, a tube or a plate used for the reaction between the sample and the antibody of the present invention, or the like can be combined, so that a kit for testing for a disease attributable to Th1 cells can also be provided. Meanwhile, in a case where the antibody preparation is an unlabeled antibody, a labeled substance (for example, secondary antibody, Protein G, Protein A, or the like) capable of binding to the antibody can be combined. Additionally, the kit for testing for a disease attributable to Th1 cells may comprise an instruction for the kit.

Further, the testing composition of the present invention can also be combined with a device for detecting the antibody of the present invention. Examples of the device include flow cytometers and microplate readers.

In the present invention, the "polynucleotide for detecting a nucleotide sequence specific to the intestinal bacterium and the like of the present invention" is not particularly limited, as long as the sequence specific to the bacterium is detected. Examples of the polynucleotide include any polynucleotides according to the following (a) and (b) each of which has a chain length of at least 15 nucleotides:

(a) a polynucleotide that is a pair of primers designed to flank the specific nucleotide sequence; and (b) a polynucleotide that is a primer or a probe capable of hybridizing to a nucleotide sequence containing the specific nucleotide sequence.

The polynucleotide of the present invention has a base sequence complementary to a nucleotide sequence of the intestinal bacterium and the like of the present invention. Herein, being "complementary" does not always have to be completely complementary, as long as the hybridization is possible. These polynucleotides have a homology of normally 80% or more, preferably 90% or more, more preferably 95% or more, and particularly preferably 100%, with the nucleotide sequence.

The "chain length" of the polynucleotide of the present invention is normally 15 to 100 nucleotides, preferably 17 to 30 nucleotides, and more preferably 20 to 25 nucleotides, in the case where the polynucleotide is used as the primer. Meanwhile, in the case where the polynucleotide is used as the probe, the chain length is normally 15 to 1000 nucleotides, and preferably 20 to 100 nucleotides.

The polynucleotide of the present invention may be a DNA or an RNA, or may have part or all of the nucleotide substituted with an artificial nucleic acid such as LNA (registered trademark, locked nucleic acid), ENA (registered trademark, 2'-O, 4'-C-Ethylene-bridged nucleic acids), GNA (glycerol nucleic acid), TNA (threose nucleic acid), or PNA (peptide nucleic acid).

Note that the polynucleotide of the present invention can be chemically synthesized by using a commercially-available automated nucleotide synthesizer or the like. Moreover, as the polynucleotide used in the test of the present invention, a polynucleotide bound to a labeling substance can be used. The labeling substance is not particularly limited, as long as the labeling substance can bind to the polynucleotide and can be detected by a chemical or optical method. Examples of the labeling substance include fluorescent dyes (such as DEAC, FITC, R6G, TexRed, Cy5), dyes (chromogens) such as DAB other than the fluorescent dyes, enzymes, and radioactive substances.

The testing composition of the present invention may comprise other pharmacologically acceptable ingredients than the above-described polynucleotide. Examples of such other ingredients include buffers, emulsifiers, suspensions, stabilizers, antiseptics, physiological salts, and the like.

Further, besides the testing composition, a preparation such as a substrate necessary for detection of the labeling substance added to the polynucleotide, a positive control or a negative control, or a buffer solution used to dilute or wash a sample can be combined, and a tube or a plate used for the reaction between the sample and the polynucleotide of the present invention, or the like can be combined, so that a kit for testing for a disease attributable to Th1 cells can also be provided. Furthermore, the kit for testing for a disease attributable to Th1 cells may comprise an instruction for the kit.

Further, the testing composition of the present invention can also be combined with a device for detecting the nucleotide sequence specific to the intestinal bacterium and the like of the present invention. Examples of the device include thermal cyclers, sequencers, and microarrays.

Moreover, the present invention also provides a method for testing for a disease attributable to Th1 cells by using the above-described antibody, polynucleotide, or testing composition. To be more specific, the present invention provides a method for testing for a disease attributable to Th1 cells, the method comprising the steps of:

bringing the antibody, polynucleotide, or testing composition into contact with a sample isolated from a subject; and detecting the presence or absence of the intestinal bacterium and the like of the present invention in an intestine, as a result of the contact.

The subject is not particularly limited, and includes animals, such as human, which may have a disease attributable to Th1 cells. Moreover, the sample isolated from such a subject is not particularly limited, either, and a fecal sample of the subject, a culture thereof, a polypeptide, a polynucleotide, a carbohydrate, or a lipid extracted therefrom, or the like is suitably used in the method of the present invention.

Examples of the method for detecting the presence or absence of the intestinal bacterium and the like of the present invention by bringing the antibody of the present invention or the testing composition comprising the antibody into contact with the sample include detection methods using an antibody (immunological methods) such as ELISA methods, immunoblotting, antibody array analyses, immunohistochemical staining, flow cytometry, imaging cytometry, radioimmunoassay, and immunoprecipitation.

Meanwhile, as the method for detecting the presence or absence of the intestinal bacterium and the like of the present invention by bringing the polynucleotide of the present invention or the testing composition comprising the polynucleotide into contact with the sample, it is possible to employ, for example, PCR (RT-PCR, real-time PCR, quantitative PCR), DNA microarray analysis, northern blotting, 16s rRNA sequencing, a new generation sequencing method (sequencing-by-synthesis, for example, sequencing using Solexa genome analyzer or Hiseq (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SoliD (registered trademark) or 5500xl manufactured by Life Technologies Corporation), bead array method, in situ hybridization, dot blot, RNase protection assay, mass spectrometry, genomic PCR, or Southern blotting.

In the present invention, "testing" a disease attributable to Th1 cells includes testing not only whether the disease has developed or not, but also the risk of the development. If the presence of the intestinal bacterium and the like of the present invention in an intestine is detected by the above-described method, it can be determined that a disease attributable to Th1 cells has not developed or that the risk of the development is low.

A disease attributable to Th1 cells in a subject is normally diagnosed by a doctor (including one instructed by the doctor). The data obtained by the method of the present invention are useful in the diagnosis by a doctor. Thus, the method of the present invention can also be described as a method for collecting and presenting data useful in a diagnosis by a doctor.

Additionally, the present invention can also provide a companion diagnostic method utilizing the above-described test method and a drug used in the companion diagnostic method. Accordingly, the present invention also provides the following.

A method for determining effectiveness of pharmaceutical and other compositions of the present invention or active ingredients thereof in treating, alleviating, or preventing a disease attributable to Th1 cells, the method comprising the steps of:

bringing the antibody, polynucleotide, or testing composition into contact with a sample isolated from a subject;

detecting the presence or absence of the intestinal bacterium and the like, as a result of the contact; and determining that the effectiveness of the pharmaceutical and other compositions of the present invention or the active ingredients thereof in treating, alleviating, or preventing the disease is high for the subject, if the presence of the bacterium is not detected in the previous step.

A method for treating, alleviating, or preventing a disease attributable to Th1 cells, the method comprising providing pharmaceutical and other compositions of the present invention or active ingredients thereof to a patient for whom the effectiveness of the pharmaceutical and other compositions or the active ingredients thereof has been determined to be high according to the above-described determination method.

A composition for treating, alleviating, or preventing a disease attributable to Th1 cells, the composition comprising, as an active ingredient, an intestinal bacterium and the like of the present invention, wherein the composition is provided to a subject for whom/which the effectiveness has been determined to be high according to the above-described determination method.

<Method for Screening Intestinal Bacterium Having Antibacterial Activity against Bacterium Capable of Inducing Th1 Cell Proliferation or Activation in Intestinal Tract>

As described above, the present inventors have also revealed for the first time that, in intestinal bacteria, there are bacteria that suppress colonization and the like of bacteria that induce Th1 cells in the intestinal tract. Therefore, the present invention provides a method for screening an intestinal bacterium having antibacterial activity against a bacterium capable of inducing Th1 cell proliferation or activation in an intestinal tract, the method comprising the following steps;

providing a non-human germ-free animal with a bacterium capable of inducing Th1 cell proliferation or activation in an intestinal tract and a test intestinal bacterium;

detecting the bacterium capable of inducing Th1 cell proliferation or activation in an intestinal tract of the non-human germ-free animal; and determining that the test intestinal bacterium is an intestinal bacterium having antibacterial activity against a bacterium capable of inducing Th1 cell proliferation or activation in an intestinal tract, if the number of bacteria detected in the previous step is reduced compared to a case where the test intestinal bacteria are not provided.

The "bacterium capable of inducing Th1 cell proliferation or activation in an intestinal tract" is as described above. The "non-human germ-free animal" means an animal born and grown under a germ-free condition, excluding human. Examples of the animals other than human include mice, rats, monkeys, pigs, cattle, horses, sheep, goats, chickens, ducks, ostriches, domesticated ducks, dogs, cats, rabbits, hamsters, and the like, but are not limited thereto. Additionally, among these animals, mice are suitably used.

The test intestinal bacteria to be provided to the non-human germ-free animal may be bacteria present in the intestines of animals. Examples of the animal include humans and non-human animals (such as mice, rats, monkeys, pigs, cattle, horses, sheep, goats, chickens, ducks, ostriches, domesticated ducks, dogs, cats, rabbits, and hamsters). In addition, the intestinal bacteria to be provided to the non-human germ-free animal may be isolated intestinal bacteria, and includes a sample containing intestinal bacteria (for example, a fecal sample of the animal or a culture thereof).

In addition, the method for "providing" a non-human animal with the test intestinal bacterium and the Th1 cell-inducible bacterium is not particularly limited. Normally, the bacteria are orally administered, but may be parenterally administered (for example, administered into an intestine). Additionally, the test intestinal bacterium and the Th1 cell-inducible bacterium may be provided simultaneously, the test intestinal bacterium may be provided to the non-human animal and then the Th1 cell-inducible bacterium may be provided to the animal, or the Th1 cell-inducible bacterium may be provided to the non-human animal and then the test intestinal bacterium may be provided to the animal.

The Th1 cell-inducible bacteria in the intestinal tract can be "detected" by detecting a nucleotide sequence specific to the Th1 cell-inducible bacteria. Examples of the detection method include PCR (RT-PCR, real-time PCR, quantitative PCR), DNA microarray analysis, northern blotting, 16s rRNA sequencing, a new generation sequencing method (sequencing-by-synthesis, for example, sequencing using Solexa genome analyzer or Hiseq (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SoliD (registered trademark) or 5500xl manufactured by Life Technologies Corporation), bead array method, in situ hybridization, dot blot, RNase protection assay, mass spectrometry, genomic PCR, or Southern blotting.

In addition, the Th1 cell-inducible bacteria in the intestinal tract can be "detected" by detecting, for example, an amino acid sequence specific to the Th1 cell-inducible bacteria. Examples of the detection method include detection methods using an antibody (immunological methods) such as ELISA methods, immunoblotting, antibody array analyses, immunohistochemical staining, flow cytometry, imaging cytometry, radioimmunoassay, and immunoprecipitation.

Moreover, the timing of the detection is not particularly limited, and can be adjusted as appropriate by those skilled in the art, depending on the type of the animal used, and so forth.

Note that if the intestinal bacterium having antibacterial activity against the bacterium capable of inducing Th1 cell proliferation or activation in an intestinal tract cannot be obtained by performing the screening method of the present invention one time, the obtained bacterium-containing sample in the intestine is provided as the next test intestinal bacterium to another non-human germ-free animal, and the above-described screening is performed multiple times, so that the intestinal bacterium having antibacterial activity can be isolated.

EXAMPLES

Hereinafter, the present invention will be described more specifically based on Examples. However, the present invention is not limited to the following Examples.

Example 1

<Colonization of Th1 Cell-Inducible Bacterium in Antibiotic-Treated Mice>

Prior to gavage of Th1 cell-inducible bacteria, the following antibiotics were administered to SPF mice (wild type C57BL/6) through the drinking water for 4 days. Moreover, mice without these antibiotics administered were also prepared.

Antibiotics: ampicillin (200 mg/L), tylosin (500 mg/L), metronidazole (500 mg/L), spectinomycin (200 mg/L), vancomycin (200 mg/L).

The Kp2H7 strain or the Ka11E12 strain, which is a Th1 cell-inducible bacterium, was cultured to log phase in LB broth, and 1 to $2\times10^8$ CFUs were used to inoculate the mice.

Feces were collected 1, 3, 7, 14, and 21 days after the gavage of Th1 cell-inducible bacteria, and DNAs were extracted therefrom. Then, these DNAs were used as templates to perform qPCR using the following primers specific to each bacterial strain, thereby evaluating the intestinal colonization level of each bacterial strain.

```
Klebsiella (ompK36-3_F:
5'-GCGACCAGACCTACATGCGT-3' [SEQ ID NO: 148],
ompK36-3_R:
5'-AGTCGAAAGAGCCCGCGTC-3' [SEQ ID NO: 149]), Kp-2H7 (sca4_298_F:
5'-AGCACTAGCGGCTGTGGTAT-3' [SEQ ID NO: 150],
sca4_298_R:
5'-ACTTACTCGGGCCCTTGATT-3' [SEQ ID NO: 151]), Ka-11E12 (group_4037_F:
5'-CTTCGCCTTCATCAGCTTCA-3' [SEQ ID NO: 152],
group_4037_R:
5'-TCATCATTAACGCGGGTCAG-3' [SEQ ID NO: 153]),
```

FIG. 1 and FIG. 2 show the obtained results.

As described in PTL 1, the present inventors have revealed that, when administered to germ-free mice, the Kp2H7 strain colonizes in their intestinal tract and induces Th1 cells. In addition, the present inventors have confirmed that the bacterial strain is a bacterial strain which is resistant to ampicillin, tylosin, metronidazole, or spectinomycin.

However, when the Kp2H7 strain was administered to SPF mice, colonization of the bacterial strain in the intestinal tract was not observed unlike the case of administration to germ-free mice, as shown in FIG. 1.

Interestingly, in the SPF mice administered with metronidazole or spectinomycin, the Kp2H7 strain was resistant to these antibiotics, but no intestinal colonization of the bacterial strain was observed. On the other hand, intestinal colonization of the Kp2H7 strain was observed in the SPF mice administered with ampicillin or tylosin (see "Amp" and "Tyl" in FIG. 1).

Additionally, as described in PTL 1, the present inventors have revealed that, when administered to germ-free mice, the Ka11E12 strain also colonizes in their intestinal tract and induces Th1 cells. Moreover, the present inventors have confirmed that the bacterial strain is a bacterial strain which is resistant to vancomycin, tylosin, or metronidazole.

However, as in the case of the Kp2H7 strain, when the Ka11E12 strain was administered to SPF mice, colonization of the bacterial strain in the intestinal tract was not observed unlike the case of administration to germ-free mice, as shown in FIG. 2.

On the other hand, colonization of the Ka11E12 strain in the intestinal tract was observed in the SPF mice administered with vancomycin or tylosin (see "VCM" and "Tyl" in FIG. 2).

The above results suggest that antibiotic exposure suppressed the resistance to intestinal colonization of oral-derived Th1 cell-inducible bacteria caused by specific bacteria in the intestinal microbiota (such as bacteria resistant to ampicillin and tylosin but susceptible to metronidazole and spectinomycin, and bacteria resistant to metronidazole but susceptible to vancomycin and tylosin), thereby enhancing the intestinal colonization.

Example 2

<Administration of Human Fecal Sample to Germ-Free Mice Inoculated with Th1 Cell-Inducible Bacteria 1>

As shown in FIG. 3, germ-free mice were inoculated with the Kp2H7 strain in the same manner as in Example 1. Then, one week after the inoculation, a human fecal sample collected from a healthy individual (#K) was orally administered. In addition, during the period of 31 to 94 days after the oral administration, ampicillin was continuously administered in the same manner as in Example 1 (hereinafter, the mice thus treated is also referred to as the "controls").

In addition, germ-free mice were treated in the same manner as for the control except for orally administering the sample treated with chloroform at a final concentration of 3% instead of the human fecal sample (hereinafter, the mice thus treated are also referred to as the "chloroform treated group").

Moreover, germ-free mice were treated in the same manner as for the control except that metronidazole was continuously administered in the same manner as in Example 1 from one day before oral administration of human fecal sample (hereinafter, the mice thus treated are also referred to as the "metronidazole administered group").

Figure 4:
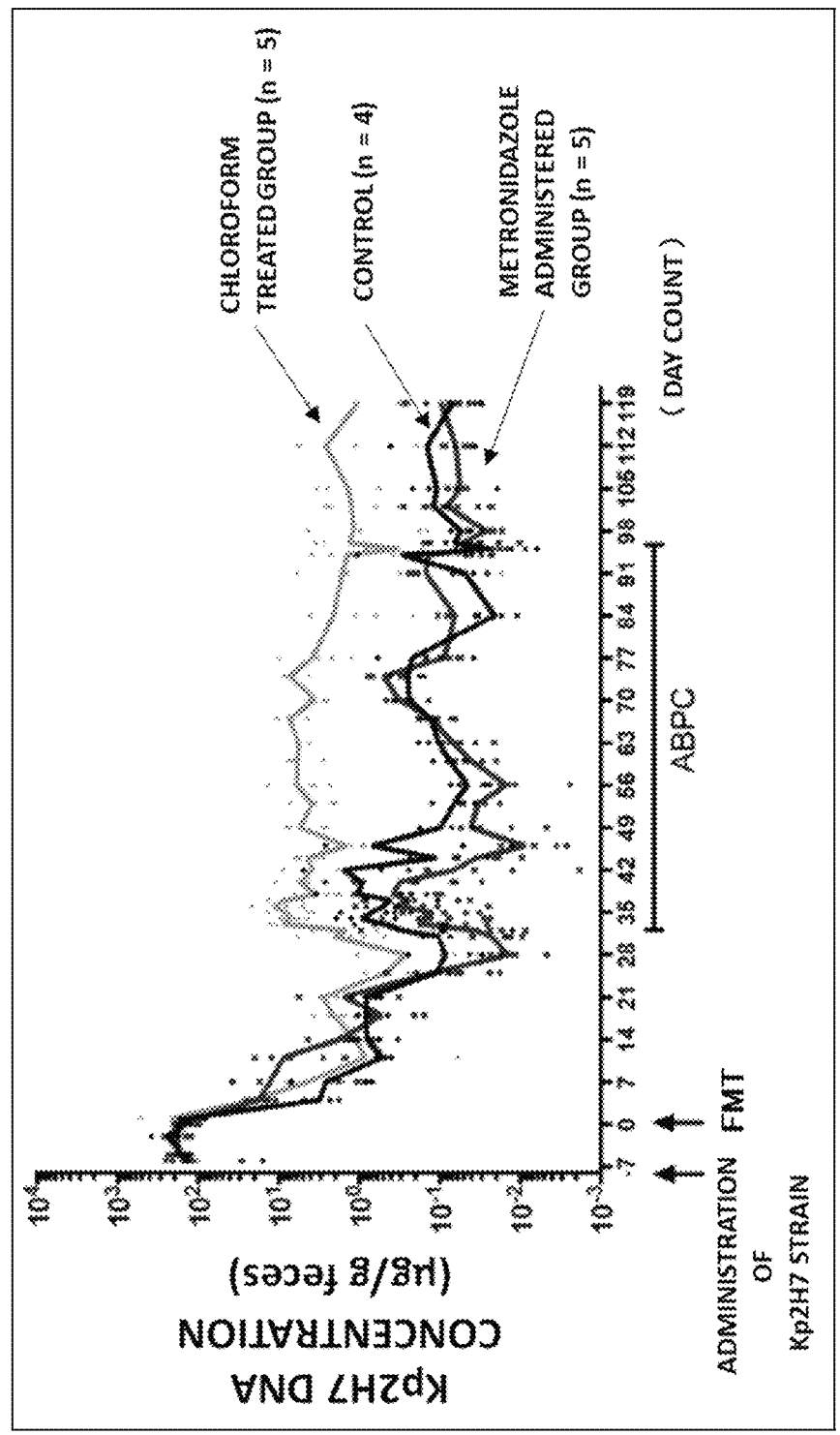
FIG. 4 is a graph illustrating the results of qPCR analysis of the change over time of the intestinal colonization level of a Kp2H7 strain in germ-free mice inoculated with the Kp2H7 strain and then fed with fecal samples derived from a healthy individual (#K).

Then, feces of the SPF mice thus treated were collected, and the intestinal colonization level of the Kp2H7 strain was evaluated by qPCR in the same manner as Example 1. FIG. 4 shows the obtained results.

As is apparent from the results shown in FIG. 4, the germ-free mice were orally administered with the Kp2H7 strain and further provided with human (healthy human) fecal samples, and as a result, intestinal colonization of the Kp2H7 strain was not observed as in the SPF mice. However, it was revealed that the Kp2H7 strain can colonize in the mouse intestine when provided with a sample obtained by treating human feces with chloroform. Meanwhile, as in the SPF mice, administration of metronidazole to germ-free mice did not cause intestinal colonization of the Kp2H7 strain.

Example 3

<Administration of Human Fecal Sample to Germ-Free Mice Inoculated with Th1 Cell-Inducible Bacteria 2>

Preparation of Fecal Sample

Feces (#K fecal sample, #F fecal sample, and #I fecal sample) provided from healthy volunteers (#K, F, and I) were diluted 5 times by weight with a glycerol PBS solution (final concentration of glycerol: 20% by volume) and filtered through a 100 µm-diameter filter, and the resultant was stored at −80° C. as a stock solution. Note that the healthy volunteer #K in the present example and the healthy individual #K in Example 2 are the same person.

Preparation of Kp2H7 Single-Bacterium-Colonized Mice

C57BL/6N Jcl gnotobiotic mice (manufactured by CLEA Japan, Inc., 4 to 8 weeks of age) were bred in a breeding vinyl isolator (sterile isolator) (manufactured by ICM Inc.; ICM-1B) for 1 week or more under free drinking and feeding conditions to acclimatize to the environment.

The Kp2H7 strain was cultured in a Schaedler blood medium, an LB medium, or an agar plate thereof in an anaerobic environment at 37° C. and 10% $CO_2$. A suspension at 200 µL of any of the above media containing $1\times10^{10}$ CFU equivalent Kp2H7 was orally administered into the stomach of mice of 8 to 11 weeks of age. Thereafter, the mice were bred in a sterile isolator for 1 week to prepare Kp2H7 single-bacterium-colonized mice.

Colonization of Bacteria by Fecal Transplantation

The stock solution of each fecal sample prepared as described above was melted at room temperature and diluted to 10 times volume with PBS. The diluted solution at 200 µL was orally administered into the stomach of Kp2H7 single-bacterium-colonized mice. Moreover, for one month, the mice were bred in a sterile isolator under free drinking and feeding conditions, and the bacteria in the transplanted feces were colonized in the mice.

Elimination of Colonized Bacteria by Administration of Antibiotic Ampicillin

After the culture for 1 month, the free drinking water was changed to a 200 mg/L aqueous solution of ampicillin, and the mice were further bred for 1 month to eliminate ampicillin non-resistant bacteria.

Measurement of Intestinal Kp2H7 Colonization Level

The qPCR measurement of CFU and intestinal bacterium genome was used to obtain the abundance ratio of Kp2H7 strains colonized in the intestine of the Kp2H7 single-bacterium-colonized mice orally administered with healthy individual fecal samples and further administered with ampicillin.

For CFU, only the Kp2H7 strain was selectively cultured by adding mouse feces suspended in PBS to a DHL medium to which ampicillin and spectinomycin were added to a final concentration of 30 µg/mL. Then, the absorbance (OD600) was calculated as an index.

In the qPCR measurement method, bacterial genomic DNA extracted from mouse feces was amplified and quantified with a Kp2H7 genome-specific primer and a universal bacterial primer, and the abundance ratio of the Kp2H7 strain in the bacteria in the mouse fecal sample was calculated.

The bacterial genome was extracted by the following steps.

To 10 mg of mouse feces, 5 times weight of PBS solution containing EDTA and glycerol (final concentration of EDTA: 10 mM, final concentration of glycerol: 20% by volume) was added, and the mixture was subjected to vigorous shaking and crushing suspension.

To 100 μL of the sample solution filtered through a 100 μm-diameter filter, 800 μL of 10 mM Tris/10 mM EDTA buffer solution obtained by dissolving 15 mg of lysozyme (manufactured by Sigma-Aldrich, Lysozyme from chicken egg white; L4919) and 5 μL of RNase (manufactured by Thermo Fisher Scientific, PureLink RNase A (20 mg/mL); 12091-021) (PH 8.0, hereinafter also referred to as "TE10") was added and shaken at 37° C. for 1 hour. Subsequently, 2,000 U of Achromopeptidase (registered trademark) (Wako; 015-09951) was added, and the mixture was shaken at 37° C. for 30 minutes for bacterium-lysis.

A 20% SDS TE10 solution at 50 μL and a TE10 solution at 50 μL obtained by dissolving proteinase K (Roche, Proteinase K, recombinant, PCR Grade; 03115852001) to a final concentration of 20 mg/ml were added and shaken at 55° C. for 60 minutes.

DNA was extracted by a liquid-liquid extraction method using Phenol/Chloroform/Isoamyl alcohol (25:24:1) (Wako; 311-90151), and bacterial genomic DNA was obtained by ethanol precipitation.

The qPCR measurement was performed by the following steps.

LightCycler (registered trademark) 480 II (Roche; 05015243001) and Thunderbird (registered trademark) SYBR (registered trademark) qPCRMix (TOYOBO; QPS-201X5) were used to perform amplification and quantification with a Kp2H7 genome-specific primer and a universal bacterial primer, and the calculated DNA concentration ratio was defined as the abundance ratio of Kp2H7.

The sequence of each primer is as follows.

```
Kp2H7 primer: Forward
(5'-AGCACTAGCGGCTGTGGTAT-3' [SEQ ID NO: 150]),

Reverse
(5'-ACTTACTCGGGCCCTTGATT-3' [SEQ ID NO: 151])
``` universal bacterial primer:

```
Forward
(5'-GGTGAATACGTTCCCGG-3' [SEQ ID NO: 154]),

Reverse
(5'-TACGGCTACCTTGTTACGACTT-3' [SEQ ID NO: 155])
```

FIGS. 5 to 8 show the obtained results (qPCR measurement results of intestinal bacterium genome).

As described above, the mice that had been intragastrically administered with 10×10$^{10}$ CFUs of Kp2H7 strains and then bred for 1 week for sufficient colonization of only the single bacterial species Kp2H7 were transplanted with the feces of healthy volunteers #F, I, and K. As a result, along with the progress of free breeding for 1 month after the treatment, the mice transplanted with any feces showed a marked elimination of the Kp2H7 strain, as shown in FIGS. 5 to 8. This suggests that all of #F, I, and K include bacterial strains having an activity of eliminating the Kp2H7 strain.

As shown by the present inventors in PTL 1, the Kp2H7 strain is a multidrug-resistant bacterium which is resistant to at least ampicillin, tylosin, spectinomycin, and metronidazole (nitroimidazole).

Figure 5:
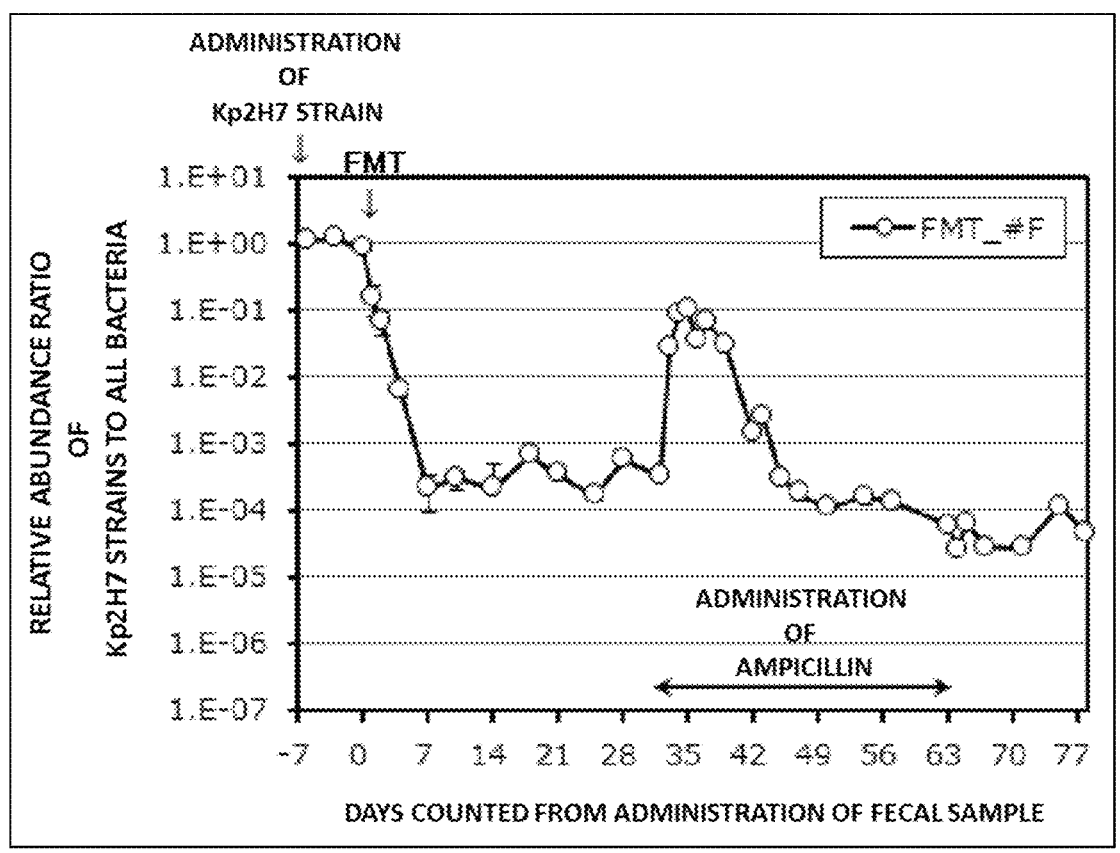
FIG. 5 is a graph illustrating the results of qPCR analysis of the change over time of the intestinal colonization level of a Kp2H7 strain in germ-free mice inoculated with the Kp2H7 strain and then fed with fecal samples derived from a healthy individual (#F).
Figure 6:
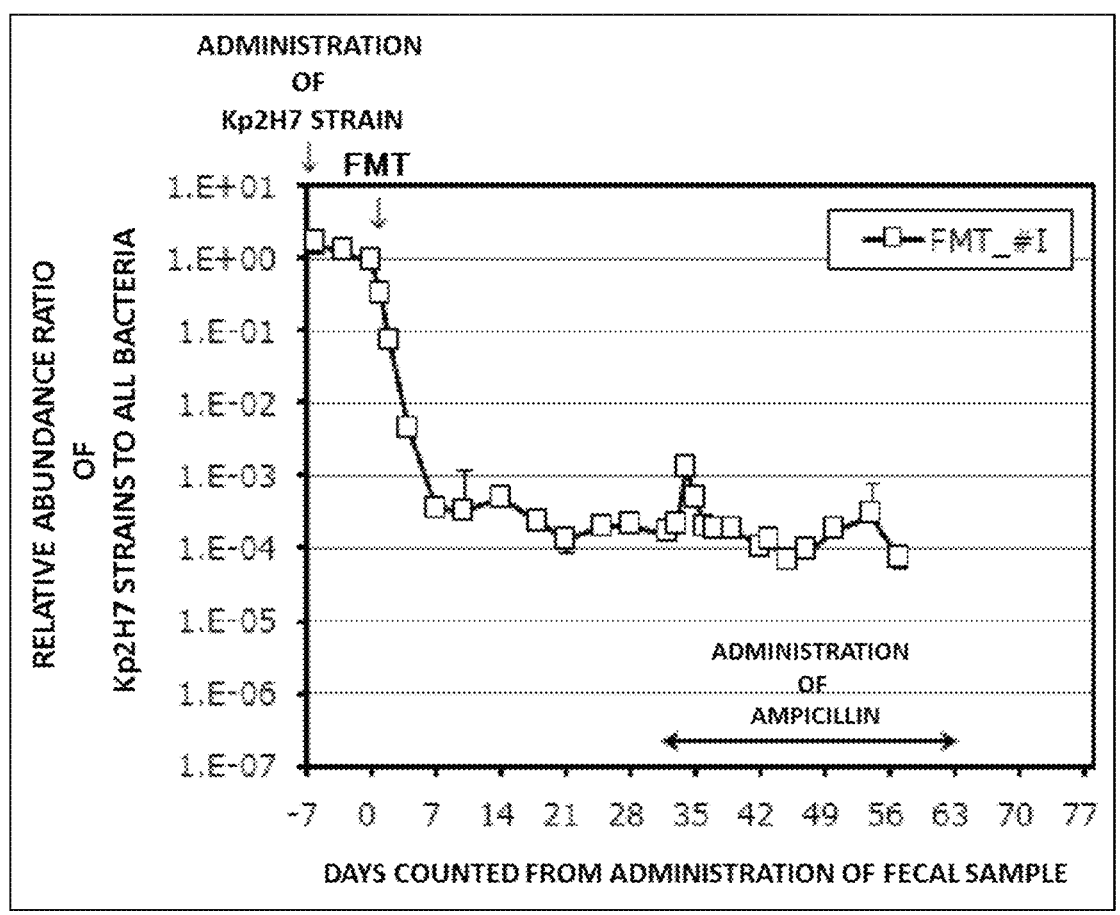
FIG. 6 is a graph illustrating the results of qPCR analysis of the change over time of the intestinal colonization level of a Kp2H7 strain in germ-free mice inoculated with the Kp2H7 strain and then fed with fecal samples derived from a healthy individual (#I).
Figure 7:
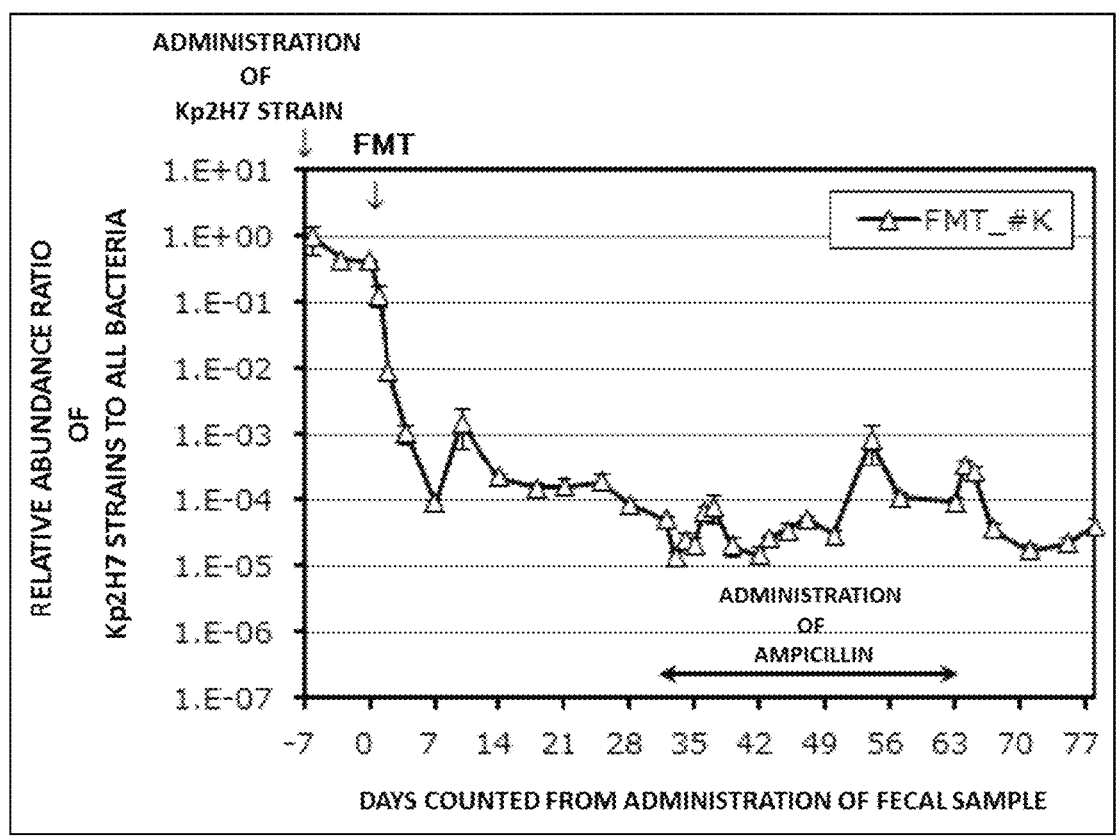
FIG. 7 is a graph illustrating the results of qPCR analysis of the change over time of the intestinal colonization level of a Kp2H7 strain in germ-free mice inoculated with the Kp2H7 strain and then fed with fecal samples derived from the healthy individual (#K).
Figure 8:
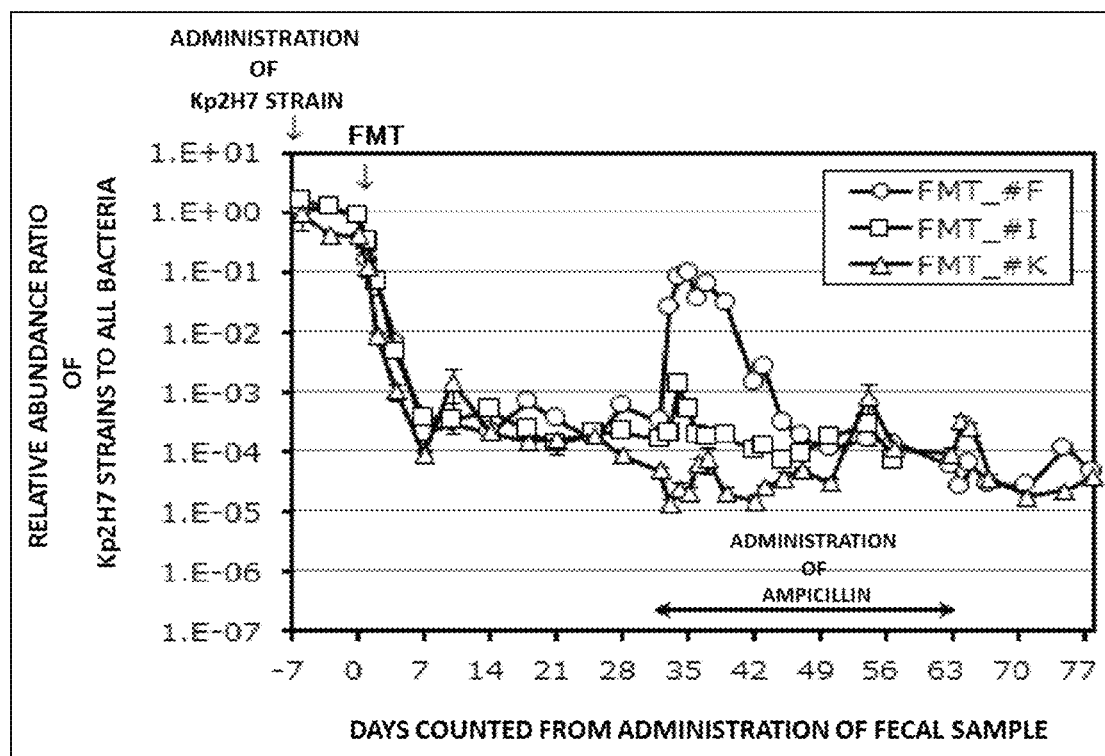
FIG. 8 is a diagram obtained by superimposing the graphs illustrated in FIGS. 5 to 7.

From one month after fecal transplantation, the mice were bred for another month while being administered with the antibiotic ampicillin. Then, as shown in FIG. 5, steep growth of the Kp2H7 strain was observed in the mice transplanted with #F feces. On the other hand, as shown in FIGS. 6 and 7, no significant change was observed in the mice transplanted with #I and K feces. This suggests that the main bacteria contained in the #F feces and involved in the elimination of colonization of the Kp2H7 strain are strains non-resistant (susceptible) to ampicillin. In addition, it is also suggested that the bacteria contained in #I and K feces and involved in the elimination of colonization of the Kp2H7 strain include at least one or more ampicillin withstandable (resistant) strains.

Example 4

Isolation 1 of Bacteria from Healthy Volunteer Feces

The frozen fecal samples derived from #I and #F prepared in Example 3 were thawed at room temperature, diluted with PBS, and cultured on an agar plate of Schaedler blood medium (manufactured by Wako; 517-45805), Luria Bertani (LB) medium (manufactured by Nacalai Tesque Inc.; 20068-75), DHL medium (manufactured by NIHON PHARMACEUTICAL CO., LTD.; 05040), or MacConkey medium (manufactured by Merck; 1.46461.0010) in an anaerobic environment at 37° C. and 10% $CO_2$, and the formed colonies were isolated.

Among the isolated bacteria, 42 types of bacteria derived from #I and 37 types of bacteria derived from #F were subjected to 16S rDNA analysis by the Sanger method to analyze the gene sequences and estimate the bacterial species. The sequencer was 3130 DNA Analyzer manufactured by Thermo Fisher Scientific, and a primer set of the following sequence was used.

```
27 Forward-mod
(5'-AGRGTTTGATYMTGGCTCAG-3' [SEQ ID NO: 156])

1492 Reverse
(5'-GGYTACCTTGTTACGACTT-3' [SEQ ID NO: 157]).
```

Example 5

Isolation 2 of Bacteria from Healthy Volunteer Feces

Kp2H7 single-bacterium-colonized mice that had been intragastrically administered with a Kp2H7 strain single bacterium and bred for 1 week for colonization of the bacterium were intragastrically administered with fecal samples derived from the healthy volunteer #K by the method according to Example 3. In addition, a fecal sample treated with chloroform by the following procedure was similarly administered intragastrically.

Chloroform treatment: A stock solution of K-derived fecal sample prepared in Example 3 was melted at room temperature. Chloroform was added to the melt to a final concentration of 3%, and the mixture was stirred with shaking at 37° C. for 1 hour, and then the chloroform was removed through nitrogen gas.

The feces-transplanted mice prepared as described above were allowed to drink either water or the following antibiotic aqueous solution freely for 2 months, and then feces were collected.

ampicillin, spectinomycin, tylosin, and metronidazole: 200 mg/L streptomycin: 50 mg/L.

After fecal collection, isolation-culture was performed by the method according to Example 4. As a result, 47 strains were isolated. In addition, different Kp2H7 single-bacterium-colonized mice were intragastrically administered with fecal samples derived from #K, and feces were collected and isolation-cultured by the above method. As a result, 68 strains were isolated.

Additionally, the gene sequence analysis of these isolated bacteria and estimation of bacterial species were carried out by the method according to Example 4.

Tables 2 to 5 below show the results obtained in Examples 4 and 5.

TABLE 2

| No. | Species | SEQ ID NO: |
|---|---|---|
| K01 | Ruminococcus sp. ID8 | 1 |
| K02 | Bacteroides sp. S-17 | 2 |
| K03 | Blautia coccoides | 3 |
| K04 | Blautia producta | 4 |
| K05 | Bilophila wadsworthia | 5 |
| K06 | Alistipes onderdonkii | 6 |
| K07 | [Clostridium] clostridioforme | 7 |
| K08 | [Clostridium] innocuum | 8 |
| K09 | Bacteroides fragilis | 9 |
| K10 | Eggerthella lenta | 10 |
| K11 | cf. Clostridium sp. MLG055 | 11 |
| K12 | Erysipelatoclostridium ramosum | 12 |
| K13 | Enterococcus faecalis | 13 |
| K14 | Bacteroides intestinalis | 14 |
| K15 | [Clostridium] symbiosum | 15 |
| K16 | [Clostridium] hylemonae | 16 |
| K17 | Hungatella hathewayi | 17 |
| K18 | Bacteroides sp. D8 | 18 |
| K19 | [Clostridium] clostridioforme | 19 |
| K20 | Flavonifractor plautii | 20 |
| K21 | Bacteroides sp. Smarlab 3302996 | 21 |
| K22 | Bacteroides thetaiotaomicron | 22 |
| K23 | Parabaderoides merdae | 23 |
| K24 | Bacteroides vulgatus | 24 |
| K25 | [Clostridium] aldenense | 25 |
| K26 | Bacteroides uniformis | 26 |
| K27 | Gordonibacter pamelaeae | 27 |
| K28 | Clostridium sp. 14505 | 28 |
| K29 | Anaerostipes caccae | 29 |
| K30 | [Ruminococcus] gnavus | 30 |
| K31 | [Ruminococcus] gnavus | 31 |
| K32 | Alistipes shahii | 32 |
| K33 | Bacteroides sp. DJF_8097 | 33 |
| K34 | Blautia sp. Ser8 | 34 |

TABLE 3

| No. | Species | SEQ ID NO: |
|---|---|---|
| K35 | Butyricicoccus pullicaecorum | 35 |
| K36 | [Clostridium] bolteae | 36 |
| K37 | Anaerotruncus sp. NML 070203 | 37 |
| K38 | Holdemania massiliensis | 38 |
| K39 | Escherichia coli | 39 |
| K40 | Agathobaculum desmolans | 40 |
| K41 | [Eubacterium] rectale | 41 |
| K42 | Lactonifactor longoviformis | 42 |
| K43 | Oscillibacter ruminantium | 43 |
| K44 | Pseudoflavonifractor capillosus | 44 |
| K45 | Streptococcus pasteurianus | 45 |
| K46 | Sutterella wadsworthensis | 46 |
| K47 | Bifidobacterium adolescentis | 47 |
| K48 | [Clostridium] clostridioforme | 48 |
| K49 | Fusicatenibacter saccharivorans | 49 |
| K50 | Hungatella hathewayi | 50 |
| K51 | Clostridium sp. TM-40 | 51 |
| K52 | Ruminococcus sp. DJF_VR70k1 | 52 |
| K53 | Ruminococcus sp. 5_1_39BFAA | 53 |
| K54 | Phascolarctobacterium faecium | 54 |
| K55 | Odoribacter splanchnicus | 55 |
| K56 | Faecalibacterium prausnitzii | 56 |
| K57 | Clostridium sp. 619 | 57 |
| K58 | Eubaderium sp. WAL 17363 | 58 |
| K59 | Alistipes finegoldii | 59 |
| K60 | Subdoligranulum sp. 4_3_54A2FAA | 60 |
| K61 | Christensenella minuta | 61 |
| K62 | Clostridium scindens | 62 |
| K63 | Enterococcus faecalis | 63 |
| K64 | Blautia coccoides | 64 |
| K65 | Alistipes ihumii | 65 |
| K66 | Intestinimonas butyriciproducens | 66 |
| K67 | Bacteroides uniformis | 67 |
| K68 | Akkermansia muciniphila | 68 |

TABLE 4

| No. | Species | SEQ ID NO: |
|---|---|---|
| F01 | Bifidobacterium longum | 69 |
| F02 | Bacteroides xylanisolvens | 70 |
| F03 | Bacteroides fragilis | 71 |
| F04 | Bacteroides uniformis | 72 |
| F05 | Bacteroides thetaiotaomicron | 73 |
| F06 | Bacteroides uniforms | 74 |
| F07 | Bacteroides sp. Smarlab 3302996 | 75 |
| F08 | Bacteroides fragilis | 76 |
| F09 | Parabacteroides goldsteinii | 77 |
| F10 | [Ruminocccus] gnavus | 78 |
| F11 | Blautia wexlerae | 79 |
| F12 | Blautia sp. canine oral taxon 143 | 80 |
| F13 | Clostridium sp. M62/1 | 81 |
| F14 | Tyzzerella nexilis | 82 |
| F15 | [Ruminococcus] gnavus | 83 |
| F16 | Anaerostipes hadrus | 84 |
| F17 | Blautia sp. YHC-4 | 85 |
| F18 | [Clostridium] bolteae | 86 |
| F19 | Blautia sp. YHC-4 | 87 |
| F20 | [Clostridium] innocuum | 88 |
| F21 | Blautia sp. Ser8 | 89 |
| F22 | [Clostridium] asparagiforme | 90 |
| F23 | [Clostridium] glycyrrhizinilyticum | 91 |
| F24 | [Clostridium] clostridioforme | 92 |
| F25 | [Clostridium] glycyrrhizinilyticum | 93 |
| F26 | Flavorefractor plautii | 94 |
| F27 | Blautia wexlerae | 95 |
| F28 | Intestinibacter bartlettii | 96 |
| F29 | [Ruminococcus] gnavus | 97 |
| F30 | Clostridium sp. TM-40 | 98 |
| F31 | [Clostridium] indolis | 99 |
| F32 | Blautia producta | 100 |
| F33 | Erysipelatoclostridium ramosum | 101 |
| F34 | Veillonella sp. 6_1_27 | 102 |
| F35 | Fusobacterium ulcerans | 103 |
| F36 | Fusobacterium ulcerans | 104 |
| F37 | Escherichia coli | 105 |

TABLE 5

| No. | Species | SEQ ID NO: |
|---|---|---|
| 101 | Bifidobacterium adolescentis | 106 |
| 102 | Bifidobacterium pseudocatenulatum | 107 |
| 103 | Bifidobacterium bifidum | 108 |
| 104 | Bifidobacterium longum | 109 |
| 105 | Collinsella aerofaciens | 110 |
| 106 | Collinsella aerofaciens | 111 |
| 107 | Bifidobacterium longum | 112 |
| 108 | Bacteroides stercoris | 113 |
| 109 | Bacteroides massiliensis | 114 |
| 110 | Bacteroides vulgatus | 115 |
| 111 | Bacteroides dorei | 116 |
| 112 | Parabacteroides merdae | 117 |
| 113 | Parabacteroides distasonis | 118 |

TABLE 5-continued

| No. | Species | SEQ ID NO: |
|---|---|---|
| 114 | Alistipes putredinis | 119 |
| 115 | Bacteroides uniformis | 120 |
| 116 | Bacteroides ovatus | 121 |
| 117 | Alistipes shahii | 122 |
| 118 | Odoribader splanchnicus | 123 |
| 119 | Faecalibacterium prausnitzii | 124 |
| 120 | Faecalibacterium prausnitzii | 125 |
| 121 | Blautia luti | 126 |
| 122 | Faecalicatena orotica | 127 |
| 123 | Ruminococcus albus | 128 |
| 124 | Faecalibacterium prausnitzii | 129 |
| 125 | Dorea longicatena | 130 |
| 126 | Dorea formicigenerans | 131 |
| 127 | Anaerostipes hadrus | 132 |
| 128 | Intestinibacter bartlettii | 133 |
| 129 | Flavonifractor plautii | 134 |
| 130 | Pseudoflavonifractor capillosus | 135 |
| 131 | [Clostridium] spirofomne | 136 |
| 132 | Megasphaera elsdenii | 137 |
| 133 | Dialister succinatiphitus | 138 |
| 134 | Acidaminococcus intestini | 139 |
| 135 | Allisonella hisfaminiformans | 140 |
| 136 | Megasphaera massiliensis | 141 |
| 137 | Sutterella wadsworthensis | 142 |
| 138 | Clostridium baratii | 143 |
| 139 | Anaeromassilibacillus senegalensis | 144 |
| 140 | Flintibacter butyricus | 145 |
| 141 | Flavonifractor plautii | 146 |
| 142 | Phocea massiliensis | 147 |

Note that the 47 strains isolated from the fecal sample derived from #K were duplicated with the 68 strains (K1 to K46 described in Tables 2 and 3) except for one strain.

Example 6

Colonization of Bacteria by Isolated Bacteria Culture Solution

The strains isolated in Examples 4 and 5 were cultured for 1 to 3 days in a Schaedler blood medium, LB medium, DHL medium, or MacConkey medium in an anaerobic environment of 37° C. and 10% $CO_2$. The bacterial solution that reached the stationary phase was mixed in equal volumes, and 200 µL thereof was orally administered into the stomach of the Kp2H7 single-bacterium-colonized mice prepared in Example 3. The mice were bred for another 1 month in a sterile isolator under free water and feed conditions to colonize the bacteria. Then, after elimination of the colonized bacteria by administration of the antibiotic ampicillin by the method described in Example 3, the intestinal Kp2H7 colonization level was measured. FIGS. 9 to 12 show the obtained results.

Figure 9:
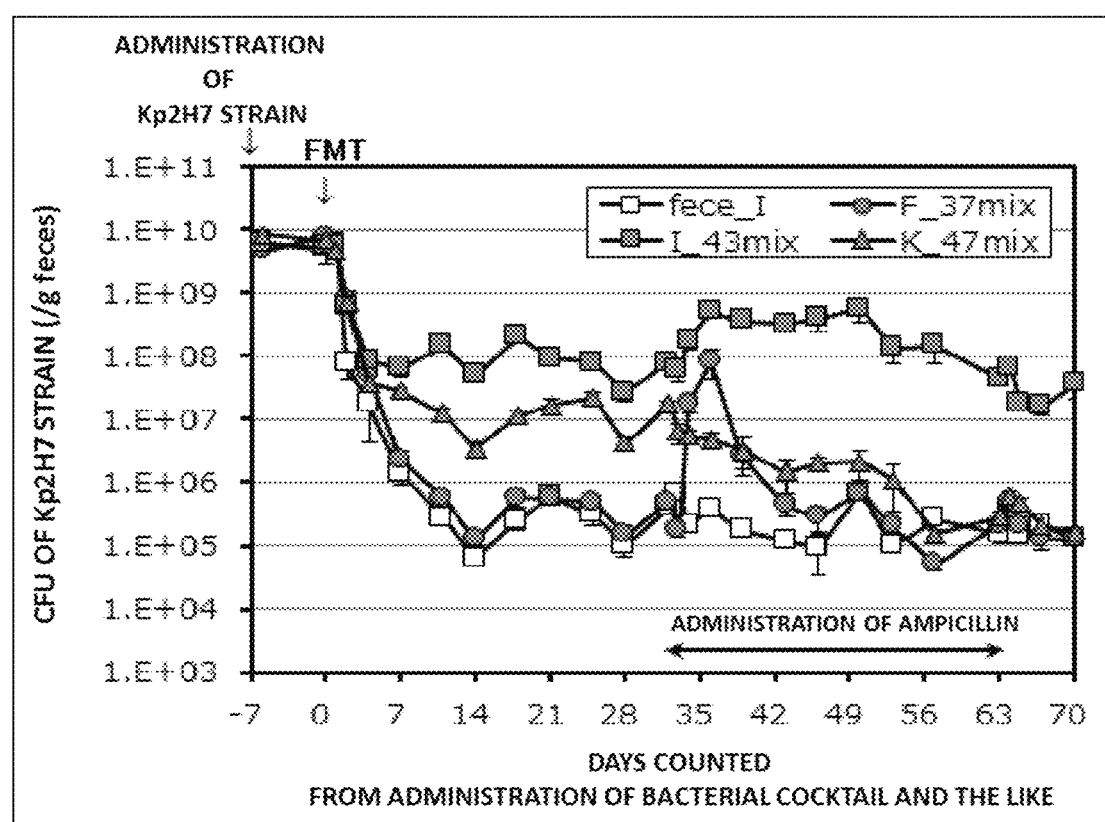
FIG. 9 is a graph illustrating in CFU the change over time of the intestinal colonization level of the Kp2H7 strain in germ-free mice inoculated with the Kp2H7 strain and then fed with a bacterial cocktail derived from the feces of a healthy individual.
Figure 10:
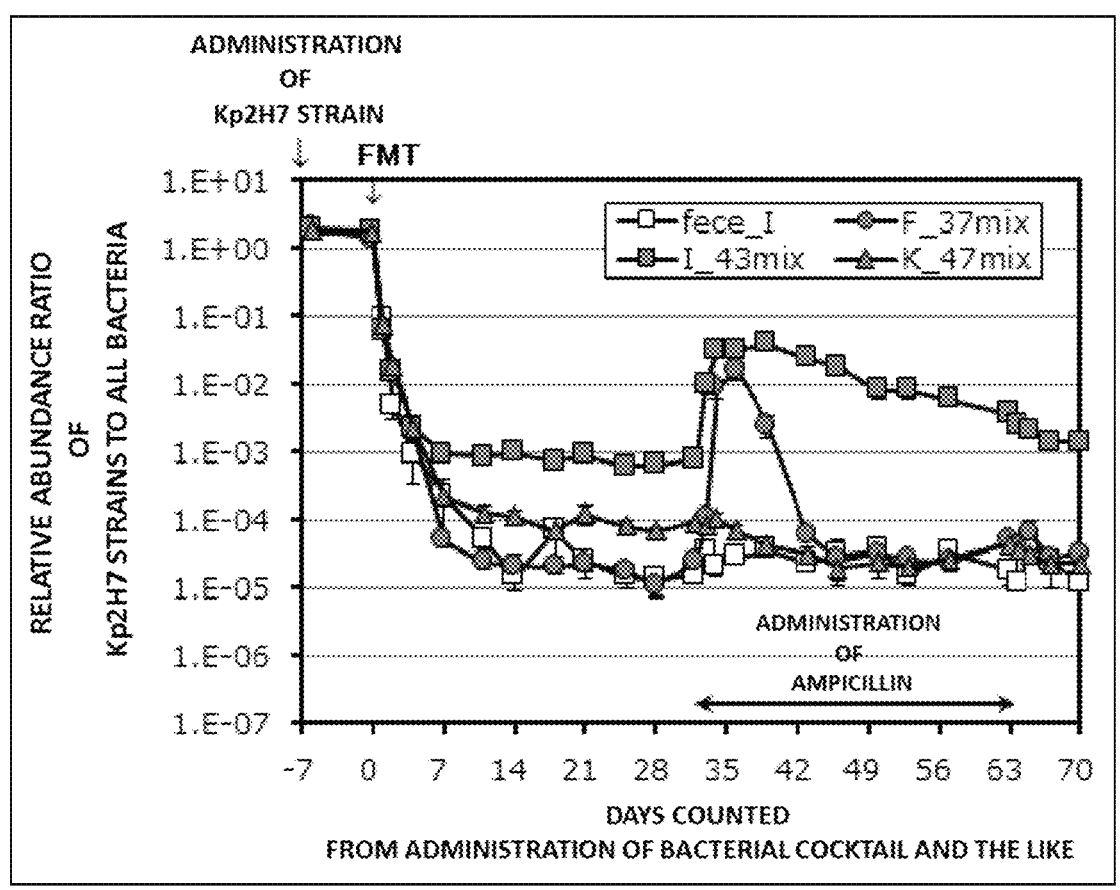
FIG. 10 is a graph illustrating the results of qPCR analysis of the change over time of the intestinal colonization level of the Kp2H7 strain in germ-free mice inoculated with the Kp2H7 strain and then fed with a bacterial cocktail derived from the feces of a healthy individual.

As described above, the mice that had been intragastrically administered with $10 \times 10^{10}$ CFUs of Kp2H7 strains and then bred for 1 week for sufficient colonization of only the single bacterial species Kp2H7 were intragastrically administered with the bacterial cocktails isolated from healthy volunteers #F, I, and K. As a result, along with the progress of free breeding for 1 month after the treatment, the mice administered with any bacterial cocktails showed a significant elimination of the Kp2H7 strain, as shown in FIGS. 9 and 10. This suggests that all of F_37mix, I_42mix, and K_47mix include bacterial strains having an activity of eliminating the Kp2H7 strain.

From one month after bacterial cocktail administration, the mice were bred for another month while being administered with the antibiotic ampicillin. Then, as shown in FIGS. 9 and 10, growth of Kp2H7 was observed in the mice administered with F_37mix and I_42mix. On the other hand, no significant change was observed in the mice transplanted with K_47mix. This suggests that the main bacteria contained in F_37mix and I_42mix and capable of eliminating colonization of the Kp2H7 strain are strains non-resistant (susceptible) to ampicillin. Meanwhile, it is also suggested that the bacteria contained in K_47mix and capable of eliminating colonization of the Kp2H7 strain include at least one or more ampicillin withstandable (resistant) strains.

In addition, when the case of administration of isolated bacteria (Example 6) is compared with the case of fecal transplantation before bacterium isolation (Example 3), the following is suggested.

The 37 bacteria isolated from #F feces and the 47 bacteria isolated from #K feces had an activity to eliminate the Kp2H7 strain, which was equal to or higher than that against the feces before isolation. In particular, the activity of F_37mix to eliminate Kp2H7 exceeded that of the Kp2H7 strain by the transplantation of #F feces before isolation. That is, it is considered that F_37mix is enriched with bacteria that inhibit the colonization of the Kp2H7 strain, or excludes bacteria that do not participate in the colonization of the Kp2H7 strain or support the colonization. Therefore, F_37mix is a bacterial cocktail effective in eliminating the Kp2H7 strain.

The 42 bacteria isolated from #I feces had a sufficient activity to eliminate Kp2H7, but did not reach the Kp2H7 elimination activity by the transplantation of #I feces before isolation. In addition, susceptibility to ampicillin, which was not observed in the case of transplantation of #I feces before isolation, was observed. That is, it is considered that I_42mix does not contain ampicillin-resistant bacteria capable of eliminating the colonization of Kp2H7, which are contained in #I feces before isolation. Therefore, I_42mix is a bacterial cocktail effective in eliminating the Kp2H7 strain.

Figure 11:
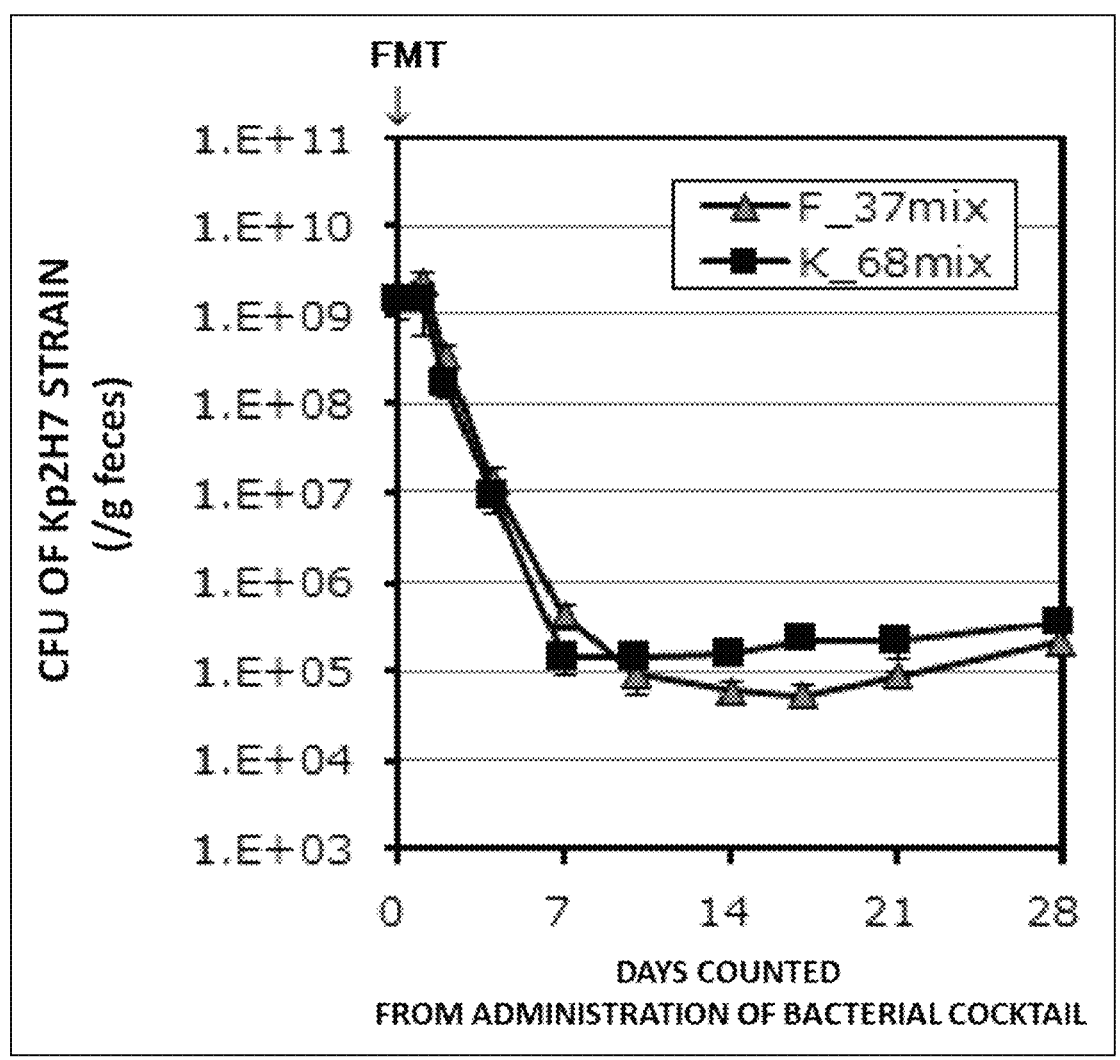
FIG. 11 is a graph illustrating in CFU the change over time of the intestinal colonization level of the Kp2H7 strain in germ-free mice inoculated with the Kp2H7 strain and fed 7 days after with a bacterial cocktail derived from the feces of a healthy individual.
Figure 12:
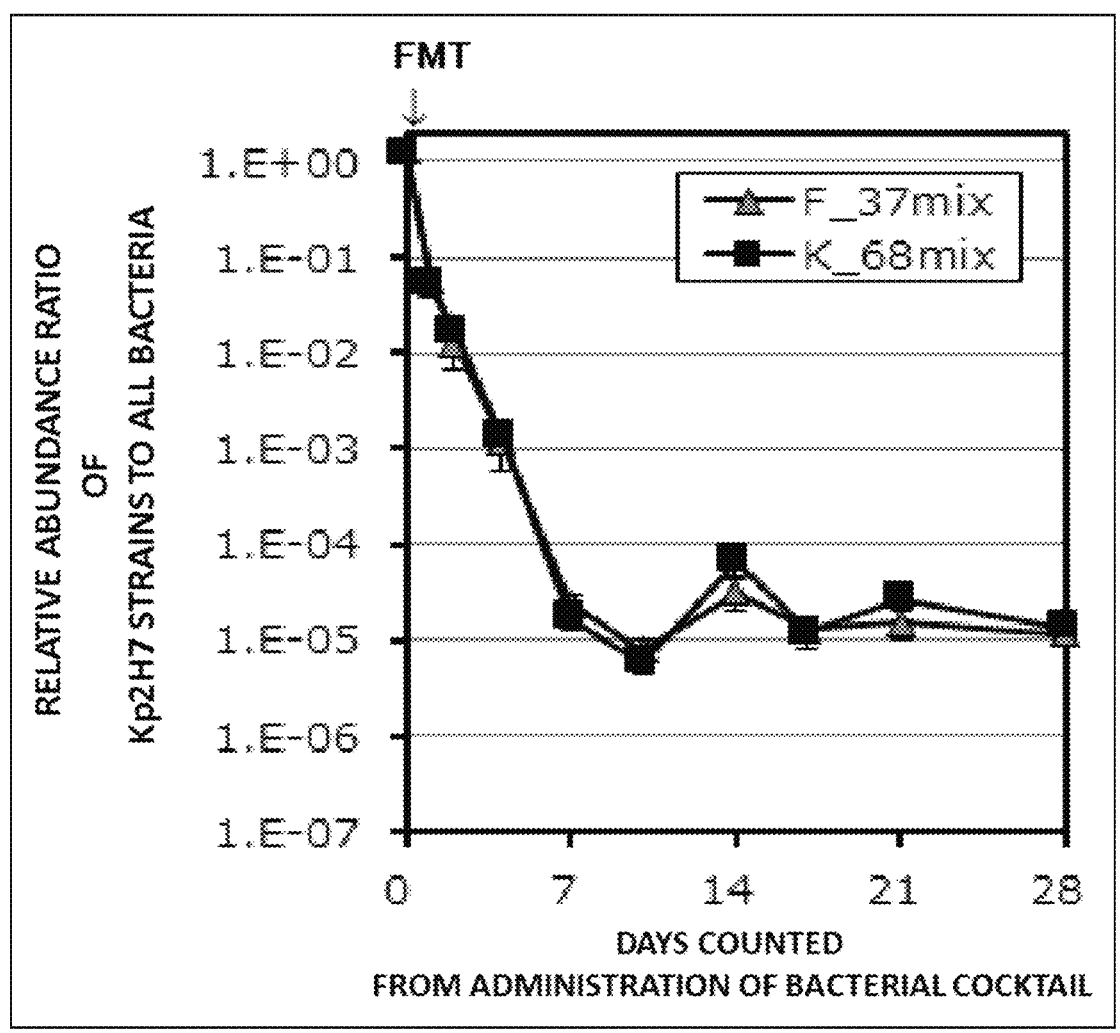
FIG. 12 is a graph illustrating the results of qPCR analysis of the change over time of the intestinal colonization level of the Kp2H7 strain in germ-free mice inoculated with the Kp2H7 strain and fed 7 days after with a bacterial cocktail derived from the feces of a healthy individual.

In addition, the mice that had been intragastrically administered with $10 \times 10^{10}$ CFUs of Kp2H7 and then bred for 1 week for sufficient colonization of only the single bacterial species Kp2H7 were intragastrically administered with K_68mix. As a result, along with the progress of free breeding for 1 month after the treatment, the elimination of Kp2H7 was observed, as shown in FIGS. 11 and 12. In addition, in K_68mix, a significant level of Kp2H7 elimination equivalent to that in the case of F_37mix was observed.

In particular, the activity of K_68mix to eliminate the Kp2H7 strain exceeded that of the Kp2H7 strain by the transplantation of #K feces before isolation. That is, it is considered that K_68mix is enriched with bacteria that inhibit the colonization of the Kp2H7 strain, or excludes bacteria that do not participate in the colonization of the Kp2H7 strain or support the colonization. Therefore, K_68mix is a bacterial cocktail effective in eliminating the Kp2H7 strain.

INDUSTRIAL APPLICABILITY

As described above, according to the present invention, suppression of the colonization and the like of Th1 cell-inducible bacteria in the intestinal tract makes it possible to suppress Th1 cell proliferation or activation, suppress intestinal immunity, and moreover treat, alleviate, or prevent a disease attributable to Th1 cells. In addition, the present invention makes it possible to test for a disease attributable to Th1 cells.

Therefore, the present invention is extremely useful in the pharmaceutical development, treatment, alleviation, prevention, and diagnosis relating to inflammatory bowel disease, autoimmune disease, chronic inflammatory disease, and the like attributable to Th1 cells.

[Sequence Listing Free Text]
SEQ ID NOs: 148 to 157
<223> Artificially synthesized primer sequence

The invention claimed is:

1. An antibacterial composition against a bacterium capable of inducing Th1 cell proliferation or activation in an intestinal tract, wherein said antibacterial composition comprises (1) a bacterium having a DNA comprising a base sequence at least 90% identical to SEQ ID NO: 69,
(2) a bacterium having a DNA comprising a base sequence at least 90% identical to SEQ ID NO: 70,
(3) a bacterium having a DNA comprising a base sequence at least 90% identical to SEQ ID NO: 71,
(4) a bacterium having a DNA comprising a base sequence at least 90% identical to SEQ ID NO: 72,
(5) a bacterium having a DNA comprising a base sequence at least 90% identical to SEQ ID NO: 73,
(6) a bacterium having a DNA comprising a base sequence at least 90% identical to SEQ ID NO: 74,
(7) a bacterium having a DNA comprising a base sequence at least 90% identical to SEQ ID NO: 75,
(8) a bacterium having a DNA comprising a base sequence at least 90% identical to SEQ ID NO: 76, (9) a bacterium having a DNA comprising a base sequence at least 90% identical to SEQ ID NO: 77,
(10) a bacterium having a DNA comprising a base sequence at least 90% identical to SEQ ID NO: 78,
(11) a bacterium having a DNA comprising a base sequence at least 90% identical to SEQ ID NO: 79,
(12) a bacterium having a DNA comprising a base sequence at least 90% identical to SEQ ID NO: 80,
(13) a bacterium having a DNA comprising a base sequence at least 90% identical to SEQ ID NO: 81,
(14) a bacterium having a DNA comprising a base sequence at least 90% identical to SEQ ID NO: 82,
(15) a bacterium having a DNA comprising a base sequence at least 90% identical to SEQ ID NO: 83,
(16) a bacterium having a DNA comprising a base sequence at least 90% identical to SEQ ID NO: 84,
(17) a bacterium having a DNA comprising a base sequence at least 90% identical to SEQ ID NO: 85,
(18) a bacterium having a DNA comprising a base sequence at least 90% identical to SEQ ID NO: 86,
(19) a bacterium having a DNA comprising a base sequence at least 90% identical to SEQ ID NO: 87,
(20) a bacterium having a DNA comprising a base sequence at least 90% identical to SEQ ID NO: 88,
(21) a bacterium having a DNA comprising a base sequence at least 90% identical to SEQ ID NO: 89,
(22) a bacterium having a DNA comprising a base sequence at least 90% identical to SEQ ID NO: 90,
(23) a bacterium having a DNA comprising a base sequence at least 90% identical to SEQ ID NO: 91,
(24) a bacterium having a DNA comprising a base sequence at least 90% identical to SEQ ID NO: 92,
(25) a bacterium having a DNA comprising a base sequence at least 90% identical to SEQ ID NO: 93,
(26) a bacterium having a DNA comprising a base sequence at least 90% identical to SEQ ID NO: 94,
(27) a bacterium having a DNA comprising a base sequence at least 90% identical to SEQ ID NO: 95,
(28) a bacterium having a DNA comprising a base sequence at least 90% identical to SEQ ID NO: 96,
(29) a bacterium having a DNA comprising a base sequence at least 90% identical to SEQ ID NO: 97,
(30) a bacterium having a DNA comprising a base sequence at least 90% identical to SEQ ID NO: 98,
(31) a bacterium having a DNA comprising a base sequence at least 90% identical to SEQ ID NO: 99,
(32) a bacterium having a DNA comprising a base sequence at least 90% identical to SEQ ID NO: 100,
(33) a bacterium having a DNA comprising a base sequence at least 90% identical to SEQ ID NO: 101,
(34) a bacterium having a DNA comprising a base sequence at least 90% identical to SEQ ID NO: 102,
(35) a bacterium having a DNA comprising a base sequence at least 90% identical to SEQ ID NO: 103,
(36) a bacterium having a DNA comprising a base sequence at least 90% identical to SEQ ID NO: 104, and
(37) a bacterium having a DNA comprising a base sequence at least 90% identical to SEQ ID NO: 105,
as an active ingredient, and wherein said antibacterial composition further comprises a medium and/or a buffer.

2. The antibacterial composition according to claim 1, which is a pharmaceutical composition.

3. An antibacterial composition against a bacterium capable of inducing Th1 cell proliferation or activation in an intestinal tract, wherein said antibacterial composition comprises
(1) a bacterium having a DNA comprising a base sequence at least 90% identical to SEQ ID NO: 69,
(2) a bacterium having a DNA comprising a base sequence at least 90% identical to SEQ ID NO: 70,
(3) a bacterium having a DNA comprising a base sequence at least 90% identical to SEQ ID NO: 71,
(4) a bacterium having a DNA comprising a base sequence at least 90% identical to SEQ ID NO: 72,
(5) a bacterium having a DNA comprising a base sequence at least 90% identical to SEQ ID NO: 73,
(6) a bacterium having a DNA comprising a base sequence at least 90% identical to SEQ ID NO: 74,
(7) a bacterium having a DNA comprising a base sequence at least 90% identical to SEQ ID NO: 75,
(8) a bacterium having a DNA comprising a base sequence at least 90% identical to SEQ ID NO: 76,
(9) a bacterium having a DNA comprising a base sequence at least 90% identical to SEQ ID NO: 77,
(10) a bacterium having a DNA comprising a base sequence at least 90% identical to SEQ ID NO: 78,
(11) a bacterium having a DNA comprising a base sequence at least 90% identical to SEQ ID NO: 79,
(12) a bacterium having a DNA comprising a base sequence at least 90% identical to SEQ ID NO: 80,
(13) a bacterium having a DNA comprising a base sequence at least 90% identical to SEQ ID NO: 81,
(14) a bacterium having a DNA comprising a base sequence at least 90% identical to SEQ ID NO: 82,
(15) a bacterium having a DNA comprising a base sequence at least 90% identical to SEQ ID NO: 83,
(16) a bacterium having a DNA comprising a base sequence at least 90% identical to SEQ ID NO: 84,
(17) a bacterium having a DNA comprising a base sequence at least 90% identical to SEQ ID NO: 85,
(18) a bacterium having a DNA comprising a base sequence at least 90% identical to SEQ ID NO: 86,
(19) a bacterium having a DNA comprising a base sequence at least 90% identical to SEQ ID NO: 87,
(20) a bacterium having a DNA comprising a base sequence at least 90% identical to SEQ ID NO: 88,
(21) a bacterium having a DNA comprising a base sequence at least 90% identical to SEQ ID NO: 89,
(22) a bacterium having a DNA comprising a base sequence at least 90% identical to SEQ ID NO: 90,
(23) a bacterium having a DNA comprising a base sequence at least 90% identical to SEQ ID NO: 91,
(24) a bacterium having a DNA comprising a base sequence at least 90% identical to SEQ ID NO: 92,
(25) a bacterium having a DNA comprising a base sequence at least 90% identical to SEQ ID NO: 93,
(26) a bacterium having a DNA comprising a base sequence at least 90% identical to SEQ ID NO: 94,
(27) a bacterium having a DNA comprising a base sequence at least 90% identical to SEQ ID NO: 95,
(28) a bacterium having a DNA comprising a base sequence at least 90% identical to SEQ ID NO: 96,
(29) a bacterium having a DNA comprising a base sequence at least 90% identical to SEQ ID NO: 97,
(30) a bacterium having a DNA comprising a base sequence at least 90% identical to SEQ ID NO: 98,
(31) a bacterium having a DNA comprising a base sequence at least 90% identical to SEQ ID NO: 99,

(32) a bacterium having a DNA comprising a base sequence at least 90% identical to SEQ ID NO: 100,
(33) a bacterium having a DNA comprising a base sequence at least 90% identical to SEQ ID NO: 101,
(34) a bacterium having a DNA comprising a base sequence at least 90% identical to SEQ ID NO: 102,
(35) a bacterium having a DNA comprising a base sequence at least 90% identical to SEQ ID NO: 103,
(36) a bacterium having a DNA comprising a base sequence at least 90% identical to SEQ ID NO: 104, and
(37) a bacterium having a DNA comprising a base sequence at least 90% identical to SEQ ID NO: 105,
and wherein said antibacterial composition is prepared in the form of a tablet and/or a capsule.

4. The antibacterial composition according to claim 3, which is a pharmaceutical composition.

* * * * *

```
                              SEQUENCE LISTING

<160> NUMBER OF SEQ ID NOS: 157

<210> SEQ ID NO 1
<211> LENGTH: 1391
<212> TYPE: DNA
<213> ORGANISM: Unknown
<220> FEATURE:
<223> OTHER INFORMATION: K01

<400> SEQUENCE: 1
gcaagtcgag cgaagcgctg ttttcagaat cttcggagga agaggacagc gactgagcgg      60
cggacgggtg agtaacgcgt gggcaacctg cctcatacag ggggataaca gttagaaatg     120
actgctaata ccgcataagc gcacgggacc gcatggtcta gtgtgaaaaa ctccggtggt     180
atgagatgga cccgcgtctg attaggtagt tggtggggta aaggcctacc aagccgacga     240
tcagtagccg acctgagagg gtgaccggcc acattgggac tgagacacgg cccaaactcc     300
tacgggaggc agcagtgggg aatattgcac aatgggggaa accctgatgc agcgacgccg     360
cgtgaaggaa gaagtatttc ggtatgtaaa cttctatcag cagggaagaa atgacggta      420 cctgagtaag aagcaccggc taaatacgtg ccagcagccg cggtaatacg tatggtgcaa     480
gcgttatccg gatttactgg gtgtaaaggg agcgtagacg gataggcaag tctggagtga     540
aaacccaggg ctcaaccctg ggactgcttt ggaaactgca gatctggagt ccggagagg     600 taagcggaat tcctagtgta gcggtgaaat gcgtagatat taggaggaac accagtggcg     660
aaggcggctt actggacggt gactgacgtt gaggctcgaa agcgtgggga gcaaacagga     720
ttagataccc tggtagtcca cgccgtaaac gatgactact aggtgtcggt gtgcaaagca     780
catcggtgcc gcagcaaacg caataagtag tccacctggg gagtacgttc gcaagaatga     840
aactcaaagg aattgacggg gacccgcaca agcggtggag catgtggttt aattcgaagc     900
aacgcgaaga accttacctg gtcttgacat ccggatgacg ggcgagtaat gtcgccgtcc     960
cttcggggca tccgagacag gtggtgcatg gttgtcgtca gctcgtgtcg tgagatgttg    1020
ggttaagtcc cgcaacgagc gcaacccttat tcttcagtag ccagcatata aggtgggcac    1080 tctgagaga ctgccaggga gaacctggag gaaggtgggg atgacgtcaa atcatcatgc    1140
cccttatggc cagggctaca cacgtgctac aatggcgtaa acaaagggaa gcgagagggt    1200
gacctgaagc gaatcccaaa aataacgtct cagttcggat tgtagtctgc aactcgacta    1260
catgaagctg gaatcgctag taatcgcgga tcagcatgcc gcggtgaata cgttcccggg    1320
tcttgtacac accgcccgtc acaccatggg agtcagtaac gcccgaagcc agtgacccaa    1380
ccttgaggag g                                                         1391

<210> SEQ ID NO 2
<211> LENGTH: 1383
<212> TYPE: DNA
<213> ORGANISM: Unknown
<220> FEATURE:
<223> OTHER INFORMATION: K02

<400> SEQUENCE: 2 tcgagggca gcattttagt ttgcttgcaa actgaagatg gcgaccggcg cacgggtgag      60
taacacgtat ccaacctgcc gataactccg gaatagcctt tcgaaagaaa gattaatacc     120
ggatagcata cgaatatcgc atgatatttt tattaaagaa tttcggttat cgatggggat     180
```

```
gcgttccatt agtttgttgg cggggtaacg gcccaccaag actacgatgg ataggggttc     240
tgagaggaag gtcccccaca ttggaactga gacacggtcc aaactcctac gggaggcagc     300
agtgaggaat attggtcaat gggcgagagc ctgaaccagc caagtagcgt gaaggatgaa     360
ggctctatgg gtcgtaaact tcttttatat gggaataaag ttttccacgt gtggaatttt     420
gtatgtacca tatgaataag gatcggctaa ctccgtgcca gcagccgcgg taatacggag     480
gatccgagcg ttatccggat ttattgggtt taaagggagc gtaggtggat tgttaagtca     540
gttgtgaaag tttgcggctc aaccgtaaaa ttgcagttga aactggcagt cttgagtaca     600
gtagaggtgg gcggaattcg tggtgtagcg gtgaaatgct tagatatcac gaagaactcc     660
gattgcgaag gcagctcact agactgttac tgacactgat gctcgaaagt gtgggtatca     720
aacaggatta ataccctggt agtccacaca agtaaacgat gaatactcgc tgtttgcgat     780
atacagtaag cggccaagcg aaagcattaa gtattccacc tggggagtac gccggcaacg     840
gtgaaactca aaggaattga cgggggcccg cacaagcgga ggaacatgtg gtttaattcg     900
atgatacgcg aggaacctta cccgggctta aattgcaaca gaatatattg gaaacagtat     960
agccgtaagg ctgttgtgaa ggtgctgcat ggttgtcgtc agctcgtgcc gtgaggtgtc    1020
ggcttaagtg ccataacgag cgcaacccct atctttagtt actaacaggt tatgctgagg    1080
actctagaga gactgccgtc gtaagatgtg aggaaggtgg ggatgacgtc aaatcagcac    1140
ggcccttacg tccggggcta cacacgtgtt acaatggggg gtacagaagg cggctacctg    1200
gtgacaggat gctaatccca aaaacctctc tcagttcgga tcgaagtctg caacccgact    1260
tcgtgaagct ggattcgcta gtaatcgcgc atcagccatg gcgcggtgaa tacgttcccg    1320
ggccttgtac acaccgcccg tcaagccatg aaagccgggg gtacctgaag tacgtaaccg    1380
caa                                                                  1383
```

<210> SEQ ID NO 3
<211> LENGTH: 1396
<212> TYPE: DNA
<213> ORGANISM: Unknown
<220> FEATURE:
<223> OTHER INFORMATION: K03

<400> SEQUENCE: 3

```
tgcagtcgag cgaagcgcta agacaggatt tcttcggatt gaagtctttg tgactgagcg      60
gcggacgggt gagtaacgcg tgggtaacct gcctcataca gggggataac agttagaaat     120
gactgctaat accgcataag cgcacaggac cgcatggtct ggtgtgaaaa actccggtgg     180
tatgagatgg acccgcgtct gattagctag ttggaggggt aacggcccac caaggcgacg     240
atcagtagcc ggcctgagag ggtgaacggc cacattggga ctgagacacg gcccagactc     300
ctacgggagg cagcagtggg gaatattgca caatggggga accctgatgc agcgacgcc     360
gcgtgaagga agaagtatct cggtatgtaa acttctatca gcaggaagaa aaatgacggt     420
acctgactaa gaagccccgg ctaactacgt gccagcagcc gcggtaatac gtaggggggca     480
agcgttatcc ggatttactg ggtgtaaagg gagcgtagac ggaagagcaa gtctgatgtg     540
aaaggctggg gcttaacccc aggactgcat tggaaactgt tgttctagag tgccggagag     600
gtaagcggaa ttcctagtgt agcggtgaaa tgcgtagata ttaggaggaa caccagtggc     660
gaaggcggct tactggacgg taactgacgt tgaggctcga aagcgtgggg agcaaacagg     720
attagatacc ctggtagtcc acgccgtaaa cgatgaatac taggtgtcgg gtggcaaagc     780
cattcggtgc cgcagcaaac gcaataagta ttccacctgg ggagtacgtt cgcaagaatg     840
```

```
aaactcaaag gaattgacgg ggacccgcac aagcggtgga gcatgtggtt taattcgaag      900
caacgcgaag aaccttacca agtcttgaca tccctctgac cgtcccgtaa cgggggcttc      960
ccttcggggc agaggagaca ggtggtgcat ggttgtcgtc agctcgtgtc gtgagatgtt     1020
gggttaagtc ccgcaacgag cgcaacccct atccttagta gccagcacat gatggtgggc     1080
actctaggga gactgccggg gataacccgg aggaaggcgg ggacgacgtc aaatcatcat     1140
gccccttatg atttgggcta cacacgtgct acaatgcgt aaacaaaggg aagcgagaca      1200
gcgatgttga gcgaatccca aaaataacgt cccagttcgg actgcagtct gcaactcgac     1260
tgcacgaagc tggaatcgct agtaatcgcg gatcagaatg ccgcggtgaa tacgttcccg     1320
ggtcttgtac acaccgcccg tcacaccatg ggagtcagta acgcccgaag tcagtgacct     1380
aaccgaaagg aaggag                                                    1396
```

<210> SEQ ID NO 4
<211> LENGTH: 1395
<212> TYPE: DNA
<213> ORGANISM: Unknown
<220> FEATURE:
<223> OTHER INFORMATION: K04

<400> SEQUENCE: 4

```
cagtcgagcg aagcgtctta gaatgatctc ttcggattga gtcttatatg actgagcggc       60
ggacgggtga gtaacgcgtg ggtaacctgc ctcatacagg gggataacag ttagaaatga      120
ctgctaatac cgcataagcg cacagggctg catggcctgg tgtgaaaaac tccggtggta      180
tgagatggac ccgcgtctga ttagctagtt ggaggggtaa cggcccacca aggcgacgat      240
cagtagccgg cctgagaggg tgaacggcca cattgggact gagacacggc ccagactcct      300
acgggaggca gcagtgggga atattgcaca atggggaaa ccctgatgca gcgacgccgc       360
gtgaaggaag aagtatctcg gtatgtaaac ttctatcagc agggaagaaa atgacggtac      420
ctgactaaga agccccggct aactacgtgc cagcagccgc ggtaatacgt aggggcaag      480 cgttatccgg atttactggg tgtaaaggga gcgtagacgg aagagcaagt ctgatgtgaa      540
aggctggggc ttaaccccag gactgcattg gaaactgttt ttctagagtg ccggagaggt      600
aagcggaatt cctagtgtag cggtgaaatg cgtagatatt aggaggaaca ccagtggcga      660
aggcggctta ctggacggta actgacgttg aggctcgaaa gcgtgggag caaacaggat      720 tagataccct ggtagtccac gccgtaaacg atgaatacta ggtgtcgggt ggcaaagcca      780
ttcggtgccg cagcaaacgc aataagtatt ccacctgggg agtacgttcg caagaatgaa      840
actcaaagga attgacgggg acccgcacaa gcggtggagc atgtggttta attcgaagca      900
acgcgaagaa ccttaccaag tcttgacatc cttctgacgt gcccgtaacg ggcattccc      960 ttcggggcag aggagacagg tggtgcatgg ttgtcgtcag ctcgtgtcgt gagatgttgg     1020
gttaagtccc gcaacgagcg caaccccat cttagtagc cagcacatca tggtgggcac     1080
tctagggaga ctgccgggga taacccggag gaaggcgggg acgacgtcaa atcatcatgc     1140
cccttatgat ttgggctaca cacgtgctac aatggcgtaa acaaagggaa gcgagacagc     1200
gatgtttagc aaatcccaaa aataacgtcc cagttcggac tgcagtctgc aactcgactg     1260
cacgaagctg gaatcgctag taatcgcgaa tcagaatgtc gcggtgaata cgttcccggg     1320
tcttgtacac accgcccgtc acaccatggg agtcagtaac gcccgaagtc agtgacccaa     1380
cctcacggag ggagc                                                    1395
```

<210> SEQ ID NO 5
<211> LENGTH: 1411
<212> TYPE: DNA
<213> ORGANISM: Unknown
<220> FEATURE:
<223> OTHER INFORMATION: K05

<400> SEQUENCE: 5

| | | | | | |
|---|---|---|---|---|---|
| gcagtcgaac | gtgaaagtcc | ttcgggacga | gtaaagtggc | gcacgggtga | gtaacgcgtg | 60 |
| gataatctac | ccttaagatg | gggataacgg | ctggaaacgg | tcgctaatac | cgaatacgct | 120 |
| cccgatttta | tcattggggg | gaaagatggc | ctctgcttgc | aagctatcgc | ttaaggatga | 180 |
| gtccgcgtcc | cattagctag | ttggcgggt | aacggcccac | caaggcgacg | atgggtagcc | 240 |
| ggtctgagag | gatgaccggc | cacactggaa | ctggaacacg | gtccagactc | ctacgggagg | 300 |
| cagcagtggg | gaatattgcg | caatgggcga | aagcctgacg | cagcgacgcc | gcgtgaggga | 360 |
| tgaaggttct | cggatcgtaa | acctctgtca | gggggaaga | aaccccctcg | tgtgaataat | 420 |
| gcgagggctt | gacggtaccc | ccaaaggaag | caccggctaa | ctccgtgcca | gcagccgcgg | 480 |
| taatacggag | ggtgcaagcg | ttaatcgaa | tcactgggcg | taaagcgcac | gtaggcggct | 540 |
| tggtaagtca | ggggtgaaat | cccacagccc | aactgtggaa | ctgcctttga | tactgccagg | 600 |
| cttgagtacc | ggagagggtg | gcggaattcc | aggtgtagga | gtgaaatccg | tagatatctg | 660 |
| gaggaacacc | ggtggcgaag | gcggccacct | ggacggtaac | tgacgctgag | gtgcgaaagc | 720 |
| gtgggtagca | aacaggatta | gatacctgg | tagtccacgc | tgtaaacgat | gggtgctggg | 780 |
| tgctgggatg | tatgtctcgg | tgccgtagct | aacgcgataa | gcaccccgcc | tggggagtac | 840 |
| ggtcgcaagg | ctgaaactca | aagaaattga | cggggcccg | cacaagcggt | ggagtatgtg | 900 |
| gtttaattcg | atgcaacgcg | aagaaccta | cccaggcttg | acatctaggg | aacccttcgg | 960 |
| aaatgaaggg | gtgcccttcg | gggagcccta | agacaggtgc | tgcatggctg | tcgtcagctc | 1020 |
| gtgccgtgag | gtgttggt | aagtcccgca | acgagcgcaa | cccctatctt | cagttgccag | 1080 |
| caggtaaggc | tgggcactct | ggagagaccg | ccccggtcaa | cggggaggaa | ggtggggacg | 1140 |
| acgtcaagtc | atcatggccc | ttacgcctgg | ggctacacac | gtactacaat | ggcgcgcaca | 1200 |
| aagggtagcg | agaccgcgag | gtggagccaa | tcccaaaaaa | cgcgtcccag | tccggattgg | 1260 |
| agtctgcaac | tcgactccat | gaagtcggaa | tcgctagtaa | ttcgagatca | gcatgctcgg | 1320 |
| gtgaatgcgt | tcccgggcct | tgtacacacc | gcccgtcaca | ccacgaaagt | cggttttacc | 1380 |
| cgaagccggt | gagctaactc | gcaagagaag | c | | | 1411 |

<210> SEQ ID NO 6
<211> LENGTH: 1383
<212> TYPE: DNA
<213> ORGANISM: Unknown
<220> FEATURE:
<223> OTHER INFORMATION: K06

<400> SEQUENCE: 6

| | | | | | |
|---|---|---|---|---|---|
| gaggggcatc | gggattgaag | cttgcttcaa | ttgccggcga | ccggcgcacg | ggtgcgtaac | 60 |
| gcgtatgtaa | cctacctata | acaggggcat | aacactgaga | aattggtact | aattccccat | 120 |
| aatattcgga | gaggcatctc | tccgggttga | aaactccggt | ggttatagat | ggacatgcgt | 180 |
| tgtattagct | agttggtgag | gtaacggctc | accaaggcaa | cgatacatag | ggggactgag | 240 |
| aggttaaccc | cccacactgg | tactgagaca | cggaccagac | tcctacggga | ggcagcagtg | 300 |
| aggaatattg | gtcaatggac | gcaagtctga | accagccatg | ccgcgtgcag | gaagacggct | 360 |

-continued

```
ctatgagttg taaactgctt ttgtacgagg gtaaactcac ctacgtgtag gtgactgaaa    420
gtatcgtacg aataaggatc ggctaactcc gtgccagcag ccgcggtaat acggaggatt    480
caagcgttat ccggatttat tgggtttaaa gggtgcgtag gcggtttgat aagttagagg    540
tgaaatcccg gggcttaact ccggaactgc ctctaatact gttagactag agagtagttg    600
cggtaggcgg aatgtatggt gtagcggtga aatgcttaga gatcatacag aacaccgatt    660
gcgaaggcag cttaccaaac tatatctgac gttgaggcac gaaagcgtgg ggagcaaaca    720
ggattagata ccctggtagt ccacgcagta acgatgata actcgttgtc ggcgatacac    780
agtcggtgac taagcgaaag cgataagtta tccacctggg ggagtacgtt cgcaagaatg    840
aaactcaaag gaattgacgg gggcccgcac aagcggagga acatgtggtt taattcgatg    900
atacgcgagg aaccttaccc gggcttgaaa gttactgacg attctggaaa caggatttcc    960
cttcggggca ggaaactagg tgctgcatgg ttgtcgtcag ctcgtgccgt gaggtgtcgg   1020
gttaagtccc ataacgagcg caaccccctac cgttagttgc catcaggtca agctgggcac   1080
tctggcggga ctgccggtgt aagccgagag gaaggtgggg atgacgtcaa atcagcacgg   1140
cccttacgtc cggggctaca cacgtgttac aatggtaggt acagagggtc gctacccgt    1200
gaggggatgc caatctcgaa agccttactctc agttcggatt ggaggctgaa acccgcctcc   1260
atgaagttgg attcgctagt aatcgcgcat cagccatggc gcggtgaata cgttcccggg   1320
ccttgtacac accgcccgtc aagccatgga agctggggggt gcctgaagtt cgtgaccgca   1380
agg                                                                1383
```

<210> SEQ ID NO 7
<211> LENGTH: 1393
<212> TYPE: DNA
<213> ORGANISM: Unknown
<220> FEATURE:
<223> OTHER INFORMATION: K07

<400> SEQUENCE: 7

```
cagtcgaacg gagttatgca gaggaagttt tcggatggaa tcggcgtaac ttagtggcgg     60
acgggtgagt aacgcgtggg aaacctgccc tgtaccgggg gataacactt agaaataggt    120
gctaataccg cataagcgca cagcttcaca tgaggcagtg tgaaaaactc cggtggtaca    180
ggatggtccc gcgtctgatt agccagttgg cagggtaacg gcctaccaaa gcgacgatca    240
gtagccggcc tgagagggtg aacggccaca ttgggactga gacacggccc aaactcctac    300
gggaggcagc agtgggggaat attgcacaat gggggaaacc ctgatgcagc gacgccgcgt    360
gagtgaagaa gtatttcggt atgtaaagct ctatcagcag ggaagaaaat gacggtacct    420
gactaagaag cccggctaa ctacgtgcca gcagccgcgg taatacgtag ggggcaagcg    480
ttatccggat ttactgggtg taaagggagc gtagacggca tgacaagcca gatgtgaaaa    540
cccagggctc aaccctggga ctgcatttgg aactgccagg ctgagtgca ggagaggtaa     600
gcggaattcc tagtgtagcg gtgaaatgcg tagatattag gaggaacacc agtggcgaag    660
gcggcttact ggactgtaac tgacgttgag gctcgaaagc gtgggagca acaggatta     720
gataccctgg tagtccacgc ggtaaacgat gattgctagg tgtaggtggg tatgacccca    780
tcggtgccgc agctaacgca ataagcaatc cacctggggg agtacgttcg caagaatgaa    840
actcaaagga attgacgggg acccgcacaa gcggtggagc atgtggttta attcgaagca    900
acgcgaagaa ccttaccaag tcttgacatc ccaatgacgt gtccgtaacg ggcattctc    960
```

| | |
|---|---|
| ttcggagcat tggagacagg tggtgcatgg ttgtcgtcag ctcgtgtcgt gagatgttgg | 1020 |
| gttaagtccc gcaacgagcg caacccttat ccttagtagc cagcaggtag agctgggcac | 1080 |
| tctagggaga ctgccgggga taacccggag gaaggcgggg atgacgtcaa atcatcatgc | 1140 |
| cccttatgat ttgggctaca cacgtgctac aatggcgtaa acaaagggaa gcgagacagt | 1200 |
| gatgttgagc aaatcccaga ataacgtct cagttcggat tgtagtctgc aactcgacta | 1260 |
| catgaagctg gaatcgctag taatcgcgaa tcagcatgtc gcggtgaata cgttcccggg | 1320 |
| tcttgtacac accgcccgtc acaccatggg agttggaaat gcccgaagcc tgtgacctaa | 1380 |
| ccgcaaggga gga | 1393 |

<210> SEQ ID NO 8
<211> LENGTH: 1402
<212> TYPE: DNA
<213> ORGANISM: Unknown
<220> FEATURE:
<223> OTHER INFORMATION: K08
<220> FEATURE:
<221> NAME/KEY: misc_feature
<222> LOCATION: (947)..(949)
<223> OTHER INFORMATION: n is a, c, g, or t
<220> FEATURE:
<221> NAME/KEY: misc_feature
<222> LOCATION: (953)..(955)
<223> OTHER INFORMATION: n is a, c, g, or t
<220> FEATURE:
<221> NAME/KEY: misc_feature
<222> LOCATION: (967)..(970)
<223> OTHER INFORMATION: n is a, c, g, or t

<400> SEQUENCE: 8

| | |
|---|---|
| caagtcgaac gaagtttcga ggaagcttgc ttccaaagag acttagtggc gaacgggtga | 60 |
| gtaacacgta ggtaacctgc ccatgtgtcc gggataactg ctggaaacgg tagctaaaac | 120 |
| cggataggta tacagagcgc atgctcagta tattaaagcg cccatcaagg cgtgaacatg | 180 |
| gatggacctg cggcgcatta gctagttggt gaggtaacgg cccaccaagg cgatgatgcg | 240 |
| tagccggcct gagagggtaa acggccacat tgggactgag acacggccca aactcctacg | 300 |
| ggaggcagca gtagggaatt ttcgtcaatg ggggaaaccc tgaacgagca atgccgcgtg | 360 |
| agtgaagaag gtcttcggat cgtaaagctc tgttgtaagt gaagaacggc tcatagagga | 420 |
| aatgctatgg gagtgacggt agcttaccag aaagccacgg ctaactacgt gccagcagcc | 480 |
| gcggtaatac gtaggtggca agcgttatcc ggaatcattg ggcgtaaagg gtgcgtaggt | 540 |
| ggcgtactaa gtctgtagta aaaggcaatg gctcaaccat tgtaagctat ggaaactggt | 600 |
| atgctggagt gcagaagagg gcgatggaat tccatgtgta gcggtaaaat gcgtagatat | 660 |
| atggaggaac accagtggcg aaggcggtcg cctggtctgt aactgacact gaggcacgaa | 720 |
| agcgtgggga gcaaatagga ttagataccc tagtagtcca cgccgtaaac gatgagaact | 780 |
| aagtgttgga ggaattcagt gctgcagtta acgcaataag ttctccgcct ggggagtatg | 840 |
| cacgcaagtg tgaaactcaa aggaattgac ggggcccgc acaagcggtg gagtatgtgg | 900 |
| tttaattcga agcaacgcga agaaccttac caggccttga catggannna annnncctag | 960 |
| agatagnnnn ataattatgg atcacacagg tggtgcatgg ttgtcgtcag ctcgtgtcgt | 1020 |
| gagatgttgg gttaagtccc gcaacgagcg caacccttgt cgcatgttac cagcatcaag | 1080 |
| ttggggactc atgcgagact gccggtgaca aaccggagga aggtggggat gacgtcaaat | 1140 |
| catcatgccc cttatggcct gggctacaca cgtactacaa tggcgaccac aaagagcagc | 1200 |
| gacacagtga tgtgaagcga atctcataaa ggtcgtctca gttcggattg aagtctgcaa | 1260 |

| | |
|---|---|
| ctcgacttca tgaagtcgga atcgctagta atcgcagatc agcatgctgc ggtgaatacg | 1320 |
| ttctcgggcc ttgtacacac cgcccgtcaa accatgggag tcagtaatac ccgaagccgg | 1380 |
| tggcataacc gtaaggagtg ag | 1402 |

<210> SEQ ID NO 9
<211> LENGTH: 1386
<212> TYPE: DNA
<213> ORGANISM: Unknown
<220> FEATURE:
<223> OTHER INFORMATION: K09

<400> SEQUENCE: 9

| | |
|---|---|
| agtcgagggg catcaggaag aaagcttgct ttctttgctg gcgaccggcg cacgggtgag | 60 |
| taacacgtat ccaacctgcc ctttactcgg ggatagcctt tcgaaagaaa gattaatacc | 120 |
| cgatggcata atgattccgc atggtttcat tattaaagga ttccggtaaa ggatggggat | 180 |
| gcgttccatt aggttgttgg tgaggtaacg gctcaccaag ccttcgatgg ataggggttc | 240 |
| tgagaggaag gtcccccaca ttggaactga gacacggtcc aaactcctac gggaggcagc | 300 |
| agtgaggaat attggtcaat gggcgctagc ctgaaccagc caagtagcgt gaaggatgaa | 360 |
| ggctctatgg gtcgtaaact tcttttatat aagaataaag tgcagtatgt atactgtttt | 420 |
| gtatgtatta tatgaataag gatcggctaa ctccgtgcca gcagccgcgg taatacggag | 480 |
| gatccgagcg ttatccggat ttattgggtt taaagggagc gtaggtggac tggtaagtca | 540 |
| gttgtgaaag tttgcggctc aaccgtaaaa ttgcagttga tactgtcagt cttgagtaca | 600 |
| gtagaggtgg gcggaattcg tggtgtagcg gtgaaatgct tagatatcac gaagaactcc | 660 |
| gattgcgaag gcagctcact ggactgcaac tgacactgat gctcgaaagt gtgggtatca | 720 |
| aacaggatta gataccctgg tagtccacac agtaaacgat gaatactcgc tgtttgcgat | 780 |
| atacagtaag cggccaagcg aaagcattaa gtattccacc tggggagtac gccggcaacg | 840 |
| gtgaaactca aaggaattga cggggacccg cacaagcgga gaacatgtg gtttaattcg | 900 |
| atgatacgcg aggaaccta cccgggctta aattgcagtg gaatgatgtg aaacatgtc | 960 |
| agtgagcaat caccgctgtg aaggtgctgc atggttgtcg tcagctcgtg ccgtgaggtg | 1020 |
| tcggcttaag tgccataacg agcgcaaccc ttatcttcag ttactaacag gtcatgctga | 1080 |
| ggactctgga gagactgccg tcgtaagatg tgaggaaggt ggggatgacg tcaaatcagc | 1140 |
| acggccctta cgtccggggc tacacacgtg ttacaatggg gggtacagaa ggcagctagc | 1200 |
| gggtgaccgt atgctaatcc caaaatcctc tctcagttcg gatcgaagtc tgcaacccga | 1260 |
| cttcgtgaag ctggattcgc tagtaatcgc gcatcagcca cggcgcggtg aatacgttcc | 1320 |
| cgggccttgt acacaccgcc cgtcaagcca tgggagccgg ggtacctga agtacgtaac | 1380 |
| cgcaag | 1386 |

<210> SEQ ID NO 10
<211> LENGTH: 1366
<212> TYPE: DNA
<213> ORGANISM: Unknown
<220> FEATURE:
<223> OTHER INFORMATION: K10

<400> SEQUENCE: 10

| | |
|---|---|
| agtcgaacga tgaaaccgcc ctcgggcgga catgaagtgg cgaacgggtg agtaacacgt | 60 |
| gaccaacctg ccccttgctc cgggacaacc ttgggaaacc gaggctaata ccggatactc | 120 |

```
ctcgcccccc tcctgggggg cccgggaaag cccagacggc aagggatggg gtcgcggccc      180
attaggtagt aggcgggggta acggcccacc tagcccgcga tgggtagccg ggttgagaga     240
ccgaccggcc acattgggac tgagatacgg cccagactcc tacgggaggc agcagtgggg     300
aattttgcgc aatgggggaa accctgacgc agcaacgccg cgtgcgggac gacggccttc     360
gggttgtaaa ccgctttcag cagggaagaa attcgacggt acctgcagaa gaagctccgg     420
ctaactacgt gccagcagcc gcggtaatac gtagggagcg agcgttatcc ggattcattg     480
ggcgtaaaga gcgcgtaggc ggcctctcaa gcgggatctc taatccgagg gctcaacccc     540
cggccggatc ccgaactggg aggctcgagt tcggtagagg caggcggaat tcccggtgta     600
gcggtggaat gcgcagatat cgggaagaac accgatggcg aaggcagcct gctgggccgc     660
aactgacgct gaggcgcgaa agctagggga gcgaacagga ttagataccc tggtagtcct     720
agccgtaaac gatggatact aggtgtgggg ggctccgccc tccgtgccgc agccaacgca     780
ttaagtatcc cgcctgggga gtacggccgc aaggctaaaa ctcaaaggaa ttgacggggg     840
cccgcacaag cagcggagca tgtggcttaa ttcgaagcaa cgcgaagaac cttaccaggg     900
cttgacatgg acgtgaagcc ggggaaaccc ggtggccgag aggagcgtcc gcaggtggtg     960
catggctgtc gtcagctcgt gtcgtgagat gttgggttaa gtcccgcaac gagcgcaacc    1020
cctgccccat gttgccagca ttaggttggg gactcatggg ggactgccgg cgtcaagccg    1080
gaggaaggtg gggacgacgt caagtcatca tgccctttat gccctgggct gcacacgtgc    1140
tacaatggcc ggtacaacgg gctgcgagac cgcgaggtcg agcgaatccc tcaaagccgg    1200
ccccagttcg gatcggaggc tgcaacccgc ctccgtgaag tcggagttgc tagtaatcgc    1260
ggatcagcat gccgcggtga atacgttccc gggccttgta cacaccgccc gtcacaccac    1320
ccgagtcgtc tgcacccgaa gccgccggcc gaacccgcaa ggggcg                    1366

<210> SEQ ID NO 11
<211> LENGTH: 1395
<212> TYPE: DNA
<213> ORGANISM: Unknown
<220> FEATURE:
<223> OTHER INFORMATION: K11

<400> SEQUENCE: 11
cagtcgaacg aagtgaagat agcttgctat tggaacttag tggcgaacgg gtgagtaaca       60
cgtagataac ctgcctgtat gaccgggata acagttggaa acgactgcta ataccggata      120
ggcagagagg aggcatctct tctctgttaa agttgggata caacgcaaac agatggatct      180
gcggtgcatt agctagttgg tgaggtaacg gcccaccaag gcgatgatgc atagccggcc      240
tgagagggcg aacggccaca ttgggactga gacacggccc aaactcctac gggaggcagc      300
agtagggaat tttcggcaat gggggaaacc ctgaccgagc aatgccgcgt gagtgaagac      360
ggccttcggg ttgtaaagct ctgttgtaag gaagaacgg catagagagg gaatgctcta      420
tgagtgacgg taccttacca gaaagccacg gctaactacg tgccagcagc cgcggtaata      480
cgtaggtggc aagcgttatc cggaattatt gggcgtaaag ggtgcgtagg cggcgagata      540
agtctgaggt aaaagcccgt ggctcaacca cggtaagcct tggaaactgt ctggctggag      600
tgcaggagag gacaatggaa ttccatgtgt agcggtaaaa tgcgtagata tatggaggaa      660
caccagtggc gaaggcggtt gtctggcctg taactgacgc tgaagcacga aagcgtgggg      720
agcaaatagg attagatacc ctagtagtcc acgccgtaaa cgatgagaac taagtgttgg      780
ggaaactcag tgctgcagtt aacgcaataa gttctccgcc tggggagtat gcacgcaagt      840
```

```
gtgaaactca aaggaattga cgggggcccg cacaagcggt ggagtatgtg gtttaattcg      900
acgcaacgcg aagaacctta ccaggccttg acatggtatc aaaggccctg agatagggga      960
gatagttatg atacacacag gtggtgcatg gttgtcgtca gctcgtgtcg tgagatgttg     1020
ggttaagtcc cgcaacgagc gcaacccttg tttctagtta ccaacagtaa gatgggggact   1080 ctagagagac tgccggtgac aaaccggagg aaggtgggga tgacgtcaaa tcatcatgcc    1140
ccttatggcc tgggctacac acgtactaca atggcgtcta caaagagcag cgagcaggtg    1200
actgtaagcg aatctcataa aggacgtctc agttcggatt gaagtctgca actcgacttc    1260
atgaagtcgg aatcgctagt aatcgcggat cagcatgccg cggtgaatac gttctcgggc    1320
cttgtacaca ccgcccgtca accatggga gttgataata cccgaagccg gtggcctaac     1380
catttatgga gggag                                                     1395

<210> SEQ ID NO 12
<211> LENGTH: 1383
<212> TYPE: DNA
<213> ORGANISM: Unknown
<220> FEATURE:
<223> OTHER INFORMATION: K12

<400> SEQUENCE: 12
cagtcgaacg cgagcacttg tgctcgagtg gcgaacgggt gagtaataca taagtaacct       60
gccctagaca gggggataac tattggaaac gatagctaag accgcatagg tacggacact      120
gcatggtgac cgtattaaaa gtgcctcaaa gcactggtag aggatggact tatggcgcat      180
tagctggttg gcggggtaac ggcccaccaa ggcgacgatg cgtagccgac ctgagagggt      240
gaccggccac actgggactg agacacggcc cagactccta cgggaggcag cagtagggaa      300
ttttcggcaa tggggaaac cctgaccgag caacgccgcg tgaaggaaga aggttttcgg      360
attgtaaact tctgttataa aggaagaacg gcggctacag gaaatggtag ccgagtgacg      420
gtactttatt agaaagccac ggctaactac gtgccagcag ccgcggtaat acgtaggtgg      480
caagcgttat ccggaattat tgggcgtaaa gagggagcag gcggcagcaa gggtctgtgg      540
tgaaagcctg aagcttaact tcagtaagcc atagaaacca ggcagctaga gtgcaggaga      600
ggatcgtgga attccatgtg tagcggtgaa atgcgtagat atatggagga acaccagtgg      660
cgaaggcgac gatctggcct gcaactgacg ctcagtcccg aaagcgtggg gagcaaatag      720
gattagatac cctagtagtc cacgccgtaa acgatgagta ctaagtgttg gatgtcaaag      780
ttcagtgctg cagttaacgc aataagtact ccgcctgagt agtacgttcg caagaatgaa      840
actcaaagga attgacgggg cccgcacaa gcggtggagc atgtggttta attcgaagca     900
acgcgaagaa ccttaccagg tcttgacata tcataaagg ctccagagat ggagagatag      960
ctatatgaga tacaggtggt gcatggttgt cgtcagctcg tgtcgtgaga tgttgggtta     1020
agtcccgcaa cgagcgcaac ccttatcgtt agttaccatc attaagttgg ggactctagc     1080
gagactgcca gtgacaagct ggaggaaggc ggggatgacg tcaaatcatc atgcccctta     1140
tgacctgggc tacacacgtg ctacaatgga tggtgcagag ggaagcgaag ccgcgaggtg     1200
aagcaaaacc cataaaacca ttctcagttc ggattgtagt ctgcaactcg actacatgaa     1260
gttggaatcg ctagtaatcg cgaatcagca tgtcgcggtg aatacgttct cgggccttgt     1320
acacaccgcc cgtcacacca cgagagttga taacacccga agccggtggc ctaaccgcaa     1380
gga                                                                  1383
```

<210> SEQ ID NO 13
<211> LENGTH: 1423
<212> TYPE: DNA
<213> ORGANISM: Unknown
<220> FEATURE:
<223> OTHER INFORMATION: K13
<220> FEATURE:
<221> NAME/KEY: misc_feature
<222> LOCATION: (4)..(4)
<223> OTHER INFORMATION: n is a, c, g, or t

<400> SEQUENCE: 13

| | | | | | |
|---|---|---|---|---|---|
| tgcnagtcga | acgcttcttt | cctcccgagt | gcttgcactc | aattggaaag | aggagtggcg | 60 |
| gacgggtgag | taacacgtgg | gtaacctacc | catcagaggg | ggataacact | tggaaacagg | 120 |
| tgctaatacc | gcataacagt | ttatgccgca | tggcataaga | gtgaaaggcg | ctttcgggtg | 180 |
| tcgctgatgg | atggacccgc | ggtgcattag | ctagttggtg | aggtaacggc | tcaccaaggc | 240 |
| cacgatgcat | agccgacctg | agagggtgat | cggccacact | gggactgaga | cacggcccag | 300 |
| actcctacgg | gaggcagcag | tagggaatct | tcggcaatgg | acgaaagtct | gaccgagcaa | 360 |
| cgccgcgtga | gtgaagaagg | ttttcggatc | gtaaaactct | gttgttagag | aagaacaagg | 420 |
| acgttagtaa | ctgaacgtcc | cctgacggta | tctaaccaga | aagccacggc | taactacgtg | 480 |
| ccagcagccg | cggtaatacg | taggtggcaa | gcgttgtccg | gatttattgg | gcgtaaagcg | 540 |
| agcgcaggcg | gtttcttaag | tctgatgtga | aagcccccgg | ctcaaccggg | agggtcatt | 600 |
| ggaaactggg | agacttgagt | gcagaagagg | agagtggaat | tccatgtgta | gcggtgaaat | 660 |
| gcgtagatat | atggaggaac | accagtggcg | aaggcggctc | tctggtctgt | aactgacgct | 720 |
| gaggctcgaa | agcgtgggga | gcaaacagga | ttagatacc | tggtagtcca | cgccgtaaac | 780 |
| gatgagtgct | aagtgttgga | gggtttccgc | ccttcagtgc | tgcagcaaac | gcattaagca | 840 |
| ctccgcctgg | ggagtacgac | cgcaaggttg | aaactcaaag | gaattgacgg | gggcccgcac | 900 |
| aagcggtgga | gcatgtggtt | taattcgaag | caacgcgaag | aaccttacca | ggtcttgaca | 960 |
| tcctttgacc | actctagaga | tagagctttc | ccttcgggga | caaagtgaca | ggtggtgcat | 1020 |
| ggttgtcgtc | agctcgtgtc | gtgagatgtt | gggttaagtc | ccgcaacgag | cgcaacccctt | 1080 |
| attgttagtt | gccatcattt | agttgggcac | tctagcgaga | ctgccggtga | caaaccggag | 1140 |
| gaaggtgggg | atgacgtcaa | atcatcatgc | cccttatgac | ctgggctaca | cacgtgctac | 1200 |
| aatgggaagt | acaacgagtc | gctagaccgc | gaggtcatgc | aaatctctta | aagcttctct | 1260 |
| cagttcggat | tgcaggctgc | aactcgcctg | catgaagccg | gaatcgctag | taatcgcgga | 1320 |
| tcagcacgcc | gcggtgaata | cgttcccggg | ccttgtacac | accgcccgtc | acaccacgag | 1380 |
| agtttgtaac | acccgaagtc | ggtgaggtaa | ccttttggga | gcc | | 1423 |

<210> SEQ ID NO 14
<211> LENGTH: 1381
<212> TYPE: DNA
<213> ORGANISM: Unknown
<220> FEATURE:
<223> OTHER INFORMATION: K14

<400> SEQUENCE: 14

| | | | | | |
|---|---|---|---|---|---|
| aagtcgaggg | gcatcatgac | ctagcaatag | gttgatggcg | accggcgcac | gggtgagtaa | 60 |
| cacgtatcca | acctgccgat | tattccggga | tagcctttcg | aaagaaagat | taatactgga | 120 |
| tagcataacg | agaaggcatc | ttcttgttat | taaagaattt | cgataatcga | tggggatgcg | 180 |
| ttccattagt | ttgttggcgg | ggtaacggcc | caccaagaca | tcgatggata | ggggttctga | 240 |

-continued

```
gaggaaggtc ccccacattg gaactgagac acggtccaaa ctcctacggg aggcagcagt      300
gaggaatatt ggtcaatgga cgagagtctg aaccagccaa gtagcgtgaa ggatgactgc      360
cctatgggtt gtaaacttct tttatatggg aataaagtgc agtatgtata ctgttttgta      420
tgtaccatac gaataaggat cggctaactc cgtgccagca gccgcggtaa tacgaggat       480 ccgagcgtta tccggattta ttgggtttaa gggagcgta ggcggattat taagtcagtt      540
gtgaaagttt gcggctcaac cgtaaaattg cagttgatac tggtagtctt gagtgcagca     600
gaggtaggcg gaattcgtgg tgtagcggtg aaatgcttag atatcacgaa gaactccgat     660
tgcgaaggca gcttactgga ctgtaactga cgctgatgct cgaaagtgtg ggtatcaaac     720
aggattagat accctggtag tccacacagt aaacgatgaa tactcgctgt tgcgatata     780 cagcaagcgg ccaagcgaaa gcattaagta ttccacctgg ggagtacgcc ggcaacggtg     840
aaactcaaag gaattgacgg gggcccgcac aagcggagga catgtggtt taattcgatg     900 atacgcgagg aaccttaccc gggcttaaat tgcaactgac ggatttggaa acagatcttc     960
cttcgggcag ttgtgaaggt gctgcatggt tgtcgtcagc tcgtgccgtg aggtgtcggc    1020
ttaagtgcca taacgagcgc aacccttatc tttagttact aacaggtcat gctgaggact    1080
ctagagagac tgccgtcgta agatgtgagg aaggtgggga tgacgtcaaa tcagcacggc    1140
ccttacgtcc ggggctacac acgtgttaca atggggggta cagaaggcag ctacacagcg    1200
atgtgatgct aatcccaaaa gcctctctca gttcggattg gagtctgcaa cccgactcca    1260
tgaagctgga ttcgctagta atcgcgcatc agccacggcg cggtgaatac gttcccgggc    1320
cttgtacaca ccgcccgtca agccatgaaa gccggggta cctgaagtac gtaaccgcaa    1380
g                                                                    1381
```

<210> SEQ ID NO 15
<211> LENGTH: 1391
<212> TYPE: DNA
<213> ORGANISM: Unknown
<220> FEATURE:
<223> OTHER INFORMATION: K15

<400> SEQUENCE: 15

```
cagtcgaacg aagcgattta acggaagttt tcggatggaa gttggattga ctgagtggcg      60
gacgggtgag taacgcgtgg gtaacctgcc ttgtactggg ggacaacagt tagaaatgac     120
tgctaatacc gcataagcgc acagtatcgc atgatacagt gtgaaaaact ccggtggtac     180
aagatggacc cgcgtctgat tagctagttg gtaaggtaac ggcttaccaa ggcgacgatc     240
agtagccgac ctgagagggt gaccggccac attgggactg agacacggcc caaactccta     300
cgggaggcag cagtggggaa tattgcacaa tgggcgaaag cctgatgcag cgacgccgcg     360
tgagtgaaga agtatttcgg tatgtaaagc tctatcagca gggaagaaaa tgacggtacc     420
tgactaagaa gccccggcta actacgtgcc agcagccgcg gtaatacgta gggggcaagc     480
gttatccgga tttactgggt gtaaagggag cgtagacggt aaagcaagtc tgaagtgaaa     540
gcccgcggct caactgcggg actgctttgg aaactgttta actggagtgt cggagaggta    600
agtggaattc ctagtgtagc ggtgaaatgc gtagatatta ggaggaacac cagtggcgaa    660
ggcgacttac tggacgataa ctgacgttga ggctcgaaag cgtggggagc aaacaggatt    720
agataccctg gtagtccacg ccgtaaacga tgaatactag gtgttgggga gcaaagctct    780
tcggtgccgt cgcaaacgca gtaagtattc cacctgggga gtacgttcgc aagaatgaaa    840
```

```
ctcaaaggaa ttgacgggga cccgcacaag cggtggagca tgtggtttaa ttcgaagcaa      900
cgcgaagaac cttaccaggt cttgacatcg atccgacggg ggagtaacgt cccctccct      960 tcggggcgga gaagacaggt ggtgcatggt tgtcgtcagc tcgtgtcgtg agatgttggg     1020
ttaagtcccg caacgagcgc aaccctattt ctaagtagcc agcggttcgg ccgggaactc     1080
ttgggagact gccagggata acctggagga aggtgggat gacgtcaaat catcatgccc      1140
cttatgatct gggctacaca cgtgctacaa tggcgtaaac aaagagaagc aagaccgcga     1200
ggtggagcaa atctcaaaaa taacgtctca gttcggactg caggctgcaa ctcgcctgca     1260
cgaagctgga atcgctagta atcgcgaatc agaatgtcgc ggtgaatacg ttcccgggtc     1320
ttgtacacac cgcccgtcac accatgggag tcagtaacgc cgaagtcag tgacccaacc     1380 gcaaggaggg a                                                         1391

<210> SEQ ID NO 16
<211> LENGTH: 1402
<212> TYPE: DNA
<213> ORGANISM: Unknown
<220> FEATURE:
<223> OTHER INFORMATION: K16

<400> SEQUENCE: 16
agtcgaacga agcaatactg tgtgaagaga ttagcttgct aagatcagaa ctttgtattg       60
actgagtggc ggacgggtga gtaacgcgtg ggcaacctgc cttacacagg gggataacag      120
ctagaaatgg ctgctaatac cgcataagac ctcagtaccg catggtagag gggtaaaaac      180
tccggtggtg taagatgggc ccgcgtctga ttaggtagtt ggtagggtaa cggcctacca      240
agccgacgat cagtagccga cctgagaggg tgaccggcca cattgggact gagacacggc      300
ccaaactcct acgggaggca gcagtgggga atattgcaca atgggggaaa ccctgatgca      360
gcgacgccgc gtgaaggatg aagtatttcg gtatgtaaac ttctatcagc agggaagaag      420
atgacggtac ctgactaaga agccccggct aactacgtgc cagcagccgc ggtaatacgt      480 aggggggcaag cgttatccgg atttactggg tgtaaaggga gcgtagacgg catggcaagt      540
ctgaagtgaa agcccggggc tcaacccegg gactgctttg gaaactgtca ggctagagtg      600
tcggagaggc aagtggaatt cctagtgtag cggtgaaatg cgtagatatt aggaggaaca      660
ccagtggcga aggcggcttg ctggacgatg actgacgttg aggctcgaaa gcgtggggag      720
caaacaggat tagataccct ggtagtccac gccgtaaacg atgattacta ggtgtcggga      780
agcaaagctt ttcggtgccg cagccaacgc aataagtaat ccacctgggg agtacgttcg      840
caagaatgaa actcaaagga attgacgggg acccgcacaa gcggtggagc atgtggttta      900
attcgaagca acgcgaagaa ccttacctga tcttgacatc ccggtgacaa agtatgtaat      960
gtactctttc ttcggaacac cggtgacagg tggtgcatgg ttgtcgtcag ctcgtgtcgt     1020
gagatgttgg gttaagtccc gcaacgagcg caacccttat ctttagtagc cagcatttga     1080
ggtgggcact ctagagagac tgccagggat aacctggagg aaggtgggga tgacgtcaaa     1140
tcatcatgcc ccttatgacc agggctacac acgtgctaca atggcgtaaa caagggaag      1200 cgaccctgtg aaggcaagca aatcccaaaa ataacgtctc agttcggatt gtagtctgca     1260
actcgactac atgaagctgg aatcgctagt aatcgcgaat cagaatgtcg cggtgaatac     1320
gttcccgggt cttgtacaca ccgcccgtca caccatggga gtcagtaacg cccgaagccg     1380
gtgacctaac cgaaaggaag ga                                             1402
```

-continued

```
<210> SEQ ID NO 17
<211> LENGTH: 1393
<212> TYPE: DNA
<213> ORGANISM: Unknown
<220> FEATURE:
<223> OTHER INFORMATION: K17
<220> FEATURE:
<221> NAME/KEY: misc_feature
<222> LOCATION: (942)..(945)
<223> OTHER INFORMATION: n is a, c, g, or t
<220> FEATURE:
<221> NAME/KEY: misc_feature
<222> LOCATION: (953)..(956)
<223> OTHER INFORMATION: n is a, c, g, or t
<220> FEATURE:
<221> NAME/KEY: misc_feature
<222> LOCATION: (1067)..(1069)
<223> OTHER INFORMATION: n is a, c, g, or t

<400> SEQUENCE: 17
gcaagtcgag cgaagcggtt tcgatgaagt tttcggatgg atttgaaatt gacttagcgg      60
cggacgggtg agtaacgcgt gggtaacctg ccttacactg ggggataaca gttagaaatg     120
actgctaata ccgcataagc gcacagggcc gcatggtctg gtgtgaaaaa ctccggtggt     180
gtaagatgga cccgcgtctg attaggtagt tggtggggta acggcccacc aagccgacga     240
tcagtagccg acctgagagg gtgaccggcc acattgggac tgagacacgg cccaaactcc     300
tacgggaggc agcagtgggg aatattggac aatgggcgaa agcctgatcc agcgacgccg     360
cgtgagtgaa gaagtatttc ggtatgtaaa gctctatcag cagggaagaa atgacggta     420 cctgactaag aagccccggc taactacgtg ccagcagccg cggtaatacg tagggggcaa     480
gcgttatccg gatttactgg gtgtaaaggg agcgtagacg gttaagcaag tctgaagtga     540
aagcccgggg ctcaacccccg gtactgcttt ggaaactgtt tgacttgagt gcaggagagg     600
taagtggaat tcctagtgta gcggtgaaat gcgtagatat taggaggaac accagtggcg     660
aaggcggctt actggactgt aactgacgtt gaggctcgaa agcgtgggga gcaaacagga     720 ttagatacccc tggtagtcca cgccgtaaac gatgaatact aggtgtcggg ggacaaagtc     780
cttcggtgcc gccgctaacg caataagtat tccacctggg gagtacgttc gcaagaatga     840
aactcaaagg aattgacggg gacccgcaca agcggtggag catgtggttt aattcgaagc     900
aacgcgaaga accttaccaa gtcttgacat cccattgaaa annnnttaac cgnnnncct     960 cttcggagca atggagacag gtggtgcatg gttgtcgtca gctcgtgtcg tgagatgttg    1020
ggttaagtcc cgcaacgagc gcaacccctta tccttagtag ccagcannna atggtgggca    1080
ctctggggag actgccaggg ataacctgga ggaaggtggg gatgacgtca atcatcatg    1140 cccccttatga tttgggctac acacgtgcta caatggcgta aacaaaggga agcaaaggag    1200
cgatctggag caaaccccaa aaataacgtc tcagttcgga ttgcaggctg caactcgcct    1260
gcatgaagct ggaatcgcta gtaatcgcga atcagaatgt cgcggtgaat acgttcccgg    1320
gtcttgtaca caccgcccgt cacaccatgg gagttggtaa cgcccgaagt cagtgaccca    1380
accgcaagga ggg                                                      1393

<210> SEQ ID NO 18
<211> LENGTH: 1389
<212> TYPE: DNA
<213> ORGANISM: Unknown
<220> FEATURE:
<223> OTHER INFORMATION: K18

<400> SEQUENCE: 18
```

| | |
|---|---|
| gtcgaggggc agcatggtct tagcttgcta aggctgatgg cgaccggcgc acgggtgagt | 60 |
| aacacgtatc caacctgccg tctactcttg gccagccttc tgaaaggaag attaatccag | 120 |
| gatggcatca tgagttcaca tgtccgcatg attaaaggta ttttccggta gacgatgggg | 180 |
| atgcgttcca ttagatagta ggcggggtaa cggcccacct agtcaacgat ggataggggt | 240 |
| tctgagagga aggtccccca cattggaact gagacacggt ccaaactcct acgggaggca | 300 |
| gcagtgagga atattggtca atgggcgatg cctgaacca gccaagtagc gtgaaggatg | 360 |
| actgccctat gggttgtaaa cttcttttat aaaggaataa agtcgggtat gcatacccgt | 420 |
| ttgcatgtac tttatgaata aggatcggct aactccgtgc cagcagccgc ggtaatacgg | 480 |
| aggatccgag cgttatccgg atttattggg tttaaaggga gcgtagatgg atgtttaagt | 540 |
| cagttgtgaa agtttgcggc tcaaccgtaa aattgcagtt gatactggat gtcttgagtg | 600 |
| cagttgaggc aggcggaatt cgtggtgtag cggtgaaatg cttagatatc acgaagaact | 660 |
| ccgattgcga aggcagcctg ctaagctgca actgacattg aggctcgaaa gtgtgggtat | 720 |
| caaacaggat tagataccct ggtagtccac acggtaaacg atgaatactc gctgtttgcg | 780 |
| atatacggca agcggccaag cgaaagcgtt aagtattcca cctggggagt acgccggcaa | 840 |
| cggtgaaact caaaggaatt gacggggcc cgcacaagcg gaggaacatg tggtttaatt | 900 |
| cgatgatacg cgaggaacct tacccgggct taaattgcac tcgaatgatc cggaaacggt | 960 |
| tcagctagca atagcgagtg tgaaggtgct gcatggttgt cgtcagctcg tgccgtgagg | 1020 |
| tgtcggctta agtgccataa cgagcgcaac ccttgttgtc agttactaac aggtgatgct | 1080 |
| gaggactctg acaagactgc catcgtaaga tgtgaggaag gtggggatga cgtcaaatca | 1140 |
| gcacggccct tacgtccggg gctacacacg tgttacaatg gggggtacag agggccgcta | 1200 |
| ccacgcgagt ggatgccaat ccctaaaacc cctctcagtt cggactggag tctgcaaccc | 1260 |
| gactccacga agctggattc gctagtaatc gcgcatcagc cacggcgcgg tgaatacgtt | 1320 |
| cccgggcctt gtacacaccg cccgtcaagc catgggagcc gggggtacct gaagtgcgta | 1380 |
| accgcgagg | 1389 |

<210> SEQ ID NO 19
<211> LENGTH: 1393
<212> TYPE: DNA
<213> ORGANISM: Unknown
<220> FEATURE:
<223> OTHER INFORMATION: K19
<220> FEATURE:
<221> NAME/KEY: misc_feature
<222> LOCATION: (1205)..(1206)
<223> OTHER INFORMATION: n is a, c, g, or t

<400> SEQUENCE: 19

| | |
|---|---|
| gcagtcgaac gaagcaatta agatgaagtt ttcggatgga atcttgattg actgagtggc | 60 |
| ggacgggtga gtaacgcgtg gataacctgc ctcacactgg gggataacag ttagaaatga | 120 |
| ctgctaatac cgcataagcg cacagtgccg catggcagtg tgtgaaaaac tccggtggtg | 180 |
| tgagatggat ccgcgtctga ttagccagtt ggcggggtaa cggcccacca aagcgacgat | 240 |
| cagtagccga cctgagaggg tgaccggcca cattgggact gagacacggc ccaaactcct | 300 |
| acgggaggca gcagtgggga atattgcaca atgggcgaaa gcctgatgca gcgacgccgc | 360 |
| gtgagtgaag aagtatttcg gtatgtaaag ctctatcagc agggaagaaa atgacggtac | 420 |
| ctgactaaga gccccggct aactacgtgc cagcagccgc ggtaatacgt agggggcaag | 480 |
| cgttatccgg atttactggg tgtaaaggga gcgtagacgg cgaagcaagt ctgaagtgaa | 540 |

-continued

```
aacccagggc tcaaccctgg gactgctttg gaaactgttt tgctagagtg tcggagaggt      600
aagtggaatt cctagtgtag cggtgaaatg cgtagatatt aggaggaaca ccagtggcga      660
aggcggctta ctggacgata actgacgttg aggctcgaaa gcgtggggag caaacaggat      720 tagatacccct ggtagtccac gccgtaaacg atgaatgcta ggtgttgggg ggcaaagccc     780
ttcggtgccg ccgcaaacgc agtaagcatt ccacctgggg agtacgttcg caagaatgaa      840
actcaaagga attgacgggg acccgcacaa gcggtggagc atgtggttta attcgaagca      900
acgcgaagaa ccttaccaag tcttgacatc ccctgacgg gccggtaacg cggccttttcc     960 ttcgggacag gggagacagg tggtgcatgg ttgtcgtcag ctcgtgtcgt gagatgttgg      1020
gttaagtccc gcaacgagcg caacccttat ccttagtagc cagcacgtga aggtgggcac      1080
tctagggaga ctgccaggga taacctggag gaaggtgggg atgacgtcaa atcatcatgc      1140
cccttatgat ttgggctaca cacgtgctac aatggcgtaa acaaagggaa gcgagacagt      1200
gatgnngagc aaatcccaaa ataacgtcc cagttcggac tgtagtctgc aacccgacta      1260
cacgaagctg gaatcgctag taatcgcgaa tcagaatgtc gcggtgaata cgttcccggg      1320
tcttgtacac accgcccgtc acaccatggg agtcagcaac gcccgaagtc agtgaccccaa    1380 ccgaaaggag gga                                                        1393

<210> SEQ ID NO 20
<211> LENGTH: 1394
<212> TYPE: DNA
<213> ORGANISM: Unknown
<220> FEATURE:
<223> OTHER INFORMATION: K20

<400> SEQUENCE: 20
tgcaagtcga acggggtgct catgacggag gattcgtcca acggattgag ttacctagtg      60
gcggacgggt gagtaacgcg tgaggaacct gccttggaga ggggaataac actccgaaag      120
gagtgctaat accgcatgat gcagttgggt cgcatggctc tgactgccaa agatttatcg      180
ctctgagatg gcctcgcgtc tgattagcta gtaggcgggg taacggccca cctaggcgac      240
gatcagtagc cggactgaga ggttgaccgg ccacattggg actgagacac ggcccagact      300
cctacgggag gcagcagtgg ggaatattgg gcaatgggcg caagcctgac ccagcaacgc      360
cgcgtgaagg aagaaggctt tcgggttgta aacttcttt gtcggggacg aaacaaatga      420
cggtacccga cgaataagcc acggctaact acgtgccagc agccgcggta atacgtaggt      480
ggcaagcgtt atccggattt actgggtgta aagggcgtgt aggcgggatt gcaagtcaga      540
tgtgaaaact gggggctcaa cctccagcct gcatttgaaa ctgtagttct tgagtgctgg      600
agaggcaatc ggaattccgt gtgtagcggt gaaatgcgta gatatacgga ggaacaccag      660
tggcgaaggc ggattgctgg acagtaactg acgctgaggc gcgaaagcgt ggggagcaaa      720
caggattaga taccctggta gtccacgccg taaacgatgg atactaggtg tggggggtct      780
gaccccctcc gtgccgcagt taacacaata agtatcccac ctggggagta cgatcgcaag      840
gttgaaactc aaaggaattg acgggggccc gcacaagcgg tggagtatgt ggtttaattc      900
gaagcaacgc gaagaacctt accagggctt gacatcccac taacgaagca gagatgcatt      960
aggtgccctt cggggaaagt ggagacaggt ggtgcatggt tgtcgtcagc tcgtgtcgtg      1020
agatgttggg ttaagtcccg caacgagcgc aacccttatt gttagttgct acgcaagagc      1080
actctagcga gactgccgtt gacaaaacgg aggaaggtgg ggacgacgtc aaatcatcat      1140
```

```
gcccccttatg tcctgggcca cacacgtact acaatggtgg ttaacagagg gaggcaatac    1200
cgcgaggtgg agcaaatccc taaaagccat cccagttcgg attgcaggct gaaacccgcc    1260
tgtatgaagt tggaatcgct agtaatcgcg gatcagcatg ccgcggtgaa tacgttcccg    1320
ggccttgtac acaccgcccg tcacaccatg agagtcggga cacccgaag tccgtagcct     1380 aaccgcaagg aggg                                                      1394

<210> SEQ ID NO 21
<211> LENGTH: 1385
<212> TYPE: DNA
<213> ORGANISM: Unknown
<220> FEATURE:
<223> OTHER INFORMATION: K21

<400> SEQUENCE: 21
agtcgagggg cagcatttta gtttgcttgc aaactaaaga tggcgaccgg cgcacgggtg     60
agtaacacgt atccaacctg ccgataactc ggggatagcc tttcgaaaga aagattaata    120
tccgatggta tattaaaacc gcatggtttt actattaaag aatttcggtt atcgatgggg    180
atgcgttcca ttagtttgtt ggcggggtaa cggcccacca agactacgat ggataggggt    240
tctgagagga aggtccccca cattggaact gagacacgg ccaaactcct acgggaggca     300
gcagtgagga atattggtca atggacgaga gtctgaacca gccaagtagc gtgaaggatg    360
actgccctat gggttgtaaa cttctttat atgggaataa agtattccac gtgtgggatt     420
ttgtatgtac catatgaata aggatcggct aactccgtgc cagcagccgc ggtaatacgg    480
aggatccgag cgttatccgg atttattggg tttaaaggga gcgtaggtgg attgttaagt    540
cagttgtgaa agtttgcggc tcaaccgtaa aattgcagtt gaaactggca gtcttgagta    600
cagtagaggt gggcggaatt cgtggtgtag cggtgaaatg cttagatatc acgaagaact    660
ccgattgcga aggcagctca ctagactgca actgacactg atgctcgaaa gtgtgggtat    720
caaacaggat tagatacccct ggtagtccac acagtaaacg atgaatactc gctgtttgcg    780
atatacagta agcggccaag cgaaagcatt aagtattcca cctggggagt acgccggcaa    840
cggtgaaact caaaggaatt gacggggggcc cgcacaagcg gaggaacatg tggtttaatt    900
cgatgatacg cgaggaacct tacccgggct taaattgcat ttgaataatc tggaaacagg    960
ttagccgcaa gcaaatgtg aaggtgctga atggttgtcg tcagctcgtg ccgtgaggtg    1020
tcggcttaag tgccataacg agcgcaaccc ttatctttag ttactaacag gtcatgctga    1080
ggactctaga gagactgccg tcgtaagatg tgaggaaggt ggggatgacg tcaaatcagc    1140
acggccctta cgtccggggc tacacacgtg ttacaatggg gggtacagaa ggcagctacc    1200
tggcgacagg atgctaatcc caaaaacctc tctcagttcg gatcgaagtc tgcaacccga    1260
cttcgtgaag ctggattcgc tagtaatcgc gcatcagcca tggcgcggtg aatacgttcc    1320
cgggccttgt acacaccgcc cgtcaagcca tgaaagccgg ggtacctga agtacgtaac    1380 cgcaa                                                               1385

<210> SEQ ID NO 22
<211> LENGTH: 1385
<212> TYPE: DNA
<213> ORGANISM: Unknown
<220> FEATURE:
<223> OTHER INFORMATION: K22

<400> SEQUENCE: 22
agtcgagggg cagcatttca gtttgcttgc aaactggaga tggcgaccgg cgcacgggtg     60
```

```
agtaacacgt atccaacctg ccgataactc ggggatagcc tttcgaaaga aagattaata    120
cccgatggta taattagacc gcatggtctt gttattaaag aatttcggtt atcgatgggg    180
atgcgttcca ttaggcagtt ggtgaggtaa cggctcacca aaccttcgat ggatagggt    240 tctgagagga aggtccccca cattggaact gagacacgt  ccaaactcct acgggaggca    300
gcagtgagga atattggtca atgggcgcag gcctgaacca gccaagtagc gtgaaggatg    360
actgccctat gggttgtaaa cttcttttat atgggaataa agttttccac gtgtggaatt    420
ttgtatgtac catatgaata aggatcggct aactccgtgc cagcagccgc ggtaatacgg    480
aggatccgag cgttatccgg atttattggg tttaaaggga gcgtaggtgg acagttaagt    540
cagttgtgaa agtttgcggc tcaaccgtaa aattgcagtt gatactggct gtcttgagta    600
cagtagaggt gggcggaatt cgtggtgtag cggtgaaatg cttagatatc acgaagaact    660
ccgattgcga aggcagctca ctggactgca actgacactg atgctcgaaa gtgtgggtat    720
caaacaggat tagataccct ggtagtccac acagtaaacg atgaatactc gctgtttgcg    780
atatacagta agcggccaag cgaaagcatt aagtattcca cctggggagt acgccggcaa    840
cggtgaaact caaaggaatt gacggggggcc cgcacaagcg gaggaacatg tggtttaatt    900
cgatgatacg cgaggaacct tacccgggct taaattgcat ttgaatatat tggaaacagt    960
atagccgtaa ggcaaatgtg aaggtgctgc atggttgtcg tcagctcgtg ccgtgaggtg   1020
tcggcttaag tgccataacg agcgcaaccc ttatctttag ttactaacag gtcatgctga   1080
ggactctaga gagactgccg tcgtaagatg tgaggaaggt ggggatgacg tcaaatcagc   1140 acggcccta  cgtccggggc tacacacgtg ttacaatggg gggtacagaa ggcagctacc   1200
tggtgacagg atgctaatcc caaaagcctc tctcagttcg gatcgaagtc tgcaacccga   1260
cttcgtgaag ctggattcgc tagtaatcgc gcatcagcca tggcgcggtg aatacgttcc   1320
cgggccttgt acacaccgcc cgtcaagcca tgaaagccgg ggtacctga  agtacgtaac   1380 cgcaa                                                                1385
```

<210> SEQ ID NO 23
<211> LENGTH: 1387
<212> TYPE: DNA
<213> ORGANISM: Unknown
<220> FEATURE:
<223> OTHER INFORMATION: K23

<400> SEQUENCE: 23

```
agtcgagggg cagcatgatt tgtagcaata cagattgatg gcgaccggcg cacgggtgag     60
taacgcgtat gcaacttacc tatcagaggg ggatagcccg gcgaaagtcg gattaatacc    120
ccataaaaca ggggtcccgc atgggaatat ttgttaaaga ttcatcgctg atagataggc    180
atgcgttcca ttaggcagtt ggcggggtaa cggcccacca aaccgacgat ggatagggt    240 tctgagagga aggtccccca cattggtact gagacacgg  ccaaactcct acgggaggca    300
gcagtgagga atattggtca atggccgaga ggctgaacca gccaagtcgc gtgaaggaag    360
aaggatctat ggtttgtaaa cttcttttat aggggaataa agtggaggac gtgtcctttt    420
ttgtatgtac cctatgaata agcatcggct aactccgtgc cagcagccgc ggtaatacgg    480
aggatgcgag cgttatccgg atttattggg tttaagggt  gcgtaggtgg tgatttaagt    540
cagcggtgaa agtttgtggc tcaaccataa aattgccgtt gaaactgggt tacttgagtg    600
tgtttgaggt aggcggaatg cgtggtgtag cggtgaaatg catagatatc acgcagaact    660
```

```
ccgattgcga aggcagctta ctaaaccata actgacactg aagcacgaaa gcgtggggat      720
caaacaggat tagataccct ggtagtccac gcagtaaacg atgattacta ggagtttgcg      780
atacaatgta agctctacag cgaaagcgtt aagtaatcca cctggggagt acgccggcaa      840
cggtgaaact caaaggaatt gacggggggcc cgcacagcgg aggaacatgt ggtttaattc      900
gatgatacgc gaggaacctt acccgggttt gaacgtagtc tgaccggagt ggaaacactc      960
tttctagcaa tagcagatta cgaggtgctg catggttgtc gtcagctcgt gccgtgaggt     1020
gtcggcttaa gtgccataac gagcgcaacc cttatcacta gttactaaca ggtgaagctg     1080
aggactctgg tgagactgcc agcgtaagct gtgaggaagg tggggatgac gtcaaatcag     1140
cacggccctt acatccgggg cgacacacgt gttacaatgg catggacaaa gggcagctac     1200
ctggtgacag gatgctaatc tccaaaccat gtctcagttc ggatcggagt ctgcaactcg     1260
actccgtgaa gctggattcg ctagtaatcg cgcatcagcc atgcgcggt gaatacgttc      1320 ccgggccttg tacacaccgc ccgtcaagcc atgggagccg ggggtacctg aagtccgtaa     1380
ccgcaag                                                               1387
```

<210> SEQ ID NO 24
<211> LENGTH: 1384
<212> TYPE: DNA
<213> ORGANISM: Unknown
<220> FEATURE:
<223> OTHER INFORMATION: K24

<400> SEQUENCE: 24

```
gtcgagggggc agcatggtct tagcttgcta aggccgatgg cgaccggcgc acgggtgagt       60
aacacgtatc caacctgccg tctactcttg gacagccttc tgaaaggaag attaatacaa      120
gatggcatca tgagtccgca tgttcacatg attaaaggta ttccggtaga cgatggggat      180
gcgttccatt agatagtagg cggggtaacg gcccacctag tcttcgatgg atagggggttc     240 tgagaggaag gtcccccaca ttggaactga gacacggtcc aaactcctac gggaggcagc      300
agtgaggaat attggtcaat gggcgagagc ctgaaccagc caagtagcgt gaaggatgac      360
tgccctatgg gttgtaaact tcttttataa aggaataaag tcgggtatgg atacccgttt     420
gcatgtactt tatgaataag gatcggctaa ctccgtgcca gcagccgcgg taatacggag      480
gatccgagcg ttatccggat ttattgggtt taaagggagc gtagatggat gtttaagtca     540
gttgtgaaag tttgcggctc aaccgtaaaa ttgcagttga tactggatat cttgagtgca     600
gttgaggcag gcggaattcg tggtgtagcg gtgaaatgct tagatatcac gaagaactcc      660
gattgcgaag gcagcctgct aagctgcaac tgacattgag gctcgaaagt gtgggtatca     720
aacaggatta gataccctgg tagtccacac ggtaaacgat gaatactcgc tgtttgcgat     780
atactgcaag cggccaagcg aaagcgttaa gtattccacc tggggagtac gccggcaacg     840
gtgaaactca aaggaattga cggggggcccg cacaagcgga ggaacatgtg gtttaattcg     900
atgatacgcg aggaacctta cccgggctta aattgcagat gaattacggt gaaagccgta     960
agccgcaagg catctgtgaa ggtgctgcat ggttgtcgtc agctcgtgcc gtgaggtgtc     1020
ggcttaagtg ccataacgag cgcaacccct tgttcagtt actaacaggt tccgctgagg     1080
actctgacaa gactgccatc gtaagatgtg aggaaggtgg ggatgacgtc aaatcagcac     1140
ggcccttacg tccggggcta cacacgtgtt acaatggggg gtacagaggg ccgctaccac     1200
gcgagtggat gccaatcccc aaaacctctc tcagttcgga ctggagtctg caacccgact     1260
ccacgaagct ggattcgcta gtaatcgcgc atcagccacg gcgcggtgaa tacgttcccg     1320
```

```
ggccttgtac acaccgcccg tcaagccatg ggagccgggg gtacctgaag tgcgtaaccg      1380
cgag                                                                   1384

<210> SEQ ID NO 25
<211> LENGTH: 1396
<212> TYPE: DNA
<213> ORGANISM: Unknown
<220> FEATURE:
<223> OTHER INFORMATION: K25
<220> FEATURE:
<221> NAME/KEY: misc_feature
<222> LOCATION: (943)..(944)
<223> OTHER INFORMATION: n is a, c, g, or t
<220> FEATURE:
<221> NAME/KEY: misc_feature
<222> LOCATION: (1072)..(1072)
<223> OTHER INFORMATION: n is a, c, g, or t
<220> FEATURE:
<221> NAME/KEY: misc_feature
<222> LOCATION: (1290)..(1290)
<223> OTHER INFORMATION: n is a, c, g, or t

<400> SEQUENCE: 25
gcagtcgaac gaagcgatct gggatgaagt tttcggatgg attcctggtt gactgagtgg        60
cggacgggtg agtaacgcgt ggataacctg cctcacactg ggggataaca gttagaaatg       120
gctgctaata ccgcataagc gcacagtacc gcatggtacg gtgtgaaaaa cccaggtggt       180
gtgagatgga tccgcgtctg attagccagt tggcgggggta acgcccacc aaagcgacga       240 tcagtagccg aacctgagagg gtgaccggcc acattgggac tgagacacgg cccaaactcc       300
tacgggaggc agcagtgggg aatattgcac aatgggcgaa agcctgatgc agcgacgccg       360
cgtgagtgaa gaagtatctc ggtatgtaaa gctctatcag cagggaagaa atgacggta        420 cctgactaag aagccccggc taactacgtg ccagcagccg cggtaatacg tagggggcaa       480
gcgttatccg gatttactgg gtgtaaaggg agcgtagacg cgacgcaag tctggagtga        540 aagcccgggg cccaaccccg ggactgcttt ggaaactgtg ctgctggagt gcaggagagg       600
taagtggaat tcctagtgta gcggtgaaat gcgtagatat taggaggaac accagtggcg       660
aaggcggctt actggactgt aactgacgtt gaggctcgaa agcgtgggga gcaaacagga       720
ttagataccc tggtagtcca cgccgtaaac gatgaatgct aggtgtcggg gggcaaagcc       780
cttcggtgcc gccgctaacg caataagcat tccacctggg gagtacgttc gcaagaatga       840
aactcaaagg aattgacggg gacccgcaca agcggtggag catgtggttt aattcgaagc       900
aacgcgaaga accttaccaa gtcttgacat cccctgaccc ggnncgtaac ggtgcccttc       960
cttcgggaca ggggagacag gtggtgcatg gttgtcgtca gctcgtgtcg tgagatgttg      1020
ggttaagtcc cgcaacgagc gcaacccctta tccttagtag ccagcacgtg anggtgggca     1080
ctctagggag actgccaggg ataacctgga ggaaggtggg gatgacgtca atcatcatg       1140 cccttatga tttgggctac acacgtgcta caatggcgta aacaaaggga ggcgaccctg       1200
cgaaggcaag caaatcccaa aaataacgtc ccagttcgga ctgtagtctg caacccgact      1260
acacgaagct ggaatcgcta gtaatcgcgn atcagaatgc cgcggtgaat acgttcccgg      1320
gtcttgtaca caccgcccgt cacaccatgg gagtcagcaa cgcccgaagt cagtgaccca     1380
accttaacag gaggga                                                    1396

<210> SEQ ID NO 26
<211> LENGTH: 1382
<212> TYPE: DNA
```

<213> ORGANISM: Unknown
<220> FEATURE:
<223> OTHER INFORMATION: K26

<400> SEQUENCE: 26

| | | | | | |
|---|---|---|---|---|---|
| gtcgaggggc | atcaggaaga | aagcttgctt | tctttgctgg | cgaccggcgc | acgggtgagt | 60 |
| aacacgtatc | caacctgccg | atgactcggg | gatagccttt | cgaaagaaag | attaataccc | 120 |
| gatggtatat | ctgaaaggca | tctttcagct | attaaagaat | ttcggtcatt | gatgggggatg | 180 |
| cgttccatta | ggttgttggc | ggggtaacgg | cccaccaagc | cgtcgatgga | tagggggttct | 240 |
| gagaggaagg | tccccacat | tggaactgag | acacggtcca | aactcctacg | ggaggcagca | 300 |
| gtgaggaata | ttggtcaatg | gacgagagtc | tgaaccagcc | aagtagcgtg | aaggatgact | 360 |
| gccctatggg | ttgtaaactt | cttttatacg | ggaataaagt | taggcacgtg | tgcctttttg | 420 |
| tatgtaccgt | atgaataagg | atcggctaac | tccgtgccag | cagccgcggt | aatacggagg | 480 |
| atccgagcgt | tatccggatt | tattgggttt | aaagggagcg | taggcggatg | cttaagtcag | 540 |
| ttgtgaaagt | ttgcggctca | accgtaaaat | tgcagttgat | actgggtgtc | ttgagtacag | 600 |
| tagaggcagg | cggaattcgt | ggtgtagcgg | tgaaatgctt | agatatcacg | aagaactccg | 660 |
| attgcgaagg | cagcttgctg | gactgtaact | gacgctgatg | ctcgaaagtg | tgggtatcaa | 720 |
| acaggattag | ataccctggt | agtccacaca | gtaaacgatg | aatactcgct | gtttgcgata | 780 |
| tacagtaagc | ggccaagcga | aagcgttaag | tattccacct | ggggagtacg | ccggcaacgg | 840 |
| tgaaactcaa | aggaattgac | gggggcccgc | acaagcggag | gaacatgtgg | tttaattcga | 900 |
| tgatacgcga | ggaaccttac | ccgggcttaa | attgcaaatg | aatgttctgg | aaacagatca | 960 |
| gccgcaaggc | atttgtgaag | gtgctgcatg | gttgtcgtca | gctcgtgccg | tgaggtgtcg | 1020 |
| gcttaagtgc | cataacgagc | gcaacccctta | tcgatagtta | ccatcaggtt | atgctgggga | 1080 |
| ctctgtcgag | actgccgtcg | taagatgtga | ggaaggtggg | gatgacgtca | aatcagcacg | 1140 |
| gcccttacgt | ccggggctac | acacgtgtta | caatgggggg | tacagaaggc | agctacacgg | 1200 |
| tgacgtgatg | ctaatcccta | aaacctctct | cagttcggat | tggagtctgc | aacccgactc | 1260 |
| catgaagctg | gattcgctag | taatcgcgca | tcagccacgg | cgcggtgaat | acgttcccgg | 1320 |
| gccttgtaca | caccgcccgt | caagccatga | agccggggg | tacctgaagt | gcgtaaccgc | 1380 |
| ga | | | | | | 1382 |

<210> SEQ ID NO 27
<211> LENGTH: 1370
<212> TYPE: DNA
<213> ORGANISM: Unknown
<220> FEATURE:
<223> OTHER INFORMATION: K27
<220> FEATURE:
<221> NAME/KEY: misc_feature
<222> LOCATION: (916)..(917)
<223> OTHER INFORMATION: n is a, c, g, or t

<400> SEQUENCE: 27

| | | | | | |
|---|---|---|---|---|---|
| tgcaagtcga | acggttaagg | cgccttcggg | cgcgaataga | gtggcgaacg | ggtgagtaac | 60 |
| acgtgaccaa | cctgccccc | tccccgggat | aacgcgagga | aacccgcgct | aataccggat | 120 |
| actccgcccc | tcccgcatgg | gaggggcggg | aaagccccga | cggagggga | tggggtcgcg | 180 |
| gcccattagg | tagacggcgg | ggcaacggcc | caccgtgcct | cgatgggta | gccgggttga | 240 |
| gagaccgacc | ggccacattg | ggactgagat | acggcccaga | ctcctacggg | aggcagcagt | 300 |
| ggggaatttt | gcgcaatggg | gggaaccctg | acgcagcaac | gccgcgtgcg | ggacgaaggc | 360 |

-continued

```
cttcgggttg taaaccgctt tcagcaggga agaagttgac ggtacctgca gaagaagccc      420
cggctaacta cgtgccagca gccgcggtaa tacgtagggg gcgagcgtta tccggattca      480
ttgggcgtaa agcgcgcgta ggcggcccgt caagcggaac ctctaacccg agggctcaac      540
ccccggtcgg gttccgaact ggcaggctcg agtttggtag aggaagatgg aattcccggt      600
gtagcggtgg aatgcgcaga tatcgggaag aacaccgatg gcgaaggcag tcttctgggc      660
catcaactga cgctgaggcg cgaaagctgg gggagcgaac aggattagat accctggtag      720
tcccagccgt aaacgatggg cgctaggtgt gggggatca tccctccgtg ccgcagccaa       780
cgcattaagc gccccgcctg gggagtacgg ccgcaaggct aaaactcaaa ggaattgacg      840
ggggcccgca caagcagcgg agcatgtggc ttaattcgaa gcaacgcgaa gaaccttacc      900
agggcttgac atgctnntga agccggggaa accggtggc cgagaggagc cagcgcaggt      960
ggtgcatggc tgtcgtcagc tcgtgtcgtg agatgttggg ttaagtcccg caacgagcgc     1020
aacccctgcc atatgttgcc agcattcagt tgggactca tatgggactg ccggcgtcaa      1080
gccggaggaa ggtggggacg acgtcaagtc atcatgccct ttatgccctg ggctgcacac     1140
gtgctacaat ggccggtaca acgggccgcg acctggcgac aggaagcgaa tccctcaaag     1200
ccggccccag ttcggatcgg aggctgcaac ccgcctccgt gaagtcggag ttgctagtaa     1260
tcgcggatca gcatgccgcg gtgaatacgt tcccgggcct tgtacacacc gcccgtcaca     1320
ccacccgagt cgtctgcacc cgaagccgcc ggccgaaccc gcaaggggcg                1370
```

<210> SEQ ID NO 28
<211> LENGTH: 1394
<212> TYPE: DNA
<213> ORGANISM: Unknown
<220> FEATURE:
<223> OTHER INFORMATION: K28
<220> FEATURE:
<221> NAME/KEY: misc_feature
<222> LOCATION: (909)..(911)
<223> OTHER INFORMATION: n is a, c, g, or t

<400> SEQUENCE: 28

```
caagtcgaac gaagcactta cttccaaatc ttcggaagag gaggtatttg actgagtggc       60
ggacgggtga gtaacgcgtg gggaacctgc cccgtaccgg gggataacag tcagaaatga      120
ctgctaatac cgcataagcg cacgaaggcg catgcttttg tgtgaaaaac tccggtggta      180
cgggatggtc cgcgtctga ttagccagtt ggcggggtaa cggcccacca aagcgacgat       240
cagtagccgg cctgagaggg tggacggcca cattgggact gagacacggc ccagactcct      300
acgggaggca gcagtgggga atattgcaca atgggggaaa ccctgatgca gcgacgccgc      360
gtgagcgaag aagtatttcg gtatgtaaag ctctgtcagc agggaagaaa atgacggtac      420
ctgaccaaga agcaccggct aaatacgtgc cagcagccgc ggtaatacgt atggtgcaag      480
cgttatccgg atttactggg tgtaaaggga gcgtagacgg aggggcaagt ctgaagtgaa      540
agcccggggc ccaaccccgg gactgctttg gaaactgtcc gtctggagtg ccggagaggt      600
aagcggaatt cccagtgtag cggtgaaatg cgtagatatt gggaggaaca ccagtggcga      660
aggcggctta ctggacggtc actgacgttg aggctcgaaa gcgtgggag caaacaggat       720 tagataccct ggtagtccac gccgtaaacg atgactacta ggtgtcgggt ggcagagcca      780
ttcggtgccg cagccaacgc agtaagtagt ccacctgggg agtacgttcg caagaatgaa      840
actcaaagga attgacgggg acccgcacaa gcggtggagc atgtggttta attcgaagca      900
```

```
acgcgaagnn ncttacctgg ccttgacatc ccctgaccg gcgcgtaatg gtgccttcc       960 ttcgggacag gggagacagg tggtgcatgg ttgtcgtcag ctcgtgtcgt gagatgttgg    1020
gttaagtccc gcaacgagcg caaccettat cttcagtagc cagcattcag gatgggcact    1080
ctggagagac tgccagggac aacctggagg aaggtgggga tgacgtcaaa tcatcatgcc    1140
ccttatggcc agggctacac acgtgctaca atggcgtaaa cagagggaag cgagcccgcg    1200 aggggagca atcccaaaa ataacgtccc agttcggact gcaggctgca acccgcctgc      1260
acgaagctgg aatcgctagt aatcgcgaat cagcatgtcg cggtgaatac gttcccgggt    1320
cttgtacaca ccgcccgtca caccatggga gtcggtaacg cccgaagtca gtgacccaac    1380
ctccgggagg gagc                                                     1394
```

<210> SEQ ID NO 29
<211> LENGTH: 1387
<212> TYPE: DNA
<213> ORGANISM: Unknown
<220> FEATURE:
<223> OTHER INFORMATION: K29
<220> FEATURE:
<221> NAME/KEY: misc_feature
<222> LOCATION: (895)..(896)
<223> OTHER INFORMATION: n is a, c, g, or t
<220> FEATURE:
<221> NAME/KEY: misc_feature
<222> LOCATION: (910)..(912)
<223> OTHER INFORMATION: n is a, c, g, or t
<220> FEATURE:
<221> NAME/KEY: misc_feature
<222> LOCATION: (942)..(946)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t

<400> SEQUENCE: 29

```
agtcgaacga agcatttagg attgaagttt tcggatggat ttcctttatg actgagtggc       60
ggacgggtga gtaacgcgtg gggaacctgc cctatacagg gggataacag ctggaaacgg      120
ctgctaatac cgcataagcg cacagaatcg catgattcag tgtgaaaagc cctggcagta      180
taggatggtc ccgcgtctga ttagctggtt ggtgaggtaa cggctcacca aggcgacgat      240
cagtagccgg cttgagagag tgaacggcca cattgggact gagacacggc ccaaactcct      300
acgggaggca gcagtgggga atattgcaca atgggggaaa ccctgatgca gcgacgccgc      360
gtgagtgaag aagtatttcg gtatgtaaag ctctatcagc agggaagaaa acagacggta      420
cctgactaag aagccccggc taactacgtg ccagcagccg cggtaatacg tagggggcaa      480
gcgttatccg gaattactgg gtgtaaaggg tgcgtaggtg gcatggtaag tcagaagtga      540
aagcccgggg cttaaccccg ggactgcttt tgaaactgtc atgctggagt gcaggagagg      600
taagcggaat tcctagtgta gcggtgaaat gcgtagatat taggaggaac accagtggcg      660
aaggcggctt actggactgt cactgacact gatgcacgaa agcgtgggga gcaaacagga      720
ttagataccc tggtagtcca cgccgtaaac gatgaatact aggtgtcggg gccgtagagg      780
cttcggtgcc gcagcaaacg cagtaagtat tccacctggg gagtacgttc gcaagaatga      840
aactcaaagg aattgacggg gacccgcaca agcggtggag catgtggttt aattnnaagc      900
aacgcgaagn nncttacctg gtcttgcat cccaatgacc gnnnnntaac cgnnttttc        960 tttcgagaca ttggagacag gtggtgcatg gttgtcgtca gctcgtgtcg tgagatgttg     1020
ggttaagtcc cgcaacgagc gcaaccccta tctttagtag ccagcattag aggtgggcac    1080
```

| | |
|---|---:|
| tctagagaga ctgccaggga taacctggag gaaggtgggg aggacgtcaa atcatcatgc | 1140 |
| cccttatggc cagggctaca cacgtgctac aatggcgtaa acaaagggaa gcgaagtcgt | 1200 |
| gaggcgaagc aaatcccaga aataacgtct cagttcggat tgtagtctgc aactcgacta | 1260 |
| catgaagctg gaatcgctag taatcgtgaa tcagaatgtc acggtgaata cgttcccggg | 1320 |
| tcttgtacac accgcccgtc acaccatggg agtcagtaac gcccgaagtc agtgacccaa | 1380 |
| ccgcaag | 1387 |

<210> SEQ ID NO 30
<211> LENGTH: 1392
<212> TYPE: DNA
<213> ORGANISM: Unknown
<220> FEATURE:
<223> OTHER INFORMATION: K30

<400> SEQUENCE: 30

| | |
|---|---:|
| gcaagtcgag cgaagcacct tgacggattt cttcggattg aagccttggt gactgagcgg | 60 |
| cggacgggtg agtaacgcgt gggtaacctg cctcatacag ggggataaca gttggaaacg | 120 |
| gctgctaata ccgcataagc gcacagtacc gcatggtacg gtgtgaaaaa ctccggtggt | 180 |
| atgagatgga cccgcgtctg attaggtagt tggtggggta acggcctacc aagccgacga | 240 |
| tcagtagccg acctgagagg gtgaccggcc acattgggac tgagacacgg cccaaactcc | 300 |
| tacgggaggc agcagtgggg aatattgcac aatggggaa accctgatgc agcgacgccg | 360 |
| cgtgagcgat gaagtatttc ggtatgtaaa gctctatcag cagggaagaa aatgacggta | 420 |
| cctgactaag aagccccggc taactacgtg ccagcagccg cggtaatacg tagggggcaa | 480 |
| gcgttatccg gatttactgg gtgtaaaggg agcgtagacg gcatggcaag ccagatgtga | 540 |
| aagcccgggg ctcaaccccg ggactgcatt tggaactgtc aggctagagt gtcggagagg | 600 |
| aaagcggaat tcctagtgta gcggtgaaat gcgtagatat taggaggaac accagtggcg | 660 |
| aaggcggctt tctggacgat gactgacgtt gaggctcgaa agcgtgggga gcaaacagga | 720 |
| ttagatacce tggtagtcca cgccgtaaac gatgaatact aggtgtcggg tggcaaagcc | 780 |
| attcggtgcc gcagcaaacg caataagtat tccacctggg gagtacgttc gcaagaatga | 840 |
| aactcaaagg aattgacggg acccgcaca agcggtggag catgtggttt aattcgaagc | 900 |
| aacgcgaaga accttacctg tcttgacat cctctgaccc gctctttaat cggagctttc | 960 |
| cttcgggaca gaggagacag gtggtgcatg gttgtcgtca gctcgtgtcg tgagatgttg | 1020 |
| ggttaagtcc cgcaacgagc gcaacccta tctttagtag ccagcatttt ggatgggcac | 1080 |
| tctagagaga ctgccaggga taacctggag gaaggtgggg atgacgtcaa atcatcatgc | 1140 |
| cccttatgac cagggctaca cacgtgctac aatggcgtaa acaaagggaa gcgagcccgc | 1200 |
| gaggggagc aaatcccaaa aataacgtct cagttcggat tgtagtctgc aactcgacta | 1260 |
| catgaagctg gaatcgctag taatcgcgaa tcagaatgtc gcggtgaata cgttcccggg | 1320 |
| tcttgtacac accgcccgtc acaccatggg agtcagtaac gcccgaagtc agtgacccaa | 1380 |
| ccgcaaggag gg | 1392 |

<210> SEQ ID NO 31
<211> LENGTH: 1394
<212> TYPE: DNA
<213> ORGANISM: Unknown
<220> FEATURE:
<223> OTHER INFORMATION: K31
<220> FEATURE:

<221> NAME/KEY: misc_feature
<222> LOCATION: (1073)..(1074)
<223> OTHER INFORMATION: n is a, c, g, or t

<400> SEQUENCE: 31

| | |
|---|---|
| cagtcgagcg aagcgctttg tgcggatttc ttcggattga agcaactgtg actgagcggc | 60 |
| ggacgggtga gtaacgcgtg ggtaacctgc ctcatacagg gggataacag ttggaaacgg | 120 |
| ctgctaatac cgcataagcg cacagtaccg catggtacgg tgtgaaaaac tccggtggta | 180 |
| tgagatggac ccgcgtctga ttaggtagtt ggtggggtaa cggcctacca aggcgacgat | 240 |
| cagtagccga cctgagaggg tgaccggcca cattgggact gagacacggc ccaaactcct | 300 |
| acgggaggca gcagtgggga atattgcaca atggggaaa ccctgatgca gcgacgccgc | 360 |
| gtgagcgatg aagtatttcg gtatgtaaag ctctatcagc agggaagaaa atgacggtac | 420 |
| ctgactaaga agccccggct aactacgtgc cagcagccgc ggtaatacgt aggggggcaag | 480 |
| cgttatccgg atttactggg tgtaaaggga gcgtagacgg catggcaagc cagatgtgaa | 540 |
| agcccggggc tcaaccccgg gactgcattt ggaactgtca ggctagagtg tcggagagga | 600 |
| aagcggaatt cctagtgtag cggtgaaatg cgtagatatt aggaggaaca ccagtggcga | 660 |
| aggcggcttt ctggacgatg actgacgttg aggctcgaaa gcgtggggag caaacaggat | 720 |
| tagataccct ggtagtccac gccgtaaacg atgaatacta ggtgtcgggt ggcaaagcca | 780 |
| ttcggtgccg cagcaaacgc aataagtatt ccacctgggg gagtacgttc gcaagaatga | 840 |
| aactcaaagg aattgacggg gacccgcaca agcggtggag catgtggttt aattcgaagc | 900 |
| aacgcgaaga accttacctg gtcttgacat ccctctgacc gctctttaat cggagctttc | 960 |
| tttcgggaca gaggagacag gtggtgcatg gttgtcgtca gctcgtgtcg tgagatgttg | 1020 |
| ggttaagtcc cgcaacgagc gcaaccccta tctttagtag ccagcattta agnngggcac | 1080 |
| tctagagaga ctgccaggga taacctggag gaaggtgggg atgacgtcaa atcatcatgc | 1140 |
| cccttatgac cagggctaca cacgtgctac aatggcgtaa acaaagggaa gcgagcccgc | 1200 |
| gaggggggagc aaatcccaaa aataacgtct cagttcggat tgtagtctgc aactcgacta | 1260 |
| catgaagctg gaatcgctag taatcgcgaa tcagaatgtc gcggtgaata cgttcccggg | 1320 |
| tcttgtacac accgcccgtc acaccatggg agtcagtaac gcccgaagtc agtgacccaa | 1380 |
| ccgcaaggag ggag | 1394 |

<210> SEQ ID NO 32
<211> LENGTH: 1383
<212> TYPE: DNA
<213> ORGANISM: Unknown
<220> FEATURE:
<223> OTHER INFORMATION: K32

<400> SEQUENCE: 32

| | |
|---|---|
| aagtcgaggg gcagcacggt gtagcaatac actggtggcg accggcgcac gggtgcgtaa | 60 |
| cgcgtatgca acctacccat aacaggggga taacactgag aaattggtac taataccccca | 120 |
| taacatcagg accggcatcg gttctggttg aaaactccgg tggttatgga tgggcatgcg | 180 |
| ttgtattagc tggttggtga ggtaacggct caccaaggca acgatacata ggggactga | 240 |
| gaggttaacc ccccacattg gtactgagac acggaccaaa ctcctacggg aggcagcagt | 300 |
| gaggaatatt ggtcaatgga cgcaagtctg aaccagccat gccgcgtgca ggaagacggc | 360 |
| tctatgagtt gtaaactgct tttgtacgag ggtaaacgct cttacgtgta agagcctgaa | 420 |
| agtatcgtac gaataaggat cggctaactc cgtgccagca gccgcggtaa tacggaggat | 480 |

```
ccaagcgtta tccggattta ttgggtttaa agggtgcgta ggcggtttga taagttagag    540
gtgaaatacc ggtgcttaac accggaactg cctctaatac tgttgaacta gagagtagtt    600
gcggtaggcg gaatgtatgg tgtagcggtg aaatgcttag agatcataca gaacaccgat    660
tgcgaaggca gcttaccaaa ctatatctga cgttgaggca cgaaagcgtg gggagcaaac    720
aggattagat accctggtag tccacgcagt aaacgatgat aactcgctgt cggcgataca    780
cagtcggcgg ctaagcgaaa gcgataagtt atccacctgg ggagtacgtt cgcaagaatg    840
aaactcaaag gaattgacgg gggcccgcac aagcggagga acatgtggtt taattcgatg    900
atacgcgagg aaccttaccc gggcttgaaa gttactgacg attctggaaa caggatttcc    960
cttcggggca ggaaactagg tgctgcatgg ttgtcgtcag ctcgtgccgt gaggtgtcgg   1020
gttaagtccc ataacgagcg caaccccta c cgttagttgc catcaggtca agctgggcac   1080
tctggcggga ctgccggtgt aagccgagag gaaggtgggg atgacgtcaa atcagcacgg   1140
cccttacgtc cggggctaca cacgtgttac aatggtaggt acagagggca gctacccagt   1200
gatgggatgc gaatctcgaa agcctatctc agttcggatc ggaggctgaa acccgcctcc   1260
gtgaagttgg attcgctagt aatcgcgcat cagccatggc gcggtgaata cgttcccggg   1320
ccttgtacac accgcccgtc aagccatgga agctgggggt gcctgaagtt cgtgaccgca   1380
agg                                                                 1383

<210> SEQ ID NO 33
<211> LENGTH: 1378
<212> TYPE: DNA
<213> ORGANISM: Unknown
<220> FEATURE:
<223> OTHER INFORMATION: K33

<400> SEQUENCE: 33
gaggggcagc atcattaaag cttgctttga tggatggcga ccggcgcacg ggtgagtaac     60
acgtatccaa cctgccgaca acactgggat agcctttcga agaaagatt aataccggat    120 ggcatagttt tcccgcatgg gataattatt aaagaatttc ggttgtcgat ggggatgcgt    180
tccattaggc agttggcggg gtaacggccc accaaaccaa cgatggatag gggttctgag    240
aggaaggtcc cccacattgg aactgagaca cggtccaaac tcctacggga ggcagcagtg    300
aggaatattg gtcaatggac gagagtctga accagccaag tagcgtgaag gatgactgcc    360 ctatggggttg taaacttctt ttatacggga ataaagttag ccacgtgtgg ctttttgtat    420
gtaccgtatg aataaggatc ggctaactcc gtgccagcag ccgcggtaat acggaggatc    480
cgagcgttat ccggatttat tgggtttaaa gggagcgtag gcgggttgtt aagtcagttg    540
tgaaagtttg cggctcaacc gtaaaattgc agttgatact ggcgaccttg agtgcaacag    600
aggtaggcgg aattcgtggt gtagcggtga aatgcttaga tatcacgaag aactccgatt    660
gcgaaggcag cttactggat tgtaactgac gctgatgctc gaaagtgtgg gtatcaaaca    720
ggattagata ccctggtagt ccacacagta aacgatgaat actcgctgtt ggcgatatac    780
ggtcagcggc caagcgaaag cattaagtat tccacctggg gagtacgccg caacggtga     840 aactcaaagg aattgacggg ggcccgcaca agcggaggaa catgtggttt aattcgatga    900
tacgcgagga accttacccg ggcttaaatt gcaactgact gaaccggaaa cggttctttc    960
ttcggacagt tgtgaaggtg ctgcatggtt gtcgtcagct cgtgccgtga ggtgtcggct   1020
taagtgccat aacgagcgca acccttatcg atagttacta gcaggtcatg ctgaggactc   1080
```

| tattgagact gccgtcgtaa gatgtgagga aggtggggat gacgtcaaat cagcacggcc | 1140 |
| cttacgtccg gggctacaca cgtgttacaa tgggggtac agaaggcagc tacacggcga | 1200 |
| cgtggtgcta atcccgaaag cctctctcag ttcggattgg agtctgcaac ccgactccat | 1260 |
| gaagctggat tcgctagtaa tcgcgcatca gccacggcgc ggtgaatacg ttcccgggcc | 1320 |
| ttgtacacac cgcccgtcaa gccatgaaag ccggggtac ctgaagtacg taaccgcg | 1378 |

<210> SEQ ID NO 34
<211> LENGTH: 1394
<212> TYPE: DNA
<213> ORGANISM: Unknown
<220> FEATURE:
<223> OTHER INFORMATION: K34

<400> SEQUENCE: 34

| cagtcgagcg aagcacttaa gtggatctct tcggattgaa acttattgtg actgagcggc | 60 |
| ggacgggtga gtaacgcgtg ggtaacctgc ctcatacagg gggataacag ttagaaatgg | 120 |
| ctgctaatac cgcataagcg cacaggaccg catggtctgg tgtgaaaaac tccggtggta | 180 |
| tgagatggac ccgcgtctga ttagctagtt ggaggggtaa cggcccacca aggcgacgat | 240 |
| cagtagccgg cctgagaggg tgaacggcca cattgggact gagacacggc ccagactcct | 300 |
| acgggaggca gcagtgggga atattgcaca atggggggaaa ccctgatgca gcgacgccgc | 360 |
| gtgaaggaag aagtatctcg gtatgtaaac ttctatcagc agggaagaaa atgacgtac | 420 |
| ctgactaaga agccccggct aactacgtgc cagcagccgc ggtaatacgt aggggggcaag | 480 |
| cgttatccgg atttactggg tgtaaaggga gcgtagacgg aagagcaagt ctgatgtgaa | 540 |
| aggctggggc ttaaccccag gactgcattg gaaactgttt ttctagagtg ccggagaggt | 600 |
| aagcggaatt cctagtgtag cggtgaaatg cgtagatatt aggaggaaca ccagtggcga | 660 |
| aggcggctta ctggacggta actgacgttg aggctcgaaa gcgtggggag caaacaggat | 720 |
| tagatacccct ggtagtccac gccgtaaacg atgaatacta ggtgtcgggt ggcaaagcca | 780 |
| ttcggtgccg cagcaaacgc aataagtatt ccacctgggg agtacgttcg caagaatgaa | 840 |
| actcaaagga attgacgggg acccgcacaa gcggtggagc atgtggttta attcgaagca | 900 |
| acgcgaagaa ccttaccaag tcttgacatc cctctgaccg gcccgtaacg ggccttccc | 960 |
| ttcggggcag aggagacagg tggtgcatgg ttgtcgtcag ctcgtgtcgt gagatgttgg | 1020 |
| gttaagtccc gcaacgagcg caacccctat ccttagtagc cagcaggtga agctgggcac | 1080 |
| tctagggaga ctgccgggga taacccggag gaaggcgggg acgacgtcaa atcatcatgc | 1140 |
| cccttatgat ttgggctaca cacgtgctac aatggcgtaa acaaagggaa gcgagacagc | 1200 |
| gatgttgagc aaatcccaaa aataacgtcc cagttcggac tgcagtctgc aactcgactg | 1260 |
| cacgaagctg gaatcgctag taatcgcgaa tcagaatgtc gcggtgaata cgttcccggg | 1320 |
| tcttgtacac accgcccgtc acaccatggg agtcagtaac gcccgaagtc agtgacccaa | 1380 |
| ccttacagga ggga | 1394 |

<210> SEQ ID NO 35
<211> LENGTH: 1392
<212> TYPE: DNA
<213> ORGANISM: Unknown
<220> FEATURE:
<223> OTHER INFORMATION: K35
<220> FEATURE:
<221> NAME/KEY: misc_feature
<222> LOCATION: (901)..(901)
<223> OTHER INFORMATION: n is a, c, g, or t

<400> SEQUENCE: 35

```
cagtcgaacg gagctcagtt ttggaaactt tcttcgggag tggaattctc gacttagtgg      60
cggacgggtg agtaacgcgt gagcaatctg cctttaagag ggggataaca gtcggaaacg     120
gctgctaata ccgcataaag cattgaattc gcatgttttc gatgccaaag gagcaatccg     180
cttttagatg agctcgcgtc tgattagcta gttggcgggg taacggccca ccaaggcgac     240
gatcagtagc cggactgaga ggttgaacgg ccacattggg actgagacac ggcccagact     300
cctacgggag gcagcagtgg ggaatattgc gcaatggggg aaaccctgac gcagcaacgc     360
cgcgtgattg aagaaggcct tcgggttgta aagatcttta atcagggacg aaacaaatga     420
cggtacctga agaataagct ccggctaact acgtgccagc agccgcggta atacgtaggg     480
agcaagcgtt atccggattt actgggtgta aagggcgcgc aggcgggccg gcaagttgga     540
agtgaaatct atgggcttaa cccataaact gctttcaaaa ctgctggtct tgagtgatgg     600
agaggcaggc ggaattccgt gtgtagcggt gaaatgcgta gatatacgga ggaacaccag     660
tggcgaaggc ggcctgctgg acattaactg acgctgaggc gcgaaagcgt ggggagcaaa     720
caggattaga taccctggta gtccacgccg taaacgatgg atactaggtg tgggaggtat     780
tgaccccttc cgtgccgcag ttaacacaat aagtatccca cctggggagt acggccgcaa     840
ggttgaaact caaaggaatt gacgggggcc cgcacaagca gtggagtatg tggtttaatt     900
ngaagcaacg cgaagaacct taccaggtct tgacatcccg atgaccgcct tagagataag     960
gcttttttc ggaacatcgg tgacaggtgg tgcatggttg tcgtcagctc gtgtcgtgag    1020
atgttgggtt aagtcccgca acgagcgcaa cccttacggt tagttgatac gcaagatcac    1080
tctagccgga ctgccgttga caaaacggag gaaggtgggg acgacgtcaa atcatcatgc    1140
cccttatgac ctgggctaca cacgtactac aatggcagtc atacagaggg aagcaaaacc    1200
gcgaggtgga gcaaatccct aaaagctgtc ccagttcaga ttgcaggctg caacccgcct    1260
gcatgaagtc ggaattgcta gtaatcgcgg atcagcatgc cgcggtgaat acgttcccgg    1320
gccttgtaca caccgcccgt cacaccatga gagccgtcaa tacccgaagt ccgtagccta    1380
accttcttgg ag                                                       1392
```

<210> SEQ ID NO 36
<211> LENGTH: 1394
<212> TYPE: DNA
<213> ORGANISM: Unknown
<220> FEATURE:
<223> OTHER INFORMATION: K36
<220> FEATURE:
<221> NAME/KEY: misc_feature
<222> LOCATION: (1068)..(1069)
<223> OTHER INFORMATION: n is a, c, g, or t

<400> SEQUENCE: 36

```
agtcgaacga agcaattaaa atgaagtttt cggatggatt tttgattgac tgagtggcgg      60
acgggtgagt aacgcgtgga taacctgcct cacactgggg gataacagtt agaaatgact     120
gctaataccg cataagcgca cagtaccgca tggtacggtg tgaaaaactc cggtggtgtg     180
agatggatcc gcgtctgatt agccagttgg cggggtaacg gcccaccaaa gcgacgatca     240
gtagccgacc tgagagggtg accggccaca ttgggactga gacacggccc aaactcctac     300
gggaggcagc agtgggggaat attgcacaat gggcgaaagc ctgatgcagc gacgccgcgt     360
gagtgaagaa gtatttcggt atgtaaagct ctatcagcag ggaagaaaat gacggtacct     420
```

| | |
|---|---|
| gactaagaag ccccggctaa ctacgtgcca gcagccgcgg taatacgtag ggggcaagcg | 480 |
| ttatccggat ttactgggtg taaagggagc gtagacggcg aagcaagtct gaagtgaaaa | 540 |
| cccagggctc aaccctggga ctgctttgga aactgttttg ctagagtgtc ggagaggtaa | 600 |
| gtggaattcc tagtgtagcg gtgaaatgcg tagatattag gaggaacacc agtggcgaag | 660 |
| gcggcttact ggacgataac tgacgttgag gctcgaaagc gtgggagca aacaggatta | 720 |
| gataccctgg tagtccacgc cgtaaacgat gaatgctagg tgttgggggg caaagccctt | 780 |
| cggtgccgtc gcaaacgcag taagcattcc acctggggag tacgttcgca agaatgaaac | 840 |
| tcaaaggaat tgacggggac ccgcacaagc ggtggagcat gtggtttaat tcgaagcaac | 900 |
| gcgaagaacc ttaccaagtc ttgacatcct cttgaccggc gtgtaacggc gccttccctt | 960 |
| cggggcaaga gagacaggtg gtgcatggtt gtcgtcagct cgtgtcgtga gatgttgggt | 1020 |
| taagtcccgc aacgagcgca acccttatcc ttagtagcca gcaggtanng ctgggcactc | 1080 |
| tagggagact gccagggata acctggagga aggtggggat gacgtcaaat catcatgccc | 1140 |
| cttatgattt gggctacaca cgtgctacaa tggcgtaaac aaagggaagc aagacagtga | 1200 |
| tgtggagcaa atcccaaaaa taacgtccca gttcggactg tagtctgcaa cccgactaca | 1260 |
| cgaagctgga atcgctagta atcgcgaatc agaatgtcgc ggtgaatacg ttcccgggtc | 1320 |
| ttgtacacac cgcccgtcac accatgggag tcagcaacgc cgaagtcag tgacccaact | 1380 |
| cgcaagagag ggag | 1394 |

<210> SEQ ID NO 37
<211> LENGTH: 1371
<212> TYPE: DNA
<213> ORGANISM: Unknown
<220> FEATURE:
<223> OTHER INFORMATION: K37

<400> SEQUENCE: 37

| | |
|---|---|
| cagtcgaacg agccgagggg agcttgctcc ccagagctag tggcggacgg gtgagtaaca | 60 |
| cgtgagcaac ctgcctttca gaggggggata acgtttggaa acgaacgcta ataccgcata | 120 |
| acataccggg accgcatgat tctggtatca aaggagcaat ccgctgaaag atgggctcgc | 180 |
| gtccgattag ctagttggcg gggtaacggc ccaccaaggc gacgatcggt agccggactg | 240 |
| agaggttgat cggccacatt gggactgaga cacggcccag actcctacgg gaggcagcag | 300 |
| tgggggatat tgcacaatgg aggaaactct gatgcagcga cgccgcgtga gggaagacgg | 360 |
| tcttcggatt gtaaacctct gtctttgggg acgataatga cggtacccaa ggaggaagct | 420 |
| ccggctaact acgtgccagc agccgcggta atacgtaggg agcgagcgtt gtccggaatt | 480 |
| actgggtgta aagggagcgt aggcgggtc tcaagtcgaa tgttaaatct accggctcaa | 540 |
| ctggtagctg cgttcgaaac tggggctctt gagtgaagta gaggcaggcg gaattcctag | 600 |
| tgtagcggtg aaatgcgtag atattaggag gaacaccagt ggcgaaggcg gcctgctggg | 660 |
| cttttactga cgctgaggct cgaaagcgtg ggagcaaac aggattagat accctggtag | 720 |
| tccacgccgt aaacgatgat tactaggtgt gggggactg accccttccg tgccggagtt | 780 |
| aacacaataa gtaatccacc tggggagtac gaccgcaagg ttgaaactca aggaattga | 840 |
| cgggggcccg cacaagcagt ggattatgtg gtttaattcg aagcaacgcg aagaacctta | 900 |
| ccaggtcttg acatcgagtg acggctctag agatagagct tccttcgggg acacaaagac | 960 |
| aggtggtgca tggttgtcgt cagctcgtgt cgtgagatgt tgggttaagt cccgcaacga | 1020 |
| gcgcaaccct tattattagt tgctacattc agttgagcac tctaatgaga ctgccgttga | 1080 |

```
caaaacggag gaaggtgggg atgacgtcaa atcatcatgc cccttatgac ctgggctaca      1140
cacgtaatac aatggcgatc aacagaggga agcaagaccg cgaggtggag caaacccta       1200 aaagtcgtct cagttcggat tgcaggctgc aactcgcctg catgaagtcg gaattgctag      1260
taatcgcgga tcagcatgcc gcggtgaata cgttcccggg ccttgtacac accgcccgtc      1320
acaccatggg agtcggtaac acccgaagtc agtagcctaa ccgcaaggag g               1371
```

<210> SEQ ID NO 38
<211> LENGTH: 1396
<212> TYPE: DNA
<213> ORGANISM: Unknown
<220> FEATURE:
<223> OTHER INFORMATION: K38

<400> SEQUENCE: 38

```
tgcagtcgaa cgctttgtaa aggagcttgc ttctttacga ggagtggcga acgggtgagt       60
aatacataag caatctgccc atcggcctgg gataacagtt ggaaacgact gctaataccg      120
gataggttag tttctggcat cagggactaa ttaaagttgg gatacaacac ggatggatga      180
gcttatggcg tattagctag taggtgaggt aacggcccac ctaggcgatg atacgtagcc      240
gacctgagag ggtgaccggc cacattggga ctgagacacg gcccaaactc ctacgggagg      300
cagcagtagg gaattttcgg caatgggcga aagcctgacc gagcaacgcc gcgtgagtga      360
agaaggcctt cgggttgtaa agctctgttg tgaaggaaga acggctcata gagggaatgc      420
tatgggagtg acggtacttt accagaaagc cacggctaac tacgtgccag cagccgcggt      480
aatacgtagg tggcgagcgt tatccggaat tattgggcgt aaagggtgcg caggcggttt      540
gaaaagttta aggtgaaagc gtggggctta accccataca gccttagaaa ctgtcagact      600
agagtacagg agagggcaat ggaattccat gtgtagcggt aaaatgcgta gatatatgga      660
ggaacaccag tggcgaaggc ggttgcctgg cctgtaactg acgctcatgc acgaaagcgt      720
ggggagcaaa taggattaga taccctagta gtccacgccg taaacgatga aactaagtg       780 ttggggaaac tcagtgctgc agttaacgca ataagttctc cgcctgggga gtatgcacgc      840
aagtgtgaaa ctcaaaggaa ttgacggggg cccgcacaag cggtggagta tgtggtttaa      900
ttcgacgcaa cgcgaagaac cttaccaggt cttgacatac caggcaaagc tatagagata      960
tagtggagga tatcctggat acaggtggtg catggttgtc gtcagctcgt gtcgtgagat     1020
gttgggttaa gtcccgcaac gagcgcaacc cttgtcttta gttactaaca ttaagttgag     1080
gactctagag agactgccgg tgacaaaccg gaggaaggtg gggatgacgt caaatcatca     1140
tgccccttat gacctgggct acacacgtac acaatggcg gatacaacga gaagcaagac     1200
agcaatgtgg agcaaacctc agaaagtccg tctcagttcg gattgaagtc tgcaacccga     1260
cttcatgaag ccggaatcgc tagtaatcgc ggatcagcat gccgcggtga atacgttctc     1320
gggccttgta cacaccgccc gtcaaaccat gagagttggc aatacccgaa gccggtggcc     1380
taaccctgca aaggga                                                      1396
```

<210> SEQ ID NO 39
<211> LENGTH: 1399
<212> TYPE: DNA
<213> ORGANISM: Unknown
<220> FEATURE:
<223> OTHER INFORMATION: K39

<400> SEQUENCE: 39

```
cagtcgaacg gtaacaggaa gcagcttgct gctttgctga cgagtggcgg acgggtgagt    60
aatgtctggg aaactgcctg atggagggg ataactactg gaaacggtag ctaataccgc   120
ataacgtcgc aagaccaaag agggggacct tagggcctct tgccatcgga tgtgcccaga   180
tgggattagc tagtaggtgg ggtaacggct cacctaggcg acgatcccta gctggtctga   240
gaggatgacc agccacactg gaactgagac acggtccaga ctcctacggg aggcagcagt   300
ggggaatatt gcacaatggg cgcaagcctg atgcagccat gccgcgtgta tgaagaaggc   360
cttcggttg taaagtactt tcagcgggga ggaagggagt aaagttaata cctttgctca   420
ttgacgttac ccgcagaaga agcaccggct aactccgtgc cagcagccgc ggtaatacgg   480
agggtgcaag cgttaatcgg aattactggg cgtaaagcgc acgcaggcgg tttgttaagt   540
cagatgtgaa atccccgggc tcaacctggg aactgcatct gatactggca agcttgagtc   600
tcgtagaggg gggtagaatt ccaggtgtag cggtgaaatg cgtagagatc tggaggaata   660
ccggtggcga aggcggcccc ctggacgaag actgacgctc aggtgcgaaa gcgtggggag   720
caaacaggat tagataccct ggtagtccac gccgtaaacg atgtcgactt ggaggttgtg   780
cccttgaggc gtggcttccg gagctaacgc gttaagtcga ccgcctgggg agtacggccg   840
caaggttaaa actcaaatga attgacgggg cccgcacaa gcggtggagc atgtggttta   900
attcgatgca acgcgaagaa ccttacctgg tcttgacatc cacggaagtt ttcagagatg   960
agaatgtgcc ttcgggaacc gtgagacagg tgctgcatgg ctgtcgtcag ctcgtgttgt  1020
gaaatgttgg gttaagtccc gcaacgagcg caacccttat cctttgttgc cagcggtccg  1080
gccgggaact caaaggagac tgccagtgat aaactggagg aaggtgggga tgacgtcaag  1140
tcatcatggc ccttacgacc agggctacac acgtgctaca atggcgcata caaagagaag  1200
cgacctcgcg agagcaagcg gacctcataa agtgcgtcgt agtccggatt ggagtctgca  1260
actcgactcc atgaagtcgg aatcgctagt aatcgtggat cagaatgcca cggtgaatac  1320
gttcccgggc cttgtacaca ccgcccgtca ccatggga gtgggttgca aaagaagtag  1380
gtagcttaac cttcgggag                                              1399

<210> SEQ ID NO 40
<211> LENGTH: 1384
<212> TYPE: DNA
<213> ORGANISM: Unknown
<220> FEATURE:
<223> OTHER INFORMATION: K40

<400> SEQUENCE: 40
agtcgaacgg ggttattttg gaaatctctt cggagatgga attcttaacc tagtggcgga    60
cgggtgagta acgcgtgagc aatctgcctt taggaggggg ataacagtcg gaaacggctg   120
ctaataccgc ataatacgtt tgggaggcat ctcttgaacg tcaaagattt tatcgccttt   180
agatgagctc gcgtctgatt agctggttgg cggggtaacg gcccaccaag gcgacgatca   240
gtagccggac tgagaggttg aacggccaca ttggactga gacacggccc agactcctac   300
gggaggcagc agtggggaat attgcgcaat gggggaaacc ctgacgcagc aacgccgcgt   360
gattgaagaa ggccttcggg ttgtaaagat ctttaatcag gacgaaaaa tgacggtacc   420
tgaagaataa gctccggcta actacgtgcc agcagccgcg gtaatacgta gggagcaagc   480
gttatccgga tttactgggt gtaaaggcgc gcaggcggg ccgcaagtt gggagtgaaa   540
tcccggggct aaccccggga actgctttca aaactgctgg tcttgagtga tggagaggca   600
ggcggaattc cgtgtgtagc ggtgaaatgc gtagatatac ggaggaacac cagtggcgaa   660
```

```
ggcggcctgc tggacattaa ctgacgctga ggcgcgaaag cgtggggagc aaacaggatt        720 agatacoctg gtagtccacg ccgtaaacga tggatactag gtgtgggagg tattgacccc        780
ttccgtgccg cagttaacac aataagtatc ccacctgggg agtacggccg caaggttgaa        840
actcaaagga attgacgggg gcccgcacaa gcagtggagt atgtggttta attcgaagca        900
acgcgaagaa ccttaccagg tcttgacatc ccgatgaccg gcgtagagat acgccctctc        960
ttcggagcat cggtgacagg tggtgcatgg ttgtcgtcag ctcgtgtcgt gagatgttgg       1020
gttaagtccc gcaacgagcg caacccttac ggttagttga tacgcaagat cactctagcc       1080
ggactgccgt tgacaaaacg gaggaaggtg ggacgacgtc aaatcatca tgcccttat         1140 gacctgggct acacacgtac tacaatggca gtcatacaga gggaagcaat accgcgaggt       1200
ggagcaaatc cctaaaagct gtcccagttc agattgcagg ctgcaacccg cctgcatgaa       1260
gtcggaattg ctagtaatcg cggatcagca tgccgcggtg aatacgttcc cgggccttgt       1320
acacaccgcc cgtcacacca tgagagccgt caatacccga agtccgtagc ctaaccgcaa       1380
gggg                                                                     1384
```

<210> SEQ ID NO 41
<211> LENGTH: 1392
<212> TYPE: DNA
<213> ORGANISM: Unknown
<220> FEATURE:
<223> OTHER INFORMATION: K41

<400> SEQUENCE: 41

```
agtcgaacga agcactttat ttgatttcct tcgggactga ttattttgtg actgagtggc         60
ggacgggtga gtaacgcgtg ggtaacctgc cttgtacagg gggataacag ttggaaacgg        120
ctgctaatac cgcataagcg cacggcatcg catgatgcag tgtgaaaaac tccggtggta        180
taagatggac ccgcgttgga ttagctagtt ggtgaggtaa cggcccacca aggcgacgat        240
ccatagccga cctgagaggg tgaccggcca cattgggact gagacacggc ccaaactcct        300 acggaggca gcagtgggga atattgcaca atgggcgaaa gcctgatgca gcgacgccgc        360
gtgagcgaag aagtatttcg gtatgtaaag ctctatcagc agggaagata atgacggtac        420
ctgactaaga agcaccggct aaatacgtgc cagcagccgc ggtaatacgt atggtgcaag        480
cgttatccgg atttactggg tgtaaaggga gcgcaggcg tgcggcaagt ctgatgtgaa         540
agcccggggc tcaaccccgg tactgcattg gaaactgtcg tactagagtg tcggaggggt        600
aagcggaatt cctagtgtag cggtgaaatg cgtagatatt aggaggaaca ccagtggcga        660
aggcggctta ctggacgata actgacgctg aggctcgaaa gcgtggggag caaacaggat        720 tagatacct ggtagtccac gccgtaaacg atgaatacta ggtgttggga agcattgctt        780
ctcggtgccg tcgcaaacgc agtaagtatt ccacctgggg agtacgttcg caagaatgaa        840
actcaaagga attgacgggg acccgcacaa gcggtggagc atgtggttta attcgaagca        900
acgcgaagaa ccttaccaag tcttgacatc cttctgaccg gtacttaacc gtaccttctc        960
ttcggagcag gagtgacagg tggtgcatgg ttgtcgtcag ctcgtgtcgt gagatgttgg       1020
gttaagtccc gcaacgagcg caacccttat ctttagtagc cagcggttcg gccgggcact       1080
ctagagagac tgccagggat aacctggagg aaggcgggga tgacgtcaaa tcatcatgcc       1140
ccttatgact gggctacaca cgtgctaca atggcgtaaa caagggaag caaagctgtg         1200 aagccgagca aatctcaaaa ataacgtctc agttcggact gtagtctgca acccgactac       1260
```

```
acgaagctgg aatcgctagt aatcgcagat cagaatgctg cggtgaatac gttcccgggt    1320
cttgtacaca ccgcccgtca caccatggga gttgggaatg cccgaagcca gtgacctaac    1380
cgaaaggaag ga                                                         1392
```

<210> SEQ ID NO 42
<211> LENGTH: 1397
<212> TYPE: DNA
<213> ORGANISM: Unknown
<220> FEATURE:
<223> OTHER INFORMATION: K42

<400> SEQUENCE: 42

```
cagtcgaacg aagcatatag agacgagtat ttcggtatga gtaactatat gactgagtgg      60
cggacgggtg agtaacgcgt ggataacctg cctcatacag ggggataaca gttagaaatg     120
actgctaata ccgcataagc gcacagtgct gcatggcaca gtgtgaaaag ctccggcggt     180
atgagatgga tccgcgtttg attagctagt tggtggggta aaggcctacc aaggcgacga     240
tcaatagccg acctgagagg gtgaccggcc acattggac tgagacacgg cccaaactcc     300
tacgggaggc agcagtgggg aatattgcac aatgggggaa accctgatgc agcgacgccg     360
cgtgaaggaa gaagtatttc ggtatgtaaa cttctatcag cagggaagaa aatgacggta     420
cctgactaag aagccccggc taattacgtg ccagcagccg cggtaatacg taagggcaa     480 gcgttatccg gatttactgg gtgtaaaggg agcgtagacg gcagtgcaag tctgatgtga     540
aagcccgggg ctcaaccccg gactgcatt ggaaactgtg cagctagagt gtcggagagg     600
taagtggaat tcctagtgta gcggtgaaat gcgtagatat taggaggaac accagtggcg     660
aaggcggctt actggacgat aactgacgtt gaggctcgaa agcgtgggga gcaaacagga     720
ttagataccc tggtagtcca cgccgtaaac gatgaatact aggtgtcggg cgccaaaggc     780
gttcggtgcc gcagcaaacg caataagtat tccacctggg gagtacgttc gcaagaatga     840
aactcaaagg aattgacggg gacccgcaca agcggtggag catgtggttt aattcgaagc     900
aacgcgaaga accttaccaa gtcttgacat ctgcctgacc ggtccgtaac aggacccttc     960
cttcgggaca ggcaagacag gtggtgcatg gttgtcgtca gctcgtgtcg tgagatgttg    1020
ggttaagtcc cgcaacgagc gcaacccctta tccttagtag ccagcaggta gagctgggca    1080 ctctaggagag actgccaggg acaacctgga ggaaggtggg gatgacgtca atcatcatg    1140 cccttatga tttgggctac acacgtgcta caatggcgta acaaaggga agcgaagggg    1200 tgacctgaag caaatcccaa aaataacgtc tcagttcgga ttgtagtctg caactcgact    1260
acatgaagct ggaatcgcta gtaatcgcga atcagaatgt cgcggtgaat acgttcccgg    1320
gtcttgtaca caccgcccgt cacaccatgg gagtcggata tgcccgaagc cggtgaccga    1380
acccgaaagg gaaggag                                                   1397
```

<210> SEQ ID NO 43
<211> LENGTH: 1388
<212> TYPE: DNA
<213> ORGANISM: Unknown
<220> FEATURE:
<223> OTHER INFORMATION: K43

<400> SEQUENCE: 43

```
agtcgaacgg agcaccttg actgaggttt cggccaaatg ataggaatgc ttagtggcgg      60
actggtgagt aacgcgtgag gaacctgcct tccagagggg gacaacagtt ggaaacgact     120
gctaataccg catgacgcat gaccgggggca tcccgggcat gtcaaagatt ttatcgctgg     180
```

```
aagatggcct cgcgtctgat tagctagatg gtggggtaac ggcccaccat ggcgacgatc    240
agtagccgga ctgagaggtt gaccggccac attgggactg agatacgcc cagactccta    300 cgggaggcag cagtggggaa tattgggcaa tggacgcaag tctgacccag caacgccgcg    360
tgaaggaaga aggctttcgg gttgtaaact tcttttgtca gggaagagta aagacggta    420 cctgacgaat aagccacggc taactacgtg ccagcagccg cggtaatacg taggtggcaa    480
gcgttgtccg gatttactgg gtgtaaaggg cgtgcagccg gccggcaag tcagatgtga    540 aatctggagg cttaacctcc aaactgcatt tgaaactgta ggtcttgagt accggagagg    600
ttatcggaat tccttgtgta gcggtgaaat gcgtagatat aaggaagaac accagtggcg    660
aaggcggata actggacggc aactgacggt gaggcgcgaa agcgtgggga gcaaacagga    720
ttagataccc tggtagtcca cgctgtaaac gatggatact aggtgtgcgg ggactgaccc    780
cctgcgtgcc gcagttaaca caataagtat cccacctggg gagtacgatc gcaaggttga    840
aactcaaagg aattgacggg gcccgcaca agcggtggag tatgtggttt aattcgaagc    900
aacgcgaaga accttaccag ggcttgacat cctactaacg aagtagagat acatcaggtg    960
cccttcgggg aaagtagaga caggtggtgc atggttgtcg tcagctcgtg tcgtgagatg   1020
ttgggttaag tcccgcaacg agcgcaaccc ctattgttag ttgctacgca agagcactct   1080
agcgagactg ccgttgacaa aacggaggaa ggtggggacg acgtcaaatc atcatgcccc   1140
ttatgtcctg ggctacacac gtaatacaat ggcggtcaac agagggaggc aaagccgcga   1200
ggcagagcaa accccccaaaa gccgtcccag ttcggatcgc aggctgcaac ccgcctgcgt   1260
gaagtcggaa tcgctagtaa tcgcggatca gcatgccgcg gtgaatacgt tcccgggcct   1320
tgtacacacc gcccgtcaca ccatgagagt cgggaacacc cgaagtccgt agcctaaccg   1380
caaggagg                                                            1388
```

<210> SEQ ID NO 44
<211> LENGTH: 1393
<212> TYPE: DNA
<213> ORGANISM: Unknown
<220> FEATURE:
<223> OTHER INFORMATION: K44

<400> SEQUENCE: 44

```
tgcagtcgaa cggagtgcct tagaaagagg attcgtccaa ttgataaggt tacttagtgg     60
cggacgggtg agtaacgcgt gaggaacctg cctcggagtg gggaataaca gaccgaaagg    120
cctgctaata ccgcatgatg cagttggacc gcatggtcct gactgccaaa gatttatcgc    180
tctgagatgg cctcgcgtct gattagcttg ttggcgggt aatggcccac caaggcgacg    240
atcagtagcc ggactgagag gttggccggc acattggga ctgagacacg gcccagactc    300
ctacgggagg cagcagtggg gaatattggg caatgggcgc aagcctgacc cagcaacgcc    360
gcgtgaagga agaaggcttt cgggttgtaa acttctttc tcaggacga acaaatgacg    420 gtacctgagg aataagccac ggctaactac gtgccagcag ccgcggtaat acgtaggtgg    480
caagcgttat ccggatttac tgggtgtaaa gggcgtgtag gcgggaaggc aagtcagatg    540
tgaaaactat gggctcaacc catagcctgc atttgaaact gttttttcttg agtgctggag    600 aggcaatcgg aattccgtgt gtagcggtga aatgcgtaga tatacggagg aacaccagtg    660
gcgaaggcga attgctggac agtaactgac gctgaggcgc gaaagcgtgg ggagcaaaca    720
ggattagata ccctggtagt ccacgctgta aacgatggat actaggtgtg ggggggtctg    780
```

| | | | |
|---|---|---|---|
| accccctccg | tgccgcagtt | aacacaataa gtatcccacc | tggggagtac gatcgcaagg | 840 |
| ttgaaactca | aaggaattga | cgggggcccg cacaagcggt | ggagtatgtg gtttaattcg | 900 |
| aagcaacgcg | aagaacctta | ccagggcttg acatcctact | aacgaagcag agatgcatta | 960 |
| ggtgcccttc | ggggaaagta | gagacaggtg gtgcatggtt | gtcgtcagct cgtgtcgtga | 1020 |
| gatgttgggt | taagtcccgc | aacgagcgca acccttattg | ttagttgcta cgcaagagca | 1080 |
| ctctagcgag | actgccgttg | acaaaacgga ggaaggcggg | gacgacgtca atcatcatg | 1140 |
| ccccttatgt | cctgggctac | acacgtacta caatggtggt | aaacagaggg aagcaagacc | 1200 |
| gcgaggtgga | gcaaatccct | aaaagccatc ccagttcgga | ttgcaggctg aaacccgcct | 1260 |
| gtatgaagtt | ggaatcgcta | gtaatcgcgg atcagcatgc | cgcggtgaat acgttcccgg | 1320 |
| gccttgtaca | caccgcccgt | cacaccatga gagtcgggaa | cacccgaagt ccgtagtcta | 1380 |
| accgcaaggg | gga | | | 1393 |

<210> SEQ ID NO 45
<211> LENGTH: 1409
<212> TYPE: DNA
<213> ORGANISM: Unknown
<220> FEATURE:
<223> OTHER INFORMATION: K45

<400> SEQUENCE: 45

| | | | |
|---|---|---|---|
| caagtagaac | gctgactact | ttagcttgct agagtagaag | gagttgcgaa cgggtgagta | 60 |
| acgcgtaggt | aacctgccta | ctagcggggg ataactattg | gaaacgatag ctaataccgc | 120 |
| ataacagtgt | ttaacacatg | ttagatgctt gaaagatgca | attgcatcac tagtagatgg | 180 |
| acctgcgttg | tattagctag | ttggtggggt aacggcccac | caaggcgacg atacatagcc | 240 |
| gacctgagag | ggtgatcggc | cacactggga ctgagacacg | gcccagactc ctacgggagg | 300 |
| cagcagtagg | gaatcttcgg | caatggggggc aaccctgacc | gagcaacgcc gcgtgagtga | 360 |
| agaaggtttt | cggatcgtaa | agctctgttg taagagaaga | acgtgtgtga gagtggaaag | 420 |
| ttcacacagt | gacggtaact | taccagaaag ggacggctaa | ctacgtgcca gcagccgcgg | 480 |
| taatacgtag | gtcccgagcg | ttgtccggat ttattgggcg | taaagcgagc gcaggcggtt | 540 |
| taataagtct | gaagttaaag | gcagtggctt aaccattgtt | cgctttggaa actgttaaac | 600 |
| ttgagtgcag | aaggggagag | tggaattcca tgtgtagcgg | tgaaatgcgt agatatatgg | 660 |
| aggaacaccg | gtggcgaaag | cggctctctg gtctgtaact | gacgctgagg ctcgaaagcg | 720 |
| tggggagcaa | acaggattag | ataccctggt agtccacgcc | gtaaacgatg agtgctaggt | 780 |
| gttaggccct | ttccggggct | tagtgccgca gctaacgcat | taagcactcc gcctggggag | 840 |
| tacgaccgca | aggttgaaac | tcaaaggaat tgacgggggc | ccgcacaagc ggtggagcat | 900 |
| gtggtttaat | tcgaagcaac | gcgaagaacc ttaccaggtc | ttgacatccc gatgctattt | 960 |
| ctagagatag | aaagtttctt | cggaacatcg gtgacaggtg | gtgcatggtt gtcgtcagct | 1020 |
| cgtgtcgtga | gatgttgggt | taagtcccgc aacgagcgca | acccctattg ttagttgcca | 1080 |
| tcatttagtt | gggcactcta | gcgagactgc cggtaataaa | ccggaggaag gtggggatga | 1140 |
| cgtcaaatca | tcatgcccct | tatgacctgg gctacacacg | tgctacaatg gttggtacaa | 1200 |
| cgagtcgcaa | gtcggtgacg | gcaagcaaat ctcttaaagc | caatctcagt tcggattgta | 1260 |
| ggctgcaact | cgcctacatg | aagtcggaat cgctagtaat | cgcggatcag cacgccgcgg | 1320 |
| tgaatacgtt | cccgggcctt | gtacacaccg cccgtcacac | cacgagagtt tgtaacaccc | 1380 |
| gaagtcggtg | aggtaaccat | ttaggagcc | | 1409 |

<210> SEQ ID NO 46
<211> LENGTH: 1395
<212> TYPE: DNA
<213> ORGANISM: Unknown
<220> FEATURE:
<223> OTHER INFORMATION: K46

<400> SEQUENCE: 46

| | | | | | | |
|---|---|---|---|---|---|---|
| caagtcgaac | ggcagcgcgg | ggagcttgct | ccctggcggc | gagtggcgca | cgggtgagta | 60 |
| atacatcgga | acgtgtcttc | tagtgggggga | taactgcccg | aaagggcagc | taataccgca | 120 |
| tgagacctga | gggtgaaagc | gggggatcgc | aagacctcgc | gctggaagag | cggccgatgt | 180 |
| ccgattagct | agttggtgag | gtaaaggctc | accaaggcga | cgatcggtag | ctggtctgag | 240 |
| aggacgacca | gccacactgg | gactgagaca | cggcccagac | tcctacggga | ggcagcagtg | 300 |
| gggaattttg | gacaatgggg | gcaaccctga | tccagccatg | ccgcgtgcag | gatgaaggtc | 360 |
| ttcggattgt | aaactgcttt | tgtcagggac | gaaaagggat | gcgataacac | cgcattccgc | 420 |
| tgacggtacc | tgaagaataa | gcaccggcta | actacgtgcc | agcagccgcg | gtaatacgta | 480 |
| gggtgcaagc | gttaatcgga | attactgggc | gtaaagcgtg | cgcaggcggt | tctgtaagat | 540 |
| agatgtgaaa | tccccgggct | caacctggga | attgcatata | tgactgcagg | acttgagttt | 600 |
| gtcagaggag | ggtggaattc | cacgtgtagc | agtgaaatgc | gtagatatgt | ggaagaacac | 660 |
| cgatggcgaa | ggcagccctc | tgggacatga | ctgacgctca | tgcacgaaag | cgtggggagc | 720 |
| aaacaggatt | agatacctg | gtagtccacg | ccctaaacga | tgtctactag | ttgttgggga | 780 |
| cgatagtcct | tggtaacgca | gctaacgcgt | gaagtagacc | gcctgggag | tacggtcgca | 840 |
| agattaaaac | tcaaaggaat | tgacggggac | ccgcacaagc | ggtggatgat | gtggattaat | 900 |
| tcgatgcaac | gcgaaaaacc | ttacctagcc | ttgacatgcc | aggaaggcct | gagagatcag | 960 |
| gccgtgcccg | caagggaatc | tggacacagg | tgctgcatgg | ctgtcgtcag | ctcgtgtcgt | 1020 |
| gagatgttgg | gttaagtccc | gcaacgagcg | caacccttgt | cattagttgc | tacgaaaggg | 1080 |
| cactctaatg | agactgccgg | tgacaaaccg | gaggaaggtg | gggatgacgt | caagtcctca | 1140 |
| tggcccttat | ggctagggcc | tcacacgtca | tacaatggtc | ggaacagagg | gaagcgaagc | 1200 |
| cgcgaggtga | agccaatccc | agaaaaccga | tcgtagtccg | gattgcagtc | tgcaactcga | 1260 |
| ctgcatgaag | tcggaatcgc | tagtaatcgc | ggatcagcat | gccgcggtga | atacgttccc | 1320 |
| gggtcttgta | cacaccgccc | gtcacaccat | gggagtgggg | ttcaccagaa | gacgtttgcc | 1380 |
| caaccgaaag | gaagg | | | | | 1395 |

<210> SEQ ID NO 47
<211> LENGTH: 1384
<212> TYPE: DNA
<213> ORGANISM: Unknown
<220> FEATURE:
<223> OTHER INFORMATION: K47

<400> SEQUENCE: 47

| | | | | | | |
|---|---|---|---|---|---|---|
| agtcgaacgg | gatcccagga | gcttgctcct | gggtgagagt | ggcgaacggg | tgagtaatgc | 60 |
| gtgaccgacc | tgccccatac | accggaatag | ctcctggaaa | cggtggtaa | tgccggatgc | 120 |
| tccagttgac | cgcatggtcc | tctgggaaag | attctatcgg | tatgggatgg | ggtcgcgtcc | 180 |
| tatcagcttg | atggcgggt | aacggcccac | catggcttcg | acgggtagcc | ggcctgagag | 240 |
| ggcgaccggc | cacattggga | ctgagatacg | gcccagactc | ctacgggagg | cagcagtggg | 300 |

```
gaatattgca caatgggcgc aagcctgatg cagcgacgcc gcgtgcggga tgacggcctt      360
cggggttgtaa accgcttttg actgggagca agcccttcgg ggtgagtgta cctttcgaat      420
aagcaccggc taactacgtg ccagcagccg cggtaatacg tagggtgcaa gcgttatccg      480
gaattattgg gcgtaaaggg ctcgtaggcg gttcgtcgcg tccggtgtga agtccatcg       540
cttaacggtg gatccgcgcc gggtacgggc gggcttgagt gcggtagggg agactggaat      600
tcccggtgta acggtggaat gtgtagatat cgggaagaac accaatggcg aaggcaggtc      660
tctgggccgt cactgacgct gaggagcgaa agcgtgggga gcgaacagga ttagataccc      720
tggtagtcca cgccgtaaac ggtggatgct ggatgtgggg accattccac ggtctccgtg      780
tcggagccaa cgcgttaagc atcccgcctg gggagtacgg ccgcaaggct aaaactcaaa      840
gaaattgacg ggggcccgca caagcggcgg agcatgcgga ttaattcgat gcaacgcgaa      900
gaaccttacc tgggcttgac atgttcccga cagccgtaga gatacggtct cccttcgggg      960
cgggttcaca ggtggtgcat ggtcgtcgtc agctcgtgtc gtgagatgtt gggttaagtc     1020
ccgcaacgag cgcaaccctc gccctgtgtt gccagcacgt cgtggtggga actcacgggg     1080
gaccgccggg gtcaactcgg aggaaggtgg ggatgacgtc agatcatcat gccccttacg     1140
tccagggctt cacgcatgct acaatggccg gtacaacggg atgcgacatc gtgaggggga     1200
gcggatccct aaaaccggt ctcagttcgg attggagtct gcaacccgac tccatgaagg     1260
cggagtcgct agtaatcgcg gatcagcaac gccgcggtga atgcgttccc gggccttgta     1320
cacaccgccc gtcaagtcat gaaagtgggt agcacccgaa gccggtggcc caaccttttg     1380
gggg                                                                   1384
```

<210> SEQ ID NO 48
<211> LENGTH: 1387
<212> TYPE: DNA
<213> ORGANISM: Unknown
<220> FEATURE:
<223> OTHER INFORMATION: K48

<400> SEQUENCE: 48

```
gtcgaacgga gctgctttga tgaagttttc ggatggattt aaaacagctt agtggcggac       60
gggtgagtaa cgcgtgggta acctgcctca cactggggga taacagttag aaatagctgc      120
taataccgca taagcgcaca gttccgcatg aacagtgtg aaaaactccg gtggtgtgag       180
atggacccgc gtctgattag ccagttggcg gggtaacggc ccaccaaagc gacgatcagt      240
agccggcctg agagggtgaa cggccacatt gggactgaga cacggcccaa actcctacgg      300
gaggcagcag tggggaatat tgcacaatgg gggaaaccct gatgcagcga cgccgcgtga      360
gtgaagaagt atttcggtat gtaaagctct atcagcaggg aagaaagtga cggtacctga      420
ataagaagcc ccggctaact acgtgccagc agccgcggta atacgtaggg ggcaagcgtt      480
atccggattt actgggtgta aagggagcgt agacggcaag gcaagtctga agtgaaagcc      540
cggtgcttaa cgccgggact gctttggaaa ctgtttggct ggagtgccgg agaggtaagc      600
ggaattccta gtgtagcggt gaaatgcgta gatattagga agaacaccag tggcgaaggc      660
ggcttactgg acggtaactg acgttgaggc tcgaaagcgt ggggagcaaa caggattaga      720
taccctggta gtccacgccg taaacgatga ttgctaggtg taggtgggta tggacccatc      780
ggtgccgcag ctaacgcaat aagcaatcca cctgggggag tacgttcgca agaatgaaac      840
tcaaaggaat tgacggggac ccgcacaagc ggtggagcat gtggtttaat tcgaagcaac      900
gcgaagaacc ttaccaggtc ttgacatccc gatgaaaaac ccgtaacggg gttccctctt      960
```

-continued

```
cggagcatcg gagacaggtg gtgcatggtt gtcgtcagct cgtgtcgtga gatgttgggt      1020
taagtcccgc aacgagcgca acccttattc ttagtagcca gcaggtaaag ctgggcactc      1080
taaggagact gccggggata acccggagga aggtggggat gacgtcaaat catcatgccc      1140
cttatgatct gggctacaca cgtgctacaa tggcgtaaca aagggaagcg agcctgcgag      1200
ggtgagcgaa tcccaaaaat aacgtcccag ttcggactgt agtctgcaac ccgactacac      1260
gaagctggaa tcgctagtaa tcgcgaatca gaatgtcgcg gtgaatacgt tcccgggtct      1320
tgtacacacc gcccgtcaca ccatgggagt cggaaatgcc cgaagtctgt gactcaaccg      1380
caaggag                                                                1387
```

<210> SEQ ID NO 49
<211> LENGTH: 1368
<212> TYPE: DNA
<213> ORGANISM: Unknown
<220> FEATURE:
<223> OTHER INFORMATION: K49

<400> SEQUENCE: 49

```
ttaaggagat tcttcggatg attcttgact gactgagcgg cggacgggtg agtaacgcgt       60
gggtgacctg ccccataccg ggggataaca gctggaaacg gctgctaata ccgcataagc      120
gcacagagct gcatggctcg gtgtgaaaaa ctccggtggt atgggatggg cccgcgtctg      180
attaggcagt tggcggggta acggcccacc aaaccgacga tcagtagccg gcctgagagg      240
gcgaccggcc acattgggac tgagacacgg cccaaactcc tacggaggc agcagtgggg      300 aatattgcac aatgggggaa accctgatgc agcgacgccg cgtgagcgaa gaagtatttc      360
ggtatgtaaa gctctatcag cagggaagat aatgacggta cctgactaag aagcccggc       420 taactacgtg ccagcagccg cggtaatacg tagggggcaa gcgttatccg gatttactgg      480
gtgtaaaggg agcgtagacg gcaaggcaag tctgatgtga aacccagggg cttaaccctg      540
ggactgcatt ggaaactgtc tggctcgagt gccggagagg taagcggaat tcctagtgta      600
gcggtgaaat gcgtagatat taggaagaac accagtggcg aaggcggctt actggacggt      660
aactgacgtt gaggctcgaa agcgtgggga gcaaacagga ttagataccc tggtagtcca      720
cgccgtaaac gatgaatgct aggtgttggg gagcaaagct cttcggtgcc gccgcaaacg      780
cattaagcat tccacctggg gagtacgttc gcaagaatga aactcaaagg aattgacggg      840
gacccgcaca agcggtggag catgtggttt aattcgaagc aacgcgaaga accttaccag      900
gtcttgacat cccgatgacc ggcccgtaac ggggccttct cttcggagca ttggagacag      960
gtggtgcatg gttgtcgtca gctcgtgtcg tgagatgttg ggttaagtcc gcaacgagc      1020 gcaacccta tcctcagtag ccagcaggtc aagctgggca ctctgtggag actgccaggg     1080
ataacctgga ggaaggtggg gatgacgtca atcatcatg ccccttatga tctgggctac      1140
acacgtgcta caatggcgta aacaaaggga ggcaaagccg cgaggtggag caaatcccaa     1200
aaataacgtc tcagttcgga ctgcagtctg caactcgact gcacgaagct ggaatcgcta      1260
gtaatcgcga atcagaatgt cgcggtgaat acgttcccgg gtcttgtaca caccgcccgt      1320
cacaccatgg gagttggtaa cgcccgaagt cagtgaccca accttcag                  1368
```

<210> SEQ ID NO 50
<211> LENGTH: 1390
<212> TYPE: DNA
<213> ORGANISM: Unknown
<220> FEATURE:

<223> OTHER INFORMATION: K50

<400> SEQUENCE: 50

| | | | | | |
|---|---|---|---|---|---|
| gtcgagcgaa | gcacttatga | tgattcttcg | gatgaatcat | ttgtgactga | gcggcggacg | 60 |
| ggtgagtaac | gcgtgagtaa | cctgcctcat | acaggggaat | aacagttaga | aatgactgct | 120 |
| aatgccgcat | aagcgcacag | ggccgcatgg | cccggtgtga | aaaactccgg | tggtatgaga | 180 |
| tggactcgcg | tctgattagc | tagttggcag | ggtaacggcc | taccaaggcg | acgatcagta | 240 |
| gccggcctga | gagggtgaac | ggccacattg | ggactgagac | acgcccaaa | ctcctacggg | 300 |
| aggcagcagt | ggggaatatt | gcacaatggg | ggaaaccctg | atgcagcgac | gccgcgtgag | 360 |
| tgaagaagta | tttcggtatg | taaagctcta | tcagcaggga | agaaaatgac | ggtacctgac | 420 |
| taagaagccc | cggctaacta | cgtgccagca | gccgcggtaa | tacgtagggg | gcaagcgtta | 480 |
| tccggattta | ctgggtgtaa | agggagcgta | gacggctttg | caagtctgac | gtgaaactcc | 540 |
| ggggctcaac | tccggaactg | cgttggaaac | tgtaaggctt | gagtgccgga | gaggtaagcg | 600 |
| gaattcctag | tgtagcggtg | aaatgcgtag | atattaggag | gaacaccagt | ggcgaaggcg | 660 |
| gcttactgga | cggcaactga | cgttgaggct | cgaaagcgtg | gggagcaaac | aggattagat | 720 |
| accctggtag | tccacgcggt | aaacgatgaa | tactaggtgt | tgggggacaa | agtccttcgg | 780 |
| tgccgccgca | aacgcattaa | gtattccacc | tggggagta | cgttcgcaag | aatgaaactc | 840 |
| aaaggaattg | acgggacccc | gcacaagcgg | tggagcatgt | ggtttaattc | gaagcaacgc | 900 |
| gaagaacctt | accaagtctt | gacatcgatt | cgacgggagt | gtaatgactc | ctttcccttc | 960 |
| ggggacgaag | aagacaggtg | gtgcatggtt | gtcgtcagct | cgtgtcgtga | gatgttgggt | 1020 |
| taagtcccgc | aacgagcgca | acccttatct | tcagtagcca | gcgagtaagg | tcgggcactc | 1080 |
| tggagagact | gccagggaca | acctggagga | aggtggggat | gacgtcaaat | catcatgccc | 1140 |
| cttatgactt | gggctacaca | cgtgctacaa | tggcgtaaac | aaagggaagc | gaacctgtga | 1200 |
| gggtgggcaa | atcccaaaaa | taacgtctca | gttcggattg | tagtctgcaa | ctcgactaca | 1260 |
| tgaagctgga | atcgctagta | atcgcgaatc | agcatgtcgc | ggtgaatacg | ttcccgggtc | 1320 |
| ttgtacacac | cgcccgtcac | accatgggag | tcggtaacgc | ccgaagtcag | tgacccaacc | 1380 |
| gcaaggaggg | | | | | | 1390 |

<210> SEQ ID NO 51
<211> LENGTH: 1382
<212> TYPE: DNA
<213> ORGANISM: Unknown
<220> FEATURE:
<223> OTHER INFORMATION: K51

<400> SEQUENCE: 51

| | | | | | |
|---|---|---|---|---|---|
| gcagtcggac | gcaatgcttc | ggcattgagt | ggcgaacggg | tgagtaagac | ataagcaacc | 60 |
| tgccctgtg | aggggataa | ctgctggaaa | cggcagctaa | gaccgcatag | gcatagagga | 120 |
| cgcatgtcga | ctatgttaaa | tatcccacgg | gatagcacag | ggatgggctt | atgacgcatt | 180 |
| agccagctgg | tgaggtaacg | gctcaccagg | gcgacgatgc | gtagccggcc | tgagagggtg | 240 |
| gacggccaca | ctgggactga | gacacggccc | agactcctac | gggaggcagc | agtagggaat | 300 |
| tttcggcaat | gggcgaaagc | ctgaccgagc | aacgccgcgt | gaaggaagaa | gtcattcgtg | 360 |
| atgtaaactt | ctgttatgaa | ggaagaacgg | cagatggagg | gaatgccatg | tgcgtgacgg | 420 |
| tacttcatga | ggaagccacg | gctaactacg | tgccagcagc | cgcggtaata | cgtaggtggc | 480 |
| gagcgttatc | cggaatcatt | gggcgtaaag | agggagcagg | cggcagtgca | ggtctgcggt | 540 |

```
gaaagaccgg agctaaactt cggtaagccg tggaaaccgc acagctagag agcatcagag      600
gatcgcggaa ttccatgtgt agcggtgaaa tgcgtagata tatggaggaa caccagtggc      660
gaaggcggcg gtctggggtg cagctgacgc tcagtcccga aagcgtgggg agcaaatagg      720
attagatacc ctagtagtcc acgccgtaaa cgatgagtgc taagtgttgg gggtcagacc      780
tcagtgctgg agttaacgca ataagcactc cgcctgagta gtacgttcgc aagaatgaaa      840
ctcaaaggaa ttgacggggg cccgcacaaa gcggtggagc atgtggttta attcgaagca      900
acgcgaagaa ccttaccagg tcttgacatg gagataaagg ccctggagac agggagatag      960
atatatctca cacaggtggt gcatggttgt cgtcagctcg tgtcgtgaga tgttgggtta     1020
agtcccgcaa cgagcgcaac ccctgttgcc agttgccagc attaggttgg ggactctggc     1080
gagactgcct ctgcaaggag gaggaaggcg ggatgacgtc aaatcatca tgccccttat      1140 gacctgggct acacacgtgc tacaatggac ggatcagagg gaggcgaagc cgcgaggtgg     1200
agcgaaaccc agaaaccgt tcacagttcg gactgcagtc tgcaactcga ctgcacgaag      1260
ctggaatcgc tagtaatcgc gaatcagcat gtcgcggtga atacgttctc gggccttgta     1320
cacaccgccc gtcacaccat gagagttggt aacacccgaa gccggtggcc caaccgcaag     1380
ga                                                                    1382
```

<210> SEQ ID NO 52
<211> LENGTH: 1388
<212> TYPE: DNA
<213> ORGANISM: Unknown
<220> FEATURE:
<223> OTHER INFORMATION: K52

<400> SEQUENCE: 52

```
agtcgaacgg gaaatatttt attgaaactt cggtggattt aatttatttc tagtggcgga       60
cgggtgagta acgcgtgggt aacctgcctt atactggggg ataacagcca gaatgactg       120 ctaataccgc ataagcgcac agaaccgcat ggttcggtgt gaaaaactcc ggtggtataa      180
gatggacccg cgttggatta gctagttggc agggcagcgg cctaccaagg cgacgatcca      240
tagccggcct gagagggtga acggccacat tgggactgag acacgcccca gactcctacg      300
ggaggcagca gtggggaata ttgcacaatg ggggaaaccc tgatgcagcg acgccgcgtg      360
aaggaagaag tatctcggta tgtaaacttc tatcagcagg gaagataatg acggtacctg      420
actaagaagc cccggctaac tacgtgccag cagccgcggt aatacgtagg gggcaagcgt      480
tatccggatt tactgggtgt aaagggagcg tagacgcgc agcaagtctg atgtgaaagg      540
caggggctta accectggac tgcattggaa actgctgtgc ttgagtgccg gaggggtaag      600
cggaattcct agtgtagcgg tgaaatgcgt agatattagg aggaacacca gtggcgaagg      660
cggcttactg gacggtaact gacgttgagg ctcgaaagcg tggggagcaa acaggattag      720
ataccctggt agtccacgcc gtaaacgatg aatactaggt gtcagggagc acagctcttt      780
ggtgccgccg caaacgcatt aagtattcca cctggggagt acgttcgcaa gaatgaaact      840
caaaggaatt gacggggacc cgcacaagcg gtggagcatg tggtttaatt cgaagcaacg      900
cgaagaacct taccaaatct tgacatccct ctgaccggga cttaaccgtc ccttt ccttc     960 gggacagggg agacaggtgg tgcatggttg tcgtcagctc gtgtcgtgag atgttgggtt     1020
aagtcccgca acgagcgcaa cccctatcct tagtagccag cacgcagtgg tgggcactct     1080
gaggagactg ccagggataa cctggaggaa ggcggggatg acgtcaaatc atcatgcccc     1140
```

| | |
|---|---|
| ttatgatttg ggctacacac gtgctacaat ggcgtaaaca aagggaagcg aacccgcgag | 1200 |
| ggtgggcaaa tctcaaaaat aacgtcccag ttcggactgc agtctgcaac tcgactgcac | 1260 |
| gaagctggaa tcgctagtaa tcgcggatca gaatgccgcg gtgaatacgt tcccgggtct | 1320 |
| tgtacacacc gcccgtcaca ccatgggagt cagtaacgcc cgaagtcagt gacctaaccg | 1380 |
| caagggag | 1388 |

<210> SEQ ID NO 53
<211> LENGTH: 1385
<212> TYPE: DNA
<213> ORGANISM: Unknown
<220> FEATURE:
<223> OTHER INFORMATION: K53

<400> SEQUENCE: 53

| | |
|---|---|
| cgaacgggaa ttatttcatt gagacttcgg tggatttgat ctatttctag tggcggacgg | 60 |
| gtgagtaacg cgtgggtaac ctgccttata caggggata acagtcagaa atggctgcta | 120 |
| ataccgcata agcgcacaga gctgcatggc tcagtgtgaa aaactccggt ggtataagat | 180 |
| ggacccgcgt tggattagct tgttggtggg gtaacggccc accaaggcga cgatccatag | 240 |
| ccggcctgag agggtgaacg gccacattgg gactgagaca cggcccagac tcctacggga | 300 |
| ggcagcagtg gggaatattg cacaatgggg gaaaccctga tgcagcgacg ccgcgtgaag | 360 |
| gaagaagtat ctcggtatgt aaacttctat cagcagggaa gatagtgacg gtacctgact | 420 |
| aagaagcccc ggctaactac gtgccagcag ccgcggtaat acgtaggggg caagcgttat | 480 |
| ccggatttac tgggtgtaaa gggagcgtag acggtgtggc aagtctgatg tgaaaggcat | 540 |
| gggctcaacc tgtggactgc attggaaact gtcatacttg agtgccggag ggtaagcgg | 600 |
| aattcctagt gtagcggtga aatgcgtaga tattaggagg aacaccagtg gcgaaggcgg | 660 |
| cttactggac ggtaactgac gttgaggctc gaaagcgtgg ggagcaaaca ggattagata | 720 |
| ccctggtagt ccacgccgta aacgatgaat actaggtgtc ggggagcatg gctcttcggt | 780 |
| gccgtcgcaa acgcagtaag tattccacct gggggagtac gttcgcaaga atgaaactca | 840 |
| aaggaattga cggggacccg cacaagcggt ggagcatgtg gtttaattcg aagcaacgcg | 900 |
| aagaaccta ccaagtcttg acatccgcct gaccgatcct taatcggatc ttttcttcgg | 960 |
| gacagacgag acaggtggtg catggttgtc gtcagctcgt gtcgtgagat gttgggttaa | 1020 |
| gtcccgcaac gagcgcaacc cctatcctca gtagccagca tttaaggtgg gcactctggg | 1080 |
| gagactgcca gggataacct ggaggaaggc ggggatgacg tcaaatcatc atgcccctta | 1140 |
| tgatttgggc tacacacgtg ctacaatggc gtaaacaaag gaagcgaga tcgtgagatg | 1200 |
| gagcaaatcc caaaaataac gtcccagttc ggactgtagt ctgcaacccg actacacgaa | 1260 |
| gctggaatcg ctagtaatcg cggatcagaa tgccgcggtg aatacgttcc cgggtcttgt | 1320 |
| acacaccgcc cgtcacacca tgggagtcag taacgcccga agtcagtgac ctaactgcaa | 1380 |
| agaag | 1385 |

<210> SEQ ID NO 54
<211> LENGTH: 1415
<212> TYPE: DNA
<213> ORGANISM: Unknown
<220> FEATURE:
<223> OTHER INFORMATION: K54

<400> SEQUENCE: 54

| | |
|---|---|
| gtcgaacgga gaattttatt tcggtagaat tcttagtggc gaacgggtga gtaacgcgta | 60 |

```
ggcaacctgc cctttagacg gggacaacat tccgaaagga gtgctaatac cggatgtgat      120
catcgtgccg catggcagga tgaagaaaga tggcctctac aagtaagcta tcgctaaagg      180
atgggcctgc gtctgattag ctagttggta gtgtaacgga ctaccaaggc gatgatcagt      240
agccggtctg agaggatgaa cggccacatt gggactgaga cacggcccaa actcctacgg      300
gaggcagcag tggggaatct tccgcaatgg acgaaagtct gacggagcaa cgccgcgtga      360
gtgatgaagg atttcggtct gtaaagctct gttgtttatg acgaacgtgc agtgtgtgaa      420
caatgcattg caatgacggt agtaaacgag gaagccacgg ctaactacgt gccagcagcc      480
gcggtaatac gtaggtggcg agcgttgtcc ggaattattg ggcgtaaaga gcatgtaggc      540
ggcttaataa gtcgagcgtg aaaatgcggg gctcaacccc gtatggcgct ggaaactgtt      600
aggcttgagt gcaggagagg aaaggggaat tcccagtgta gcggtgaaat gcgtagatat      660
tgggaggaac accagtggcg aaggcgcctt tctggactgt gtctgacgct gagatgcgaa      720
agccagggta gcgaacggga ttagataccc cggtagtcct ggccgtaaac gatgggtact      780
aggtgtagga ggtatcgacc ccttctgtgc cggagttaac gcaataagta ccccgcctgg      840
ggagtacggc cgcaaggttg aaactcaaag gaattgacgg gggcccgcac aagcggtgga      900
gtatgtggtt taattcgacg caacgcgaag aaccttacca aggcttgaca ttgattgaac      960
gctctagaga tagagctttc ccttcgggga caagaaaaca ggtggtgcat ggctgtcgtc     1020
agctcgtgtc gtgagatgtt gggttaagtc cgcaacgagc gcaacccct atcctatgtt     1080 accagcaagt aaagttgggg actcatggga gactgccagg gacaacctgg aggaaggcgg     1140
ggatgacgtc aagtcatcat gccccttatg tcttgggcta cacacgtact acaatggtcg     1200
gaaacagagg gaagcgaagc cgcgaggcag agcaaacccc agaaacccga tctcagttcg     1260
gatcgcaggc tgcaacccgc ctgcgtgaag tcggaatcgc tagtaatcgc aggtcagcat     1320
actgcggtga atacgttccc gggccttgta cacaccgccc gtcacaccac gaaagttggt     1380
aacacccgaa gccggtgagg taacctatta ggagc                               1415
```

<210> SEQ ID NO 55
<211> LENGTH: 1366
<212> TYPE: DNA
<213> ORGANISM: Unknown
<220> FEATURE:
<223> OTHER INFORMATION: K55

<400> SEQUENCE: 55

```
atgaggtagc aataccttga tggcgaccgg cgcacgggtg agtaacgcgt atgcaacctg       60
cctgataccg gggtatagcc catggaaacg tggattaaca ccccatagta cttttatcct      120
gcatgggatg tgagttaaat gttcaaggta tcggatgggc atgcgtccta ttagttagtt      180
ggcggggtaa cagcccacca agacgatgat aggtagggt tctgagagga aggtccccca      240
cattggaact gagacacggt ccaaactcct acggaggca gcagtgagga atattggtca      300
atggacgaga gtctgaacca gccaagtcgc gtgagggaag actgccctat ggggttgtaaa     360 cctctttttat aagggaagaa taagttctac gtgtagaatg atgcctgtac cttatgaata      420
agcatcggct aactccgtgc cagcagccgc ggtaatacgg aggatgcgag cgttatccgg      480
atttattggg tttaaagggt gcgtaggcgg tttattaagt tagtggttaa atatttgagc      540
taaactcaat tgtgccatta atactggtaa actggagtac agacgaggta ggcggaataa      600
gttaagtagc ggtgaaatgc atagatataa cttagaactc cgatagcgaa ggcagcttac      660
```

| | |
|---|---|
| cagactgtaa ctgacgctga tgcacgagag cgtgggtagc gaacaggatt agataccctg | 720 |
| gtagtccacg ccgtaaacga tgctcactgg ttctgtgcga tatattgtac gggattaagc | 780 |
| gaaagtatta agtgagccac ctggggagta cgtcggcaac gatgaaactc aaaggaattg | 840 |
| acgggggccc gcacaagcgg aggaacatgt ggtttaattc gatgatacgc gaggaacctt | 900 |
| acctgggttt aaatgggaaa tgtcgtattt ggaaacagat attctcttcg gagcgttttt | 960 |
| caaggtgctg catggttgtc gtcagctcgt gccgtgaggt gtcgggttaa gtcccataac | 1020 |
| gagcgcaacc cttaccgtta gttgctagca tgtaatgatg agcactctaa cgggactgcc | 1080 |
| accgtaaggt gagaggaagg cggggatgac gtcaaatcag cacggccctt acacccaggg | 1140 |
| ctacacacgt gttacaatgg ccggtacaga gggccgctac caggtgactg gatgccaatc | 1200 |
| tcaaaagccg gtcgtagttc ggattggagt ctgtaacccg actccatgaa gttggattcg | 1260 |
| ctagtaatcg cgcatcagcc atggcgcggt gaatacgttc ccgggccttg tacacaccgc | 1320 |
| ccgtcaagcc atggaagccg ggggtgcctg aagtccgtaa ccgcga | 1366 |

<210> SEQ ID NO 56
<211> LENGTH: 1364
<212> TYPE: DNA
<213> ORGANISM: Unknown
<220> FEATURE:
<223> OTHER INFORMATION: K56
<220> FEATURE:
<221> NAME/KEY: misc_feature
<222> LOCATION: (923)..(924)
<223> OTHER INFORMATION: n is a, c, g, or t
<220> FEATURE:
<221> NAME/KEY: misc_feature
<222> LOCATION: (1349)..(1349)
<223> OTHER INFORMATION: n is a, c, g, or t
<220> FEATURE:
<221> NAME/KEY: misc_feature
<222> LOCATION: (1351)..(1352)
<223> OTHER INFORMATION: n is a, c, g, or t

<400> SEQUENCE: 56

| | |
|---|---|
| tcgaacgagc gagagagagc ttgctttctc gagcgagtgg cgaacgggtg agtaacgcgt | 60 |
| gaggaacctg cctcaaagag ggggacaaca gttggaaacg actgctaata ccgcataagc | 120 |
| ccacgggtcg gcatcgacca gagggaaaag gagcaatccg ctttgagatg gcctcgcgtc | 180 |
| cgattagcta gttggtgagg taacggccca ccaaggcgac gatcggtagc cggactgaga | 240 |
| ggttgaacgg ccacattggg actgagacac ggcccagact cctacgggag gcagcagtgg | 300 |
| ggaatattgc acaatggggg aaaccctgat gcagcgacgc cgcgtggagg aagaaggtct | 360 |
| tcggattgta aactcctgtt gttggggaag ataatgacgg tacccaacaa ggaagtgacg | 420 |
| gctaactacg tgccagcagc cgcggtaaaa cgtaggtcac aagcgttgtc cggaattact | 480 |
| gggtgtaaag ggagcgcagg cgggaagaca agttggaagt gaaatctatg ggctcaaccc | 540 |
| ataaactgct ttcaaaactg tttttcttga gtagtgcaga ggtaggcgga attcccggtg | 600 |
| tagcggtgga atgcgtagat atcggaggaa caccagtggc gaaggcggc ctactgggca | 660 |
| ccaactgacg ctgaggctcg aaagtgtggg tagcaaacag gattagatac cctggtagtc | 720 |
| cacaccgtaa acgatgatta ctaggtgttg gaggattgac cccttcagtg ccgcagttaa | 780 |
| cacaataagt aatccacctg gggagtacga ccgcaaggtt gaaactcaaa ggaattgacg | 840 |
| ggggcccgca caagcagtgg agtatgtggt ttaattcgac gcaacgcgaa gaaccttacc | 900 |
| aagtcttgac atcccttgac agnnatagaa atatgttttc tcttcggagc aaggagacag | 960 |
| gtggtgcatg gttgtcgtca gctcgtgtcg tgagatgttg ggttaagtcc cgcaacgagc | 1020 |

```
gcaacccctta tggtcagtta ctacgcaaga ggactctggc cagactgccg ttgacaaaac    1080
ggaggaaggt ggggatgacg tcaaatcatc atgcccttta tgacttgggc tacacacgta    1140
ctacaatggc gttaaacaaa gagaagcaag accgcgaggt ggagcaaaac tcagaaacaa    1200
cgtcccagtt cggactgcag gctgcaactc gcctgcacga agtcggaatt gctagtaatc    1260
gtggatcagc atgccacggt gaatacgttc ccgggccttg tacacaccgc ccgtcacacc    1320
atgagagccg gggggacccg aagtcggtng nntaaccgca agga                     1364
```

<210> SEQ ID NO 57
<211> LENGTH: 1391
<212> TYPE: DNA
<213> ORGANISM: Unknown
<220> FEATURE:
<223> OTHER INFORMATION: K57

<400> SEQUENCE: 57

```
tgcagtcgaa cggagtgctc atgacagagg attcgtccaa tggagtgagt tacttagtgg     60
cggacgggtg agtaacgcgt gagtaacctg ccttggagtg gggaataaca ggtggaaaca    120
tctgctaata ccgcatgatg cagttgggtc gcatggctct gactgccaaa gatttatcgc    180
tctgagatgg actcgcgtct gattagctgg ttggcggggt aacggcccac caaggcgacg    240
atcagtagcc ggactgagag gttggccggc cacattggga ctgagacacg cccagactc    300 ctacgggagg cagcagtggg gaatattggg caatgggcgc aagcctgacc cagcaacgcc    360
gcgtgaagga agaaggcttt cgggttgtaa acttctttc tcaggacga agcaagtgac    420 ggtacctgag gaataagcca cggctaacta cgtgccagca gccgcggtaa tacgtaggtg    480
gcgagcgtta tccggattta ctgggtgtaa agggcgtgta ggcgggactg caagtcagat    540
gtgaaaacca tgggctcaac ctgtggcctg catttgaaac tgtagttctt gagtactgga    600
gaggcagacg gaattcctag tgtagcggtg aaatgcgtag atattaggag gaacaccagt    660
ggcgaaggcg gtctgctgga cagcaactga cgctgaggcg cgaaagcgtg gggagcaaac    720
aggattagat accctggtag tccacgctgt aaacgatgga tactaggtgt gggggggtctg    780 accccctccg tgccgcagtt aacacaataa gtatcccacc tggggagtac gatcgcaagg    840
ttgaaactca aaggaattga cggggggccc cacaagcggt ggagtatgtg gtttaattcg    900
aagcaacgcg aagaacctta ccagggcttg acatcccggt gaccggtgta gagatacacc    960
ttcttcttcg gaagcgccgg tgacaggtgg tgcatggttg tcgtcagctc gtgtcgtgag   1020
atgttgggtt aagtcccgca acgagcgcaa cccttattgt tagttgctac gcaagagcac   1080
tctagcgaga ctgccgttga caaaacggag gaaggtgggg acgacgtcaa atcatcatgc   1140
cccttatgtc ctgggccaca cacgtactac aatggtggtc aacagaggga agcaagaccg   1200
cgaggtggag caaacccccta aaagccatcc cagttcggat tgcaggctgc aactcgcctg   1260
tatgaagttg gaatcgctag taatcgcgga tcagcatgcc gcggtgaata cgttcccggg   1320
ccttgtacac accgcccgtc acaccatgag agtcgggaac acccgaagtc cgtagcctaa   1380
ccgcaagggg g                                                       1391
```

<210> SEQ ID NO 58
<211> LENGTH: 1377
<212> TYPE: DNA
<213> ORGANISM: Unknown
<220> FEATURE:
<223> OTHER INFORMATION: K58

<400> SEQUENCE: 58

```
gcaagtcgag cgagaagctt tgaactgacg cttcggttga tgatcaaagt ggaaagcggc        60
ggacgggtga gtaacgcgta ggcaacctgc cctttgcaga gggatagcct cgggaaaccg       120
ggattaaaac ctcataacgc acaactgaga catcttggat gtgccaaaga tttatcggca       180
gaggatgggc ctgcgtctga ttagttagtt ggtggggtaa cggcctacca aggcgacgat       240
cagtagccga cctgagaggg tgatcggcca cattggaact gagacacggt ccaaactcct       300
acgggaggca gcagtgggga atattgcaca atggggaaa ccctgatgca gcaacgccgc        360
gtgaaggatg aaggcccttg ggtcgtaaac ttctgttcta ggggaagata gtgacgtac        420
cttaggagca agtcccggct aactacgtgc cagcagccgc ggtaatacgt aggggggcaag      480
cgttatccgg aattattggg cgtaaagagt acgtaggtgg ttacctaagc aaggggttta      540
aggcaatggc ttaactattg ttcgccccct gaactgggct acttgagtgc aggagaggaa       600
agcggaattc ctagtgtagc ggtgaaatgc gtagatatta ggaggaacac cagtggcgaa       660
ggcggctttc tggactgtaa ctgacactga ggtacgaaag cgtggggagc aaacaggatt       720
agatacctg gtagtccacg ccgtaaacga tgagcactag gtgtcggggt cgcaagactt       780
cggtgccgca gttaacgcaa taagtgctcc gcctggggag tacgttcgca agaatgaaac       840
tcaaaggaat tgacggggac ccgcacaagc agcggagcat gtggtttaat tcgaagcaac       900
gcgaagaacc ttaccagggc ttgacatctt cctgacagac ccttaaacgg tccttcttc       960
ggacaggaaa acaggtggt gcatggttgt cgtcagctcg tgtcgtgaga tgttgggtta     1020
agtcccgcaa cgagcgcaac ccttgctgtt agttgccatc attaagttgg cactctaac      1080
gggactgccg gggataactc ggaggaaggt ggggatgacg tcaaatcatc atgccccta      1140
tgttctgggc tacacacgtg ctacaatggc cggtacaaag aggaagcgag accgcgaggt     1200
ggagcgaatc tcaaaagccg gtcccagttc ggattgcagg ctgcaactcg cctgcatgaa     1260
gtcggagttg ctagtaatcg cgaatcagaa tgtcgcggtg aatgcgttcc cgggtcttgt     1320
acacaccgcc cgtcacacca tggaagttgg gggcgcccga agttggcagg caaatat        1377
```

<210> SEQ ID NO 59
<211> LENGTH: 1373
<212> TYPE: DNA
<213> ORGANISM: Unknown
<220> FEATURE:
<223> OTHER INFORMATION: K59

<400> SEQUENCE: 59

```
cgaggggcag cgcggagagt agcaatactt tggaggcgac cggcgcacgg gtgcgtaacg        60
cgtatgcaac ctacctttaa caggggcata acactgagaa attggtacta attccccata       120
acattcgaga aggcatcttc ttgggttaaa aactccggtg gttaaagatg ggcatgcgtt       180
gtattagcta gttggtgagg taacggctca ccaaggcgac gatacatagg gggactgaga       240
ggttaacccc ccacattggt actgagacac ggaccaaact cctacgggag gcagcagtga       300
ggaatattgg tcaatggacg caagtctgaa ccagccatgc cgcgtgcagg aagacggctc       360
tatgagttgt aaactgcttt tgtactaggg taaacgcttc tacgtgtagg agtctgaaag       420
tatagtacga ataaggatcg gctaactccg tgccagcagc cgcggtaata cggaggatcc       480
aagcgttatc cggatttatt gggtttaaag ggtgcgtagg cggtttgata agttagaggt       540
gaaataccgg ggctcaactc cggaactgcc tctaatactg ttgaactaga gagtagttgc       600
ggtaggcgga atgtatggtg tagcggtgaa atgcttagag atcatacaga acaccgattg       660
```

| | |
|---|---|
| cgaaggcagc ttaccaaact atatctgacg ttgaggcacg aaagcgtggg gagcaaacag | 720 |
| gattagatac cctggtagtc cacgcagtaa acgatgataa ctcgttgtcg gcgatacaca | 780 |
| gtcggtgact aagcgaaagc gataagttat ccacctgggg agtacgttcg caagaatgaa | 840 |
| actcaaagga attgacgggg gcccgcacaa gcggaggaac atgtggttta attcgatgat | 900 |
| acgcgaggaa ccttacccgg gcttgaaagt tagtgacgat tctggaaaca ggatttccct | 960 |
| tcggggcacg aaactaggtg ctgcatggtt gtcgtcagct cgtgccgtga ggtgtcgggt | 1020 |
| taagtcccat aacgagcgca acccctaccg ttagttgcca tcaggtcaag ctgggcactc | 1080 |
| tggcgggact gccggtgtaa gccgagagga aggtggggat gacgtcaaat cagcacggcc | 1140 |
| cttacgtccg gggctacaca cgtgttacaa tggtaggtac agagggccgc tacccgcga | 1200 |
| ggggatgcca atctcgaaag cctatctcag ttcggatcgg aggctgaaac ccgcctccgt | 1260 |
| gaagttggat tcgctagtaa tcgcgcatca gccatggcgc ggtgaatacg ttcccgggcc | 1320 |
| ttgtacacac cgcccgtcaa gccatggaag ctgggggtgc ctgaagttcg tga | 1373 |

```
<210> SEQ ID NO 60
<211> LENGTH: 1384
<212> TYPE: DNA
<213> ORGANISM: Unknown
<220> FEATURE:
<223> OTHER INFORMATION: K60

<400> SEQUENCE: 60
```

| | |
|---|---|
| gtcgaacgga gctgttttct ctgaagtttt cggatggaag agagttcagc ttagtggcga | 60 |
| acgggtgagt aacacgtgag caacctgcct ttcagtgggg acaacattt ggaaacgaat | 120 |
| gctaataccg cataagacca cagtgtcgca tggcacaggg gtcaaaggat ttatccgctg | 180 |
| aaagatgggc tcgcgtccga ttagctagat ggtgaggtaa cggcccacca tggcgacgat | 240 |
| cggtagccgg actgagaggt tgaacggcca cattgggact gagacacggc ccagactcct | 300 |
| acgggaggca gcagtgggga atattgcaca atggggaaa ccctgatgca gcgacgccgc | 360 |
| gtggaggaag aaggtcttcg gattgtaaac tcctgtccca ggggacgata atgacggtac | 420 |
| cctgggagga agcaccggct aactacgtgc cagcagccgc ggtaaaacgt agggtgcaag | 480 |
| cgttgtccgg aattactggg tgtaaaggga gcgcaggcgg attggcaagt tgggagtgaa | 540 |
| atctatgggc tcaacccata aattgctttc aaaactgtca gtcttgagtg gtgtagaggt | 600 |
| aggcggaatt cccggtgtag cggtggaatg cgtagatatc gggaggaaca ccagtggcga | 660 |
| aggcggccta ctgggcacta actgacgctg aggctcgaaa gcatgggtag caaacaggat | 720 |
| tagataccct ggtagtccat gccgtaaacg atgattacta ggtgtgggag gattgacccc | 780 |
| ttccgtgccg cagttaacac aataagtaat ccacctgggg agtacgaccg caaggttgaa | 840 |
| actcaaagga attgacgggg gcccgcacaa gcagtggagt atgtggttta attcgaagca | 900 |
| acgcgaagaa ccttaccagg tcttgacatc ggatgcatac ctaagagatt agggaagtcc | 960 |
| ttcgggacat ccagacaggt ggtgcatggt tgtcgtcagc tcgtgtcgtg agatgttggg | 1020 |
| ttaagtcccg caacgagcgc aacccttatc gttagttact acgcaagagg actagcga | 1080 |
| gactgccgtt gacaaaacgg aggaaggtgg ggatgacgtc aaatcatcat gccctttatg | 1140 |
| acctgggcta cacacgtact acaatggcta ttaacagaga gaagcgatac cgcgaggtgg | 1200 |
| agcaaacctc acaaaaatag tctcagttcg gatcgcaggc tgcaacccgc ctgcgtgaag | 1260 |
| ccggaattgc tagtaatcgc ggatcagcat gccgcggtga atacgttccc gggccttgta | 1320 |

```
cacaccgccc gtcacaccat gagagccggg gggacccgaa gtcggtagtc taaccgcaag    1380
gagg                                                                1384

<210> SEQ ID NO 61
<211> LENGTH: 1394
<212> TYPE: DNA
<213> ORGANISM: Unknown
<220> FEATURE:
<223> OTHER INFORMATION: K61

<400> SEQUENCE: 61
agtcgaacga agttgctctt tgtgaagccc tcgggtggaa ctgcgagtat acttagtggc      60
ggacgggtga gtaacgcgtg agcaatctgc cctgcaatgg gggacaacag ttggaaacga    120
ctgctaatac cgcatgagac cacgaaaccg catggttttg aggtaaaagg atttattcga    180
tgcaggatga gctcgcgtcc cattagatag ttggtgaggt aacggccac caagtcaacg     240 atgggtagcc gacctgagag ggtgatcggc cacactggaa ctgagacacg gtccagactc    300
ctacgggagg cagcagtggg gaatattggg caatggggga acccctgacc cagcaacgcc    360
gcgtgaggga agaaggtctt cggattgtaa acctttgtcc tatgggacga aacaaatgac    420
ggtaccatag gaggaagctc cggctaacta cgtgccagca gccgcggtaa tacgtaggga    480
gcaagcgttg tccggaatta ctgggcgtaa agggtgcgta ggtggctatg taagtcagat    540
gtgaaagacc gggcttaac cccggggttg catttgaaac tgtgtggctt gagtacagga     600
gagggaagtg gaattcctag tgtagcggtg aaatgcgtag atattaggag gaacaccagt    660
ggcgaaggcg acttctctgga ctgtaactga cactgaagca cgaaagcgtg gggagcaaac   720
aggattagat accctggtag tccacgccgt aaacgatgga tactaggtgt ggggcccgat    780
agggttccgt gccgaagcta acgcattaag tatcccgcct ggggagtacg atcgcaaggt    840
tgaaactcaa aggaattgac gggggcccgc acaagcagcg agcatgtgg tttaattcga    900 agcaacgcga agaaccttac caaggcttga catcctctga cgactgtaga gatacagttt    960
cccttcgggg cagagagaca ggtggtgcat ggttgtcgtc agctcgtgtc gtgagatgtt   1020
gggttaagtc ccgcaacgag cgcaacccctt attgctagtt gccagcgcgt aaaggcggga   1080
actctagtga gactgccggg gacaactcgg aggaaggtgg ggacgacgtc aaatcatcat   1140
gccccttatg tcttgggcta cacacgtgct acaatggccg gtacaaaggg cagcgaaccc   1200
gtaaggggaa gcgaatctca aaaagccggt cccagttcgg attgtgggct gcaacccgcc   1260
cacatgaagt cggagttgct agtaatcgcg aatcagcatg tcgcggtgaa tgcgttcccg   1320
ggccttgtac acaccgcccg tcacaccacg gaagttggga gcaccgaag ccagtggctt    1380 aaccgtaagg agag                                                    1394

<210> SEQ ID NO 62
<211> LENGTH: 1388
<212> TYPE: DNA
<213> ORGANISM: Unknown
<220> FEATURE:
<223> OTHER INFORMATION: K62

<400> SEQUENCE: 62
aacgaagcgc ttccgcctga tttctcttcgg agatgaaggc ggctgcgact gagtggcgga      60
cgggtgagta acgcgtgggc aacctgccctt gcactggggg ataacagcca gaaatggctg    120
ctaataccgc ataagaccga agcgccgcat ggcgctgcgc ccaaagcccc ggcggtgcaa    180
gatgggcccg cgtctgatta ggtagttggc ggggtaacgg cccaccaagc cgacgatcag    240
```

```
tagccgacct gagagggtga ccggccacat tgggactgag acacggccca gactcctacg    300
ggaggcagca gtggggaata ttgcacaatg ggggaaaccc tgatgcagcg acgccgcgtg    360
aaggatgaag tatttcggta tgtaaacttc tatcagcagg gaagaagatg acggtacctg    420
actaagaagc cccggctaac tacgtgccag cagccgcggt aatacgtagg gggcaagcgt    480
tatccggatt tactgggtgt aaagggagcg tagacggcga tgcaagccag atgtgaaagc    540
ccggggctca accccgggac tgcatttgga actgcgtggc tggagtgtcg gagaggcagg    600
cggaattcct agtgtagcgg tgaaatgcgt agaatattag gaggaacacc agtggcgaag    660
gcggcctgct ggacgatgac tgacgttgag gctcgaaagc gtggggagca acaggatta    720 gatacctgg tagtccacgc cgtaaacgat gactactagg tgtcgggtgg caaggccatt    780
cggtgccgca gcaaacgcaa taagtagtcc acctggggga gtacgttcgc aagaatgaaa    840
ctcaaaggaa ttgacgggga cccgcacaag cggtggagca tgtggtttaa ttcgaagcaa    900
cgcgaagaac cttacctgat cttgacatcc cgatgccaaa gcgcgtaacg cgctctttct    960
tcggaacatc ggtgacaggt ggtgcatggt tgtcgtcagc tcgtgtcgtg agatgttggg   1020
ttaagtcccg caacgagcgc aaccccctatc ttcagtagcc agcattccgg atgggcactc   1080
tggagagact gccagggaca acctggagga aggtgggat gacgtcaaat catcatgccc   1140
cttatgacca gggctacaca cgtgctacaa tggcgtaaac aaagggaggc gaacccgcga   1200
gggtgggcaa atcccaaaaa taacgtctca gttcggattg tagtctgcaa ctcgactaca   1260
tgaagctgga atcgctagta atcgcgaatc agaatgtcgc ggtgaatacg ttcccgggtc   1320
ttgtacacac cgcccgtcac accatgggag tcagtaacgc ccgaagccgg tgacccaacc   1380
cgcaaggg                                                            1388
```

<210> SEQ ID NO 63
<211> LENGTH: 1415
<212> TYPE: DNA
<213> ORGANISM: Unknown
<220> FEATURE:
<223> OTHER INFORMATION: K63

<400> SEQUENCE: 63

```
agtcgaacgc ttctttcctc ccgagtgctt gcactcaatt ggaaagagga gtggcggacg     60
ggtgagtaac acgtgggtaa cctacccatc agaggggat aacacttgga aacaggtgct    120
aataccgcat aacagtttat gccgcatggc ataagagtga aggcgctttc gggtgtcgc    180 tgatggatgg acccgcggtg cattagctag ttggtgaggt aacggctcac caaggccacg    240
atgcatagcc gacctgagag ggtgatcggc cacactggga ctgagacacg gcccagactc    300
ctacgggagg cagcagtagg gaatcttcgg caatggacga aagtctgacc gagcaacgcc    360
gcgtgagtga agaaggtttt cggatcgtaa aactctgttg ttagagaaga caaggacgt    420 tagtaactga acgtcccctg acggtatcta accagaaagc cacggctaac tacgtgccag    480
cagccgcggt aatacgtagg tggcaagcgt tgtccggatt tattgggcgt aaagcgagcg    540
caggcggttt cttaagtctg atgtgaaagc cccggctca accggggagg gtcattggaa    600
actgggagac ttgagtgcag aagaggagag tggaattcca tgtgtagcgg tgaaatgcgt    660
agatatatgg aggaacacca gtggcgaagg cggctctctg gtctgtaact gacgctgagg    720
ctcgaaagcg tggggagcaa acaggattag ataccctggt agtccacgcc gtaaacgatg    780
agtgctaagt gttggagggt ttccgccctt cagtgctgca gcaaacgcat taagcactcc    840
```

```
gcctggggag tacgaccgca aggttgaaac tcaaaggaat tgacggggc ccgcacaagc      900 ggtggagcat gtggtttaat tcgaagcaac gcgaagaacc ttaccaggtc ttgacatcct      960
ttgaccactc tagagataga gctttcccct tcggggacaaa gtgacaggtg gtgcatggtt    1020
gtcgtcagct cgtgtcgtga gatgttgggt taagtcccgc aacgagcgca acccttattg    1080
ttagttgcca tcatttagtt gggcactcta gcgagactgc cggtgacaaa ccggaggaag    1140
gtggggatga cgtcaaatca tcatgcccct tatgacctgg gctacacacg tgctacaatg    1200
ggaagtacaa cgagtcgcta accgcgagg tcatgcaaat ctcttaaagc ttctctcagt    1260
tcggattgca ggctgcaact cgcctgcatg aagccggaat cgctagtaat cgcggatcag    1320
cacgccgcgg tgaatacgtt cccgggcctt gtacacaccg cccgtcacac acgagagtt    1380 tgtaacaccc gaagtcggtg aggtaacctt tttgg                               1415
```

<210> SEQ ID NO 64  
<211> LENGTH: 1392  
<212> TYPE: DNA  
<213> ORGANISM: Unknown  
<220> FEATURE:  
<223> OTHER INFORMATION: K64

<400> SEQUENCE: 64

```
agtcgagcga agcgctaaga caggatttct tcggattgaa gtctttgtga ctgagcggcg       60
gacgggtgag taacgcgtgg gtaacctgcc tcatacaggg ggataacagt tagaaatgac     120
tgctaatacc gcataagcgc acaggaccgc atggtctggt gtgaaaaact ccggtggtat     180
gagatggacc cgcgtctgat tagctagttg gaggggtaac ggcccaccaa ggcgacgatc     240
agtagccggc ctgagagggt gaacggccac attgggactg agacacggcc cagactccta     300
cgggaggcag cagtggggaa tattgcacaa tggggaaac cctgatgcag cgacgccgcg      360
tgaaggaaga agtatctcgg tatgtaaact tctatcagca gggaagaaaa tgacggtacc     420
tgactaagaa gccccggcta actacgtgcc agcagccgcg gtaatacgta gggggcaagc     480
gttatccgga tttactgggt gtaaagggag cgtagacgga agagcaagtc tgatgtgaaa     540
ggctggggct taaccccagg actgcattgg aaactgttgt tctagagtgc ggagaggta     600 agcggaattc ctagtgtagc ggtgaaatgc gtagatatta ggaggaacac cagtggcgaa    660
ggcggcttac tggacggtaa ctgacgttga ggctcgaaag cgtggggagc aaacaggatt     720
agataccctg gtagtccacg ccgtaaacga tgaatactag gtgtcgggtg gcaaagccat     780
tcggtgccgc agcaaacgca ataagtattc cacctgggga gtacgttcgc aagaatgaaa    840
ctcaaaggaa ttgacgggga cccgcacaag cggtggagca tgtggtttaa ttcgaagcaa    900
cgcgaagaac cttaccaagt cttgacatcc tctctgaccgt cccgtaacgg ggcttccct    960 tcggggcaga ggagacaggt ggtgcatggt tgtcgtcagc tcgtgtcgtg agatgttggg    1020
ttaagtcccg caacgagcgc aacccttatc cttagtagcc agcacatgat ggtgggcact    1080
ctagggagac tgccggggat aacccggagg aaggcgggga cgacgtcaaa tcatcatgcc    1140
ccttatgatt tgggctacac acgtgctaca atggcgtaaa caagggaag cgagacagcg    1200 atgttgagcg aatcccaaaa ataacgtccc agttcggact gcagtctgca actcgactgc    1260
acgaagctgg aatcgctagt aatcgcggat cagaatgccg cggtgaatac gttcccgggt    1320
cttgtacaca ccgcccgtca caccatggga gtcagtaacg cccgaagtca gtgacctaac    1380
cgaaaggaag ga                                                        1392
```

<210> SEQ ID NO 65
<211> LENGTH: 1388
<212> TYPE: DNA
<213> ORGANISM: Unknown
<220> FEATURE:
<223> OTHER INFORMATION: K65

<400> SEQUENCE: 65

| | | | | | |
|---|---|---|---|---|---|
| aagtcgaggg | gcagcggatg | gagtgcttcg | gtactcctgc | cggcgaccgg | cggacgggtg | 60 |
| cgtaacgcgt | atgcaacctg | ccttcaacag | ggggataatc | cgaagaaatt | tggtctaata | 120 |
| ccccataata | ttccgacagg | catctgtcgg | agttgaaagc | ttcggtggtt | ggagatgggc | 180 |
| atgcgttgta | ttagctggat | ggtgaggtaa | cggctcacca | tggcgatgat | acataggggg | 240 |
| actgagaggt | tttcccccca | cactggtact | gagacacgga | ccagactcct | acgggaggca | 300 |
| gcagtgagga | atattggtca | atggacggaa | gtctgaacca | gccatgccgc | gtgcaggatg | 360 |
| aatgtgctat | gcattgtaaa | ctgcttttgt | acgagggtaa | acccagatac | gcgtatctgc | 420 |
| ttgaaagtat | cgtacgaata | aggatcggct | aactccgtgc | cagcagccgc | ggtaatacgg | 480 |
| aggatccgag | cgttatccgg | atttattggg | tttaaggggt | gcgtaggctg | ttttttaagt | 540 |
| tagaggtgaa | agctcgacgc | tcaacgtcga | aattgcctct | gatactgaga | gactagagtg | 600 |
| tagttgcgga | aggcggaatg | tgtggtgtag | cggtgaaatg | cttagatatc | acacagaaca | 660 |
| ccgattgcga | aggcagcttt | ccaagctatt | actgacgctg | aggcacgaaa | gcgtggggag | 720 |
| cgaacaggat | tagataccct | ggtagtccac | gcagtaaacg | atgataactc | gttgccggcg | 780 |
| atacacagtc | ggtgacttag | cgaaagcgtt | aagttatcca | cctgggggag | tacgttcgca | 840 |
| agaatgaaac | tcaaaggaat | tgacggggc | ccgcacaagc | ggaggaacat | gtggtttaat | 900 |
| tcgatgatac | gcgaggaacc | ttaccегggc | ttgaaagtta | gcgacggatc | gagaaatcgg | 960 |
| tcttccctac | ggggcgcgaa | actaggtgct | gcatggttgt | cgtcagctcg | tgccgtgagg | 1020 |
| tgtcgggtta | agtcccataa | cgagcgcaac | ccctaccgtt | agttgccatc | aggtcaagct | 1080 |
| gggcactcta | gcgggactgc | cggtgtaagc | cgagaggaag | gtggggatga | cgtcaaatca | 1140 |
| gcacggccct | tacgtccggg | gcgacacacg | tgttacaatg | gccggtacag | agggtagcta | 1200 |
| cctggtgaca | ggatgccaat | ctcgaaagcc | ggtctcagtt | cggattggag | gctgaaactc | 1260 |
| gcctccatga | agttggattc | gctagtaatc | gcgcatcagc | catggcgcgg | tgaatacgtt | 1320 |
| cccgggcctt | gtacacaccg | cccgtcaagc | catgggagtt | gggggtgcct | gaagtacgtg | 1380 |
| accgcaag | | | | | | 1388 |

<210> SEQ ID NO 66
<211> LENGTH: 1388
<212> TYPE: DNA
<213> ORGANISM: Unknown
<220> FEATURE:
<223> OTHER INFORMATION: K66

<400> SEQUENCE: 66

| | | | | | |
|---|---|---|---|---|---|
| gtcgaacgga | gcacccctga | cggagttttc | ggacaacgaa | agggaatgct | tagtggcgga | 60 |
| cgggtgagta | acgcgtgagt | aacctgcctt | ggagtgggga | ataacagccg | gaaacggctg | 120 |
| ctaataccgc | atgatgtatc | tggatcgcat | ggttctggat | accaaagatt | tatcgctctg | 180 |
| agatggactc | gcgtctgatt | agctagttgg | tgaggtaatg | gctcaccaag | gcgacgatca | 240 |
| gtagccggac | tgagaggttg | gccggccaca | ttgggactga | gacacggccc | agactcctac | 300 |
| gggaggcagc | agtggggaat | attggcaat | gggcgaaagc | ctgacccagc | aacgccgcgt | 360 |

```
gaaggaagaa ggccctcggg ttgtaaactt cttttgtcag ggacgaagca agtgacggta      420
cctgacgaat aagccacggc taactacgtg ccagcagccg cggtaatacg taggtggcaa      480
gcgttatccg gatttactgg gtgtaaaggg cgtgtaggcg ggagtgcaag tcagatgtga      540
aaactatggg ctcaacccat agcctgcatt tgaaactgta cttcttgagt gatggagagg      600
caggcggaat tccctgtgta gcggtgaaat gcgtagatat agggaggaac accagtggcg      660
aaggcggcct gctggacatt aactgacgct gaggcgcgaa agcgtgggga gcaaacagga      720 ttagatacccc tggtagtcca cgccgtaaac gatggatact aggtgtgggg ggtctgaccc      780
cctccgtgcc gcagttaaca caataagtat cccacctggg gagtacgatc gcaaggttga      840
aactcaaagg aattgacggg ggcccgcaca agcggtggag tatgtggttt aattcgaagc      900
aacgcgaaga accttaccag gacttgacat cctactaacg aagcagagat gcataaggtg      960
cccttcgggg aaagtagaga caggtggtgc atggttgtcg tcagctcgtg tcgtgagatg     1020
ttgggttaag tcccgcaacg agcgcaaccc ttattgttag ttgctacgca agagcactct     1080
agcgagactg ccgttgacaa aacggaggaa ggtggggacg acgtcaaatc atcatgcccc     1140
ttatgtcctg ggccacacac gtactacaat ggcggtcaac agagggaagc aaagccgcga     1200
ggtggagcaa atccctaaaa gccgtcccag ttcggattgc aggctgaaac tcgcctgtat     1260
gaagtcggaa tcgctagtaa tcgcggatca gcatgccgcg gtgaatacgt tcccgggcct     1320
tgtacacacc gcccgtcaca ccatgagagt cgggaacacc cgaagtccgt agcctaacag     1380
caatgggg                                                              1388
```

<210> SEQ ID NO 67
<211> LENGTH: 1380
<212> TYPE: DNA
<213> ORGANISM: Unknown
<220> FEATURE:
<223> OTHER INFORMATION: K67

<400> SEQUENCE: 67

```
tcgagggggca gcatgaactt agcttgctaa gtttgatggc gaccggcgca cgggtgagta       60
acacgtatcc aacctgccga tgactcgggg atagcctttc gaaagaaaga ttaatacccg      120
atggcataat tcttccgcat ggtagaacta ttaaagaatt tcggtcatcg atgggatgc       180 gttccattag gttgttggcg gggtaacggc ccaccaagcc ttcgatggat aggggttctg      240
agaggaaggt cccccacatt ggaactgaga cacggtccaa actcctacgg gaggcagcag      300
tgaggaatat tggtcaatgg acgagagtct gaaccagcca gtagcgtga aggatgactg      360 ccctatgggt tgtaaacttc ttttatacgg gaataaagtg aggcacgtgt gcctttttgt      420
atgtaccgta tgaataagga tcggctaact ccgtgccagc agccgcggta atacggagga      480
tccgagcgtt atccggattt attgggttta aagggagcgt aggcggacgc ttaagtcagt      540
tgtgaaagtt tgcggctcaa ccgtaaaatt gcagttgata ctgggtgtct tgagtacagt      600
agaggcaggc ggaattcgtg gtgtagcggt gaaatgctta gatatcacga agaactccga      660
ttgcgaaggc agcttgctgg actgtaactg acgctgatgc tcgaaagtgt gggtatcaaa      720
caggattaga taccctggta gtccacacag taaacgatga atactcgctg tttgcgatat      780
acagtaagcg gccaagcgaa agcgttaagt attccacctg gggagtacgc cggcaacggt      840
gaaactcaaa ggaattgacg ggggcccgca caagcggagg aacatgtggt ttaattcgat      900
gatacgcgag gaaccttacc cgggcttgaa ttgcaactga atgatgtgga gacatgtcag      960
ccgcaaggca gttgtgaagg tgctgcatgg ttgtcgtcag ctcgtgccgt gaggtgtcgg     1020
```

```
cttaagtgcc ataacgagcg caacccttat cgatagttac catcaggtta tgctggggac    1080
tctgtcgaga ctgccgtcgt aagatgtgag gaaggtgggg atgacgtcaa atcagcacgg    1140
cccttacgtc cggggctaca cacgtgttac aatgggggt acagaaggca gctacacggc     1200
gacgtgatgc taatccctaa agcctctctc agttcggatt ggagtctgca acccgactcc    1260
atgaagctgg attcgctagt aatcgcgcat cagccacggc gcggtgaata cgttcccggg    1320
ccttgtacac accgcccgtc aagccatgaa agccgggggt acctgaagtg cgtaaccgca    1380
```

<210> SEQ ID NO 68
<211> LENGTH: 1370
<212> TYPE: DNA
<213> ORGANISM: Unknown
<220> FEATURE:
<223> OTHER INFORMATION: K68
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (1352)..(1352)
<223> OTHER INFORMATION: n is a, c, g, or t

<400> SEQUENCE: 68

```
agtcgnacga gagaattgct agcttgctaa taattctcta gtggcgcacg ggtgagtaac    60
acgtgagtaa cctgcccca agagtgggat agccccggga aactgggatt aataccgcat     120
aaaatcgcaa gattaaagca gcaatgcgct tggggatggg ctcgcgtcct attagttagt    180
tggtgaggta acggctcacc aaggcgatga cgggtagccg gtctgagagg atgtccggcc    240
acactggaac tgagacacgg tccagacacc tacgggtggc agcagtcgag aatcattcac    300 aatggggaa accctgatgg tgcgacgccg cgtggggaa tgaaggtctt cggattgtaa     360 accctgtca tgtgggagca aattaaaaag atagtaccac aagaggaaga acggctaac     420 tctgtgccag cagccgcggt aatacagagg tctcaagcgt tgttcggaat cactgggcgt    480
aaagcgtgcg taggcggttt cgtaagtcgt gtgtgaaagg cggggctca accccggac      540 tgcacatgat actgcgagac tagagtaatg gagggggaac cggaattctc ggtgtagcag    600
tgaaatgcgt agatatcgag aggaacactc gtggcgaagg cgggttcctg gacattaact    660
gacgctgagg cacgaaggcc aggggagcga aaggggattag ataccctgt agtcctggca    720 gtaaacggtg cacgcttggt gtgcgggaa tcgacccccct gcgtgccgga gctaacgcgt    780
taagcgtgcc gcctggggga gtacggtcgc aagattaaaa ctcaaagaaa ttgacgggga    840
cccgcacaag cggtggagta tgtggcttaa ttcgatgcaa cgcgaagaac cttacctggg    900
cttgacatgt aatgaacaac atgtgaaagc atgcgactct tcggaggcgt acacaggtg    960 ctgcatggcc gtcgtcagct cgtgtcgtga gatgtttggt taagtccagc aacgagcgca   1020 accctgttg ccagttacca gcacgtaaag gtgggactc tggcgagact gcccagatca     1080
actgggagga aggtggggac gacgtcaggt cagtatggcc cttatgccca gggctgcaca   1140
cgtactacaa tgcccagtac agaggggcc gaagccgcga ggcggaggaa atcctaaaaa   1200
ctgggcccag ttcggactgt aggctgcaac ccgcctacac gaagccggaa tcgctagtaa   1260
tggcgcatca gctacggcgc cgtgaatacg ttcccgggtc ttgtacacac cgcccgtcac   1320
atcatggaag ccggtcgcac ccgaagtatc tnaagccaac cgcaaggagg             1370
```

<210> SEQ ID NO 69

```
<211> LENGTH: 1382
<212> TYPE: DNA
<213> ORGANISM: Unknown
<220> FEATURE:
<223> OTHER INFORMATION: F01

<400> SEQUENCE: 69
cagtcgaacg ggatccatca ggctttgctt ggtggtgaga gtggcgaacg ggtgagtaat      60
gcgtgaccga cctgccccat acaccggaat agctcctgga aacgggtggt aatgccggat     120
gctccagttg atcgcatggt cttctgggaa agctttcgcg gtatgggatg gggtcgcgtc     180
ctatcagctt gacggcgggg taacggccca ccgtggcttc gacgggtagc cggcctgaga     240
gggcgaccgg ccacattggg actgagatac ggcccagact cctacgggag gcagcagtgg     300
ggaatattgc acaatgggcg caagcctgat gcagcgacgc cgcgtgaggg atggaggcct     360
tcgggttgta aacctctttt atcggggagc aagcgagagt gagtttaccc gttgaataag     420
caccggctaa ctacgtgcca gcagccgcgg taatacgtag ggtgcaagcg ttatccggaa     480
ttattgggcg taaagggctc gtaggcggtt cgtcgcgtcc ggtgtgaaag tccatcgctt     540
aacggtggat ccgcgccggg tacggcgggc ttgagtgcg taggggaga ctggaattcc      600
cggtgtaacg gtggaatgtg tagatatcgg aagaacacc aatggcgaag gcaggtctct     660
gggccgttac tgacgctgag gagcgaaagc gtggggagcg aacaggatta gataccctgg     720
tagtccacgc cgtaaacggt ggatgctgga tgtggggccc gttccacggg ttccgtgtcg     780
gagctaacgc gttaagcatc ccgcctgggg agtacggccg caaggctaaa actcaaagaa     840
attgacgggg gcccgcacaa gcggcggagc atgcggatta attcgatgca acgcgaagaa     900
ccttacctgg gcttgacatg ttcccgacgg tcgtagagat acggcttccc ttcggggcgg     960
gttcacaggt ggtgcatggt cgtcgtcagc tcgtgtcgtg agatgttggg ttaagtcccg    1020
caacgagcgc aaccctcgcc ccgtgttgcc agcggattat gccgggaact cacggggac     1080
cgccggggtt aactcggagg aaggtgggga tgacgtcaga tcatcatgcc ccttacgtcc    1140
agggcttcac gcatgctaca atggccggta caacgggatg cgacgcggcg acgcggagcg    1200
gatccctgaa aaccggtctc agttcggatc gcagtctgca actcgactgc gtgaaggcgg    1260
agtcgctagt aatcgcgaat cagcaacgtc gcggtgaatg cgttcccggg ccttgtacac    1320
accgcccgtc aagtcatgaa agtgggcagc acccgaagcc ggtggcctaa ccccttgtgg    1380
ga                                                                   1382

<210> SEQ ID NO 70
<211> LENGTH: 1382
<212> TYPE: DNA
<213> ORGANISM: Unknown
<220> FEATURE:
<223> OTHER INFORMATION: F02

<400> SEQUENCE: 70
tcgaggggca gcattttagt ttgcttgcaa actaaagatg gcgaccggcg cacgggtgag      60
taacacgtat ccaacctgcc gataactcgg ggatagcctt tcgaaagaaa gattaatatc     120
cgatagtata ttaaaaccgc atggttttac tattaaagaa tttcggttat cgatggggat     180
gcgttccatt agtttgttgg cggggtaacg gcccaccaag actacgatgg atagggttc      240
tgagaggaag gtcccccaca ttggaactga gacacggtcc aaactcctac gggaggcagc     300
agtgaggaat attggtcaat ggacgagagt ctgaaccagc caagtagcgt gaaggatgac     360
tgccctatgg gttgtaaact tcttttatat gggaataaag tattccacgt gtgggatttt     420
```

```
gtatgtacca tatgaataag gatcggctaa ctccgtgcca gcagccgcgg taatacggag      480
gatccgagcg ttatccggat ttattgggtt taaagggagc gtaggtggat tgttaagtca      540
gttgtgaaag tttgcggctc aaccgtaaaa ttgcagttga actggcagtc cttgagtaca      600
gtagaggtgg gcggaattcg tggtgtagcg gtgaaatgct tagatatcac gaagaactcc      660
gattgcgaag gcagctcact agactgcaac tgacactgat gctcgaaagt gtgggtatca      720
aacaggatta gataccctgg tagtccacac agtaaacgat gaatactcgc tgtttgcgat      780
atacagtaag cggccaagcg aaagcattaa gtattccacc tggggagtac gccggcaacg      840
gtgaaactca aaggaattga cgggggcccg cacaagcgga ggaacatgtg gtttaattcg      900
atgatacgcg aggaaccttac cccgggctta aattgcattt gaataatctg gaaacaggtt      960
agccgcaagg caaatgtgaa ggtgctgcat ggttgtcgtc agctcgtgcc gtgaggtgtc     1020
ggcttaagtg ccataacgag cgcaacccttatctttagtt actaacaggt catgctgagg     1080
actctagaga gactgccgtc gtaagatgtg aggaaggtgg ggatgacgtc aaatcagcac     1140
ggcccttacg tccggggcta cacacgtgtt acaatggggg gtacagaagg cagctacctg     1200
gcgacaggat gctaatccca aaaacctctc tcagttcgga tcgaagtctg caaccccgact     1260 tcgtgaagct ggattcgcta gtaatcgcgc atcagccatg gcgcggtgaa tacgttcccg     1320
ggccttgtac acaccgcccg tcaagccatg aaagccgggg gtacctgaag tacgtaaccg     1380
ca                                                                     1382

<210> SEQ ID NO 71
<211> LENGTH: 1386
<212> TYPE: DNA
<213> ORGANISM: Unknown
<220> FEATURE:
<223> OTHER INFORMATION: F03

<400> SEQUENCE: 71
aagtcgaggg gcatcaggaa gaaagcttgc tttctttgct ggcgaccggc gcacgggtga       60
gtaacacgta tccaacctgc cctttactcg gggatagcct ttcgaaagaa agattaatac      120
ccgatggtat aattattccg catggtttga ttattaaagg attccggtaa aggatgggga      180
tgcgttccat taggttgttg gtgaggtaac ggctcaccaa gccttcgatg gatagggggtt     240 ctgagaggaa ggtcccccac attggaactg agacacggtc caaactccta cgggaggcag      300
cagtgaggaa tattggtcaa tgggcgatgg cctgaaccag ccaagtagcg tgaaggatga      360
aggctctatg ggtcgtaaac ttcttttata ttagaataaa gtgcagtatg tatactgttt      420
tgtatgtata atatgaataa ggatcggcta actccgtgcc agcagccgcg gtaatacgga      480
ggatccgagc gttatccgga tttattgggt taaagggagc gtaggtgga ctggtaagtc       540 agttgtgaaa gtttgcggct caaccgtaaa attgcagttg atactgtcag tcttgagtac      600
agtagaggtg ggcggaattc gtggtgtagc ggtgaaatgc ttagatatca cgaagaactc      660
cgattgcgaa ggcagctcac tggactgcaa ctgacactga tgctcgaaag tgtgggtatc      720
aaacaggatt agatacctg gtagtccaca cagtaaacga tgaatactcg ctgtttgcga       780
tatacagtaa gcggccaagc gaaagcatta agtattccac tggggagta cgccggcaac       840 ggtgaaactc aaaggaattg acgggggccc gcacaagcgg aggaacatgt ggtttaattc      900
gatgatacgc gaggaacctt acccgggctt aaattgcagt ggaatgatgt ggaaacatgt      960
cagtgagcaa tcaccgctgt gaaggtgctg catggttgtc gtcagctcgt gccgtgaggt     1020
```

-continued

```
gtcggcttaa gtgccataac gagcgcaacc cttatcttta gttactaaca ggtcatgctg    1080
aggactctag agagactgcc gtcgtaagat gtgaggaagg tggggatgac gtcaaatcag    1140
cacggccctt acgtccgggg ctacacacgt gttacaatgg ggggtacaga aggcagctac    1200
ctggtgacag gatgctaatc ccaaaagcct ctctcagttc ggatcgaagt ctgcaacccg    1260
acttcgtgaa gctggattcg ctagtaatcg cgcatcagcc acgcgcggt gaatacgttc     1320 ccgggccttg tacacaccgc ccgtcaagcc atgggagccg ggggtacctg aagtacgtaa    1380
ccgcaa                                                               1386
```

<210> SEQ ID NO 72
<211> LENGTH: 1380
<212> TYPE: DNA
<213> ORGANISM: Unknown
<220> FEATURE:
<223> OTHER INFORMATION: F04

<400> SEQUENCE: 72

```
tcgaggggca gcatgaactt agcttgctaa gtttgatggc gaccggcgca cgggtgagta    60
acacgtatcc aacctgccga tgactcgggg atagcctttc gaaagaaaga ttaatacccg    120
atggcataat tcttccgcat ggtagaatta ttaaagaatt tcggtcatcg atggggatgc    180
gttccattag gttgttggcg gggtaacggc ccaccaagcc ttcgatggat aggggttctg    240
agaggaaggt cccccacatt ggaactgaga cacggtccaa actcctacgg gaggcagcag    300
tgaggaatat tggtcaatgg acgagagtct gaaccagcca gtagcgtgaa ggatgactg     360 ccctatgggt tgtaaacttc ttttatacgg gaataaagtg aggcacgtgt gcctttttgt    420
atgtaccgta tgaataagga tcggctaact ccgtgccagc agccgcggta atacggagga    480
tccgagcgtt atccggattt attgggttta aaggagcgt aggcggacgc ttaagtcagt     540
tgtgaaagtt tgcggctcaa ccgtaaaatt gcagttgata ctgggtgtct tgagtacagt    600
agaggcaggc ggaattcgtg gtgtagcggt gaaatgctta gatatcacga gaactccga     660 ttgcgaaggc agcttgctgg actgtaactg acgctgatgc tcgaaagtgt gggtatcaaa    720
caggattaga taccctggta gtccacacag taaacgatga atactcgctg tttgcgatat    780
acagtaagcg gccaagcgaa agcgttaagt attccacctg gggagtacgc cggcaacggt    840
gaaactcaaa ggaattgacg ggggcccgca caagcggagg aacatgtggt ttaattcgat    900
gatacgcgag gaaccttacc cgggcttgaa ttgcaactga atgatgtgga gacatgtcag    960
ccgcaaggca gttgtgaagg tgctgcatgg ttgtcgtcag ctcgtgccgt gaggtgtcgg    1020
cttaagtgcc ataacgagcg caacccttat cgatagttac catcaggtta tgctggggac    1080
tctgtcgaga ctgccgtcgt aagatgtgag gaaggtgggg atgacgtcaa atcagcacgg    1140
cccttacgtc cggggctaca cacgtgttac aatgggggt acagaaggca gctacacggc    1200
gacgtgatgc taatcccgaa agcctctctc agttcggatt ggagtctgca acccgactcc    1260
atgaagctgg attcgctagt aatcgcgcat cagccacggc gcggtgaata cgttcccggg    1320
ccttgtacac accgcccgtc aagccatgaa agccggggt acctgaagtg cgtaaccgca    1380
```

<210> SEQ ID NO 73
<211> LENGTH: 1384
<212> TYPE: DNA
<213> ORGANISM: Unknown
<220> FEATURE:
<223> OTHER INFORMATION: F05

<400> SEQUENCE: 73

```
agtcgagggg cagcatttca gtttgcttgc aaactggaga tggcgaccgg cgcacgggtg      60
agtaacacgt atccaacctg ccgataactc ggggatagcc tttcgaaaga aagattaata     120
cccgatggta taatcagacc gcatggtctt gttattaaag aatttcggtt atcgatgggg     180
atgcgttcca ttaggcagtt ggtgaggtaa cggctcacca aaccttcgat ggataggggt     240
tctgagagga aggtccccca cattggaact gagacacggt ccaaactcct acgggaggca     300
gcagtgagga atattggtca atgggcgcag gcctgaacca gccaagtagc gtgaaggatg     360
actgccctat gggttgtaaa cttctttat atgggaataa agttttccac gtgtggaatt      420
ttgtatgtac catatgaata aggatcggct aactccgtgc cagcagccgc ggtaatacgg     480
aggatccgag cgttatccgg atttattggg tttaagggga gcgtaggtgg acagttaagt     540
cagttgtgaa agtttgcggc tcaaccgtaa aattgcagtt gatactggct gtcttgagta     600
cagtagaggt gggcggaatt cgtggtgtag cggtgaaatg cttagatatc acgaagaact     660
ccgattgcga aggcagctca ctggactgca actgacactg atgctcgaaa gtgtgggtat     720
caaacaggat tagataccct ggtagtccac acagtaaacg atgaatactc gctgtttgcg     780
atatacagta agcggccaag cgaaagcatt aagtattcca cctggggagt acgccggcaa     840
cggtgaaact caaaggaatt gacggggggcc cgcacaagcg aggaacatg tggtttaatt       900 cgatgatacg cgaggaacct tacccgggct taaattgcat ttgaatatat tggaaacagt     960
atagccgtaa ggcaaatgtg aaggtgctgc atggttgtcg tcagctcgtg ccgtgaggtg    1020
tcggcttaag tgccataacg agcgcaaccc ttatctttag ttactaacag gtcatgctga    1080
ggactctaga gagactgccg tcgtaagatg tgaggaaggt ggggatgacg tcaaatcagc    1140
acggccctta cgtccggggc tacacacgtg ttacaatggg gggtacagaa ggcagctacc    1200
tggtgacagg atgctaatcc caaaagcctc tctcagttcg gatcgaagtc tgcaacccga    1260
cttcgtgaag ctggattcgc tagtaatcgc gcatcagcca tggcgcgtg aatacgttcc      1320 cgggccttgt acacaccgcc cgtcaagcca tgaaagccgg gggtacctga agtacgtaac    1380
cgca                                                                  1384
```

<210> SEQ ID NO 74
<211> LENGTH: 1383
<212> TYPE: DNA
<213> ORGANISM: Unknown
<220> FEATURE:
<223> OTHER INFORMATION: F06

<400> SEQUENCE: 74

```
agtcgagggg cagcatgaac ttagcttgct aagtttgatg gcgaccggcg cacgggtgag      60
taacacgtat ccaacctgcc gatgactcgg ggatagcctt tcgaaagaaa gattaatacc     120
cgatggcata attcttccgc atggtagaat tattaaagaa tttcggtcat cgatgggat      180 gcgttccatt aggttgttgg cggggtaacg gcccaccaag ccttcgatgg ataggggttc     240
tgagaggaag gtcccccaca ttggaactga gacacggtcc aaactcctac gggaggcagc     300
agtgaggaat attggtcaat ggacgagagt ctgaaccagc caagtagcgt gaaggatgac     360
tgccctatgg gttgtaaact tcttttatac gggaataaag tgaggcacgt gtgccttttt     420
gtatgtaccg tatgaataag gatcggctaa ctccgtgcca gcagccgcgg taatacggag     480
gatccgagcg ttatccggat ttattgggtt taagggagc gtaggcggac gcttaagtca      540
gttgtgaaag tttgcggctc aaccgtaaaa ttgcagttga tactgggtgt cttgagtaca     600
```

| | |
|---|---|
| gtagaggcag gcggaattcg tggtgtagcg gtgaaatgct tagatatcac gaagaactcc | 660 |
| gattgcgaag gcagcttgct ggactgtaac tgacgctgat gctcgaaagt gtgggtatca | 720 |
| aacaggatta gataccctgg tagtccacac agtaaacgat gaatactcgc tgtttgcgat | 780 |
| atacagtaag cggccaagcg aaagcgttaa gtattccacc tggggagtac gccggcaacg | 840 |
| gtgaaactca aaggaattga cgggggcccg cacaagcgga ggaacatgtg gtttaattcg | 900 |
| atgatacgcg aggaacctta cccgggcttg aattgcaact gaatgatgtg gagacatgtc | 960 |
| agccgcaagg cagttgtgaa ggtgctgcat ggttgtcgtc agctcgtgcc gtgaggtgtc | 1020 |
| ggcttaagtg ccataacgag cgcaaccctt atcgatagtt accatcaggt tatgctgggg | 1080 |
| actctgtcga gactgccgtc gtaagatgtg aggaaggtgg ggatgacgtc aaatcagcac | 1140 |
| ggcccttacg tccggggcta cacacgtgtt acaatggggg gtacagaagg cagctacacg | 1200 |
| gcgacgtgat gctaatcccg aaagcctctc tcagttcgga ttggagtctg caacccgact | 1260 |
| ccatgaagct ggattcgcta gtaatcgcgc atcagccacg gcgcggtgaa tacgttcccg | 1320 |
| ggccttgtac acaccgcccg tcaagccatg aaagccgggg tacctgaag tgcgtaaccg | 1380 |
| caa | 1383 |

<210> SEQ ID NO 75
<211> LENGTH: 1382
<212> TYPE: DNA
<213> ORGANISM: Unknown
<220> FEATURE:
<223> OTHER INFORMATION: F07

<400> SEQUENCE: 75

| | |
|---|---|
| cgagggcag catttcagtt tgcttgcaaa ctggagatgg cgaccggcgc acgggtgagt | 60 |
| aacacgtatc caacctgccg ataactcggg gatagccttt cgaaagaaag attaatatcc | 120 |
| gatggtatat ttctcccgca tgagagagat attaaagaat ttcggttatc gatggggatg | 180 |
| cgttccatta gtttgttggc ggggtaacgg cccaccaaga ctacgatgga taggggttct | 240 |
| gagaggaagg tcccccacat tggaactgag acacggtcca aactcctacg ggaggcagca | 300 |
| gtgaggaata ttggtcaatg gacgagagtc tgaaccagcc aagtagcgtg aaggatgact | 360 |
| gcccctatggg ttgtaaactt cttttatatg ggaataaaat gttccacgtg tgggattttg | 420 |
| tatgtaccat atgaataagg atcggctaac tccgtgccag cagccgcggt aatacggagg | 480 |
| atccgagcgt tatccggatt tattgggttt aaagggagcg taggtggatt gttaagtcag | 540 |
| ttgtgaaagt ttgcggctca accgtaaaat tgcagttgaa actggcagtc ttgagtacag | 600 |
| tagaggtggg cggaattcgt ggtgtagcgg tgaaatgctt agatatcacg aagaactccg | 660 |
| attgcgaagg cagctcacta gactggtcac tgacactgag gctcgaaagt gtgggtatca | 720 |
| aacaggatta gataccctgg tagtccacac agtaaacgat gaatactcgc tgtttgcgat | 780 |
| atacagcaag cggccaagcg aaagcattaa gtattccacc tggggagtac gccggcaacg | 840 |
| gtgaaactca aaggaattga cgggggcccg cacaagcgga ggaacatgtg gtttaattcg | 900 |
| atgatacgcg aggaacctta cccgggctta aattgcattt gaatatagtg gaaacattat | 960 |
| agccgcaagg caaatgtgaa ggtgctgcat ggttgtcgtc agctcgtgcc gtgaggtgtc | 1020 |
| ggcttaagtg ccataacgag cgcaaccctt atcttcagtt actaacaggt catgctgagg | 1080 |
| actctggaga gactgccgtc gtaagatgtg aggaaggtgg ggatgacgtc aaatcagcac | 1140 |
| ggcccttacg tccggggcta cacacgtgtt acaatggggg gtacagaagg ccgctacctg | 1200 |
| gtgacaggat gccaatccca aaaacctctc tcagttcgga tcgaagtctg caacccgact | 1260 |

```
tcgtgaagct ggattcgcta gtaatcgcgc atcagccatg gcgcggtgaa tacgttcccg    1320
ggccttgtac acaccgcccg tcaagccatg aaagccgggg gtacctgaag tacgtaaccg    1380
ca                                                                   1382
```

<210> SEQ ID NO 76
<211> LENGTH: 1386
<212> TYPE: DNA
<213> ORGANISM: Unknown
<220> FEATURE:
<223> OTHER INFORMATION: F08

<400> SEQUENCE: 76

```
gtcgaggggc atcaggaaga aagcttgctt tctttgctgg cgaccggcgc acgggtgagt     60
aacacgtatc caacctgccc tttactcggg gatagccttt cgaaagaaag attaataccc    120
gatggtataa ttattccgca tggtttgatt attaaaggat tccggtaaag gatggggatg    180
cgttccatta ggttgttggt gaggtaacgg ctcaccaagc cttcgatgga taggggttct    240
gagaggaagg tcccccacat tggaactgag acacggtcca aactcctacg ggaggcagca    300
gtgaggaata ttggtcaatg ggcgatggcc tgaaccagcc aagtagcgtg aaggatgaag    360
gctctatggg tcgtaaactt cttttatatt agaataaagt gcagtatgta tactgttttg    420
tatgtataat atgaataagg atcggctaac tccgtgccag cagccgcggt aatacgagg     480 atccgagcgt tatccggatt tattgggttt aagggagcg taggtggact ggtaagtcag    540
ttgtgaaagt ttgcggctca accgtaaaat tgcagttgat actgtcagtc ttgagtacag    600
tagaggtggg cggaattcgt ggtgtagcgg tgaaatgctt agatatcacg aagaactccg    660
attgcgaagg cagctcactg gactgcaact gacactgatg ctcgaaagtg tgggtatcaa    720
acaggattag ataccctggt agtccacaca gtaaacgatg aatactcgct gtttgcgata    780
tacagtaagc ggccaagcga aagcattaag tattccacct ggggagtacg ccggcaacgg    840
tgaaactcaa aggaattgac gggggcccgc acaagcggag gaacatgtgg tttaattcga    900
tgatacgcga ggaaccttac ccgggcttaa attgcagtgg aatgatgtgg aaacatgtca    960
gtgagcaatc accgctgtga aggtgctgca tggttgtcgt cagctcgtgc cgtgaggtgt   1020
cggcttaagt gccataacga gcgcaacccc tatctttagt tactaacagg tcatgctgag   1080
gactctagag agactgccgt cgtaagatgt gaggaaggtg gggatgacgt caaatcagca   1140
cggcccttac gtccggggct acacacgtgt tacaatgggg ggtacagaag gcagctacct   1200
ggtgacagga tgctaatccc aaaagcctct ctcagttcgg atcgaagtct gcaacccgac   1260
ttcgtgaagc tggattcgct agtaatcgcg catcagccac ggcgcggtga atacgttccc   1320
gggccttgta cacaccgccc gtcaagccat gggagccggg ggtacctgaa gtacgtaacc   1380
gcaagg                                                              1386
```

<210> SEQ ID NO 77
<211> LENGTH: 1384
<212> TYPE: DNA
<213> ORGANISM: Unknown
<220> FEATURE:
<223> OTHER INFORMATION: F09

<400> SEQUENCE: 77

```
gtcgaggggc agcacgatgt agcaatacat tggtggcgac cggcgcacgg gtgagtaacg     60
cgtatgcaac ctacctatca gaggggaata acccggcgaa agtcggacta ataccgcata    120
```

| | |
|---|---|
| aaacaggggt tccacatgga aatatttgtt aaagaattat cgctgataga tgggcatgcg | 180 |
| ttccattaga tagttggtga ggtaacggct caccaagtcc acgatggata ggggttctga | 240 |
| gaggaaggtc ccccacactg gtactgagac acggaccaga ctcctacggg aggcagcagt | 300 |
| gaggaatatt ggtcaatggg cgagagcctg aaccagccaa gtcgcgtgaa ggatgaagga | 360 |
| tctatggttt gtaaacttct tttatatggg aataaagtga ggaacgtgtt ccttttttgta | 420 |
| tgtaccatat gaataagcat cggctaactc cgtgccagca gccgcggtaa tacgaggat | 480 |
| gcgagcgtta tccggattta ttgggtttaa agggtgcgta ggtggttaat taagtcagcg | 540 |
| gtgaaagttt gtggctcaac cataaaattg ccgttgaaac tggttgactt gagtatattt | 600 |
| gaggtaggcg gaatgcgtgg tgtagcggtg aaatgcatag atatcacgca gaactccgat | 660 |
| tgcgaaggca gcttactaaa ctataactga cactgaagca cgaaagcgtg gggatcaaac | 720 |
| aggattagat accctggtag tccacgcagt aaacgatgat tactagctgt ttgcgataca | 780 |
| cagtaagcgg cacagcgaaa gcgttaagta atccacctgg ggagtacgcc ggcaacggtg | 840 |
| aaactcaaag gaattgacgg gggcccgcac aagcggagga acatgtggtt taattcgatg | 900 |
| atacgcgagg aaccttaccc gggtttgaac gcattcggac cggagtggaa acacttcttc | 960 |
| tagcaatagc cgtttgcgag gtgctgcatg gttgtcgtca gctcgtgccg tgaggtgtcg | 1020 |
| gcttaagtgc cataacgagc gcaaccctta tcactagtta ctaacaggtc atgctgagga | 1080 |
| ctctagtgag actgccagcg taagctgtga ggaaggtggg gatgacgtca aatcagcacg | 1140 |
| gcccttacat ccggggcgac acacgtgtta caatggtggg gacaaagggc agctaccgtg | 1200 |
| tgagcggatg ctaatctcca aaccccatct cagttcggat cgaagtctgc aacccgactt | 1260 |
| cgtgaagctg gattcgctag taatcgcgca tcagccatgg cgcggtgaat acgttcccgg | 1320 |
| gccttgtaca caccgcccgt caagccatgg gagttgggggg tacctaaagt ccgtaaccgc | 1380 |
| aagg | 1384 |

<210> SEQ ID NO 78
<211> LENGTH: 1387
<212> TYPE: DNA
<213> ORGANISM: Unknown
<220> FEATURE:
<223> OTHER INFORMATION: F10

<400> SEQUENCE: 78

| | |
|---|---|
| gtcgagcgaa gcaccttgac ggatttcttc ggattgaagc cttggtgact gagcggcgga | 60 |
| cgggtgagta acgcgtgggt aacctgcctc atacaggggg ataacagttg gaaacggctg | 120 |
| ctaataccgc ataagcgcac agtaccgcat ggtacggtgt gaaaaactcc ggtggtatga | 180 |
| gatggacccg cgtctgatta ggtagttggt ggggtaacgg cctaccaagc cgacgatcag | 240 |
| tagccgacct gagagggtga ccggccacat tgggactgag acacggccca aactcctacg | 300 |
| ggaggcagca gtgggggaata ttgcacaatg ggggaaaccc tgatgcagcg acgccgcgtg | 360 |
| agcgatgaag tatttcggta tgtaaagctc tatcagcagg aagaaaatg acggtacctg | 420 |
| actaagaagc cccggctaac tacgtgccag cagccgcggt aatacgtagg ggcaagcgt | 480 |
| tatccggatt tactgggtgt aaagggagcg tagacggcat ggcaagccag atgtgaaagc | 540 |
| ccggggctca accccgggac tgcatttgga actgtcaggc tagagtgtcg gagaggaaag | 600 |
| cggaattcct agtgtagcgg tgaaatgcgt agatattagg aggaacacca gtggcgaagg | 660 |
| cggctttctg gacgatgact gacgttgagg ctcgaaagcg tggggagcaa acaggattag | 720 |
| ataccctggt agtccacgcc gtaaacgatg aatactaggt gtcgggtggc aaagccattc | 780 |

| | |
|---|---:|
| ggtgccgcag caaacgcaat aagtattcca cctggggagt acgttcgcaa gaatgaaact | 840 |
| caaaggaatt gacggggacc cgcacaagcg gtggagcatg tggtttaatt cgaagcaacg | 900 |
| cgaagaacct tacctggtct tgacatccct ctgaccgctc tttaatcgga gctttccttc | 960 |
| gggacagagg agacaggtgg tgcatggttg tcgtcagctc gtgtcgtgag atgttgggtt | 1020 |
| aagtcccgca acgagcgcaa ccctatctt tagtagccag cattttggat gggcactcta | 1080 |
| gagagactgc cagggataac ctggaggaag gtggggatga cgtcaaatca tcatgcccct | 1140 |
| tatgaccagg gctacacacg tgctacaatg gcgtaaacaa agggaagcga gcccgcgagg | 1200 |
| gggagcaaat cccaaaaata acgtctcagt tcggattgta gtctgcaact cgactacatg | 1260 |
| aagctggaat cgctagtaat cgcgaatcag aatgtcgcgg tgaatacgtt cccgggtctt | 1320 |
| gtacaccg cccgtcacac catgggagtc agtaacgccc gaagtcagtg acccaaccgc | 1380 |
| aaggagg | 1387 |

<210> SEQ ID NO 79
<211> LENGTH: 1392
<212> TYPE: DNA
<213> ORGANISM: Unknown
<220> FEATURE:
<223> OTHER INFORMATION: F11

<400> SEQUENCE: 79

| | |
|---|---:|
| cagtcgaacg ggaatcactt cattgagact tcggtggatt tgatttagat tctagtggcg | 60 |
| gacgggtgag taacgcgtgg gtaacctgcc ttatacaggg ggataacagt cagaaatgac | 120 |
| tgctaatacc gcataagcgc acaggaccgc atggtccggt gtgaaaaact ccggtggtat | 180 |
| aagatggacc cgcgttggat tagcttgttg gtggggtaac ggcccaccaa ggcgacgatc | 240 |
| catagccggc ctgagagggt gaacggccac attgggactg agacacggcc cagactccta | 300 |
| cgggaggcag cagtggggaa tattgcacaa tgggggaaac cctgatgcag cgacgccgcg | 360 |
| tgaaggaaga agtatctcgg tatgtaaact tctatcagca gggaagatag tgacggtacc | 420 |
| tgactaagaa gcccggcta actacgtgcc agcagccgcg gtaatacgta ggggcaagc | 480 |
| gttatccgga tttactgggt gtaaagggag cgtagacggt gtggcaagtc tgatgtgaaa | 540 |
| ggcatgggct caacctgtgg actgcattgg aaactgtcat acttgagtgc cggaggggta | 600 |
| agcggaattc ctagtgtagc ggtgaaatgc gtagatatta ggaggaacac cagtggcgaa | 660 |
| ggcggcttac tggacggtaa ctgacgttga ggctcgaaag cgtggggagc aaacaggatt | 720 |
| agataccctg gtagtccacg ccgtaaacga tgaatactag gtgtcgggtg gcatggccat | 780 |
| tcggtgccgt cgcaaacgca gtaagtattc cacctgggga gtacgttcgc aagaatgaaa | 840 |
| ctcaaaggaa ttgacgggga cccgcacaag cggtggagca tgtggtttaa ttcgaagcaa | 900 |
| cgcgaagaac cttaccaagt cttgacatcc ctctgaccga ctcttaaccg agtctttcct | 960 |
| tcgggacaga ggagacaggt ggtgcatggt tgtcgtcagc tcgtgtcgtg agatgttggg | 1020 |
| ttaagtcccg caacgagcgc aaccccctatc ctcagtagcc agcaagttaa gttgggcact | 1080 |
| ctgtggagac tgccagggat aacctggagg aaggcgggga tgacgtcaaa tcatcatgcc | 1140 |
| ccttatgatt tgggctacac acgtgctaca atggcgtaaa caagggaag cgagattgtg | 1200 |
| agatggagca atcccaaaa ataacgtccc agttcggact gtagtctgca acccgactac | 1260 |
| acgaagctgg aatcgctagt aatcgcggat cagaatgccg cggtgaatac gttcccgggt | 1320 |
| cttgtacaca ccgcccgtca caccatggga gtcagtaacg cccgaagtca gtgacctaac | 1380 |

```
tgcaaagaag ga                                                           1392

<210> SEQ ID NO 80
<211> LENGTH: 1388
<212> TYPE: DNA
<213> ORGANISM: Unknown
<220> FEATURE:
<223> OTHER INFORMATION: F12

<400> SEQUENCE: 80
gtcgaacgaa gcacttgaat ggaattcttc ggaaggaagc tcaagtgact gagtggcgga         60
cgggtgagta acgcgtgggt aacctgcctc atacagggggg ataacagtta gaaatgactg       120
ctaataccgc ataagcacac gtgatcgcat gatcgagtgt gaaaaactcc ggtggtatga       180
gatggacccg cgtctgatta gctagttggt ggggtaatgg cccaccaagg cgacgatcag       240
tagccggcct gagagggtga acggccacat tgggactgag acacgcccca aactcctacg       300
ggaggcagca gtggggaata ttgcacaatg ggggaaaccc tgatgcagcg acgccgcgtg       360
aaggatgaag tatttcggta tgtaaacttc tatcagcagg gaagaaaatg acggtacctg       420
actaagaagc cccggctaac tacgtgccag cagccgcggt aatacgtagg gggcaagcgt       480
tatccggatt tactgggtgt aaagggagcg tagacgcag tgcaagtctg aagtgaaagc        540
ccggggctca accccgggac tgctttggaa actgtgcagc tagagtgtcg gagaggcaag       600
cggaattcct agtgtagcgg tgaaatgcgt agatattagg aggaacacca gtggcgaagg       660
cggcttgctg gacgatgact gacgttgagg ctcgaaagcg tggggagcaa acaggattag       720 atacccttggt agtccacgcc gtaaacgatg actactaggt gtcggggagc aaagctcttc      780
ggtgccgcag ccaacgcaat aagtagtcca cctggggagt acgttcgcaa gaatgaaact       840
caaaggaatt gacggggacc cgcacaagcg gtggagcatg tggtttaatt cgaagcaacg       900
cgaagaacct tacctgctct tgacatccct ctgaccgctc tttaatcgga gctttccttc       960
gggacagagg agacaggtgg tgcatggttg tcgtcagctc gtgtcgtgag atgttgggtt      1020
aagtcccgca acgagcgcaa ccctatctt cagtagccag cggcaaggcc gggcactctg      1080
gagagactgc cagggataac ctggaggaag gtggggatga cgtcaaatca tcatgcccct      1140
tatgagcagg gctacacacg tgctacaatg gcgtaaacaa agggaagcag agtcgtgagg      1200
ccgagcaaat cccaaaaata acgtctcagt tcggattgta gtctgcaact cgactacatg      1260
aagctggaat cgctagtaat cgcgaatcag aatgtcgcgg tgaatacgtt cccgggtctt      1320
gtacacaccg cccgtcacac catgggagtc agtaacgccc gaagtcagtg acccaaccgc      1380
aaggaggg                                                              1388

<210> SEQ ID NO 81
<211> LENGTH: 1380
<212> TYPE: DNA
<213> ORGANISM: Unknown
<220> FEATURE:
<223> OTHER INFORMATION: F13

<400> SEQUENCE: 81
gagcgaagcg gtctggagga agttttcgga tggaatccgg attgactgag cggcggacgg         60
gtgagtaacg cgtgggtaac ctgcctcata caggggggata acagttagaa atggctgcta       120
ataccgcata agcgcacagc ttcgcatgga gcagtgtgaa aaactccggt ggtatgagat        180
ggacccgcgt ctgattagct ggttggtaag gtaacggctt accaaggcga cgatcagtag       240
ccgacctgag agggtgaccg gccacattgg gactgagaca cggcccaaac tcctacggga       300
```

```
ggcagcagtg gggaatattg cacaatgggg gaaaccctga tgcagcgacg ccgcgtgagt      360
gaagaagtat ttcggtatgt aaagctctat cagcagggaa gaaaatgacg gtacctgact      420
aagaagcccc ggctaactac gtgccagcag ccgcggtaat acgtagggg caagcgttat      480 ccggatttac tgggtgtaaa gggagcgtag acggcatagc aagtctggag tgaaagcccg      540
gggctcaacc ccgtactgc tttggaaact gttaagctag agtgctggag aggtaagtgg      600
aattcctagt gtagcggtga aatgcgtaga tattaggagg aacaccagtg gcgaaggcgg      660
cttactggac agtaactgac gttgaggctc gaaagcgtgg ggagcaaaca ggattagata      720
ccctggtagt ccacgccgta acgatgaat actaggtgtt ggtgggcaaa gcccatcggt      780
gccgccgcaa acgcaataag tattccacct ggggagtacg ttcgcaagaa tgaaactcaa      840
aggaattgac ggggacccgc acaagcggtg gagcatgtgg tttaattcga agcaacgcga      900
agaaccttac caagtcttga catcggaatg accgggaagt aatgttccct tctctacgga      960
gcattctaga caggtggtgc atggttgtcg tcagctcgtg tcgtgagatg ttgggttaag     1020
tcccgcaacg agcgcaaccc ttatccttag tagccagcag taagatgggc actctaggga     1080
gactgccagg gataacctgg aggaaggtgg ggatgacgtc aaatcatcat gccccttatg     1140
atttgggcta cacacgtgct acaatggcgt aaacaaagag aggcgagcct gcgaggggga     1200
gcgaatctca aaaataacgt cccagttcgg actgtagtct gcaacccgac tacacgaagc     1260
tggaatcgct agtaatcgcg aatcagaatg tcgcggtgaa tacgttcccg ggtcttgtac     1320
acaccgcccg tcacaccatg ggagtcagca acgcccgaag tcagtgactc aaccgaaagg     1380
```

<210> SEQ ID NO 82
<211> LENGTH: 1388
<212> TYPE: DNA
<213> ORGANISM: Unknown
<220> FEATURE:
<223> OTHER INFORMATION: F14

<400> SEQUENCE: 82

```
agtcgaacga agcgcttaaa cggatttctt cggattgaag ttttgtgac tgagtggcgg       60 acgggtgagt aacgcgtggg taacctgcct catacagggg gataacagtt agaaatgact      120
gctaataccg cataagcgca cagtgctgca tggcacagtg tgaaaaactc cggtggtatg      180
agatggaccc gcgtctgatt agctagttgg tggggtaacg gcctaccaag gcgacgatca      240
gtagccggcc tgagagggtg aacggccaca ttgggactga gacacggccc aaactcctac      300
gggaggcagc agtgggggaat attgcacaat ggggggaaacc ctgatgcagc gacgccgcgt     360
gagcgaagaa gtatttcggt atgtaaagct ctatcagcag ggaagaaaat gacggtacct      420
gactaagaag caccggctaa atacgtgcca gcagccgcgg taatacgtat ggtgcaagcg      480
ttatccggat ttactgggtg taagggagc gtagacggtt gtgtaagtct gatgtgaaag      540 cccgggctc aaccccggga ctgcattgga aactatgtaa ctagagtgtc ggagaggtaa      600
gcggaattcc tagtgtagcg gtgaaatgcg tagatattag gaggaacacc agtggcgaag      660
gcggcttact ggacgatcac tgacgttgag gctcgaaagc gtggggagca aacaggatta      720
gataccctgg tagtccacgc cgtaaacgat gactactagg tgtcggggag caaagctctt      780
cggtgccgca gcaaacgcaa taagtagtcc acctggggag tacgttcgca agaatgaaac      840
tcaaaggaat tgacgggac ccgcacaagc ggtggagcat gtggtttaat tcgaagcaac      900
gcgaagaacc ttacctggtc ttgacatccc ggtgaccggc aagtaatgtt gccttctctt      960
```

| | |
|---|---|
| cgggacaccg gtgacaggtg gtgcatggtt gtcgtcagct cgtgtcgtga gatgttgggt | 1020 |
| taagtcccgc aacgagcgca acccctatct tcagtagcca gcatttaagg tgggcactct | 1080 |
| ggagagactg ccagggataa cctggaggaa ggtggggatg acgtcaaatc atcatgcccc | 1140 |
| ttatgaccag ggctacacac gtgctacaat ggcgtaaaca aagggaagcg aacctgtgag | 1200 |
| gggaagcaaa tctcaaaaat aacgtctcag ttcggattgt agtctgcaac tcgactacat | 1260 |
| gaagctggaa tcgctagtaa tcgcgaatca gcatgtcgcg gtgaatacgt tcccgggtct | 1320 |
| tgtacacacc gcccgtcaca ccatgggagt cagtaacgcc cgaagtcagt gacccaaccg | 1380 |
| taaggagg | 1388 |

<210> SEQ ID NO 83
<211> LENGTH: 1391
<212> TYPE: DNA
<213> ORGANISM: Unknown
<220> FEATURE:
<223> OTHER INFORMATION: F15

<400> SEQUENCE: 83

| | |
|---|---|
| cagtcgagcg aagcaccttg acggatttct tcggattgaa gccttggtga ctgagcggcg | 60 |
| gacgggtgag taacgcgtgg gtaacctgcc tcatacaggg ggataacagt tggaaacggc | 120 |
| tgctaatacc gcataagcgc acagtaccgc atggtacggt gtgaaaaact ccggtggtat | 180 |
| gagatggacc cgcgtctgat taggtagttg gtggggtaac ggcctaccaa gccgacgatc | 240 |
| agtagccgac ctgagagggt gaccggccac attgggactg agacacggcc caaactccta | 300 |
| cgggaggcag cagtggggaa tattgcacaa tgggggaaac cctgatgcag cgacgccgcg | 360 |
| tgagcgatga agtatttcgg tatgtaaagc tctatcagca gggaagaaaa tgacggtacc | 420 |
| tgactaagaa gccccggcta actacgtgcc agcagccgcg gtaatacgta gggggcaagc | 480 |
| gttatccgga tttactgggt gtaaagggag cgtagacggc atggcaagcc agatgtgaaa | 540 |
| gcccggggct caaccccggg actgcatttg gaactgtcag gctagagtgt cggagaggaa | 600 |
| agcggaattc ctagtgtagc ggtgaaatgc gtagatatta ggaggaacac cagtggcgaa | 660 |
| ggcggctttc tggacgatga ctgacgttga ggctcgaaag cgtggggagc aaacaggatt | 720 |
| agataccctg gtagtccacg ccgtaaacga tgaatactag gtgtcgggtg caaagccat | 780 |
| tcggtgccgc agcaaacgca ataagtattc cacctgggga gtacgttcgc aagaatgaaa | 840 |
| ctcaaaggaa ttgacgggga cccgcacaag cggtggagca tgtggtttaa ttcgaagcaa | 900 |
| cgcgaagaac cttacctggt cttgacatcc ctctgaccgc tctttaatcg agctttcct | 960 |
| tcgggacaga ggagacaggt ggtgcatggt tgtcgtcagc tcgtgtcgtg agatgttggg | 1020 |
| ttaagtcccg caacgagcgc aaccccctatc tttagtagcc agcattttgg atgggcactc | 1080 |
| tagagagact gccagggata acctggagga aggtggggat gacgtcaaat catcatgccc | 1140 |
| cttatgacca gggctacaca cgtgctacaa tggcgtaaac aaagggaagc gagcccgcga | 1200 |
| gggggagcaa atcccaaaaa taacgtctca gttcggattg tagtctgcaa ctcgactaca | 1260 |
| tgaagctgga atcgctagta atcgcgaatc agaatgtcgc ggtgaatacg ttcccgggtc | 1320 |
| ttgtacacac cgcccgtcac accatgggag tcagtaacgc ccgaagtcag tgacccaacc | 1380 |
| gcaaggaggg a | 1391 |

<210> SEQ ID NO 84
<211> LENGTH: 1391
<212> TYPE: DNA
<213> ORGANISM: Unknown

<220> FEATURE:
<223> OTHER INFORMATION: F16

<400> SEQUENCE: 84

```
agtcgaacga aacaccttat ttgattttct tcggaactga agatttggtg attgagtggc      60
ggacgggtga gtaacgcgtg ggtaacctgc cctgtacagg gggataacag tcagaaatga     120
ctgctaatac cgcataagac cacagcaccg catggtgcag gggtaaaaac tccggtggta     180
caggatggac ccgcgtctga ttagctggtt ggtgaggtaa cggctcacca aggcgacgat     240
cagtagccgg cttgagagag tgaacggcca cattgggact gagacacggc ccaaactcct     300
acgggaggca gcagtgggga atattgcaca atggggaaa ccctgatgca gcgacgccgc      360
gtgagtgaag aagtatttcg gtatgtaaag ctctatcagc agggaagaaa atgacggtac     420
ctgactaaga agccccggct aactacgtgc cagcagccgc ggtaatacgt aggggcaag      480
cgttatccgg aattactggg tgtaaagggt gcgtaggtgg tatggcaagt cagaagtgaa     540
aacccagggc ttaactctgg gactgctttt gaaactgtca gactagagtg caggagaggt     600
aagcggaatt cctagtgtag cggtgaaatg cgtagatatt aggaggaaca tcagtggcga     660
aggcggctta ctggactgaa actgacactg aggcacgaaa gcgtgggag caaacaggat      720
tagatacccc t ggtagtccac gccgtaaacg atgaatacta ggtgtcgggg ccgtagaggc    780
ttcggtgccg cagccaacgc agtaagtatt ccacctgggg agtacgttcg caagaatgaa     840
actcaaagga attgacgggg acccgcacaa gcggtggagc atgtggttta attcgaagca     900
acgcgaagaa ccttacctgg tcttgacatc cttctgaccg gtccttaacc ggaccttttcc    960
ttcgggacag gagtgacagg tggtgcatgg ttgtcgtcag ctcgtgtcgt gagatgttgg    1020
gttaagtccc gcaacgagcg caaccccttat ctttagtagc cagcatataa ggtgggcact   1080
ctagagagac tgccagggat aacctggagg aaggtgggga cgacgtcaaa tcatcatgcc    1140
ccttatgacc agggctacac acgtgctaca atggcgtaaa cagagggaag cagcctcgtg    1200
agagtgagca aatcccaaaa ataacgtctc agttcggatt gtagtctgca actcgactac    1260
atgaagctgg aatcgctagt aatcgcgaat cagaatgtcg cggtgaatac gttcccgggt    1320
cttgtacaca ccgcccgtca caccatggga gtcagtaacg cccgaagtca gtgacccaac    1380
cgtaaggagg g                                                         1391
```

<210> SEQ ID NO 85
<211> LENGTH: 1423
<212> TYPE: DNA
<213> ORGANISM: Unknown
<220> FEATURE:
<223> OTHER INFORMATION: F17
<220> FEATURE:
<221> NAME/KEY: misc_feature
<222> LOCATION: (965)..(966)
<223> OTHER INFORMATION: n is a, c, g, or t
<220> FEATURE:
<221> NAME/KEY: misc_feature
<222> LOCATION: (974)..(976)
<223> OTHER INFORMATION: n is a, c, g, or t
<220> FEATURE:
<221> NAME/KEY: misc_feature
<222> LOCATION: (984)..(986)
<223> OTHER INFORMATION: n is a, c, g, or t
<220> FEATURE:
<221> NAME/KEY: misc_feature
<222> LOCATION: (990)..(991)
<223> OTHER INFORMATION: n is a, c, g, or t
<220> FEATURE:
<221> NAME/KEY: misc_feature
<222> LOCATION: (998)..(1000)

<223> OTHER INFORMATION: n is a, c, g, or t
<220> FEATURE:
<221> NAME/KEY: misc_feature
<222> LOCATION: (1002)..(1004)
<223> OTHER INFORMATION: n is a, c, g, or t
<220> FEATURE:
<221> NAME/KEY: misc_feature
<222> LOCATION: (1101)..(1103)
<223> OTHER INFORMATION: n is a, c, g, or t

<400> SEQUENCE: 85

```
caggatgaac gctggcggcg tgcttaacac atgcaagtcg aacggggaac attttatgga      60
agcttcggtg gaaatagctt gttcctagtg gcggacgggt gagtaacgcg tgggtaacct     120
gcctcacact gggggataac agtcagaaat gactgctaat accgcataag cgcacaggac     180
tgcatgattc agtgtgaaaa actccggtgg tgtgagatgg acccgcgttg gattagccag     240
ttggcagggt aacggcctac caaagcgacg atccatagcc ggcctgagag ggtggacggc     300
cacattggga ctgagacacg gcccagactc ctacgggagg cagcagtggg gaatattgca     360
caatggggga accctgatgc agcgacgccg cgtgaagga agaagtatct cggtatgtaa      420
acttctatca gcagggaaga aaatgacggt acctgactaa gaagcccgg ctaactacgt     480
gccagcagcc gcggtaatac gtaggggca agcgttatcc ggatttactg ggtgtaaagg     540
gagcgtagac ggagcagcaa gtctgatgtg aaaggcgggg gctcaacccc cggactgcat     600
tggaaactgt tgatcttgag taccggagag gtaagcggaa ttcctagtgt agcggtgaaa     660
tgcgtagata ttaggaggaa caccagtggc gaaggcggct tactggacgg taactgacgt     720
tgaggctcga aagcgtgggg agcaaacagg attagatacc ctggtagtcc acgccgtaaa     780
cgatgaatac taggtgtcgg gtggcagagc cattcggtgc cgcagcaaac gcagtaagta     840
ttccacctgg ggagtacgtt cgcaagaatg aaactcaaag gaattgacgg ggacccgcac     900
aagcggtgga gcatgtggtt taattcgaag caacgcgaag aaccttacca agtcttgaca     960
tcccnntgac cggnnngtaa cgtnnncttn ncttcggnnn annngagaca ggtggtgcat    1020
ggttgtcgtc agctcgtgtc gtgagatgtt gggttaagtc ccgcaacgag cgcaacccct    1080
atccttagta gccagcggtt nnnccgggca ctctgaggag actgccaggg ataacctgga    1140
ggaaggcggg gatgacgtca atcatcatg cccccttatga tttgggctac acacgtgcta    1200
caatggcgta aacaaaggga agcgagagtg tgagcttaag caaatcccaa aaataacgtc    1260
ccagttcgga ctgcagtctg caactcgact gcacgaagct ggaatcgcta gtaatcgcgg    1320
atcagaatgc cgcggtgaat acgttcccgg gtcttgtaca caccgcccgt cacaccatgg    1380
gagtcagtaa cgcccgaagt cagtgaccga accgaaagga cgg                      1423
```

<210> SEQ ID NO 86
<211> LENGTH: 1426
<212> TYPE: DNA
<213> ORGANISM: Unknown
<220> FEATURE:
<223> OTHER INFORMATION: F18

<400> SEQUENCE: 86

```
aggatgaacg ctggcggcgt gcctaacaca tgcaagtcga acgaagcaat taaaatgaag      60
ttttcggatg gattttttgat tgactgagtg gcggacgggt gagtaacgcg tggataacct    120
gcctcacact gggggataac agttagaaat gactgctaat accgcataag cgcacagtac    180
cgcatggtac ggtgtgaaaa actccggtgg tgtgagatgg atccgcgtct gattagccag    240
ttggcggggt aacggcccac caaagcgacg atcagtagcc gacctgagag ggtgaccggc    300
```

```
cacattggga ctgagacacg gcccaaactc ctacgggagg cagcagtggg gaatattgca      360
caatgggcga aagcctgatg cagcgacgcc gcgtgagtga agaagtattt cggtatgtaa      420
agctctatca gcagggaaga aaatgacggt acctgactaa gaagcccggg ctaactacgt      480
gccagcagcc gcggtaatac gtaggggcca agcgttatcc ggatttactg ggtgtaaagg      540
gagcgtagac ggcgaagcaa gtctgaagtg aaaacccagg gctcaaccct gggactgctt      600
tggaaactgt tttgctagag tgtcggagag gtaagtggaa ttcctagtgt agcggtgaaa      660
tgcgtagata ttaggaggaa caccagtggc gaaggcggct tactggacga taactgacgt      720
tgaggctcga aagcgtgggg agcaaacagg attagatacc ctggtagtcc acgccgtaaa      780
cgatgaatgc taggtgttgg ggggcaaagc ccttcggtgc cgtcgcaaac gcagtaagca      840
ttccacctgg ggagtacgtt cgcaagaatg aaactcaaag gaattgacgg gacccgcac       900 aagcggtgga gcatgtggtt taattcgaag caacgcgaag aaccttacca agtcttgaca      960
tcctcttgac cggcgtgtaa cggcgccttc ccttcggggc aagagagaca ggtggtgcat     1020
ggttgtcgtc agctcgtgtc gtgagatgtt gggttaagtc ccgcaacgag cgcaacccett    1080 atccttagta gccagcaggt agagctgggc actctaggga gactgccagg ataacctgg      1140 aggaaggtgg ggatgacgtc aaatcatcat gccccttatg atttgggcta cacacgtgct     1200
acaatggcgt aaacaaaggg aagcaagaca gtgatgtgga gcaaatccca aaaataacgt     1260
cccagttcgg actgtagtct gcaacccgac tacacgaagc tggaatcgct agtaatcgcg     1320
aatcagaatg tcgcggtgaa tacgttcccg ggtcttgtac acaccgcccg tcacaccatg     1380
ggagtcagca acgcccgaag tcagtgaccc aactcgcaag agaggg                   1426

<210> SEQ ID NO 87
<211> LENGTH: 1420
<212> TYPE: DNA
<213> ORGANISM: Unknown
<220> FEATURE:
<223> OTHER INFORMATION: F19
<220> FEATURE:
<221> NAME/KEY: misc_feature
<222> LOCATION: (1402)..(1402)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t

<400> SEQUENCE: 87
cggatgaacg ctggcggcgt gcttaacaca tgcaagtcga acggggatta ttttgacaga       60
gacttcggtt gaagtcgtta taatcctagt ggcggacggg tgagtaacgc gtgggtaacc      120
tgcctcacac tggggataa cagtcagaaa tgactgctaa taccgcataa gcgcacggga       180
ctgcatggtt cagtgtgaaa actccggtg gtgtgagatg acccgcgtt ggattagcca        240 gttggcaggt aacggccta ccaaagcgac gatccatagc cggcctgaga gggtggacgg       300
ccacattggg actgagacac ggcccagact cctacgggag gcagcagtgg ggaatattgc      360
acaatggggg aaaccctgat gcagcgacgc cgcgtgaagg aagaagtatc tcggtatgta     420
aacttctatc agcagggaag aaaatgacgg tacctgacta agaagcccg gctaactacg      480 tgccagcagc cgcggtaata cgtaggggc aagcgttatc cggattact gggtgtaaag      540 ggagcgtaga cggagcagca agtctgatgt gaaaggcggg ggctcaaccc ccggactgca     600
ttggaaactg ttgatcttga gtaccggaga ggtaagcgga attcctagtg tagcggtgaa    660
```

```
atgcgtagat attaggagga acaccagtgg cgaaggcggc ttactggacg gtaactgacg      720
tgaggctcga aagcgtggga gcaaacagga ttagatacCC tggtagtcca cgccgtaaac      780
gatgaatact aggtgtcggg tggcagagcc attcggtgcc gcagcaaacg cagtaagtat      840
tccacctggg gagtacgttc gcaagaatga aactcaaagg aattgacggg acccgcaca       900
agcggtggag catgtggttt aattcgaagc aacgcgaaga accttaccaa gtcttgacat      960
ccctctgacc ggtgagtaac gtcacctttc cttcgggaca gaggagacag gtggtgcatg     1020
gttgtcgtca gctcgtgtcg tgagatgttg ggttaagtcc cgcaacgagc gcaaccccta     1080
tccttagtag ccagcggttt ggccgggcac tctgaggaga ctgccaggga taacctggag     1140
gaaggcgggg atgacgtcaa atcatcatgc cccttatgat ttgggctaca cacgtgctac     1200
aatggcgtaa acaaagggaa gcgagagtgt gagcttaagc aaatcccaaa ataacgtcc      1260
cagttcggac tgcagtctgc aactcgactg cacgaagctg gaatcgctag taatcgcgga     1320
tcagaatgcc gcggtgaata cgttcccggg tcttgtacac accgcccgtc acaccatggg     1380
agtcagtaac gcccgaagtc antnaccgaa ccgaaaggac                            1420
```

```
<210> SEQ ID NO 88
<211> LENGTH: 1397
<212> TYPE: DNA
<213> ORGANISM: Unknown
<220> FEATURE:
<223> OTHER INFORMATION: F20
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (947)..(947)
<223> OTHER INFORMATION: n is a, c, g, or t
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (965)..(968)
<223> OTHER INFORMATION: n is a, c, g, or t

<400> SEQUENCE: 88
```

```
agtcgaacga agtttcgagg aagcttgctt ccaaagagac ttagtggcga acgggtgagt       60
aacacgtagg taacctgccc atgtgtccgg gataactgct ggaaacggta gctaaaaccg      120
gataggtata cagagcgcat gctcagtata ttaaagcgcc catcaaggcg tgaacatgga      180
tggacctgcg gcgcattagc tagttggtga ggtaacggcc caccaaggcg atgatgcgta      240
gccggcctga gagggtaaac ggccacattg ggactgagac acggcccaaa ctcctacggg      300
aggcagcagt agggaatttt cgtcaatggg ggaaaccctg aacgagcaat gccgcgtgag      360
tgaagaaggt cttcggatcg taaagctctg ttgtaagtga agaacggctc atagaggaaa      420
tgctatggga gtgacggtag cttaccagaa agccacggct aactacgtgc cagcagccgc      480
ggtaatacgt aggtggcaag cgttatccgg aatcattggg cgtaaagggt gcgtaggtgg      540
cgtactaagt ctgtagtaaa aggcaatggc tcaaccattg taagctatgg aaactggtat      600
gctggagtgc agaagagggc gatggaattc catgtgtagc ggtaaaatgc gtagatatat      660
ggaggaacac cagtggcgaa ggcggtcgcc tggtctgtaa ctgacactga ggcacgaaag      720
cgtgggagc aaataggatt agataccta gtagtccacg ccgtaaacga tgagaactaa       780
gtgttggagg aattcagtgc tgcagttaac gcaataagtt ctccgcctgg ggagtatgca      840
```

```
cgcaagtgtg aaactcaaag gaattgacgg gggcccgcac aagcggtgga gtatgtggtt      900
taattcgaag caacgcgaag aaccttacca ggccttgaca tgganananaaa tantctagag    960 atagnnnnat aattatggat cacacaggtg gtgcatggtt gtcgtcagct cgtgtcgtga     1020
gatgttgggt taagtcccgc aacgagcgca acccttgtcg catgttacca gcatcaagtt    1080
ggggactcat gcgagactgc cggtgacaaa ccggaggaag gtggggatga cgtcaaatca    1140
tcatgcccct tatggcctgg gctacacacg tactacaatg gcgaccacaa agagcagcga    1200
cacagtgatg tgaagcgaat ctcataaagg tcgtctcagt tcggattgaa gtctgcaact    1260
cgacttcatg aagtcggaat cgctagtaat cgcagatcag catgctgcgg tgaatacgtt    1320
ctcgggcctt gtacacaccg cccgtcaaac catgggagtc agtaatacc c gaagccggtg   1380 gcataaccgt aaggagt                                                   1397

<210> SEQ ID NO 89
<211> LENGTH: 1392
<212> TYPE: DNA
<213> ORGANISM: Unknown
<220> FEATURE:
<223> OTHER INFORMATION: F21

<400> SEQUENCE: 89
agtcgagcga agcacttaag tggatctctt cggattgaag cttatttgac tgagcggcgg      60
acgggtgagt aacgcgtggg taacctgcct catacagggg gataacagtt agaaatggct    120
gctaataccg cataagcgca caggaccgca tggtctggtg tgaaaaactc cggtggtatg    180
agatggaccc gcgtctgatt agctagttgg aggggtaacg gcccaccaag gcgacgatca    240
gtagccggcc tgagagggtg aacggccaca ttgggactga gacacggccc agactcctac    300
gggaggcagc agtggggaat attgcacaat ggggaaacc ctgatgcagc gacgccgcgt    360
gaaggaagaa gtatctcggt atgtaaactt ctatcagcag gaagaaaat gacggtacct    420 gactaagaag ccccggctaa ctacgtgcca gcagccgcgg taatacgtag ggggcaagcg    480
ttatccggat ttactgggtg taaagggagc gtagacggaa gagcaagtct gatgtgaaag    540
gctgggcctt aaccccagga ctgcattgga aactgttttt ctagagtgcc ggagaggtaa    600
gcggaattcc tagtgtagcg gtgaaatgcg tagatattag gaggaacacc agtggcgaag    660
gcggcttact ggacggtaac tgacgttgag gctcgaaagc gtggggagca acaggatta    720 gataccctgg tagtccacgc cgtaaacgat gaatactagg tgtcgggtgg caaagccatt    780
cggtgccgca gcaaacgcaa taagtattcc acctggggag tacgttcgca agaatgaaac    840
tcaaaggaat tgacggggac ccgcacaagc ggtggagcat gtggtttaat tcgaagcaac    900
gcgaagaacc ttaccaagtc ttgacatccc tctgaccggc cgtaacggg gccttccctt    960 cggggcagag gagacaggtg gtgcatggtt gtcgtcagct cgtgtcgtga gatgttgggt   1020
taagtcccgc aacgagcgca acccctatcc ttagtagcca gcaggtgaag ctgggcactc   1080
tagggagact gccggggata acccggagga aggcgggac gacgtcaaat catcatgccc   1140
cttatgattt gggctacaca cgtgctacaa tggcgtaaac aaagggaagc gagacagcga   1200
tgttgagcaa atcccaaaaa taacgtccca gttcggactg cagtctgcaa ctcgactgca   1260
cgaagctgga atcgctagta atcgcgaatc agaatgtcgc ggtgaatacg ttcccgggtc   1320
ttgtacacac cgcccgtcac accatggag tcagtaacgc ccgaagtcag tgacccaacc   1380
ttataggagg ga                                                      1392
```

```
<210> SEQ ID NO 90
<211> LENGTH: 1382
<212> TYPE: DNA
<213> ORGANISM: Unknown
<220> FEATURE:
<223> OTHER INFORMATION: F22

<400> SEQUENCE: 90
gaacgaagca ttttaggatg aagttttcgg atggattctg agatgactga gtggcggacg      60
ggtgagtaac acgtggataa cctgcctcac actgggggac aacagttaga aatgactgct     120
aataccgcat aagcgcacag taccgcatgg tacggtgtga aaaactccgg tggtgtgaga     180
tggatccgcg tctgattagc cagttggcgg ggtaacggcc caccaaagcg acgatcagta     240
gccgacctga gagggtgacc ggccacattg ggactgagac acggcccaaa ctcctacggg     300
aggcagcagt ggggaatatt gcacaatggg cgaaagcctg atgcagcgac gccgcgtgag     360
tgaagaagta tttcggtatg taaagctcta tcagcaggga agataatgac ggtacctgac     420
taagaagccc cggctaacta cgtgccagca gccgcggtaa tacgtagggg gcaagcgtta     480
tccggattta ctgggtgtaa agggagcgta gacggcatgg caagtctgaa gtgaaaaccc     540
agggctcaac cctgggactg ctttggaaac tgtcaagcta gagtgcagga gaggtaagtg     600
gaattcctag tgtagcggtg aaatgcgtag atattaggag gaacaccagt ggcgaaggcg     660
gcttactgga ctgtaactga cgttgaggct cgaaagcgtg gggagcaaac aggattagat     720
accctggtag tccacgccgt aaacgatgag tgctaggtgt tggggggcaa agcccttcgg     780
tgccgtcgca aacgcaataa gcactccacc tggggagtac gttcgcaaga atgaaactca     840
aaggaattga cggggacccg cacaagcggt ggagcatgtg gtttaattcg aagcaacgcg     900 aagaaccctta ccaagtcttg acatcctctt gaccggcgtg taacgcgcc tttccttcgg     960 gacaagagag acaggtggtg catggttgtc gtcagctcgt gtcgtgagat gttgggttaa    1020
gtcccgcaac gagcgcaacc cttatcctta gtagccagca ttaagatggg cactctaggg    1080
agactgccag gacaacctg gaggaaggtg gggatgacgt caaatcatca tgccccttat    1140
gatttgggct acacacgtgc tacaatggcg taaacaaagg gaagcgaccc tgcgaaggtg    1200
agcaaatctc aaaaataacg tcccagttcg gactgtagtc tgcaacccga ctacacgaag    1260
ctggaatcgc tagtaatcgc gaatcagaat gtcgcggtga atacgttccc gggtcttgta    1320
cacaccgccc gtcacaccat gggagtcagc aacgcccgaa gtcagtgacc caaccgaaag    1380
ga                                                                   1382

<210> SEQ ID NO 91
<211> LENGTH: 1386
<212> TYPE: DNA
<213> ORGANISM: Unknown
<220> FEATURE:
<223> OTHER INFORMATION: F23

<400> SEQUENCE: 91
tcgaacgaag cactttaccg gatttcttcg ggatgaaagt tttgtgactg agtggcggac      60
gggtgagtaa cgcgtgggta acctgcctca tacaggggga taacagttag aaatgactgc     120
taataccgca taagaccaca ggattgcatg atccggtggt aaaaactccg gtggtatgag     180
atggacccgc gtctgattag gtagttggtg gggtaacggc tcaccaagcc gacgatcagt     240
agccgacctg agagggtgac cggccacatt gggactgaga cacggcccaa actcctacgg     300
gaggcagcag tggggaatat tgcacaatgg gggaaaccct gatgcagcga cgccgcgtga     360
```

```
gcgatgaagt atttcggtat gtaaagctct atcagcaggg aagaaaatga cggtacctga      420
ctaagaagca ccggctaaat acgtgccagc agccgcggta atacgtatgg tgcaagcgtt      480
atccggattt actgggtgta aagggagcgt agacggagag gcaagtctga tgtgaaaacc      540
cggggctcaa ccccgggact gcattggaaa ctgttttcct agagtgtcgg agaggtaagt      600
ggaattccta gtgtagcggt gaaatgcgta gatattagga ggaacaccag tggcgaaggc      660
ggcttactgg acgatgactg acgttgaggc tcgaaagcgt ggggagcaaa caggattaga      720
taccctggta gtccacgccg taaacgatga ctgctaggtg tcgggaggca aagcctttcg      780
gtgccgcagc aaacgcaata agcagtccac ctggggagta cgttcgcaag aatgaaactc      840
aaaggaattg acgggaccc gcacaagcgg tggagcatgt ggtttaattc gaagcaacgc      900
gaagaacctt acctgccctt gacatccggc tgaccggcga gtaatgtcgc ctttccttcg      960
ggacagccga gacaggtggt gcatggttgt cgtcagctcg tgtcgtgaga tgttgggtta     1020
agtcccgcaa cgagcgcaac ccttatcttt agtagccagc atttcggatg gcactctag      1080 agagactgcc agggataacc tggaggaagg tggggatgac gtcaaatcat catgccctt      1140 atgggcaggg ctacacacgt gctacaatgg cgtaaacaaa gggaggcaag cctgcgaggg     1200
tgagcaaatc ccaaaaataa cgtctcagtt cggattgtag tctgcaactc gactacatga     1260
agctggaatc gctagtaatc gcgaatcaga atgtcgcggt gaatacgttc ccgggtcttg     1320 tacaccgc ccgtcacacc atgggagttg gtaacgcccg aagtcagtga cccaaccgta     1380
aggagg                                                                1386

<210> SEQ ID NO 92
<211> LENGTH: 1391
<212> TYPE: DNA
<213> ORGANISM: Unknown
<220> FEATURE:
<223> OTHER INFORMATION: F24
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (936)..(940)
<223> OTHER INFORMATION: n is a, c, g, or t
<220> FEATURE:
<221> NAME/KEY: misc_feature
<222> LOCATION: (948)..(950)
<223> OTHER INFORMATION: n is a, c, g, or t
<220> FEATURE:
<221> NAME/KEY: misc_feature
<222> LOCATION: (953)..(957)
<223> OTHER INFORMATION: n is a, c, g, or t
<220> FEATURE:
<221> NAME/KEY: misc_feature
<222> LOCATION: (968)..(970)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t

<400> SEQUENCE: 92
gtcgaacgaa gttacgacag aggaagtttt cggatggaat cggtataact tagtggcgga       60
cgggtgagta acgcgtggga aacctgccct gtaccggggg ataacactta gaaataggtg      120
ctaataccgc ataagcgcac ggaaccgcat ggttgtgtgt gaaaaactcc ggtggtacag      180
gatggtcccg cgtctgatta gccagttggc agggtaacgg cctaccaaag cgacgatcag      240
```

```
tagccggcct gagagggtga acggccacat tgggactgag acacggccca aactcctacg      300
ggaggcagca gtggggaata ttgcacaatg ggggaaaccc tgatgcagcg acgccgcgtg      360
agtgaagaag tatttcggta tgtaaagctc tatcagcagg gaagaaaatg acggtacctg      420
actaagaagc cccggctaac tacgtgccag cagccgcggt aatacgtagg ggcaagcgt       480 tatccggatt tactgggtgt aaagggagcg tagacggcat ggcaagccag atgtgaaaac      540
ccagggctca accttgggat tgcatttgga actgccaggc tggagtgcag gagaggtaag      600
cggaattcct agtgtagcgg tgaaatgcgt agatattagg aggaacacca gtggcgaagg      660
cggcttactg gactgtaact gacgttgagg ctcgaaagcg tggggagcaa acaggattag      720
ataccctggt agtccacgcg gtaaacgatg attgctaggt gtaggtgggt atggacccat      780
cggtgccgca gctaacgcaa taagcaatcc acctggggag tacgttcgca agaatgaaac      840
tcaaaggaat tgacggggac ccgcacaagc ggtggagcat gtggtttaat tcgaagcaac      900
gcgaagaacc ttaccaagtc ttgacatccc nttgannnnn ttgtaaannn gcnnnnnctt      960
cgggacannn gagacaggtg gtgcatggtt gtcgtcagct cgtgtcgtga atgttgggt       1020 taagtcccgc aacgagcgca acccttattc ttagtagcca gcaggtgnag ctgggcactc      1080
taaggagact gccggggata acccggagga aggcggggat gacgtcaaat catcatgccc      1140
cttatgattt gggctacaca cgtgctacaa tggcgtaaac aaagggaagc gagacagtga      1200
tgtggagcaa atcccagaaa taacgtctca gttcggattg tagtctgcaa ctcgactaca      1260
tgaagctgga atcgctagta atcgcgaatc agcatgtcgc ggtgaatacg ttcccgggtc      1320
ttgtacacac cgcccgtcac accatgggag ttggaaatgc ccgaagtctg tgacctaacc      1380
gaaagggagg a                                                          1391
```

<210> SEQ ID NO 93
<211> LENGTH: 1388
<212> TYPE: DNA
<213> ORGANISM: Unknown
<220> FEATURE:
<223> OTHER INFORMATION: F25

<400> SEQUENCE: 93

```
gtcgaacgaa gcactttacc ggatttcttc gggatgaaag ttttgtgact gagtggcgga      60
cgggtgagta acgcgtgggt aacctgcctc atacagggggg ataacagtta gaaatgactg     120
ctaataccgc ataagaccac aggattgcat gatccggtgg taaaaactcc ggtggtatga      180
gatggacccg cgtctgatta ggtagttggt ggggtaacgg ctcaccaagc cgacgatcag      240
tagccgacct gagagggtga ccggccacat tgggactgag acacggccca aactcctacg      300
ggaggcagca gtggggaata ttgcacaatg ggggaaaccc tgatgcagcg acgccgcgtg      360
agcgatgaag tatttcggta tgtaaagctc tatcagcagg gaagaaaatg acggtacctg      420
actaagaagc accggctaaa tacgtgccag cagccgcggt aatacgtatg gtgcaagcgt      480
tatccggatt tactgggtgt aaagggagcg tagacggaga ggcaagtctg atgtgaaaac      540
ccggggctca accccgggac tgcattggaa actgtttttc tagagtgtcg gagaggtaag      600
tggaattcct agtgtagcgg tgaaatgcgt agatattagg aggaacacca gtggcgaagg      660
cggcttactg gacgatgact gacgttgagg ctcgaaagcg tggggagcaa acaggattag      720
ataccctggt agtccacgcc gtaaacgatg actgctaggt gtcgggaggc aaagcctttc      780
ggtgccgcag caaacgcaat aagcagtcca cctggggagt acgttcgcaa gaatgaaact      840
caaaggaatt gacggggacc cgcacaagcg gtggagcatg tggtttaatt cgaagcaacg      900
```

```
cgaagaacct tacctgccct tgacatccgg ctgaccggcg agtaatgtcg cctttccttc    960
gggacagccg agacaggtgg tgcatggttg tcgtcagctc gtgtcgtgag atgttgggtt   1020
aagtcccgca acgagcgcaa cccttatctt tagtagccag catttcggat gggcactcta   1080
gagagactgc cagggataac ctggaggaag gtggggatga cgtcaaatca tcatgcccct   1140
tatgggcagg gctacacacg tgctacaatg gcgtaaacaa agggaggcaa gcctgcgagg   1200
gtgagcaaat cccaaaaata acgtctcagt tcggattgta gtctgcaact cgactacatg   1260
aagctggaat cgctagtaat cgcgaatcag aatgtcgcgg tgaatacgtt cccgggtctt   1320
gtacacaccg cccgtcacac catgggagtt ggtaacgccc gaagtcagtg acccaaccgt   1380
aaggaggg                                                            1388
```

<210> SEQ ID NO 94
<211> LENGTH: 1386
<212> TYPE: DNA
<213> ORGANISM: Unknown
<220> FEATURE:
<223> OTHER INFORMATION: F26

<400> SEQUENCE: 94

```
tcgaacgggg tgctcatgac ggaggattcg tccaacggat tgagttacct agtggcggac     60
gggtgagtaa cgcgtgagga acctgccttg gagaggggaa taacactccg aaaggagtgc    120
taataccgca tgatgcagtt gggtcgcatg gctctgactg ccaaagattt atcgctctga    180
gatggcctcg cgtctgatta gctagtaggc ggggtaacgg cccacctagg cgacgatcag    240
tagccggact gagaggttga ccggccacat tgggactgag acacggccca gactcctacg    300
ggaggcagca gtggggaata ttgggcaatg gcgcaagcc tgacccagca cgccgcgtg     360 aaggaagaag gctttcgggt tgtaaacttc ttttgtcggg gacgaaacaa atgacggtac    420
ccgacgaata agccacggct aactacgtgc cagcagccgc ggtaatacgt aggtggcaag    480
cgttatccgg atttactggg tgtaaagggc gtgtaggcgg gattgcaagt cagatgtgaa    540 aactggggc tcaacctcca gcctgcattt gaaactgtag ttcttgagtg ctggagaggc    600
aatcggaatt ccgtgtgtag cggtgaaatg cgtagatata cggaggaaca ccagtggcga    660
aggcggattg ctggacagta actgacgctg aggcgcgaaa gcgtgggag caaacaggat    720 tagatacccct ggtagtccac gccgtaaacg atggatacta ggtgtggggg gtctgacccc    780
ctccgtgccg cagttaacac aataagtatc ccacctgggg agtacgatcg caaggttgaa    840
actcaaagga attgacgggg gcccgcacaa gcggtggagt atgtggttta attcgaagca    900
acgcgaagaa ccttaccagg gcttgacatc ccactaacga agcagagatg cattaggtgc    960
ccttcgggga aagtggagac aggtggtgca tggttgtcgt cagctcgtgt cgtgagatgt   1020
tgggttaagt cccgcaacga gcgcaaccct tattgttagt tgctacgcaa gagcactcta   1080
gcgagactgc cgttgacaaa acggaggaag gtggggacga cgtcaaatca tcatgcccct   1140
tatgtcctgg gccacacacg tactacaatg gtggttaaca gagggaggca ataccgcgag   1200
gtggagcaaa tccctaaaag ccatcccagt tcggattgca ggctgaaacc cgcctgtatg   1260
aagttggaat cgctagtaat cgcggatcag catgccgcgg tgaatacgtt cccgggcctt   1320
gtacacaccg cccgtcacac catgagagtc gggaacaccc gaagtccgta gcctaaccgc   1380
aaggag                                                              1386
```

<210> SEQ ID NO 95

```
<211> LENGTH: 1392
<212> TYPE: DNA
<213> ORGANISM: Unknown
<220> FEATURE:
<223> OTHER INFORMATION: F27

<400> SEQUENCE: 95
cagtcgaacg ggaatcactt cattgagact tcggtggatt tgatttagat tctagtggcg      60
gacgggtgag taacgcgtgg gtaacctgcc ttatacaggg ggataacagt cagaaatgac     120
tgctaatacc gcataagcgc acaggaccgc atggtccggt gtgaaaaact ccggtggtat     180
aagatggacc cgcgttggat tagcttgttg gtggggtaac ggcccaccaa ggcgacgatc     240
catagccggc ctgagagggt gaacggccac attgggactg agacacggcc cagactccta     300
cgggaggcag cagtggggaa tattgcacaa tgggggaaac cctgatgcag cgacgccgcg     360
tgaaggaaga agtatctcgg tatgtaaact tctatcagca gggaagatag tgacggtacc     420
tgactaagaa gccccggcta actacgtgcc agcagccgcg gtaatacgta ggggcaagc     480
gttatccgga tttactgggt gtaaagggag cgtagacggt gtggcaagtc tgatgtgaaa     540
ggcatgggct caacctgtgg actgcattgg aaactgtcat acttgagtgc cggaggggta     600
agcggaattc ctagtgtagc ggtgaaatgc gtagatatta ggaggaacac cagtggcgaa     660
ggcggcttac tggacggtaa ctgacgttga ggctcgaaag cgtggggagc aaacaggatt     720
agataccctg gtagtccacg ccgtaaacga tgaatactag gtgtcgggtg gcatggccat     780
tcggtgccgt cgcaaacgca gtaagtattc cacctggggg agtacgttcg caagaatgaa     840
actcaaagga attgacgggg acccgcacaa gcggtggagc atgtggttta attcgaagca     900
acgcgaagaa ccttaccaag tcttgacatc cctctgaccg actcttaacc gagtcttttcc    960
ttcgggacag aggagacagg tggtgcatgg ttgtcgtcag ctcgtgtcgt gagatgttgg    1020
gttaagtccc gcaacgagcg caaccccctat cctcagtagc cagcaagtta agttgggcac    1080
tctgtggaga ctgccaggga taacctggag gaaggcgggg atgacgtcaa atcatcatgc    1140
cccttatgat ttgggctaca cacgtgctac aatggcgtaa acaaagggaa gcgagattgt    1200
gagatggagc aaatcccaaa aataacgtcc cagttcggac tgtagtctgc aacccgacta    1260
cacgaagctg gaatcgctag taatcgcgga tcagaatgcc gcggtgaata cgttcccggg    1320
tcttgtacac accgcccgtc acaccatggg agtcagtaac gcccgaagtc agtgacctaa    1380
ctgcaaagaa gg                                                       1392

<210> SEQ ID NO 96
<211> LENGTH: 1394
<212> TYPE: DNA
<213> ORGANISM: Unknown
<220> FEATURE:
<223> OTHER INFORMATION: F28
<220> FEATURE:
<221> NAME/KEY: misc_feature
<222> LOCATION: (25)..(25)
<223> OTHER INFORMATION: n is a, c, g, or t

<400> SEQUENCE: 96
tgcagtcgag cgatactctt cgganaagag cggcggacgg gtgagtaacg cgtgggtaac      60
ctgccctgta cacacggata acataccgaa aggtatgcta atacgggata acataagaaa     120
ttcgcatgtt tttcttatca aagctccggc ggtacaggat ggaccgcgt ctgattagct     180
agttggtgag gtaacggctc accaaggcga cgatcagtag ccgacctgag agggtgatcg     240
gccacattgg aactgagaca cggtccaaac tcctacggga ggcagcagtg gggaatattg     300
```

```
cacaatgggc gaaagcctga tgcagcaacg ccgcgtgagc gatgaaggcc ttcgggtcgt    360
aaagctctgt cctcaaggaa gataatgacg gtacttgagg aggaagcccc ggctaactac    420
gtgccagcag ccgcggtaat acgtaggggg ctagcgttat ccggatttac tgggcgtaaa    480
gggtgcgtag gcggtctttt aagtcaggag tgaaaggcta cggctcaacc gtagtaagct    540
cttgaaactg gaggacttga gtgcaggaga ggagagtgga attcctagtg tagcggtgaa    600
atgcgtagat attaggagga acaccagtag cgaaggcggc tctctggact gtaactgacg    660
ctgaggcacg aaagcgtggg gagcaaacag gattagatac cctggtagtc cacgccgtaa    720
acgatgagta ctagctgtcg gaggttaccc ccttcggtgg cgcagctaac gcattaagta    780
ctccgcctgg ggagtacgct cgcaagagtg aaactcaaag gaattgacgg gacccgcac    840 aagtagcgga gcatgtggtt taattcgaag caacgcgaag aaccttacct aagcttgaca    900
tccttttgac cgatgcctaa tcgcatcttt cccttcgggg acagaagtga caggtggtgc    960
atggttgtcg tcagctcgtg tcgtgagatg ttgggttaag tcccgcaacg agcgcaaccc   1020
ttgcctttag ttgccatcat taagttgggc actctagagg gactgccagg gataacctgg   1080
aggaaggtgg ggatgacgtc aaatcatcat gccccttatg cttagggcta cacacgtgct   1140
acaatgggtg gtacagaggg cagcgaagtc gtgaggccaa gctaatccct aaagccatt    1200 ctcagttcgg attgtaggct gaaactcgcc tacatgaagc tggagttact agtaatcgca   1260
gatcaaaatg ctgcggtgaa tgcgttcccg ggtcttgtac acaccgcccg tcacaccatg   1320
ggagttgggg gcgcccgaag ccggctagct aaccttttgg aagcggtcgt cgaaggtgaa   1380
accaataact gggg                                                    1394

<210> SEQ ID NO 97
<211> LENGTH: 1392
<212> TYPE: DNA
<213> ORGANISM: Unknown
<220> FEATURE:
<223> OTHER INFORMATION: F29
<220> FEATURE:
<221> NAME/KEY: misc_feature
<222> LOCATION: (1046)..(1046)
<223> OTHER INFORMATION: n is a, c, g, or t
<220> FEATURE:
<221> NAME/KEY: misc_feature
<222> LOCATION: (1071)..(1072)
<223> OTHER INFORMATION: n is a, c, g, or t

<400> SEQUENCE: 97
cagtcgagcg aagcactttt gcggatttct tcggattgaa gcaattgtga ctgagcggcg     60
gacgggtgag taacgcgtgg gtaacctgcc tcatacaggg ggataacagt tggaaacggc    120
tgctaatacc gcataagcgc acagtaccgc atggtaccgt gtgaaaaact ccggtggtat    180
gagatggacc cgcgtctgat tagctagttg gtggggtaac ggcctaccaa ggcgacgatc    240
agtagccgac ctgagagggt gaccggccac attgggactg agacacggcc caaactccta    300
cgggaggcag cagtggggaa tattgcacaa tgggggaaac cctgatgcag cgacgccgcg    360
tgagcgatga agtatttcgg tatgtaaagc tctatcagca gggaagaaaa tgacggtacc    420
tgactaagaa gccccggcta actacgtgcc agcagccgcg gtaatacgta gggggcaagc    480
gttatccgga tttactgggt gtaaagggag cgtagacggc atggcaagcc agatgtgaaa    540
gcccggggct caaccccggg actgcatttg gaactgtcag gctagagtgt cggagaggaa    600
agcggaattc ctagtgtagc ggtgaaatgc gtagatatta ggaggaacac cagtggcgaa    660
```

| | |
|---|---|
| ggcggctttc tggacgatga ctgacgttga ggctcgaaag cgtggggagc aaacaggatt | 720 |
| agataccctg gtagtccacg ccgtaaacga tgaatactag gtgtcgggtg caaagccat | 780 |
| tcggtgccgc agcaaacgca ataagtattc cacctgggga gtacgttcgc aagaatgaaa | 840 |
| ctcaaaggaa ttgacgggga cccgcacaag cggtggagca tgtggtttaa ttcgaagcaa | 900 |
| cgcgaagaac cttacctggt cttgacatcc ctctgaccgc tctttaatcg gagctttcct | 960 |
| tcgggacaga ggagacaggt ggtgcatggt tgtcgtcagc tcgtgtcgtg agatgttggg | 1020 |
| ttaagtcccg caacgagcgc aacccntatc tttagtagcc agcatttaag nngggcactc | 1080 |
| tagagagact gccagggata acctggagga aggtggggat gacgtcaaat catcatgccc | 1140 |
| cttatgacca gggctacaca cgtgctacaa tggcgtaaac aaagggaagc gagcccgcga | 1200 |
| gggggagcaa atcccaaaaa taacgtctca gttcggattg tagtctgcaa ctcgactaca | 1260 |
| tgaagctgga atcgctagta atcgcgaatc agaatgtcgc ggtgaatacg ttcccgggtc | 1320 |
| ttgtacacac cgcccgtcac accatgggag tcagtaacgc ccgaagtcag tgacccaacc | 1380 |
| gcaaggaggg ag | 1392 |

<210> SEQ ID NO 98
<211> LENGTH: 1378
<212> TYPE: DNA
<213> ORGANISM: Unknown
<220> FEATURE:
<223> OTHER INFORMATION: F30

<400> SEQUENCE: 98

| | |
|---|---|
| gtcggacgca atgcttcggc attgagtggc gaacgggtga gtaagacata agcaacctgc | 60 |
| ccctgtgagg gggataactg ctggaaacgg cagctaagac cgcataggca tagaggacgc | 120 |
| atgtcgacta tgttaaatat cccacgggat agcacaggga tgggcttatg acgcattagc | 180 |
| cagctggtga ggtaacggct caccagggcg acgatgcgta gccggcctga gagggtggac | 240 |
| ggccacactg gactgagaca cggcccagac tcctacgggg aggcagcagt agggaatttt | 300 |
| cggcaatggg cgaaagcctg accgagcaac gccgcgtgaa ggaagaagtc attcgtgatg | 360 |
| taaacttctg ttatgaagga agaacggcag atggagggaa tgccatgtgc gtgacggtac | 420 |
| ttcatgagga agccacggct aactacgtgc cagcagccgc ggtaatacgt aggtggcgag | 480 |
| cgttatccgg aatcattggg cgtaaagagg gagcaggcgg cagtgcaggt ctgcggtgaa | 540 |
| agaccggagc taaacttcgg taagccgtgg aaaccgcaca gctagagagc atcagaggat | 600 |
| cgcggaattc catgtgtagc ggtgaaatgc gtagatatat ggaggaacac cagtggcgaa | 660 |
| ggcggcggtc tggggtgcag ctgacgctca gtcccgaaag cgtggggagc aaataggatt | 720 |
| agataccctg gtagtccacg ccgtaaacga tgagtgctaa gtgttggggg tcagacctca | 780 |
| gtgctggagt taacgcaata agcactccgc ctgagtagta cgttcgcaag aatgaaactc | 840 |
| aaaggaattg acggggcccc gcacaagcgg tggagcatgt ggtttaattc gaagcaacgc | 900 |
| gaagaacctt accaggtctt gacatggaga taaaggccct ggagacaggg agatagatat | 960 |
| atctcacaca ggtggtgcat ggttgtcgtc agctcgtgtc gtgagatgtt gggttaagtc | 1020 |
| ccgcaacgag cgcaaccccct gttgccagtt gccagcatta ggttgggac tctggcgaga | 1080 |
| ctgcctctgc aaggaggagg aaggcgggga tgacgtcaaa tcatcatgcc cttatgacc | 1140 |
| tgggctacac acgtgctaca atggacggat cagaggagg cgaagccgcg aggtggagcg | 1200 |
| aaacccagaa acccgttcac agttcggact gcagtctgca actcgactgc acgaagctgg | 1260 |
| aatcgctagt aatcgcgaat cagcatgtcg cggtgaatac gttctcgggc cttgtacaca | 1320 |

```
ccgcccgtca caccatgaga gttggtaaca cccgaagccg gtggcccaac cgcaagga    1378
```

<210> SEQ ID NO 99
<211> LENGTH: 1392
<212> TYPE: DNA
<213> ORGANISM: Unknown
<220> FEATURE:
<223> OTHER INFORMATION: F31

<400> SEQUENCE: 99

```
gtcgaacgaa gcattttgga aggaagtttt cggatggaat tccttaatga ctgagtggcg     60
gacgggtgag taacgcgtgg ggaacctgcc ctatacaggg gataacagc tggaaacggc    120
tgctaatacc gcataagcgc acagaatcgc atgattcggt gtgaaaagct ccggcagtat    180
aggatggtcc cgcgtctgat tagctggttg gcggggtaac ggcccaccaa ggcgacgatc    240
agtagccggc ttgagagagt ggacggccac attgggactg agacacggcc caaactccta    300
cgggaggcag cagtggggaa tattgcacaa tggggggaaac cctgatgcag cgacgccgcg    360
tgagtgaaga agtatttcgg tatgtaaagc tctatcagca gggaagaaaa agacggtac    420
ctgactaaga agccccggct aactacgtgc cagcagccgc ggtaatacgt agggggcaag    480
cgttatccgg aattactggg tgtaaagggt gcgtaggtgg catggtaagt cagaagtgaa    540
agcccggggc ttaaccccgg gactgctttt gaaactgtca tgctgagtg caggagaggt    600
aagcggaatt cctagtgtag cggtgaaatg cgtagatatt aggaggaaca ccagtggcga    660
aggcggctta ctggactgtc actgactg atgcacgaaa gcgtggggag caaacaggat    720
tagataccct ggtagtccac gccgtaaacg atgaatacta ggtgtcgggg ccgtagaggc    780
ttcggtgccg cagcaaacgc agtaagtatt ccacctgggg agtacgttcg caagaatgaa    840
actcaaagga attgacgggg acccgcacaa gcggtggagc atgtggttta attcgaagca    900
acgcgaagaa ccttacctgg tcttgacatc taactgaccg gttcgtaatg gaccttttcc    960
ttcgggacag ttaagacagg tggtgcatgg ttgtcgtcag ctcgtgtcgt gagatgttgg   1020
gttaagtccc gcaacgagcg caaccccctat ctttagtagc cagcatataa ggtgggcact   1080
ctagagagac tgccagggat aacctggagg aaggtgggga cgacgtcaaa tcatcatgcc   1140
ccttatggcc agggctacac acgtgctaca atggcgtaaa caaagggaag cgaagtcgtg   1200
aggcgaagca aatcccagaa ataacgtctc agttcggatt gtagtctgca actcgactac   1260
atgaagctgg aatcgctagt aatcgtgaat cagaatgtca cggtgaatac gttcccgggt   1320
cttgtacaca ccgcccgtca caccatggga gtcagtaacg cccgaagtca gtgacccaac   1380
cttataggag gg                                                       1392
```

<210> SEQ ID NO 100
<211> LENGTH: 1391
<212> TYPE: DNA
<213> ORGANISM: Unknown
<220> FEATURE:
<223> OTHER INFORMATION: F32
<220> FEATURE:
<221> NAME/KEY: misc_feature
<222> LOCATION: (951)..(952)
<223> OTHER INFORMATION: n is a, c, g, or t

<400> SEQUENCE: 100

```
gtcgagcgaa gcactaagac ggatttcttc ggattgaagt ctttgtgact gagcggcgga     60
cgggtgagta acgcgtgggt aacctgcctc atacaggggg ataacagtta gaaatgactg    120
```

```
ctaataccgc ataagcgcac aggaccgcat ggtctggtgt gaaaaactcc ggtggtatga      180
gatggacccg cgtctgatta gctagttgga ggggtaacgg cccaccaagg cgacgatcag      240
tagccggcct gagagggtga acggccacat tgggactgag acacggccca gactcctacg      300
ggaggcagca gtggggaata ttgcacaatg ggggaaaccc tgatgcagcg acgccgcgtg      360
aaggaagaag tatctcggta tgtaaacttc tatcagcagg gaagaaaatg acggtacctg      420
actaagaagc cccggctaac tacgtgccag cagccgcggt aatacgtagg gggcaagcgt      480
tatccggatt tactgggtgt aaagggagcg tagacggaag agcaagtctg atgtgaaagg      540
ctggggctta accccaggac tgcattggaa actgttgttc tagagtgccg gagaggtaag      600
cggaattcct agtgtagcgg tgaaatgcgt agatattagg aggaacacca gtggcgaagg      660
cggcttactg gacggtaact gacgttgagg ctcgaaagcg tggggagcaa acaggattag      720
ataccctggt agtccacgcc gtaaacgatg aatactaggt gtcgggtggc aaagccattc      780
ggtgccgcag caaacgcaat aagtattcca cctggggagt acgttcgcaa gaatgaaact      840
caaaggaatt gacggggacc cgcacaagcg gtggagcatg tggtttaatt cgaagcaacg      900
cgaagaacct taccaagtct tgacatccct ctgaccgtcc cgtaacgggg nnttcccttc      960
ggggcagagg agacaggtgg tgcatggttg tcgtcagctc gtgtcgtgag atgttgggtt     1020
aagtcccgca acgagcgcaa cccttatcct tagtagccag cacatgatgg tgggcactct     1080
agggagactg ccggggataa cccggaggaa ggcgggacg acgtcaaatc atcatgcccc      1140
ttatgatttg ggctacacac gtgctacaat ggcgtaaaca agggaagcg agacagcgat     1200 gttgagcgaa tcccaaaaat aacgtcccag ttcggactgc agtctgcaac tcgactgcac     1260
gaagctggaa tcgctagtaa tcgcggatca gaatgccgcg gtgaatacgt tcccgggtct     1320
tgtacacacc gcccgtcaca ccatgggagt cagtaacgcc cgaagtcagt gacctaaccg     1380
aaaggaagga g                                                          1391
```

<210> SEQ ID NO 101
<211> LENGTH: 1381
<212> TYPE: DNA
<213> ORGANISM: Unknown
<220> FEATURE:
<223> OTHER INFORMATION: F33

<400> SEQUENCE: 101

```
agtcgaacgc gagcacttgt gctcgagtgg cgaacgggtg agtaatacat aagtaacctg       60
ccctagacag ggggataact attggaaacg atagctaaga ccgcataggt acggacactg      120
catggtgacc gtattaaaag tgcctcaaag cactggtaga ggatggactt atggcgcatt      180
agctggttgg cggggtaacg gcccaccaag gcgacgatgc gtagccgacc tgagagggtg      240
accggccaca ctgggactga gacacggccc agactcctac gggaggcagc agtagggaat      300
tttcggcaat gggggaaacc ctgaccgagc aacgccgcgt gaaggaagaa ggttttcgga      360
ttgtaaactt ctgttataaa ggaagaacgg cggctacagg aaatggtagc cgagtgacgg      420
tactttatta gaaagccacg gctaactacg tgccagcagc cgcggtaata cgtaggtggc      480
aagcgttatc cggaattatt gggcgtaaag agggagcagg cggcagcaag ggtctgtggt      540
gaaagcctga agcttaactt cagtaagcca tagaaaccag gcagctagag tgcaggagag      600
gatcgtggaa ttccatgtgt agcggtgaaa tgcgtagata tatggaggaa caccagtggc      660
gaaggcgaca tctggcctg caactgacgc tcagtcccga aagcgtgggg agcaaatagg      720
attagatacc ctagtagtcc acgccgtaaa cgatgagtac taagtgttgg atgtcaaagt      780
```

-continued

```
tcagtgctgc agttaacgca ataagtactc cgcctgagta gtacgttcgc aagaatgaaa      840
ctcaaaggaa ttgacggggg cccgcacaag cggtggagca tgtggtttaa ttcgaagcaa      900
cgcgaagaac cttaccaggt cttgacatac tcataaaggc tccagagatg gagagatagc      960
tatatgagat acaggtggtg catggttgtc gtcagctcgt gtcgtgagat gttgggttaa     1020
gtcccgcaac gagcgcaacc cttatcgtta gttaccatca ttaagttggg gactctagcg     1080
agactgccag tgacaagctg gaggaaggcg gggatgacgt caaatcatca tgccccttat     1140
gacctgggct acacacgtgc tacaatggat ggtgcagagg gaagcgaagc cgcgaggtga     1200
agcaaaaccc ataaaaccat tctcagttcg gattgtagtc tgcaactcga ctacatgaag     1260
ttggaatcgc tagtaatcgc gaatcagcat gtcgcggtga atacgttctc gggccttgta     1320
cacaccgccc gtcacaccac gagagttgat aacacccgaa gccggtggcc taaccgcaag     1380
g                                                                    1381
```

<210> SEQ ID NO 102
<211> LENGTH: 1424
<212> TYPE: DNA
<213> ORGANISM: Unknown
<220> FEATURE:
<223> OTHER INFORMATION: F34
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (554)..(555)
<223> OTHER INFORMATION: n is a, c, g, or t

<400> SEQUENCE: 102

```
gcagtcgaac gaagagcgat ggaagcttgc ttctatcaat cttagtggcg aacgggtgag       60
taacgcgtaa tcaacctgcc cttcagaggg ggacaacagt tggaaacgac tgctaatacc      120
gcatacgatc taatctcggc atcgaggata gatgaaaggt ggcctctacn tgtaagctat      180
cactgaagga ggggattgcg tctgattagc tagttggagg ggtaacggcc caccaaggcg      240
atgatcagta gccggtctga gaggatgaac ggccacattg gactgagaca cggcccaga      300 ctcctacggg aggcagcagt ggggaatctt ccgcaatgga cgaaagtctg acggagcaac      360
gccgcgtgag tgatgacggc cttcgggttg taaagctctg ttaatcggga cgaaaggcct      420
tcttgcgaat agtgagaagg attgacggta ccggaataga aagccacggc taactacgtg      480
ccagcagccg cggtaatacg taggtggcaa gcgttgtccg gaattattgg gcgtaaagcg      540
cgcgcaggcg gatnngtcag tctgtcttaa agttcggggg cttaaccccg tgatgggatg      600
gaaactgctg atctagagta tcggagagga agtggaatt cctagtgtag cggtgaaatg      660
cgtagatatt aggaagaaca ccagtggcga aggcgacttt ctggacgaaa actgacgctg      720
aggcgcgaaa gccaggggag cgaacgggat tagatacccc ggtagtcctg gccgtaaacg      780
atgggtacta ggtgtaggag gtatcgaccc cttctgtgcc ggagttaacg caataagtac      840
cccgcctggg gagtacgacc gcaaggttga aactcaaagg aattgacggg gcccgcaca      900 agcggtggag tatgtggttt aattcgacgc aacgcgaaga accttaccag gtcttgacat      960
tgatggacag aaccagagat ggttcctctt cttcggaagc cagaaaacag gtggtgcacg     1020
gttgtcgtca gctcgtgtcg tgagatgttg ggttaagtcc gcaacgagcg caacccccta     1080
tcttatgttg ccagcactta aggtgggaac tcatgagag actgccgcag acaatgcgga     1140
```

| | |
|---|---:|
| ggaaggcggg gatgacgtca atcatcatg cccttatga cctgggctac acacgtacta | 1200 |
| caatgggagt taatagacgg aagcgagatc gcgagatgga gcaaacccga gaaacactct | 1260 |
| ctcagttcgg atcgtaggct gcaactcgcc tacgtgaagt cggaatcgct agtaatcgca | 1320 |
| ggtcagcata ctgcggtgaa tacgttcccg ggccttgtac acaccgcccg tcacaccacg | 1380 |
| aaagtcggaa gtgcccaaag ccggtggggt aaccttcggg agcc | 1424 |

<210> SEQ ID NO 103
<211> LENGTH: 1361
<212> TYPE: DNA
<213> ORGANISM: Unknown
<220> FEATURE:
<223> OTHER INFORMATION: F35

<400> SEQUENCE: 103

| | |
|---|---:|
| gtctacttga tccttcgggt gaaggtggcg gacgggtgag taacgcgtaa agaacttgcc | 60 |
| ttacagactg ggacaacatt tggaaacgaa tgctaatacc ggatattatg attgggtcgc | 120 |
| atgatctggt tatgaaagct atatgcgctg tgagagagct ttgcgtccca ttagttagtt | 180 |
| ggtgaggtaa cggctcacca agacgatgat gggtagccgg cctgagaggg tgaacggcca | 240 |
| caagggact gagacacggc ccttactcct acgggaggca gcagtgggga atattggaca | 300 |
| atggaccaaa agtctgatcc agcaattctg tgtgcacgat gaagtttttc ggaatgtaaa | 360 |
| gtgctttcag ttgggaagaa gtcagtgacg gtaccaacag aagaagcgac ggctaaaatac | 420 |
| gtgccagcag ccgcggtaat acgtatgtcg caagcgttat ccggatttat gggcgtaaa | 480 |
| gcgcgtctag gcggcttagt aagtctgatg tgaaaatgcg gggctcaacc ccgtattgcg | 540 |
| ttggaaactg ctaaactaga gtactggaga ggtaggcgga actacaagtg tagaggtgaa | 600 |
| attcgtagat atttgtagga atgccgatgg ggaagccagc ctactggaca gatactgacg | 660 |
| ctaaagcgcg aaagcgtggg tagcaaacag gattagatac cctggtagtc cacgccgtaa | 720 |
| acgatgatta ctaggtgttg ggggtcgaac ctcagcgccc aagctaacgc gataagtaat | 780 |
| ccgcctgggg agtacgtacg caagtatgaa actcaaagga attgacgggg acccgcacaa | 840 |
| gcggtggagc atgtggttta attcgacgca acgcgaggaa ccttaccagc gtttgacatc | 900 |
| ccaagaagtt aacagagatg ttttcgtgcc tcttcggagg aacttggtga caggtggtgc | 960 |
| atggctgtcg tcagctcgtg tcgtgagatg ttgggttaag tcccgcaacg agcgcaaccc | 1020 |
| ctttcgtatg ttaccatcat taagttgggg actcatgcga gactgcctgc gatgagcagg | 1080 |
| aggaaggtgg ggatgacgtc aagtcatcat gcccttata cgctgggcta cacacgtgct | 1140 |
| acaatgggta gtacagagag ctgcaaacct gcgagggtaa gctaatctca taaaactatt | 1200 |
| cttagttcgg attgtactct gcaactcgag tacatgaagt tggaatcgct agtaatcgca | 1260 |
| aatcagctat gttgcggtga atacgttctc gggtcttgta cacaccgccc gtcacaccac | 1320 |
| gagagttggt tgcacctgaa gtaacaggcc taaccgtaag g | 1361 |

<210> SEQ ID NO 104
<211> LENGTH: 1362
<212> TYPE: DNA
<213> ORGANISM: Unknown
<220> FEATURE:
<223> OTHER INFORMATION: F36

<400> SEQUENCE: 104

| | |
|---|---:|
| agtctacttg atccttcggg tgaaggtggc ggacgggtga gtaacgcgta agaacttgc | 60 |
| cttacagact gggacaacat ttggaaacga atgctaatac cggatattat gattgggtcg | 120 |

```
catgatctgg ttatgaaagc tatatgcgct gtgagagagc tttgcgtccc attagttagt      180
tggtgaggta acggctcacc aagacgatga tgggtagccg gcctgagagg gtgaacggcc      240
acaaggggac tgagacacgg cccttactcc tacgggaggc agcagtgggg aatattggac      300 aatgaccaa aagtctgatc cagcaattct gtgtgcacga tgaagttttt cggaatgtaa       360
agtgctttca gttgggaaga agtcagtgac ggtaccaaca gaagaagcga cggctaaata      420
cgtgccagca gccgcggtaa tacgtatgtc gcaagcgtta ccggattta ttgggcgtaa       480 agcgcgtcta ggcggcttag taagtctgat gtgaaaatgc ggggctcaac cccgtattgc      540
gttggaaact gctaaactag agtactggag aggtaggcgg aactacaagt gtagaggtga      600
aattcgtaga tatttgtagg aatgccgatg gggaagccag cctactggac agatactgac      660
gctaaagcgc gaaagcgtgg gtagcaaaca ggattagata ccctggtagt ccacgccgta      720
aacgatgatt actaggtgtt gggggtcgaa cctcagcgcc caagctaacg cgataagtaa      780
tccgcctggg gagtacgtac gcaagtatga aactcaaagg aattgacggg acccgcaca      840 agcggtggag catgtggttt aattcgacgc aacgcgagga accttaccag cgtttgacat      900
cccaagaagt taacagagat gttttcgtgc ctcttcggag gaacttggtg acaggtggtg      960
catggctgtc gtcagctcgt gtcgtgagat gttgggttaa gtcccgcaac gagcgcaacc     1020
cctttcgtat gttaccatca ttaagttggg gactcatgcg agactgcctg cgatgagcag     1080
gaggaaggtg gggatgacgt caagtcatca tgccccttat acgctgggct acacacgtgc     1140
tacaatgggt agtacagaga gctgcaaacc tgcgagggta agctaatctc ataaaactat     1200
tcttagttcg gattgtactc tgcaactcga gtacatgaag ttggaatcgc tagtaatcgc     1260
aaatcagcta tgttgcggtg aatacgttct cgggtcttgt acacaccgcc cgtcacacca     1320
cgagagttgg ttgcacctga gtaacaggc ctaaccgtaa gg                         1362
```

<210> SEQ ID NO 105
<211> LENGTH: 1397
<212> TYPE: DNA
<213> ORGANISM: Unknown
<220> FEATURE:
<223> OTHER INFORMATION: F37

<400> SEQUENCE: 105

```
agtcgaacgg taacaggaag cagcttgctg ctttgctgac gagtggcgga cgggtgagta       60
atgtctggga aactgcctga tgagggggga taactactgg aaacggtagc taataccgca      120
taacgtcgca agaccaaaga gggggacctt cgggcctctt gccatcggat gtgcccagat      180
gggattagct agtaggtggg gtaacggctc acctaggcga cgatccctag ctggtctgag      240
aggatgacca gccacactgg aactgagaca cggtccagac tcctacggga ggcagcagtg      300
gggaatattg cacaatgggc gcaagcctga tgcagccatg ccgcgtgtat gaagaaggcc      360
ttcgggttgt aaagtacttt cagcggggag aagggagta aagttaatac ctttgctcat      420
tgacgttacc cgcagaagaa gcaccggcta actccgtgcc agcagccgcg gtaatacgga      480
gggtgcaagc gttaatcgga attactgggc gtaaagcgca cgcaggcggt ttgttaagtc      540
agatgtgaaa tccccgggct caacctggga actgcatctg atactggcaa gcttgagtct      600
cgtagagggg ggtagaattc caggtgtagc ggtgaaatgc gtagagatct ggaggaatac      660
cggtggcgaa ggcggcccc tggacgaaga ctgacgctca ggtgcgaaag cgtgggagc       720 aaacaggatt agataccctg gtagtccacg ccgtaaacga tgtcgacttg gaggttgtgc      780
```

-continued

```
ccttgaggcg tggcttccgg agctaacgcg ttaagtcgac cgcctgggga gtacggccgc    840
aaggttaaaa ctcaaatgaa ttgacggggg cccgcacaag cggtggagca tgtggtttaa    900
ttcgatgcaa cgcgaagaac cttacctggt cttgacatcc acggaagttt tcagagatga    960
gaatgtgcct tcgggaaccg tgagacaggt gctgcatggc tgtcgtcagc tcgtgttgtg   1020
aaatgttggg ttaagtcccg caacgagcgc aaccccttatc ctttgttgcc agcggtccgg   1080
ccgggaactc aaaggagact gccagtgata aactggagga aggtggggat gacgtcaagt   1140
catcatggcc cttacgacca gggctacaca cgtgctacaa tggcgcatac aaagagaagc   1200
gacctcgcga gagcaagcgg acctcataaa gtgcgtcgta gtccggattg gagtctgcaa   1260
ctcgactcca tgaagtcgga atcgctagta atcgtggatc agaatgccac ggtgaatacg   1320
ttcccgggcc ttgtacacac cgcccgtcac accatgggag tgggttgcaa agaagtagg   1380 tagcttaacc ttcggga                                                  1397
```

```
<210> SEQ ID NO 106
<211> LENGTH: 1339
<212> TYPE: DNA
<213> ORGANISM: Unknown
<220> FEATURE:
<223> OTHER INFORMATION: I01
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (308)..(309)
<223> OTHER INFORMATION: n is a, c, g, or t
<220> FEATURE:
<221> NAME/KEY: misc_feature
<222> LOCATION: (311)..(313)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1286)..(1286)
<223> OTHER INFORMATION: n is a, c, g, or t

<400> SEQUENCE: 106
ctgggtgaga gtggcgaacg ggtgagtaat gcgtgaccga cctgccccat acaccggaat     60
agctcctgga aacgggtggt aatgccgat gctccagttg gatgcatgtc cttctgggaa    120
agattcatcg gtatgggang ggtcgcgtc ctatcagctt gatggcgggg taacggccca    180
ccatggcttc cacgggtagc cggcctgaga gggcgaccgg ccacattggg actgagntac   240
ggcccagnct cctacgggag gcagcagtgg ggaatattgc acaatgggcg caagcctgat   300
gcagcgannc nnngtgcggg atgacggcct tcggttgta aaccgctttt gactgggagc    360
```

```
aagcccttcg gggtgagtgt acctttcgaa taagcaccgg ctaactacgt gccagcagcc      420
gcggtaatac gtaaggtgca agcgttatcc ggaattattg ggcgtaaagg gctcgtaagc      480
ggttcgtcnc gtccggtgtg aaagtccatc gcttaacggt ggatccgcgc cgggtacggg      540
cgggcttgag tgcggtaggg gagactggaa ttcccggtgt aacggtggaa tgtgtagata      600
tcgggaagaa caccaatggc gaaggcaggt ctctgggccg tcactgacgc tgaggagcga      660
aagcgtgggg agcgaacagg attagatacc ctggtagtcc acgccgtaaa cggtggatgc      720
tggatgtggg gaccattcca cggtctccgt gtcggagcca acgcgttaag catcccgcct      780
ggggagtacg gccgcaaggc taaaactcaa agaaattgac gggggcccgc acaagcggcg      840
gagcatgcgg attaattcga tgcaacgcga agaaccttac ctgggcttga catgttcccg      900
acagccgtag agatacggtt tcccttcggg gcgggttcac aggtggtgca tggtcgtcgt      960
cagctcgtgt cgtgagatgt tgggttaagt cccgcaacga gcgcaaccct cgccctgtgt     1020
tgccagcacg tcgtggtggg aactcacggg ggaccgccgg ggtcaactcg gaggaaggtg     1080
gggatgacgt cagatcatca tgccccttac gtccagggct tcacgcatgc tacaatggcc     1140
ggtacaacgg gatgcganac cgcgaggtgg agcggatccc ttaaaaccgg tctcagttcg     1200
gattggagtc tgcaacccga ctccatgaag gcggagtcgc tagtaatcgc ggatcagcaa     1260
cgccgcggtg aatgcgttcc cggncnttgt acacaccgcc cgtcaagtca tgaaagtggg     1320
tagcacccga agccggtgg                                                  1339

<210> SEQ ID NO 107
<211> LENGTH: 1346
<212> TYPE: DNA
<213> ORGANISM: Unknown
<220> FEATURE:
<223> OTHER INFORMATION: I02
<220> FEATURE:
<221> NAME/KEY: misc_feature
<222> LOCATION: (911)..(913)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t

<400> SEQUENCE: 107
ttgcttggtg gtgagagtgg cgaacgggtg agtaatgcgt gaccgacctg ccccatacac       60
cggaatagct cctggaaacg ggtggtaatg ccggatgctc cgactcctcg catggggtgt      120
cgggaaagat ttcatcggta tgggatgggg tcgcgtccta tcaggtagtc ggcggggtaa      180
cggcccaccg agcctacgac gggtagccgg cctgagaggg cgaccggcca cattgggact      240
gagatacggc ccagactcct acgggaggca gcagtgggga atattgcaca atgggcgcaa      300
gcctgatgca gcgacgccgc gtgcgggatg acggccttcg ggttgtaaac cgcttttgat      360
cgggagcaag ccttcgggtg agtgtaccct tcgaataagc accggctaac tacgtgccag      420
cagccgcggt aatacgtagg gtgcaagcgt tatccggaat tattgggcgt aaagggctcg      480
taggcggttc gtcgcgtccg gtgtgaaagt ccatcgctta cggtggatc tgcgccgggt      540 acgggcgggc tggagtgcgg taggga gac tggaattccc ggtgtaacgg tggaatgtgt      600
agatatcggg aagaacacca atggcgaagg cagg tctctg ggccgttact gacgctgagg      660
agcgaaagcg tggggagcga acaggattag ataccctggt agtccacgcc gtaaacggtg      720
gatgctggat gtggggcccg ttccacgggt tccgtgtcgg agctaacgcg ttaagcatcc      780
```

| | |
|---|---|
| cgcctgggga gtacggccgc aaggctaaaa ctcaaagaaa ttgacggggg cccgcacaag | 840 |
| cggcggagca tgcggattaa ttcgatgcaa cgcgaagaac cttacctggg cttgacatgt | 900 |
| tcccgacagc nnnagagata tgncctccct tcggggcggg ttcacaggtg gtgcatggtc | 960 |
| gtcgtcagct cgtgtcgtga gatgttgggt taagtcccgc aacgagcgca accctcgccc | 1020 |
| tgtgttgcca gcacgtcgtg gtgggaactc acggggacc gccgggtca actcggagga | 1080 |
| aggtggggat gacgtcagat catcatgccc cttacgtcca gggcttcacg catgctacaa | 1140 |
| tggccggtac aacgggatgc gacacggcga cgtggagcgg atccctgaaa accggtctca | 1200 |
| gttcggattg gagtctgcaa cccgactcca tgaaggcgga gtcgctagta atcgcggatc | 1260 |
| agcaacgccg cggtgaatgc gttcccgggc cttgtacaca ccgcccgtca agtcatgaaa | 1320 |
| gtgggtagca cccgaagccg gtggcc | 1346 |

<210> SEQ ID NO 108
<211> LENGTH: 1353
<212> TYPE: DNA
<213> ORGANISM: Unknown
<220> FEATURE:
<223> OTHER INFORMATION: I03

<400> SEQUENCE: 108

| | |
|---|---|
| aagcttgctt ggtggtgaga gtggcgaacg ggtgagtaat gcgtgaccga cctgccccat | 60 |
| gctccggaat agctcctgga aacggtggt aatgccggat gttccacatg atcgcatgtg | 120 |
| attgtgggaa agattctatc ggcgtgggat ggggtcgcgt cctatcagct tgttggtgag | 180 |
| gtaacggctc accaaggctt cgacgggtag ccggcctgag agggcgaccg gccacattgg | 240 |
| gactgagata cggcccagac tcctacggga ggcagcagtg gggaatattg cacaatgggc | 300 |
| gcaagcctga tgcagcgacg ccgcgtgagg gatggaggcc ttcgggttgt aaacctcttt | 360 |
| tgtttgggag caagccttcg ggtgagtgta cctttcgaat aagcgccggc taactacgtg | 420 |
| ccagcagccg cggtaatacg tagggcgcaa gcgttatccg gatttattgg cgtaaaggg | 480 |
| ctcgtaggcg gctcgtcgcg tccggtgtga agtccatcg cttaacggtg gatctgcgcc | 540 |
| gggtacgggc gggctggagt gcggtagggg agactggaat tcccggtgta acggtggaat | 600 |
| gtgtagatat cggaagaac accgatggcg aaggcaggtc tctgggccgt cactgacgct | 660 |
| gaggagcgaa agcgtgggga gcgaacagga ttagatacc tggtagtcca cgccgtaaac | 720 |
| ggtggacgct ggatgtgggg cacgttccac gtgttccgtg tcggagctaa cgcgttaagc | 780 |
| gtcccgcctg gggagtacgg ccgcaaggct aaaactcaaa gaaattgacg ggggcccgca | 840 |
| caagcggcgg agcatgcgga ttaattcgat gcaacgcgaa gaaccttacc tgggcttgac | 900 |
| atgttcccga cgacgccaga gatggcgttt cccttcgggg cggttcaca ggtggtgcat | 960 |
| ggtcgtcgtc agctcgtgtc gtgagatgtt gggttaagtc ccgcaacgag cgcaaccctc | 1020 |
| gccccgtgtt gccagcacgt tatggtggga actcacgggg gaccgccggg gttaactcgg | 1080 |
| aggaaggtgg ggatgacgtc agatcatcat gccccttacg tccagggctt cacgcatgct | 1140 |
| acaatggccg gtacagcggg atgcgacatg gcgacatgga gcggatccct gaaaaccggt | 1200 |
| ctcagttcgg atcggagcct gcaacccggc tccgtgaagg cggagtcgct agtaatcgcg | 1260 |
| gatcagcaac gccgcggtga atgcgttccc gggccttgta cacaccgccc gtcaagtcat | 1320 |
| gaaagtgggc agcacccgaa gccggtggcc taa | 1353 |

<210> SEQ ID NO 109
<211> LENGTH: 1338

<210> SEQ ID NO 109
<211> LENGTH: 1338
<212> TYPE: DNA
<213> ORGANISM: Unknown
<220> FEATURE:
<223> OTHER INFORMATION: I04

<400> SEQUENCE: 109

| | | | | | |
|---|---|---|---|---|---|
| ggtggtgaga | gtggcgaacg | ggtgagtaat | gcgtgaccga | cctgccccat | acaccggaat | 60 |
| agctcctgga | aacgggtggt | aatgccggat | gctccagttg | atcgcatggt | cttctgggaa | 120 |
| agctttcgcg | gtatgggatg | gggtcgcgtc | ctatcagctt | gacggcgggg | taacggccca | 180 |
| ccgtggcttc | gacgggtagc | cggcctgaga | gggcgaccgg | ccacattggg | actgagatac | 240 |
| ggcccagact | cctacgggag | gcagcagtgg | ggaatattgc | acaatgggcg | caagcctgat | 300 |
| gcagcgacgc | cgcgtgaggg | atggaggcct | tcggttgta | aacctctttt | atcggggagc | 360 |
| aagcgagagt | gagtttaccc | gttgaataag | caccggctaa | ctacgtgcca | gcagccgcgg | 420 |
| taatacgtag | ggtgcaagcg | ttatccggaa | ttattgggcg | taaagggctc | gtaggcggtt | 480 |
| cgtcgcgtcc | ggtgtgaaag | tccatcgctt | aacgtggat | ccgcgccggg | tacgggcggg | 540 |
| cttgagtgcg | gtaggggaga | ctggaattcc | cggtgtaacg | gtggaatgtg | tagatatcgg | 600 |
| gaagaacacc | aatggcgaag | gcaggtctct | gggccgttac | tgacgctgag | gagcgaaagc | 660 |
| gtggggagcg | aacaggatta | gataccctgg | tagtccacgc | cgtaaacggt | ggatgctgga | 720 |
| tgtgggccc | gttccacggg | ttccgtgtcg | gagctaacgc | gttaagcatc | ccgcctgggg | 780 |
| agtacggccg | caaggctaaa | actcaaagaa | attgacgggg | gcccgcacaa | gcggcggagc | 840 |
| atgcggatta | attcgatgca | acgcgaagaa | ccttacctgg | gcttgacatg | ttcccgacgg | 900 |
| tcgtagagat | gcggcttccc | ttcggggcgg | gttcacaggt | ggtgcatggt | cgtcgtcagc | 960 |
| tcgtgtcgtg | agatgttggg | ttaagtcccg | caacgagcgc | aaccctcgcc | ccgtgttgcc | 1020 |
| agcggattat | gccgggaact | cacggggac | cgccggggtt | aactcggagg | aaggtgggga | 1080 |
| tgacgtcaga | tcatcatgcc | ccttacgtcc | agggcttcac | gcatgctaca | atggccggta | 1140 |
| caacgggatg | cgacgcggcg | acgcggagcg | gatccctgaa | aaccggtctc | agttcggatc | 1200 |
| gcagtctgca | actcgactgc | gtgaaggcg | agtcgctagt | aatcgcgaat | cagcaacgtc | 1260 |
| gcggtgaatg | cgttcccggg | ccttgtacac | accgcccgtc | aagtcatgaa | agtgggcagc | 1320 |
| acccgaagcc | ggtggcct | | | | | 1338 |

<210> SEQ ID NO 110
<211> LENGTH: 1326
<212> TYPE: DNA
<213> ORGANISM: Unknown
<220> FEATURE:
<223> OTHER INFORMATION: I05

<400> SEQUENCE: 110

| | | | | | |
|---|---|---|---|---|---|
| gatagaagcg | agtggcgaac | ggctgagtaa | cacgtggaga | acctgccccc | tccccgggga | 60 |
| tagccgcccg | aaaggacggg | taataccgga | taccccgggg | tgccgcatgg | cacccggct | 120 |
| aaagccccga | cgggagggga | tggctccgcg | gcccatcagg | tagacggcgg | ggtgacggcc | 180 |
| caccgtgccg | acaacgggta | gccgggttga | gagaccgacc | ggccagattg | ggactgagac | 240 |
| acggcccaga | ctcctacggg | aggcagcagt | ggggaatctt | gcgcaatggg | gggaaccctg | 300 |
| acgcagcgac | gccgcgtgcg | ggacggaggc | cttcgggtcg | taaaccgctt | tcagcaggga | 360 |
| agagtcaaga | ctgtacctgc | agaagaagcc | ccggctaact | acgtgccagc | agccgcggta | 420 |
| atacgtaggg | ggcgagcgtt | atccggattc | attgggcgta | aagcgcgcgt | aggcggcccg | 480 |

```
gcaggccggg ggtcgaagcg gggggctcaa ccccccgaag cccccggaac ctccgcggct    540
tgggtccggt aggggagggt ggaacacccg gtgtagcggt ggaatgcgca gatatcgggt    600
ggaacaccgg tggcgaaggc ggccctctgg gccgagaccg acgctgaggc gcgaaagctg    660
ggggagcgaa caggattaga taccctggta gtcccagccg taaacgatgg acgctaggtg    720 tgggggacg atcccccgt gccgcagcca acgcattaag cgtcccgcct ggggagtacg    780
gccgcaaggc taaaactcaa aggaattgac ggggcccgc acaagcagcg gagcatgtgg    840
cttaattcga agcaacgcga agaaccttac cagggcttga catatgggtg aagcggggga    900
gaccccgtgg ccgagaggag cccatacagg tggtgcatgg ctgtcgtcag ctcgtgtcgt    960
gagatgttgg gttaagtccc gcaacgagcg caaccccgc gcgtgttgc catcgggtga   1020 tgccgggaac ccacgcggga ccgccgccgt caaggcggag gagggcgggg acgacgtcaa   1080
gtcatcatgc cccttatgcc ctgggctgca cacgtgctac aatggccggt acagagggat   1140
gccaccccgc gaggggagc ggatcccgga aagccggccc cagttcggat tgggggctgc   1200
aacccgcccc catgaagtcg gagttgctag taatcgcgga tcagcatgcc gcggtgaatg   1260
cgttcccggg ccttgtacac accgcccgtc acaccacccg agtcgtctgc acccgaagtc   1320
gccggc                                                              1326

<210> SEQ ID NO 111
<211> LENGTH: 729
<212> TYPE: DNA
<213> ORGANISM: Unknown
<220> FEATURE:
<223> OTHER INFORMATION: I06
<220> FEATURE:
<221> NAME/KEY: misc_feature
<222> LOCATION: (13)..(13)
<223> OTHER INFORMATION: n is a, c, g, or t

<400> SEQUENCE: 111
acctgccttc ggncagaagc gagtggcgaa cggctgagta acacgtggag aacctgcccc     60
ctcccccggg atagccgccc gaaaggacgg gtaataccgg ataccccggg gtgccgcatg    120
gcaccccggc taaagccccg acgggagggg atggctccgc ggcccatcag gtagacggcg    180
gggtgacggc ccaccgtgcc gacaacgggt agccgggttg agagaccgac cggccagatt    240
gggactgaga cacggcccag actcctacgg gaggcagcag tggggaatct tgcgcaatgg    300
ggggaaccct gacgcagcga cgccgcgtgc gggacggagg ccttcgggtc gtaaaccgct    360
ttcagcaggg aagagtcaag actgtacctg cagaagaagc cccggctaac tacgtgccag    420
cagccgcggt aatacgtagg gggcgagcgt tatccggatt cattgggcgt aaagcgcgcg    480
taggcggccc ggcaggccgg gggtcgaagc gggggggctca accccctcgaa gccccggaa    540 cctccgcggc ttgggtccgg taggggaggg tggaacaccc ggtgtagcgg tggaatgcgc    600
agatatcggg tggaacaccg gtggcgaagg cggccctctg ggccgagacc gacgctgagg    660
cgcgaaagct gggggagcga acaggattag ataccctggt agtcccagcc gtaaacgatg    720
gacgctagg                                                            729

<210> SEQ ID NO 112
<211> LENGTH: 1338
<212> TYPE: DNA
<213> ORGANISM: Unknown
<220> FEATURE:
<223> OTHER INFORMATION: I07

<400> SEQUENCE: 112
```

```
gtggtgagag tggcgaacgg gtgagtaatg cgtgaccgac ctgccccata caccggaata    60
gctcctggaa acgggtggta atgccggatg ctccagttga tcgcatggtc ttctgggaaa   120
gctttcgcgg tatgggatgg ggtcgcgtcc tatcagcttg acggcggggt aacggcccac   180
cgtggcttcg acgggtagcc ggcctgagag ggcgaccggc cacattggga ctgagatacg   240
gcccagactc ctacgggagg cagcagtggg gaatattgca caatgggcgc aagcctgatg   300
cagcgacgcc gcgtgaggga tgaggccctt cgggttgtaa acctctttta tcggggagca   360
agcgagagtg agtttacccg ttgaataagc accggctaac tacgtgccag cagccgcggt   420
aatacgtagg gtgcaagcgt tatccggaat tattgggcgt aaagggctcg taggcggttc   480
gtcgcgtccg gtgtgaaagt ccatcgctta acggtggatc cgcgccgggt acgggcgggc   540
ttgagtgcgg taggggagac tggaattccc ggtgtaacgg tggaatgtgt agatatcggg   600
aagaacacca atggcgaagg caggtctctg ggccgttact gacgctgagg agcgaaagcg   660 tgggagcga acaggattag ataccctggt agtccacgcc gtaaacggtg gatgctggat    720
gtggggcccg ttccacgggt tccgtgtcgg agctaacgcg ttaagcatcc gcctgggga    780 gtacggccgc aaggctaaaa ctcaaagaaa ttgacggggg cccgcacaag cggcggagca   840
tgcggattaa ttcgatgcaa cgcgaagaac cttacctggg cttgacatgt tcccgacggt   900
cgtagagatg cggcttccct tcggggcggg ttcacaggtg gtgcatggtc gtcgtcagct   960
cgtgtcgtga gatgttgggt taagtcccgc aacgagcgca accctcgccc cgtgttgcca  1020
gcggattatg ccgggaactc acgggggacc gccggggtta actcggagga aggtggggat  1080
gacgtcagat catcatgccc cttacgtcca gggcttcacg catgctacaa tggccggtac  1140
aacgggatgc gacgcggcga cgcggagcgg atccctgaaa accggtctca gttcggatcg  1200
cagtctgcaa ctcgactgcg tgaaggcgga gtcgctagta atcgcgaatc agcaacgtcg  1260
cggtgaatgc gttcccgggc cttgtacaca ccgcccgtca agtcatgaaa gtgggcagca  1320
cccgaagccg gtggccta                                                1338

<210> SEQ ID NO 113
<211> LENGTH: 1337
<212> TYPE: DNA
<213> ORGANISM: Unknown
<220> FEATURE:
<223> OTHER INFORMATION: I08
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (117)..(119)
<223> OTHER INFORMATION: n is a, c, g, or t

<400> SEQUENCE: 113
ttgatggatg cgaccggcg cacgggtgag taacacgtat ccaacctgcc gacaacactg     60
ggatagcctt tcgaaagaaa gattaatacc ggatggcata attantccgc atgggannnt   120
tattaaagaa tttcggttgt cgatggggat gcgttccatt aggcagttgg cggggtaacg   180
gcccaccaaa ccaacgatgg ataggggttc tgagaggaag gtcccccaca ttggaactga   240
gacacggtcc aaactcctac gggaggcagc agtgaggaat attggtcaat ggacgagagt   300
ctgaaccagc caagtagcgt gaaggatgac tgccctatgg gttgtaaact tcttttatac   360
gggaataaag ttagccacgt gtggcttttt gtatgtaccg tatgaataag gatcggctaa   420
```

```
ctccgtgcca gcagccgcgg taatacggag gatccgagcg ttatccggat ttattgggtt      480
taaagggagc gtaggcgggt tgttaagtca gttgtgaaag tttgcggctc aaccgtaaaa      540
ttgcagttga tactggcgac cttgagtgca acagaggtag gcggaattcg tggtgtagcg      600
gtgaaatgct tagatatcac gaagaactcc gattgcgaag gcagcttact ggattgtaac      660
tgacgctgat gctcgaaagt gtgggtatca acaggatta gataccctgg tagtccacac      720
agtaaacgat gaatactcgc tgttggcgat atactgtcag cggccaagcg aaagcattaa      780
gtattccacc tggggagtac gccggcaacg gtgaaactca aaggaattga cgggggcccg      840
cacaagcgga ggaacatgtg gtttaattcg atgatacgcg aggaacctta cccgggctta      900
aattgcaact gacggaatcg gaaacggttc tttcttcgga cagttgtgaa ggtgctgcat      960
ggttgtcgtc agctcgtgcc gtgaggtgtc ggcttaagtg ccataacgag cgcaaccctt     1020
acgggtagtt accatcaggt tatgctgggg actctacccg gactgccgtc gtaagatgtg     1080
aggaaggtgg ggatgacgtc aaatcagcac ggcccttacg tccggggcta cacacgtgtt     1140 acaatgggggg gtacagaagg cagctacacg gcgacgtggt gctaatcccg aaagcctctc     1200
tcagttcgga ttggagtctg caacccgact ccatgaagct ggattcgcta gtaatcgcgc     1260
atcagccacg gcgcggtgaa tacgttcccg ggccttgtac acaccgcccg tcaagccatg     1320
aaagccgggg gtacctg                                                    1337

<210> SEQ ID NO 114
<211> LENGTH: 1353
<212> TYPE: DNA
<213> ORGANISM: Unknown
<220> FEATURE:
<223> OTHER INFORMATION: I09

<400> SEQUENCE: 114
ttagcttgct aaggccgatg gcgaccggcg cacgggtgag taacgcgtat ccaacctgcc       60
ttacactctt ggacagcctt ctgaaaggga gattaataca agatgttatc atgagtaagc      120 atttttcgcat gattaaaggt ttaccggtgt aagatgggga tgcgttccat tagatagtag      180
gcggggtaac ggcccaccta gtcttcgatg gatagggggtt ctgagaggaa ggtccccac      240 attggaactg agacacggtc caaactccta cgggaggcag cagtgaggaa tattggtcaa      300
tggacgagag tctgaaccag ccaagtagcg tgaaggatga aggttctatg gattgtaaac      360
ttcttttata cgggaataaa cgaatccacg cgtggatttt tgcatgtacc gtatgaataa      420
ggatcggcta actccgtgcc agcagccgcg gtaatacgga ggatccgagc gttatccgga      480
tttattgggt ttaaagggag cgtagatggg ttgttaagtc agttgtgaaa gtttgcggct      540
caaccgtaaa attgcaattg atactggcag tcttgagtac agttgaggta ggcggaattc      600
gtggtgtagc ggtgaaatgc ttagatatca cgaagaactc cgattgcgaa ggcagcttac      660
taacctgtaa ctgacattga tgctcgaaag tgtgggtatc aaacaggatt agataccctg      720
gtagtccaca cggtaaacga tgaatactcg ctgtaggcga tatacggtct gcggccaagc      780
gaaagcatta agtattccac ctggggagta cgccggcaac ggtgaaactc aaaggaattg      840 acggggggccc gcacaagcgg aggaacatgt ggtttaattc gatgatacgc gaggaacctt      900
acccgggctt aaattgcaac cgaatatggc ggaaacgcca tagctagcaa tagcggttgt      960
gaaggtgctg catggttgtc gtcagctcgt gccgtgaggt gtcggcttaa gtgccataac     1020
gagcgcaacc cttgccgata gttactaaca ggttatgctg aggactctgt cgggactgcc     1080
atcgtaagat gtgaggaagg tggggatgac gtcaaatcag cacggcccct acgtccgggg     1140
```

```
ctacacacgt gttacaatgg ggggtacaga gggctgctac cacgcaagtg gatgccaatc    1200
ccaaaaacct ctctcagttc ggattgaagt ctgcaacccg acttcatgaa gctggattcg    1260
ctagtaatcg cgcatcagcc acggcgcggt gaatacgttc ccgggccttg tacacaccgc    1320
ccgtcaagcc atgggagccg ggggtacctg aag                                 1353

<210> SEQ ID NO 115
<211> LENGTH: 1350
<212> TYPE: DNA
<213> ORGANISM: Unknown
<220> FEATURE:
<223> OTHER INFORMATION: I10

<400> SEQUENCE: 115
cttagcttgc taaggccgat ggcgaccggc gcacgggtga gtaacacgta tccaacctgc      60
cgtctactct tggacagcct tctgaaagga agattaatac aagatggcat catgagtccg     120
catgttcaca tgattaaagg tattccggta gacgatgggg atgcgttcca ttagatagta     180
ggcggggtaa cggcccacct agtcttcgat ggatagaggt tctgagagga aggtccccca     240
cattggaact gagacacggt ccaaactcct acgggaggca gcagtgagga atattggtca     300
atgggcgaga gcctgaacca gccaagtagc gtgaaggatg actgccctat gggttgtaaa     360
cttcttttat aaaggaataa agtcgggtat ggataccgt tgcatgtac tttatgaata      420 aggatcggct aactccgtgc cagcagccgc ggtaatacgg aggatccgag cgttatccgg     480
atttattggg tttaaaggga gcgtagatgg atgtttaagt cagttgtgaa agtttgcggc     540
tcaaccgtaa aattgcagtt gatactggat atcttgagtg cagttgaggc aggcggaatt     600
cgtggtgtag cggtgaaatg cttagatatc acgaagaact ccgattgcga aggcagcctg     660
ctaagctgca actgacattg aggctcgaaa gtgtgggtat caaacaggat tagataccct     720
ggtagtccac acggtaaacg atgaatactg ctgtttgcg atatactgca agcggccaag     780
cgaaagcgtt aagtattcca cctggggagt acgccggcaa cggtgaaact caaaggaatt     840
gacgggggcc cgcacaagcg gaggaacatg tggtttaatt cgatgatacg cgaggaacct     900
tacccgggct taaattgcag atgaattacg gtgaaagccg taagccgcaa ggcatctgtg     960
aaggtgctgc atggttgtcg tcagctcgtg ccgtgaggtg tcggcttaag tgccataacg    1020
agcgcaaccc ttgttgtcag ttactaacag gttccgctga ggactctgac aagactgcca    1080
tcgtaagatg tgaggaaggt ggggatgacg tcaaatcagc acggccctta cgtccggggc    1140
tacacacgtg ttacaatggg gggtacagag gccgctacc acgcgagtgg atgccaatcc     1200
ccaaaacctc tctcagttcg gactggagtc tgcaacccga ctccacgaag ctggattcgc    1260
tagtaatcgc gcatcagcca cggcgcgtg aatacgttcc cgggccttgt acacaccgcc     1320
cgtcaagcca tgggagccgg gggtacctga                                    1350

<210> SEQ ID NO 116
<211> LENGTH: 1356
<212> TYPE: DNA
<213> ORGANISM: Unknown
<220> FEATURE:
<223> OTHER INFORMATION: I11

<400> SEQUENCE: 116
tcttagcttg ctaaggctga tggcgaccgg cgcacgggtg agtaacacgt atccaacctg      60
ccgtctactc ttggccagcc ttctgaaagg aagattaatc caggatggga tcatgagttc     120
```

| | |
|---|---|
| acatgtccgc atgattaaag gtattttccg gtagacgatg gggatgcgtt ccattagata | 180 |
| gtaggcgggg taacggccca cctagtcaac gatggatagg ggttctgaga ggaaggtccc | 240 |
| ccacattgga actgagacac ggtccaaact cctacgggag gcagcagtga ggaatattgg | 300 |
| tcaatgggcg atggcctgaa ccagccaagt agcgtgaagg atgactgccc tatgggttgt | 360 |
| aaacttcttt tataaaggaa taaagtcggg tatgcatacc cgtttgcatg tactttatga | 420 |
| ataaggatcg gctaactccg tgccagcagc cgcggtaata cggaggatcc gagcgttatc | 480 |
| cggatttatt gggtttaaag ggagcgtaga tggatgttta agtcagttgt gaaagtttgc | 540 |
| ggctcaaccg taaaattgca gttgatactg gatgtcttga gtgcagttga ggcaggcgga | 600 |
| attcgtggtg tagcggtgaa atgcttagat atcacgaaga actccgattg cgaaggcagc | 660 |
| ctgctaagct gcaactgaca ttgaggctcg aaagtgtggg tatcaaacag gattagatac | 720 |
| cctggtagtc cacacggtaa acgatgaata ctcgctgttt gcgatatacg gcaagcggcc | 780 |
| aagcgaaagc gttaagtatt ccacctgggg agtacgccgg caacggtgaa actcaaagga | 840 |
| attgacgggg gcccgcacaa gcggaggaac atgtggttta attcgatgat acgcgaggaa | 900 |
| ccttacccgg gcttaaattg cactcgaatg atccggaaac ggttcagcta gcaatagcga | 960 |
| gtgtgaaggt gctgcatggt tgtcgtcagc tcgtgccgtg aggtgtcggc ttaagtgcca | 1020 |
| taacgagcgc aacccttgtt gtcagttact aacaggtgat gctgaggact ctgacaagac | 1080 |
| tgccatcgta agatgtgagg aaggtgggga tgacgtcaaa tcagcacggc ccttacgtcc | 1140 |
| ggggctacac acgtgttaca atgggggta cagagggccg ctaccacgcg agtggatgcc | 1200 |
| aatcccaa accctctca gttcggactg gagtctgcaa cccgactcca cgaagctgga | 1260 |
| ttcgctagta atcgcgcatc agccacggcg cggtgaatac gttcccgggc cttgtacaca | 1320 |
| ccgcccgtca agccatggga gccggggta cctgaa | 1356 |

<210> SEQ ID NO 117
<211> LENGTH: 1353
<212> TYPE: DNA
<213> ORGANISM: Unknown
<220> FEATURE:
<223> OTHER INFORMATION: I12
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 117

| | |
|---|---|
| tgtagnanta cagattgatg gcgaccggcg cacgggtgag taacgcgtat gcaacttacc | 60 |
| tatcagaggg ggatagcccg gcgaaagtcg gattaatacc ccataaaaca ggggtcccgc | 120 |
| atgggaatat ttgttaaaga ttcatcgctg atagataggc atgcgttcca ttaggcagtt | 180 |
| ggcggggtaa cggcccacca aaccgacgat ggatagggt tctgagagga aggtccccca | 240 |
| cattggtact gagacacgga ccaaactcct acgggaggca gcagtgagga atattggtca | 300 |
| atggccgaga ggctgaacca gccaagtcgc gtgaaggaag aaggatctat ggtttgtaaa | 360 |
| cttcttttat aggggaataa agtggaggac gtgtccttt ttgtatgtac cctatgaata | 420 |
| agcatcggct aactccgtgc cagcagccgc ggtaatacgg aggatgcgag cgttatccgg | 480 |
| atttattggg tttaaagggt gcgtaggtgg tgatttaagt cagcggtgaa agtttgtggc | 540 |
| tcaaccataa aattgccgtt gaaactgggt tacttgagtg tgtttgaggt aggcggaatg | 600 |

| | |
|---|---|
| cgtggtgtag cggtgaaatg catagatatc acgcagaact ccgattgcga aggcagctta | 660 |
| ctaaaccata actgacactg aagcacgaaa gcgtggggat caaacaggat tagatacsct | 720 |
| ggtagtccac gcagtaaacg atgattacta ggagtttgcg atacaatgta agctctacag | 780 |
| cgaaagcgtt aagtaatcca cctggggagt acgccggcaa cggtgaaact caaaggaatt | 840 |
| gacggggggcc cgcacaagcg gaggaacatg tggtttaatt cgatgatacg cgaggaacct | 900 |
| tacccgggtt tgaacgtagt ctgaccggag tggaaacact ccttctagca atagcagatt | 960 |
| acgaggtgct gcatggttgt cgtcagctcg tgccgtgagg tgtcggctta agtgccataa | 1020 |
| cgagcgcaac ccttatcact agttactaac aggtgaagct gaggactctg gtgagactgc | 1080 |
| cagcgtaagc tgtgaggaag gtggggatga cgtcaaatca gcacggccct tacatccggg | 1140 |
| gcgacacacg tgttacaatg gcatggacaa agggcagcta cctggcgaca ggatgctaat | 1200 |
| ctccaaacca tgtctcagtt cggatcggag tctgcaactc gactccgtga agctggattc | 1260 |
| gctagtaatc gcgcatcagc catggcgcgg tgaatacgtt cccgggcctt gtacacaccg | 1320 |
| cccgtcaagc catgggagcc gggggtacct gaa | 1353 |

<210> SEQ ID NO 118
<211> LENGTH: 824
<212> TYPE: DNA
<213> ORGANISM: Unknown
<220> FEATURE:
<223> OTHER INFORMATION: I13

<400> SEQUENCE: 118

| | |
|---|---|
| ggcgaccggc gcacgggtga gtaacgcgta tgcaacttac ctatcagagg gggataaccc | 60 |
| ggcgaaagtc ggactaatac cgcatgaagc aggggcccccg catggggata tttgctaaag | 120 |
| attcatcgct gatagatagg catgcgttcc attaggcagt tggcggggta acggcccacc | 180 |
| aaaccgacga tggataggggg ttctgagagg aaggtccccc acattggtac tgagacacgg | 240 |
| accaaactcc tacgggaggc agcagtgagg aatattggtc aatgggcgta agcctgaacc | 300 |
| agccaagtcg cgtgagggat gaaggttcta tggatcgtaa acctctttta taagggaata | 360 |
| aagtgcggga cgtgtcctgt tttgtatgta ccttatgaat aaggatcggc taactccgtg | 420 |
| ccagcagccg cggtaatacg gaggatccga gcgttatccg gatttattgg gtttaaaggg | 480 |
| tgcgtaggcg gccttttaag tcagcggtga agtctgtgg ctcaaccata gaattgccgt | 540 |
| tgaaactggg gggcttgagt atgtttgagg caggcggaat gcgtggtgta gcggtgaaat | 600 |
| gcttagatat cacgcagaac cccgattgcg aaggcagcct gccaagccat gactgacgct | 660 |
| gatgcacgaa agcgtgggga tcaaacagga ttagataccc tggtagtcca cgcagtaaac | 720 |
| gatgatcact agctgtttgc gatacagtgt aagcggcaca gcgaaagcgt taagtgatcc | 780 |
| acctggggag tacgccggca acggtgaaac tcaaaggaat tgac | 824 |

<210> SEQ ID NO 119
<211> LENGTH: 1348
<212> TYPE: DNA
<213> ORGANISM: Unknown
<220> FEATURE:
<223> OTHER INFORMATION: I14

<400> SEQUENCE: 119

| | |
|---|---|
| gatagcaata tctatggtgg cgaccggcgc acgggtgcgt aacgcgtatg caacctacct | 60 |
| ttaacagggg gataacactg agaaattggt actaatacc cataatatca tagaaggcat | 120 |

```
cttttatggt tgaaaattcc gatggttaga gatgggcatg cgttgtatta gctagttggt      180
ggggtaacgg ctcaccaagg cgacgataca taggggact gagaggttaa ccccccacac      240
tggtactgag acacggacca gactcctacg ggaggcagca gtgaggaata ttggtcaatg      300
gacgcaagtc tgaaccagcc atgccgcgtg caggatgacg gctctatgag ttgtaaactg      360
cttttgtacg agggtaaacg cagatacgtg tatctgtctg aaagtatcgt acgaataagg      420
atcggctaac tccgtgccag cagccgcggt aatacggagg attcaagcgt tatccggatt      480
tattgggttt aaagggtgcg taggcggttt gataagttag aggtgaaatt cgggggctca      540
accctgaacg tgcctctaat actgttgagc tagagagtag ttgcggtagg cggaatgtat      600
ggtgtagcgg tgaaatgctt agagatcata cagaacaccg attgcgaagg cagcttacca      660
aactatatct gacgttgagg cacgaaagcg tggggagcaa acaggattag ataccctggt      720
agtccacgca gtaaacgatg ataactcgtt gtcggcgata cacagtcggt gactaagcga      780
aagcgataag ttatccacct ggggagtacg ttcgcaagaa tgaaactcaa aggaattgac      840
gggggcccgc acaagcggag gaacatgtgg tttaattcga tgatacgcga ggaaccttac      900
ccgggcttga agttagcga cgattcttga aagaggattt ccttcgggg cgcgaaacta      960 ggtgctgcat ggttgtcgtc agctcgtgcc gtgaggtgtc gggttaagtc ccataacgag     1020
cgcaacccct accgttagtt gccatcaggt gaagctgggc actctggcgg gactgccggt     1080
gtaagccgag aggaaggtgg ggatgacgtc aaatcagcac ggcccttacg tccggggcta     1140
cacacgtgtt acaatggtag gtacagaggg cagctaccca gcgatgggat gcgaatctcg     1200
aaagcctatc tcagttcgga ttggaggctg aaacccgcct ccatgaagtt ggattcgcta     1260
gtaatcgcgc atcagccatg gcgcggtgaa tacgttcccg ggccttgtac acaccgcccg     1320
tcaagccatg ggagccgggg gtgcctga                                       1348

<210> SEQ ID NO 120
<211> LENGTH: 1337
<212> TYPE: DNA
<213> ORGANISM: Unknown
<220> FEATURE:
<223> OTHER INFORMATION: I15
<220> FEATURE:
<221> NAME/KEY: misc_feature
<222> LOCATION: (838)..(839)
<223> OTHER INFORMATION: n is a, c, g, or t

<400> SEQUENCE: 120
ttctttgctg gcgaccggcg cacgggtgag taacacgtat ccaacctgcc gatgactcgg       60
ggatagcctt tcgaaagaaa gattaatacc cgatggtata tctgaaaggc atctttcagc      120
tattaaagaa tttcggtcat tgatggggat gcgttccatt aggttgttgg cggggtaacg      180
gcccaccaag ccatcgatgg ataggggttc tgagaggaag gtcccccaca ttggaactga      240
gacacggtcc aaactcctac gggaggcagc agtgaggaat attggtcaat ggacgagagt      300
ctgaaccagc caagtagcgt gaaggatgac tgccctatgg gttgtaaact tcttttatac      360
gggaataaag ttgggcacgt gtgccttttt gtatgtaccg tatgaataag gatcggctaa      420
ctccgtgcca gcagccgcgg taatacggag gatccgagcg ttatccggat ttattgggtt      480
taaagggagc gtaggcggat gcttaagtca gttgtgaaag tttgcggctc aaccgtaaaa      540
ttgcagttga tactgggtgt cttgagtaca gtagaggcag gcggaattcg tggtgtagcg      600
gtgaaatgct tagatatcac gaagaactcc gattgcgaag gcagcttgct ggactgtaac      660
tgacgctgat gctcgaaagt gtgggtatca acaggattag atacccgtgg tagtccacac      720
```

```
agtaaacgat gaatactcgc tgtttgcgat atacagtaag cggccaagcg aaagcgttaa      780
gtattccacc tggggagtac gccggcaacg gtgaaactca aaggaattga cgggggcnng      840
cacaagcgga ggaacatgtg gtttaattcg atgatacgcg aggaacctta cccgggctta      900
aattgcaaat gaatgttctg gaaacagatc agccgcaagg catttgtgaa ggtgctgcat      960
ggttgtcgtc agctcgtgcc gtgaggtgtc ggcttaagtg ccataacgag cgcaaccctt     1020
atcgatagtt accatcaggt tatgctgggg actctgtcga gactgccgtc gtaagatgtg     1080
aggaaggtgg ggatgacgtc aaatcagcac ggcccttacg tccggggcta cacacgtgtt     1140
acaatggggg gtacagaagg cagctacacg gcgacgtgat gctaatccct aaaacctctc     1200
tcagttcgga ttggagtctg caacccgact ccatgaagct ggattcgcta gtaatcgcgc     1260
atcagccacg gcgcggtgaa tacgttcccg ggccttgtac acaccgcccg tcaagccatg     1320
aaagccgggg gtacctg                                                    1337

<210> SEQ ID NO 121
<211> LENGTH: 1343
<212> TYPE: DNA
<213> ORGANISM: Unknown
<220> FEATURE:
<223> OTHER INFORMATION: I16
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (110)..(113)
<223> OTHER INFORMATION: n is a, c, g, or t
<220> FEATURE:
<221> NAME/KEY: misc_feature
<222> LOCATION: (337)..(338)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t

<400> SEQUENCE: 121
cttgnanact gaagatggcg accggcgcac gggtgagtaa cacgtatcca acctgccgat       60
aactccggaa tagcctttcg aaagaaagat taataccgga tagcatacgn nnntcgcatg      120
atatttttat taaagaattt cggttatcga tggggatgcg ttccattagt ttgttggcgg      180
ggtaacggcc caccaagact acgatggata ggggttctga gaggaaggtc ccccacattg      240
gaactgagac acggtccaaa ctcctacggg aggcagcagt gaggaatatt ggtcaatggg      300
cgagagcctg aaccagccaa gtagcgtgaa ggatganngc tctatgggtc gtaaacttct      360

tttatatggg aataaagttt tccacgtgtg gaattttgta tgtaccatat gaataaggat      420
cggctaactc cgtgccagca gccgcggtaa tacggaggat ccgagcgtta ccggattta      480

ttgggtttaa agggagcgta ggtggattgt taagtcagtt gtgaaagttt gcggctcaac      540
cgtaaaattg cagttgaaac tggcagtctt gagtacagta gaggtgggcg gaattcgtgg      600

tgtagcggtg aaatgcttag atatcacgaa gaactccgat tgcgaaggca gctcactaga      660
ctgtcactga cactgatgct cgaaagtgtg gtatcaaac aggattagat accctggtag      720

tccacacagt aaacgatgaa tactcgctgt ttgcgatata cagtaagcgg ccaagcgaaa      780
```

-continued

| | |
|---|---|
| gcattaagta ttccacctgg ggagtacgcc ggcaacggtg aaactcaaag gaattgacgg | 840 |
| gggcccgcac aagcggagga acatgtggtt taattcgatg atacgcgagg aaccttaccc | 900 |
| gggcttaaat tgcaacagaa tatattggaa acagtatagc cgtaaggctg ttgtgaaggt | 960 |
| gctgcatggt tgtcgtcagc tcgtgccgtg aggtgtcggc ttaagtgcca taacgagcgc | 1020 |
| aaccctatc tttagttact aacaggtcat gctgaggact ctagagagac tgccgtcgta | 1080 |
| agatgtgagg aaggtgggga tgacgtcaaa tcagcacggc ccttacgtcc ggggctacac | 1140 |
| acgtgttaca atgggggta cagaaggcan ctacctggtg acaggatgct aatcccaaaa | 1200 |
| acctctctca gttcggatcg aagtctgcaa cccgacttcg tgaagctgga ttcgctagta | 1260 |
| atcgcgcatc agccatggcg cggtgaatac gttcccgggc cttgtacaca ccgcccgtca | 1320 |
| agccatgaaa gccgggggta cct | 1343 |

<210> SEQ ID NO 122
<211> LENGTH: 1335
<212> TYPE: DNA
<213> ORGANISM: Unknown
<220> FEATURE:
<223> OTHER INFORMATION: I17

<400> SEQUENCE: 122

| | |
|---|---|
| gggtggcgac cggcgcacgg gtgcgtaacg cgtatgcaac ctacccataa caggggata | 60 |
| acactgagaa attggtacta ataccccata acatcagaac cggcatcggt tttggttgaa | 120 |
| aactccggtg ttatggatg ggcatgcgtt gtattagctg gttggtgagg taacggctca | 180 |
| ccaaggcaac gatacatagg gggactgaga ggttaacccc ccacattggt actgagacac | 240 |
| ggaccaaact cctacgggag gcagcagtga ggaatattgg tcaatggacg caagtctgaa | 300 |
| ccagccatgc cgcgtgcagg aagacggctc tatgagttgt aaactgcttt tgtacgaggg | 360 |
| taaacgcttc tacgtgtagg agcctgaaag tatcgtacga ataaggatcg ctaactccg | 420 |
| tgccagcagc cgcggtaata cggaggatcc aagcgttatc cggatttatt gggtttaaag | 480 |
| ggtgcgtagg cggtttgata agttagaggt gaaataccgg tgcttaacac cggaactgcc | 540 |
| tctaatactg ttgaactaga gagtagttgc ggtaggcgga atgtatggtg tagcggtgaa | 600 |
| atgcttagag atcatacaga acaccgattg cgaaggcagc ttaccaaact atatctgacg | 660 |
| ttgaggcacg aaagcgtggg gagcaaacag gattagatac cctggtagtc cacgcagtaa | 720 |
| acgatgataa ctcgctgtcg gcgatacaca gtcggcggct aagcgaaagc gataagttat | 780 |
| ccacctgggg agtacgttcg caagaatgaa actcaaagga attgacgggg gcccgcacaa | 840 |
| gcggaggaac atgtggttta attcgatgat acgcgaggaa ccttacccgg gcttgaaagt | 900 |
| tactgacgat tctggaaaca ggatttccct tcggggcagg aaactaggtg ctgcatggtt | 960 |
| gtcgtcagct cgtgccgtga ggtgtcgggt taagtcccat aacgagcgca acccctaccg | 1020 |
| ttagttgcca tcaggtcaag ctgggcactc tggcggact gccggtgtaa gccgagagga | 1080 |
| aggtggggat gacgtcaaat cagcacggcc cttacgtccg gggctacaca cgtgttacaa | 1140 |
| tggtaggtac agagggcagc tacccagtga tgggatgcga atctcgaaag cctatctcag | 1200 |
| ttcggatcgg aggctgaaac ccgcctccgt gaagttggat tcgctagtaa tcgcgcatca | 1260 |
| gccatggcgc ggtgaatacg ttcccgggcc ttgtacacac cgcccgtcaa gccatggaag | 1320 |
| ctgggggtgc ctgaa | 1335 |

<210> SEQ ID NO 123
<211> LENGTH: 1309

<212> TYPE: DNA
<213> ORGANISM: Unknown
<220> FEATURE:
<223> OTHER INFORMATION: I18

<400> SEQUENCE: 123

```
cgtatgcaac ctgcccgata ccggggtata gcccatggaa acgtggatta acaccccata    60
gtactttat cctgcatggg atgtgagtta aatgttcaag gtatcggatg ggcatgcgtc   120
ctattagtta gttggcgggg taacagccca ccaagacgat gataggtagg ggttctgaga   180
ggaaggtccc ccacattgga actgagacac ggtccaaact cctacgggag gcagcagtga   240
ggaatattgg tcaatggacg taagtctgaa ccagccaagt cgcgtgaggg aagactgccc   300
tatgggttgt aaacctcttt tataagggaa gaataagttc tacgtgtaga atgatgcctg   360
taccttatga ataagcatcg gctaactccg tgccagcagc cgcggtaata cggaggatgc   420
gagcgttatc cggatttatt gggtttaaag ggtgcgtagg cggtttatta agttagtggt   480
taaatatttg agctaaactc aattgtgcca ttaatactgg taaactggag tacagacgag   540
gtaggcggaa taagttaagt agcggtgaaa tgcatagata taacttagaa ctccgatagc   600
gaaggcagct taccagactg taactgacgc tgatgcacga gagcgtgggt agcgaacagg   660
attagatacc ctggtagtcc acgccgtaaa cgatgctcac tggttctgtg cgatatattg   720
tacgggatta agcgaaagta ttaagtgagc cacctgggga gtacgtcggc aacgatgaaa   780
ctcaaaggaa ttgacggggg cccgcacaag cggaggaaca tgtggtttaa ttcgatgata   840
cgcgaggaac cttacctggg tttaaatggg aaatgtcgta tttggaaaca gatattctct   900
tcggagcgtt tttcaaggtg ctgcatggtt gtcgtcagct cgtgccgtga ggtgtcgggt   960
taagtcccat aacgagcgca acccttaccg ttagttgcta gcatgtaatg atgagcactc  1020
taacgggact gccaccgtaa ggtgagagga aggcgggat gacgtcaaat cagcacggcc  1080
cttacaccca gggctacaca cgtgttacaa tggccggtac agagggccgc taccaggtga  1140
ctggatgcca atctcaaaag ccggtcgtag ttcggattgg agtctgtaac ccgactccat  1200
gaagttggat tcgctagtaa tcgcgcatca gccatggcgc ggtgaatacg ttcccgggcc  1260
ttgtacacac cgcccgtcaa gccatggaag ccggggggtgc ctgaagtcc             1309
```

<210> SEQ ID NO 124
<211> LENGTH: 1339
<212> TYPE: DNA
<213> ORGANISM: Unknown
<220> FEATURE:
<223> OTHER INFORMATION: I19
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (190)..(191)
<223> OTHER INFORMATION: n is a, c, g, or t
<220> FEATURE:
<221> NAME/KEY: misc_feature
<222> LOCATION: (911)..(911)
<223> OTHER INFORMATION: n is a, c, g, or t

<400> SEQUENCE: 124

```
agagagcttn ctttctcgag cgagtggcga acgggtgagt aacgcgtgag gaacctgcct      60
caaagagggg gacaacagtt ggaaacgact gctaataccg cataagccca cgggtcggca     120
tcgnncagag ggaaaaggag caatccgctt tgagatggcc tcgcgtccga ttagctagtt     180
ggngaggtan nggcccacca aggcgacgat cggtagccgg actgagaggt tgaacggcca     240
cattgggact gagacacggc ccagactcct acgggaggca gcagtgggga atattgcaca     300
atgggggaaa ccctgatgca gcgacgccgc gtggaggaag aaggtcttcg gattgtaaac     360
tcctgttgtt ggggaagata atgacggtac ccaacaagga agtgacgct aactacgtgc      420
cagcagccgc ggtaaaacgt aggtcacaag cgttgtccgg aattactggg tgtaaaggga     480
gcgcaggcgg gaagacaagt tggaagtgaa atctatgggc tcaacccata aactgctttc     540
aaaactgttt ttcttgagta gtgcagaggt aggcggaatt cccggtgtag cggtggaatg     600
cgtagatatc gggaggaaca ccagtggcga aggcggccta ctgggcacca actgacgctg     660
aggctcgaaa gtgtgggtag caaacaggat tagatacccct ggtagtccac accgtaaacg    720
atgattacta ggtgttggag gattgacccc ttcagtgccg cagttaacac aataagtaat     780
ccacctgggg agtacgaccg caaggttgaa actcaaagga attgacgggg cccgcacaa      840
gcagtggagt atgtggttta attcgacgca acgcgaagaa ccttaccaag tcttgacatc     900
ccttgacaga natagaaata tgttttctct tcggagcaag gagacaggtg gtgcatggtt     960
gtcgtcagct cgtgtcgtga gatgttgggt taagtcccgc aacgagcgca accttatgg    1020
tcagttacta cgcaagagga ctctggccag actgccgttg acaaaacgga ggaaggtggg   1080
gatgacgtca aatcatcatg ccctttatga cttgggctac acacgtacta caatggcgtt   1140
aaacaaagag aagcaagacc gcgaggtgga gcaaaactca gaaacaacgt cccagttcgg   1200
actgcaggct gcaactcgcc tgcacgaagt cggaattgct agtaatcgtg gatcagcatg   1260
ccacggtgaa tacgttcccg ggccttgtac acaccgcccg tcacaccatg agagccgggg   1320
ggacccgaag tcggtagtc                                                1339
```

<210> SEQ ID NO 125
<211> LENGTH: 1339
<212> TYPE: DNA
<213> ORGANISM: Unknown
<220> FEATURE:
<223> OTHER INFORMATION: I20
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (1337)..(1337)
<223> OTHER INFORMATION: n is a, c, g, or t

<400> SEQUENCE: 125

```
gagagagctt gctttctcga gcgagtggcg aacgggtgag taacgcgtga ggaacctgcc      60
tcaaagaggg ggacaacagt tggaaacgac tgctaatacc gcataagccc acgggtcggc    120
atcgaccaga gggaaaagga gtaatccgct ttgagatggc ctcgcgtccg attagctagt    180
tggtgaggta anggcccacc aaggnnacga tcggtagccg gactgagagg ttgaacggcc    240
acattgggac tgagacacgg cccagactcc tacgggaggc agcagtgggg aatattgcac    300
```

```
aatgggggaa accctgatgc agcgacgccg cgtggaggaa gaaggtcttc ggattgtaaa        360
ctcctgttgt tggggaagat aatgacgtta cccaacaagg aagtgacggc taactacgtg        420
ccagcagccg cggtaaaacg taggtcacaa gcgttgtccg gaattactgg gtgtaaaggg        480
agcgcaggcg ggaagacaag ttggaagtga aatctatggg ctcaacccat aaactgcttt        540
caaaactgtt tttcttgagt agtgcagagg taggcggaat tcccggtgta gcggtggaat        600
gcgtagatat cgggaggaac accagtggcg aaggcggcct actgggcacc aactgacgct        660
gaggctcgaa agtgtgggta gcaaacagga ttagataccc tggtagtcca caccgtaaac        720
gatgattact aggtgttgga ggattgaccc cttcagtgcc gcagttaaca caataagtaa        780
tccacctggg gagtacgacc gcaaggttga aactcaaagg aattgacggg ggcccgcaca        840
agcagtggag tatgtggttt aattcgacgc aacgcgaaga accttaccaa gtcttgacat        900
cccttgacag acatagaaat atgttttctc ttcggagcaa ggagacaggt ggtgcatggt        960
tgtcgtcagc tcgtgtcgtg agatgttggg ttaagtcccg caacgagcgc aacccttatg       1020
gtcagttact acgcaagagg actctggcca gactgccgtt gacaaaacgg aggaaggtgg       1080
ggatgacgtc aaatcatcat gccctttatg acttgggcta cacacgtact acaatggcgt       1140
taaacaaaga gaagcaagac cgcgaggtgg agcaaaactc agaaacaacg tcccagttcg       1200
gactgcaggc tgcaactcgc ctgcacgaag tcggaattgc tagtaatcgt ggatcagcat       1260
gccacggtga atacgttccc gggccttgta cacaccgccc gtcacaccat gagagccggg       1320
gggacccgaa gtcggtngt                                                    1339

<210> SEQ ID NO 126
<211> LENGTH: 1354
<212> TYPE: DNA
<213> ORGANISM: Unknown
<220> FEATURE:
<223> OTHER INFORMATION: I21
<220> FEATURE:
<221> NAME/KEY: misc_feature
<222> LOCATION: (184)..(187)
<223> OTHER INFORMATION: n is a, c, g, or t
<220> FEATURE:
<221> NAME/KEY: misc_feature
<222> LOCATION: (573)..(574)
<223> OTHER INFORMATION: n is a, c, g, or t
<220> FEATURE:
<221> NAME/KEY: misc_feature
<222> LOCATION: (752)..(755)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t

<400> SEQUENCE: 126
cattgagact tcggtggatt tgatctattt ctagtggcgg acgggtgagt aacgcgtggg         60
taacctgcct tatacagggg gataacagtc agaaatggct gctaataccg cataagcgca        120
cagagctgca tggctcagtg tgaaaaactc cggtggtata agatggaccc gcgttggatt        180
agcnnnntgg tggggtaacg gcccaccaag gcgacgatcc atagccggcc tgagagggtg        240
aacggccaca ttgggactga gacacggccc agactcctac gggaggcagc agtgggaat        300 attgcacaat gggggaaacc ctgatgcagc gacgccgcgt gaaggaagaa gtatctcggt        360
atgtaaactt ctatcagcag ggaagatagt gacggtacct gactaagaag ccccggctaa        420
ctacgtgcca gcagccgcgg taatacgtag gggcaagcg ttatccggat ttactgggtg        480
```

```
taaagggagc gtagacggtg tggcaagtct gatgtgaaag gcatgggctc aacctgtgga      540
ctgcattgga aactgtcata cttgagtgcc ggnngggtaa gcggaattcc tagtgtagcg      600
gtgaaatgcg tagatattag gaggaacacc agtggcgaag gcggcttact ggacggtaac      660
tgacgttgag gctcgaaagc gtggggagca aacaggatta gataccctgg tagtccacgc      720
cgtaaacgat gaatactagg tgtcggggag cnnnnctctt cggtgccgtc gcaaacgcag      780
taagtattcc acctggggag tacgttcgca agaatgaaac tcaaaggaat tgacggggac      840
ccgcacaagc ggtggagcat gtggtttaat tcgaagcaac gcgaagaacc ttaccaagtc      900
ttgacatccg cctgaccgat ccttaaccgg atctttcctt cgggacaggc gagacaggtg      960
gtgcatggtt gtcgtcagct cgtgtcgtga tgttgggt taagtcccgc aacgagcgca      1020 accccctatcc tcagtagcca gcatttaagg tgggcactct ggggagactg ccagggataa     1080
cctggaggaa ggcgggatg acgtcaaatc atcatgcccc ttatgatttg ggctacacac      1140
gtgctacaat ggcgtaaaca aagggaagcg agatnntgag atggagcaaa tcccaaaaat      1200
aacgtcccag ttcggactgt agtctgcaac ccgactacac gaagctggaa tcgctagtaa      1260
tcgcggatca gaatgccgcg gtgaatacgt tcccgggtct tgtacacacc gcccgtcaca      1320
ccatgggagt cagtaacgcc cgaagtcagt gacc                                  1354

<210> SEQ ID NO 127
<211> LENGTH: 1264
<212> TYPE: DNA
<213> ORGANISM: Unknown
<220> FEATURE:
<223> OTHER INFORMATION: I22
<220> FEATURE:
<221> NAME/KEY: misc_feature
<222> LOCATION: (144)..(145)
<223> OTHER INFORMATION: n is a, c, g, or t

<400> SEQUENCE: 127
ttacttggat ttcttcggaa tgacgagtat tgtgactgag cggcggacgg gtgagtaacg       60
cgtgggtaac ctgcctcata caggggggata acagttagaa atgactgcta ataccgcata     120
agaccacagc accgcatggt gcanngggtaa aaactccggt ggtatgagat ggacccgcgt     180
ctgattagct ggttggtggg gtaacggcct accaaggcga cgatcagtag ccggcctgag     240
agggcgaccg gccacattgg gactgagaca cggcccaaac tcctacggga ggcagcagtg     300
gggaatattg cacaatgggg gaaaccctga tgcagcgacg ccgcgtgaag gaagaagtat     360
ttcggtatgt aaacttctat cagcaggaa gaaaatgacg gtacctgact aagaagcccc      420
ggctaactac gtgccagcag ccgcggtaat acgtaggggg cccgttttc tagagtgtcg      480 gagaggtaag cggaattcct agtgtagcgg tgaaatgcgt agatattagg aggaacacca     540
gtggcgaagg cggcttactg gacgatgact gacgttgagg ctcgaaagcg tggggagcaa     600
acaggattag ataccctggt agtccacgcc gtaaacgatg actactaggt gtcgggtggc      660
aaagccattc ggtgccgcag caaacgcaat aagtagtcca cctggggagt acgttcgcaa     720
gaatgaaact caaaggaatt gacggggacc cgcacaagcg gtggagcatg tggtttaatt     780
cgaagcaacg cgaagaacct tacctgctct tgacatcccg gtgaccgctc cgtaatggga     840
gcttttcttc ggaacaccgg agacaggtgg tgcatggttg tcgtcagctc gtgtcgtgag     900
atgttgggtt aagtcccgca acgagcgcaa ccccctatctt cagtagccag cggtttggcc     960
gggcactctg gagagactgc cagggataac ctggaggaag gtggggatga cgtcaaatca    1020
tcatgcccct tatgagcagg gctacacacg tgctacaatg gcgtaaacaa agggaggcga    1080
```

```
actcgcgagg gtaagcaaat cccaaaaata acgtctcagt tcggattgta gtctgcaact    1140
cgactacatg aagctggaat cgctagtaat cgcgaatcag aatgtcgcgg tgaatacgtt    1200
cccgggtctt gtacacaccg cccgtcacac catgggagtc agtaacgccc gaagtcagtg    1260
accc                                                                 1264

<210> SEQ ID NO 128
<211> LENGTH: 1340
<212> TYPE: DNA
<213> ORGANISM: Unknown
<220> FEATURE:
<223> OTHER INFORMATION: I23

<400> SEQUENCE: 128
gagaagcttg cttttctgat ctagtggcgg acgggtgagt aacacgtgag caatctgcct      60
ttcagagggg gataccgatt ggaaacgatc gttaataccg cataatataa ttgaaccgca     120
tgatttgatt atcaaagatt tatcgctgaa agatgagctc gcgtctgatt agctagttgg     180
taaggtaacg gcttaccaag gcgacgatca gtagccggac tgagaggttg atcggccaca     240
ttgggactga gacacggccc agactcctac gggaggcagc agtggggaat attgcacaat     300
ggaggaaact ctgatgcagc gatgccgcgt gagggaagaa ggttttagga ttgtaaacct     360
ctgtcttcag ggacgaaaaa tgacggtacc tgaggaggaa gctccggcta actacgtgcc     420
agcagccgcg gtaatacgta gggagcgagc gttgtccgga attactgggt gtaaagggag     480
cgtaggcggg atcgcaagtc agatgtgaaa actatgggct taacccataa actgcatttg     540
aaactgtggt tcttgagtga agtagaggta agcggaattc ctagtgtagc ggtgaaatgc     600
gtagatatta ggaggaacat cagtggcgaa ggcggcttac tgggctttaa ctgacgctga     660
ggctcgaaag cgtggggagc aaacaggatt agataccctg gtagtccacg ccgtaaacga     720
tgattactag gtgtgggggg actgaccccct tccgtgccgc agcaaacgca ataagtaatc     780
cacctgggga gtacgaccgc aaggttgaaa ctcaaaggaa ttgacggggg cccgcacaag     840
cagtggagta tgtggattaa ttcgaagcaa cgcgaagaac cttaccaggt cttgacatcg     900
tatgcatagc tcagagatga gtgaaatctc ttcgagaca tatagacagg tggtgcatgg     960
ttgtcgtcag ctcgtgtcgt gagatgttgg gttaagtccc gcaacgagcg caacccttac    1020
tgttagttgc tacgcaagag cactctagca ggactgccgt tgacaaacg gaggaaggtg    1080 gggatgacgt caaatcatca tgccccttat gacctgggcc tcacacgtac tacaatggct    1140
gtcaacagag ggatgcaaag ccgcgaggtg gagcgaaccc ctaaaagcag tcttagttcg    1200
gattgtaggc tgcaacccgc ctacatgaag tcggaattgc tagtaatcgc agatcagcat    1260
gctgcggtga atacgttccc gggccttgta cacaccgccc gtcacgccat gggagtcggt    1320
aacacccgaa gcctgtagtc                                                1340

<210> SEQ ID NO 129
<211> LENGTH: 1337
<212> TYPE: DNA
<213> ORGANISM: Unknown
<220> FEATURE:
<223> OTHER INFORMATION: I24
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (113)..(115)
```

<223> OTHER INFORMATION: n is a, c, g, or t
<220> FEATURE:
<221> NAME/KEY: misc_feature
<222> LOCATION: (123)..(125)
<223> OTHER INFORMATION: n is a, c, g, or t
<220> FEATURE:
<221> NAME/KEY: misc_feature
<222> LOCATION: (1155)..(1156)
<223> OTHER INFORMATION: n is a, c, g, or t
<220> FEATURE:
<221> NAME/KEY: misc_feature
<222> LOCATION: (1336)..(1336)
<223> OTHER INFORMATION: n is a, c, g, or t

<400> SEQUENCE: 129

```
agagagcttg ctttctcgag cgagtggcga acgggtgagt aacgcgtgag gannctgcct      60
caaagagggg gacaacagtt ggaaacgact gctaataccg cataagccca cgnnnccgca     120
tgnnncagag ggaaaaggag taatccgctt tgagatggcc tcgcgtccga ttagctagtt     180
ggtgaggtaa cggcccacca aggcgacgat cggtagccgg actgagaggt tgaacggcca     240
cattgggact gagacacggc ccagactcct acggaggca gcagtgggga atattgcaca      300
atgggggaaa ccctgatgca gcgacgccgc gtggaggaag aaggtcttcg gattgtaaac     360
tcctgttgtt ggggaagata atgacggtac ccaacaagga agtgacggct aactacgtgc     420
cagcagccgc ggtaaaacgt aggtcacaag cgttgtccgg aattactggg tgtaaaggga     480
gcgcaggcgg aagacaagt tggaagtgaa atctatgggc tcaacccata aactgctttc     540
aaaactgttt ttcttgagta gtgcagaggt aggcggaatt cccggtgtag cggtggaatg     600
cgtagatatc gggaggaaca ccagtggcga aggcggccta ctgggcacca actgacgctg     660
aggctcgaaa gtgtgggtag caaacaggat tagataccct ggtagtccac accgtaaacg     720
atgattacta ggtgttggag gattgacccc ttcagtgccg cagttaacac aataagtaat     780
ccacctgggg agtacgaccg caaggttgaa actcaaagga attgacgggg cccgcacaa      840
gcagtggagt atgtggttta attcgacgca acgcgaagaa ccttaccaag tcttgacatc     900
ccttgacaga catagaaata tgtaatctct tcggagcaag gagacaggtg gtgcatggtt     960
gtcgtcagct cgtgtcgtga gatgttgggt taagtcccgc aacgagcgca acccttatgg    1020
tcagttacta cgcaagagga ctctggccag actgccgttg acaaaacgga ggaaggtggg    1080
gatgacgtca atcatcatg ccctttatga cttgggctac acacgtacta caatggcgtt    1140
aaacaaagag aagcnngacc gcgaggtgga gcaaaactca gaaacaacgt cccagttcgg    1200
actgcaggct gcaactcgcc tgcacgaagt cggaattgct agtaatcgtg gatcagcatg    1260
ccacggtgaa tacgttcccg ggccttgtac acaccgcccg tcacaccatg agagccgggg    1320
ggacccgaag tcggtng                                                   1337
```

<210> SEQ ID NO 130
<211> LENGTH: 1353
<212> TYPE: DNA
<213> ORGANISM: Unknown
<220> FEATURE:
<223> OTHER INFORMATION: I25
<220> FEATURE:
<221> NAME/KEY: misc_feature
<222> LOCATION: (570)..(572)
<223> OTHER INFORMATION: n is a, c, g, or t

<400> SEQUENCE: 130

```
gattcttcgg atgaagactt ttgtgactga gcggcggacg ggtgagtaac gcgtgggtaa      60
cctgcctcat acagggggat aacagttaga aatgactgct aataccgcat aagaccacgg     120
```

```
taccgcatgg tacagtggta aaaactccgg tggtatgaga tggacccgcg tctgattagg      180
tagttggtgg ggtaacggcc taccaagccg acgatcagta gccgacctga gagggtgacc      240
ggccacattg ggactgagac acggcccaga ctcctacggg aggcagcagt ggggaatatt      300
gcacaatgga ggaaactctg atgcagcgac gccgcgtgaa ggatgaagta tttcggtatg      360
taaacttcta tcagcaggga agaaaatgac ggtacctgac taagaagccc cggctaacta      420
cgtgccagca gccgcggtaa tacgtagggg gcaagcgtta tccggattta ctgggtgtaa      480
agggagcgta gacggcacgg caagccagat gtgaaagccc ggggctcaac cccgggactg      540
catttggaac tgctgagcta gagtgtcggn nnggcaagtg gaattcctag tgtagcggtg      600
aaatgcgtag atattaggag gaacaccagt ggcgaaggcg gcttgctgga cgatgactga      660
cgttgaggct cgaaagcgtg gggagcaaac aggattagat accctggtag tccacgccgt      720
aaacgatgac tgctaggtgt cgggtggcaa agccattcgg tgccgcagct aacgcaataa      780
gcagtccacc tggggagtac gttcgcaaga atgaaactca aaggaattga cggggacccg      840
cacaagcggt ggagcatgtg gtttaattcg aagcaacgcg aagaaccttta cctgatcttg      900 acatcccgat gaccgcttcg taatggaagc ttttcttcgg aacatcggtg acaggtggtg      960
catggttgtc gtcagctcgt gtcgtgagat gttgggttaa gtcccgcaac gagcgcaacc     1020
cctatcttca gtagccagca ggttaagctg ggcactctgg agagactgcc agggataacc     1080
tggaggaagg tggggatgac gtcaaatcat catgccccctt atgaccaggg ctacacacgt     1140
gctacaatgg cgtaaacaaa gagaagcgaa ctcgcgaggg taagcaaatc tcaaaaataa     1200
cgtctcagtt cggattgtag tctgcaactc gactacatga agctggaatc gctagtaatc     1260
gcagatcaga atgctgcggt gaatacgttc ccgggtcttg tacacaccgc ccgtcacacc     1320
atgggagtca gtaacgcccg aagtcagtga ccc                                  1353

<210> SEQ ID NO 131
<211> LENGTH: 1361
<212> TYPE: DNA
<213> ORGANISM: Unknown
<220> FEATURE:
<223> OTHER INFORMATION: I26
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (939)..(940)
<223> OTHER INFORMATION: n is a, c, g, or t
<220> FEATURE:
<221> NAME/KEY: misc_feature
<222> LOCATION: (1052)..(1053)
<223> OTHER INFORMATION: n is a, c, g, or t
<220> FEATURE:
<221> NAME/KEY: misc_feature
<222> LOCATION: (1357)..(1357)
<223> OTHER INFORMATION: n is a, c, g, or t

<400> SEQUENCE: 131 cttaagtttng attcttcgga tgaagacttt tgtgactgag cggcggacgg gtgagtaacg       60
cgtgggtaac ctgcctcata caggggggata acagttagaa atggctgcta ataccgcata      120
agaccacagt actgcatggt acagtggtaa aaactccggt ggtatgagat ggacccgcgt      180
ctgattaggt agttggtgag gtaacggccc accaagccga cgatcagtag ccgacctgag      240
agggtgaccg gccacattgg gactgagaca cggcccagac tcctacggga ggcagcagtg      300
```

| | |
|---|---|
| gggaatattg cacaatgggc gaaagcctga tgcagcgacg ccgcgtgaag gatgaagtat | 360 |
| ttcggtatgt aaacttctat cagcagggaa gaaaatgacg gtacctgact aagaagcccc | 420 |
| ggctaactac gtgccagcag ccgcggtaat acgtaggggg caagcgttat ccggatttac | 480 |
| tgggtgtaaa gggagcgtag acggctgtgc aagtctgaag tgaaaggcat gggctcaacc | 540 |
| tgtggactgc tttggaaact gtgcagctag agtgtcggag aggtaagtgg aattcctagt | 600 |
| gtagcggtga aatgcgtaga tattaggagg aacaccagtg gcgaaggcgg cttactggac | 660 |
| gatgactgac gttgaggctc gaaagcgtgg ggagcaaaca ggattagata ccctggtagt | 720 |
| ccacgccgta aacgatgact gctaggtgtc gggtagcaaa gctattcggt gccgcagcta | 780 |
| acgcaataag cagtccacct ggggagtacg ttcgcaagaa tgaaactcaa aggaattgac | 840 |
| ggggacccgc acaagcggtg gagcatgtgg tttaattcga agcaacgcga gaaccttac | 900 |
| ctgatcttga catcccgatg accgcttcgt aatggaagnn tttcttcgga acatcggtga | 960 |
| caggtggtgc atggttgtcg tcagctcgtg tcgtgagatg ttgggttaag tcccgcaacg | 1020 |
| agcgcaaccc ttatcttcag tagccagcat tnnggatggg cactctggag agactgccag | 1080 |
| ggataacctg gaggaaggtg gggatgacgt caaatcatca tgccccttat gaccagggct | 1140 |
| acacacgtgt acaatggcg taaacaaagg gaagcagagc cgcgaggccg agcaaatctc | 1200 |
| aaaaataacg tctcagttcg gattgtagtc tgcaactcga ctacatgaag ctggaatcgc | 1260 |
| tagtaatcgc agatcagaat gctgcggtga atacgttccc gggtcttgta cacaccgccc | 1320 |
| gtcacaccat gggagtcagt aacgcccgaa gtcagtnacc c | 1361 |

<210> SEQ ID NO 132
<211> LENGTH: 1345
<212> TYPE: DNA
<213> ORGANISM: Unknown
<220> FEATURE:
<223> OTHER INFORMATION: I27

<400> SEQUENCE: 132

| | |
|---|---|
| tttcttcgga actgaagatt tggtgattga gtggcggacg ggtgagtaac gcgtgggtaa | 60 |
| cctgccctgt acaggggat aacagtcaga aatgactgct aataccgcat aagaccacag | 120 |
| caccgcatgg tgcaggggta aaaactccgg tggtacagga tggacccgcg tctgattagc | 180 |
| tggttggtga ggtaacggct caccaaggcg acgatcagta gccggcttga gagagtgaac | 240 |
| ggccacattg ggactgagac acggcccaaa ctcctacggg aggcagcagt ggggaatatt | 300 |
| gcacaatggg ggaaaccctg atgcagcgac gccgcgtgag tgaagaagta tctcggtatg | 360 |
| taaagctcta tcagcaggga agaaaatgac ggtacctgac taagaagccc cggctaacta | 420 |
| cgtgccagca gccgcggtaa tacgtagggg gcaagcgtta ccggaatta ctgggtgtaa | 480 |
| agggtgcgta ggtggtatgg caagtcagaa gtgaaacccc agggcttaac tctgggactg | 540 |
| cttttgaaac tgtcagactg gagtgcagga gaggtaagcg gaattcctag tgtagcggtg | 600 |
| aaatgcgtag atattaggag gaacatcagt ggcgaaggcg gcttactgga ctgaaactga | 660 |
| cactgaggca cgaaagcgtg gggagcaaac aggattagat accctggtag tccacgccgt | 720 |
| aaacgatgaa tactaggtgt cggggccgta gaggcttcgg tgccgcagcc aacgcagtaa | 780 |
| gtattccacc tggggagtac gttcgcaaga atgaaactca aaggaattga cggggacccg | 840 |
| cacaagcggt ggagcatgtg gtttaattcg aagcaacgcg aagaaccttac ctggtcttg | 900 |
| acatccttct gaccggtcct taaccggacc tttccttcgg gacaggagag acaggtggtg | 960 |
| catggttgtc gtcagctcgt gtcgtgagat gttgggttaa gtcccgcaac gagcgcaacc | 1020 |

```
cctatcttta gtagccagca tatcaggtgg gcactctaga gagactgcca gggataacct      1080
ggaggaaggt ggggacgacg tcaaatcatc atgcccctta tgaccagggc tacacacgtg      1140
ctacaatggc gtaaacagag ggaagcagcc tcgtgagagt gagcaaatcc caaaaataac      1200
gtctcagttc ggattgtagt ctgcaactcg actacatgaa gctggaatcg ctagtaatcg      1260
cgaatcagaa tgtcgcggtg aatacgttcc cgggtcttgt acaccgccc cgtcacacca      1320 tgggagtcag taacgcccga agtca                                            1345

<210> SEQ ID NO 133
<211> LENGTH: 400
<212> TYPE: DNA
<213> ORGANISM: Unknown
<220> FEATURE:
<223> OTHER INFORMATION: I28
<220> FEATURE:
<221> NAME/KEY: misc_feature
<222> LOCATION: (63)..(68)
<223> OTHER INFORMATION: n is a, c, g, or t
<220> FEATURE:
<221> NAME/KEY: misc_feature
<222> LOCATION: (120)..(121)
<223> OTHER INFORMATION: n is a, c, g, or t

<400> SEQUENCE: 133
gcggcggacg ggtgagtaac gcgtgggtaa cctgccctgt acacacggat aacataccga       60
aannnnnnct aatacgggat aacataagaa attcgcatgt ttttcttatc aaagctccgn      120
nggtacagga tggacccgcg tctgattagc tagttggtga ggtaacggct caccaaggcg      180
acgatcagta gccgacctga gagggtgatc ggccacattg gaactgagac acggtccaaa      240
ctcctacggg aggcagcagt ggggaatatt gcacaatggg cgaaagcctg atgcagcaac      300
gccgcgtgag caatgaaggc cttcgggtcg taaagctctg tcctcaagga agataatgac      360
ggtacttgag gaggaagccc cggctaacta cgtgccagca                            400

<210> SEQ ID NO 134
<211> LENGTH: 1366
<212> TYPE: DNA
<213> ORGANISM: Unknown
<220> FEATURE:
<223> OTHER INFORMATION: I29

<400> SEQUENCE: 134
gggtgctcat gacggaggat tcgtccaacg gattgagtta cctagtggcg gacgggtgag       60
taacgcgtga ggaacctgcc ttggagaggg gaataacact ccgaaaggag tgctaatacc      120
gcatgatgca gttgggtcgc atggctctga ctgccaaaga tttatcgctc tgagatggcc      180
tcgcgtctga ttagctagta ggcggggtaa cggcccacct aggcgacgat cagtagccgg      240
actgagaggt tgaccggcca cattgggact gagacacggc ccagactcct acgggaggca      300
gcagtgggga atattgggca atgggcgcaa gcctgaccca gcaacgccgc gtgaaggaag      360
aaggctttcg ggttgtaaac ttcttttgtc ggggacgaaa caaatgacgg tacctgacga      420
ataagccacg gctaactacg tgccagcagc cgcggtaata cgtaggtggc aagcgttatc      480
cggatttact gggtgtaaag ggcgtgtagg cgggattgca agtcagatgt gaaaactggg      540
ggctcaacct ccagcctgca tttgaaactg tagttcttga gtgctggaga ggcaatcgga      600
attccgtgtg tagcggtgaa atgcgtagat atacggagga acaccagtgg cgaaggcgga      660
ttgctggaca gtaactgacg ctgaggcgcg aaagcgtggg gagcaaacag gattagatac      720
```

```
cctggtagtc cacgccgtaa acgatggata ctaggtgtgg ggggtctgac ccctccgtg      780 ccgcagttaa cacaataagt atcccacctg gggagtacga tcgcaaggtt gaaactcaaa      840
ggaattgacg ggggcccgca caagcggtgg agtatgtggt ttaattcgaa gcaacgcgaa      900
gaaccttacc agggcttgac atcccactaa cgaggcagag atgcgttagg tgcccttcgg      960
ggaaagtgga gacaggtggt gcatggttgt cgtcagctcg tgtcgtgaga tgttgggtta     1020
agtcccgcaa cgagcgcaac ccttattgtt agttgctacg caagagcact ctagcgagac     1080
tgccgttgac aaaacggagg aaggtgggga cgacgtcaaa tcatcatgcc ccttatgtcc     1140
tgggccacac acgtactaca atggtggtaa acagagggag gcaataccgc gaggtggagc     1200
aaatccctaa aagccatccc agttcggatt gcaggctgaa acccgcctgt atgaagttgg     1260
aatcgctagt aatcgcggat cagcatgccg cggtgaatac gttcccgggc cttgtacaca     1320
ccgcccgtca caccatgaga gtcgggaaca cccgaagtcc gtagcc                    1366

<210> SEQ ID NO 135
<211> LENGTH: 1358
<212> TYPE: DNA
<213> ORGANISM: Unknown
<220> FEATURE:
<223> OTHER INFORMATION: I30

<400> SEQUENCE: 135
ttagaaagag gattcgtcca attgataagg ttacttagtg gcggacgggt gagtaacgcg       60
tgaggaacct gcctcggagt ggggaataac agaccgaaag gcctgctaat accgcatgat      120
gcagttggac cgcatggtcc tgactgccaa agatttatcg ctctgagatg gcctcgcgtc      180
tgattagctt gttggcgggg taatggccca ccaaggcgac gatcagtagc cggactgaga      240
ggttggccgg ccacattggg actgagacac ggcccagact cctacgggag gcagcagtgg      300
ggaatattgg gcaatgggcg caagcctgac ccagcaacgc cgcgtgaagg aagaaggctt      360
tcgggttgta aacttctttt ctcagggacg aacaaatgac ggtacctgag gaataagcca      420
cggctaacta cgtgccagca gccgcggtaa tacgtaggtg gcaagcgtta tccggattta      480
ctgggtgtaa agggcgtgta ggcgggaagg caagtcagat gtgaaaacta tgggctcaac      540
ccatagcctg catttgaaac tgttttcctt gagtgctgga gaggcaatcg gaattccgtg      600
tgtagcggtg aaatgcgtag atatacggag gaacaccagt ggcgaaggcg gattgctgga      660
cagtaactga cgctgaggcg cgaaagcgtg gggagcaaac aggattagat accctggtag      720
tccacgctgt aaacgatgga tactaggtgt gggggggtctg acccctccg tgccgcagtt      780 aacacaataa gtatcccacc tggggagtac gatcgcaagg ttgaaactca aaggaattga      840
cgggggcccg cacaagcggt ggagtatgtg gtttaattcg aagcaacgcg aagaacctta      900
ccagggcttg acatcctact aacgaagcag agatgcatta ggtgcccttc ggggaaagta      960
gagacaggtg gtgcatggtt gtcgtcagct cgtgtcgtga gatgttgggt taagtcccgc     1020
aacgagcgca acccttattg ttagttgcta cgcaagagca ctctagcgag actgccgttg     1080
acaaaacgga ggaaggcggg gacgacgtca atcatcatg cccttatgt cctgggctac     1140 acacgtacta caatggtggt aaacagaggg aagcaagacc gcgaggtgga gcaaatccct     1200
aaaagccatc ccagttcgga ttgcaggctg aaacccgcct gtatgaagtt ggaatcgcta     1260
gtaatcgcgg atcagcatgc cgcggtgaat acgttcccgg gccttgtaca caccgcccgt     1320
cacaccatga gagtcgggaa cacccgaagt ccgtagtc                             1358
```

```
<210> SEQ ID NO 136
<211> LENGTH: 1342
<212> TYPE: DNA
<213> ORGANISM: Unknown
<220> FEATURE:
<223> OTHER INFORMATION: I31

<400> SEQUENCE: 136
ggcgaacggg tgagtaatac ataagtaacc tggcatctac aggggataa  ctgatggaaa      60
cgtcagctaa gaccgcatag gtgtagagat cgcatgaact ctatatgaaa agtgctacgg     120
gactggtaga tgatggactt atggcgcatt agctggttgg tagggtaacg gcctaccaag     180
gcgacgatgc gtagccgacc tgagagggtg accggccaca ctgggactga gacacggccc     240
agactcctac gggaggcagc agtagggaat tttcggcaat gggggaaacc ctgaccgagc     300
aacgccgcgt gaaggaagaa gtaattcgtt atgtaaactt ctgtcataga ggaagaacgg     360
tggatatagg gaatgatatc caagtgacgg tactctataa gaaagccacg gctaactacg     420
tgccagcagc cgcggtaata cgtaggtggc gagcgttatc cggaattatt gggcgtaaag     480
agggagcagg cggcactaag ggtctgtggt gaaagatcga agcttaactt cggtaagcca     540
tggaaaccgt agagctagag tgtgtgagag gatcgtggaa ttccatgtgt agcggtgaaa     600
tgcgtagata tatggaggaa caccagtggc gaaggcgacg atctggcgca taactgacgc     660
tcagtcccga aagcgtgggg agcaaatagg attagatacc ctagtagtcc acgccgtaaa     720
cgatgagtac taagtgttgg gagtcaaatc tcagtgctgc agttaacgca ataagtactc     780
cgcctgagta gtacgttcgc aagaatgaaa ctcaaaggaa ttgacggggg cccgcacaag     840
cggtggagca tgtggtttaa ttcgaagcaa cgcgaagaac cttaccaggt cttgacatcg     900
atctaaaggc tccagagatg gagagatagc tatagaaag  acaggtggtg catggttgtc     960
gtcagctcgt gtcgtgagat gttgggttaa gtcccgcaac gagcgcaacc cctgttgcca    1020
gttgccagca ttaagttggg gactctggcg agactgccgg tgacaagccg aggaaggcg    1080
gggatgacgt caaatcatca tgcccttat gacctgggct acacacgtgc tacaatggac    1140
agagcagagg gaagcgaagc cgcgaggtgg agcgaaaccc ataaaactgt tctcagttcg    1200
gactgcagtc tgcaactcga ctgcacgaag atggaatcgc tagtaatcgc gaatcagcat    1260
gtcgcggtga atacgttctc gggccttgta cacaccgccc gtcacaccat gagagtcggt    1320
aacacccgaa gccggtggcc ta                                             1342

<210> SEQ ID NO 137
<211> LENGTH: 1390
<212> TYPE: DNA
<213> ORGANISM: Unknown
<220> FEATURE:
<223> OTHER INFORMATION: I32
<220> FEATURE:
<221> NAME/KEY: misc_feature
<222> LOCATION: (921)..(923)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (990)..(991)
<223> OTHER INFORMATION: n is a, c, g, or t
```

<400> SEQUENCE: 137

```
atgagaagct tgcttcttat tgattcgagt ggcaaacggg tgagtaacgc gtaagcaacc      60
tgcccttcag atggggacaa cagctggaaa cggctgctaa taccgaatac gttcttttg     120
tcgcatggca gagggaagaa agggaggctc ttcggagctt tcgctgaagg aggggcttgc    180
gtctgattag ctagttggag gggtaacggc ccaccaaggc gacgatcagt agccggtctg    240
agaggatgaa cggccacatt gggactgaga cacggcccag actcctacgg gaggcagcag    300
tggggaatct tccgcaatgg acgaaagtct gacggagcaa cgccgcgtga acgatgacgg    360
ccttcgggtt gtaaagttct gttatacggg acgaatggcg tagcggtcaa tacccgttac    420
gagtgacggt accgtaagag aaagccacgg ctaactacgt gccagcagcc gcggtaatac    480
gtaggtggca agcgttgtcc ggaattattg ggcgtaaagg cgcgcaggc ggcgtcgtaa     540
gtcggtctta aaagtgcggg gcttaacccc gtgagggac cgaaactgcg atgctagagt     600
atcggagagg aaagcggaat tcctagtgta gcggtgaaat gcgtagatat taggaggaac    660
accagtggcg aaagcggctt tctggacgac aactgacgct gaggcgcgaa agccagggga    720
gcaaacggga ttagataccc cggtagtcct ggccgtaaac gatggatact aggtgtagga    780
ggtatcgacc ccttctgtgc cggagttaac gcaataagta tcccgcctgg ggagtacggc    840
cgcaaggctg aaactcaaag gaattgacgg gggcccgcac aagcggtgga gtatgtggtt    900
taattcgacg caacgcgaag nnncttacca agccttgaca ttgattgcta tggatagaga    960
tatccagttc cncttcggag ganaagaaan naggtggtgc acggctgtcg tcagctcgtg   1020
tcgtgagatg ttgggttaag tcccgcaacg agcgcaaccc ctatcttctg ttaccagcgg   1080
ttcggccggg gactcaggag agactgccgc agacaatgcg gaggaaggcg gggatgacgt   1140
caagtcatca tgccccttat ggcttgggct acacacgtac tacaatggct cttaatagag   1200
ggaagcgaag gagcgatccg gagcaaaccc caaaaacaga gtcccagttc ggattgcagg   1260
ctgcaactcg cctgcatgaa gcaggaatcg ctagtaatcg caggtcagca tactgcggtg   1320
aatacgttcc cgggccttgt acacaccgcc cgtcacacca cgaaagtcat tcacacccga   1380
agccggtgag                                                          1390
```

<210> SEQ ID NO 138
<211> LENGTH: 1373
<212> TYPE: DNA
<213> ORGANISM: Unknown
<220> FEATURE:
<223> OTHER INFORMATION: I33

<400> SEQUENCE: 138

```
atctagtggc aaacgggtga gtaacacgta aacaacctgc cttcaggatg gggacaacag      60
acggaaacga ctgctaatac cgaatacgtt ccttaggtcg catgactta ggaagaaagg      120
gtggcctcta cttgtaagct atcgcctgaa gaggggtttg cgtctgatta ggtagttggt    180
gaggtaacgg cccaccaagc cgacgatcag tagccggtct gagaggatga acggccacac    240
tggaactgag acacggtcca gactcctacg ggaggcagca gtgggaatc ttccgcaatg     300
ggcgaaagcc tgacggagca acgccgcgtg agtgatgacg ccttcgggt tgtaaagctc     360
tgtgatcggg gacgaacggt cagcagacga atactctgct gaagtgacgg tacccgaata    420
gcaagccacg gctaactacg tgccagcagc cgcggtaata cgtaggtggc aagcgttgtc    480
cggaattatt gggcgtaaag cgcgcgcagg cggcttctta agtccatctt aaaagtgcgg    540
ggcttaaccc cgtgatggga tggaaactga gaggctggag tatcggagag gaaagtggaa    600
```

```
ttcctagtgt agcggtgaaa tgcgtagaga ttaggaagaa caccggtggc gaaggcgact      660
ttctggacga caactgacgc tgaggcgcga aagcgtgggg agcaaacagg attagatacc      720
ctggtagtcc acgccgtaaa cgatgaatac taggtgtagg aggtatcgac cccttctgtg      780
ccggagctaa cacaataagt attccgcctg ggaagtacga tcgcaagatt aaaactcaaa      840
ggaattgacg ggggcccgca caagcggtgg agtatgtggt ttaattcgac gcaacgcgaa      900
gaaccttacc aggtcttgac attgatcgct attccaagaa attggaagtt ctccttcggg      960
agacgagaaa acaggtggtg cacggctgtc gtcagctcgt gtcgtgagat gttgggttaa     1020
gtcccgcaac gagcgcaacc cctatcttat gttaccagca cgttatggtg gggactcatg     1080
agagaccgcc gcggacaacg cggaggaagg tggggatgac gtcaagtcat catgccccat     1140
atgacctggg ctacacacgt actacaatgg gtgtcaacaa agagaagcga agccgcgagg     1200
cagagcaaac ctcaaaaaca cacccccagt tcagattgca ggctgcaacc cgcctgcatg     1260
aagtaggaat cgctagtaat cgcgggtcag cataccgcgg tgaatacgtt cccgggcctt     1320
gtacacaccg cccgtcacac tatgagagtc agaaacaccc gaagccggtg agg            1373
```

<210> SEQ ID NO 139
<211> LENGTH: 1366
<212> TYPE: DNA
<213> ORGANISM: Unknown
<220> FEATURE:
<223> OTHER INFORMATION: I34

<400> SEQUENCE: 139

```
ttcttagtgg cgaacgggtg agtaacgcgt gggcaacctg ccctccagtt ggggacaaca       60
ttccgaaagg gatgctaata ccgaatgtgc tccctcctcc gcatggagga gggaggaaag      120
atggcctctg cttgcaagct atcgctggaa gatgggcccg cgtctgatta gctagttggt      180
ggggtaacgg ctcaccaagg cgatgatcag tagccggtct gagaggatga acggccacat      240
tgggactgag acacggccca aactcctacg ggaggcagca gtggggaatc ttccgcaatg      300
gacgaaagtc tgacggagca acgccgcgtg agtgatgaag gtcttcggat tgtaaaactc      360
tgttgttagg gacgaaagca ccgtgttcga acaggtcatg gtgttgacgg tacctaacga      420
ggaagccacg gctaactacg tgccagcagc cgcggtaata cgtaggtggc aagcgttgtc      480
cggaattatt gggcgtaaag agcatgtagg cgggctttta agtctgacgt gaaaatgcgg      540
ggcttaaccc cgtatggcgt tggatactgg aagtcttgag tgcaggagag gaaaggggaa      600
ttcccagtgt agcggtgaaa tgcgtagata ttgggaggaa caccagtggc gaaggcgcct      660
ttctggactg tgtctgacgc tgagatgcga aagccagggt agcaaacggg attagatacc      720
ccggtagtcc tggccgtaaa cgatggatac taggtgtagg aggtatcgac cccttctgtg      780
ccggagttaa cgcaataagt atccgcctg ggactacga tcgcaagatt gaaactcaaa       840
ggaattgacg ggggcccgca caagcggtgg agtatgtggt ttaattcgac gcaacgcgaa      900
gaaccttacc aaggcttgac attgagtgaa agacctagag ataggtccct cccttcgggg      960
acacgaaaac aggtggtgca tggctgtcgt cagctcgtgt cgtgagatgt tgggttaagt     1020
cccgcaacga gcgcaacccc tatcctatgt taccagcgcg taatgcggg gactcatagg     1080 agactgccag ggtaacttg gaggaaggcg gggatgacgt caagtcatca tgccccttat     1140
gtcttgggct acacacgtac tacaatggtc ggcaacaaag gcagcgaaa ccgcgaggtg     1200 gagcaaatcc cagaaacccg accccagttc ggatcgtagg ctgcaacccg cctacgtgaa     1260
```

<210> SEQ ID NO 140
<211> LENGTH: 1387
<212> TYPE: DNA
<213> ORGANISM: Unknown
<220> FEATURE:
<223> OTHER INFORMATION: I35
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t

<400> SEQUENCE: 140

```
gttggaatcg ctagtaatcg caggtcagca tactgcggtg aatacgttcc cgggccttgt   1320
acacaccgcc cgtcacacca cgaaagttgg taacacccga agccgg                   1366
```

```
cttgctcttt nttggattct agtggcaaac gggtgagtaa cacgtaaaca acctgccttc     60
aggatgggga caacagacgg aaacgactgc taataccgaa taccttccaa tttccgcatg   120
gagataggaa gaaagggtgg cctctacttg taagctatcg cctgaagagg ggtttgcgtc   180
tgattagctn gttggtgagg taacggccca ccaaggcgac gatcagtagc cggtctgaga   240
ggatgaacgg ccacactgga actgagacac ggtccagact cctacgggag gcagcagtgg   300
ggaatcttcc gcaatggacg aaagtctgac ggagcaacgc cgcgtgaacg atgaaggtct   360
tcggattgta aagttctgtg atccgggacg aaggcattna ttgagaacat tgattgatgt   420
tgacggtacc ggaaaagcaa gccacggcta actacgtgcc agcagccgcg gtaatacgta   480
ggtggcaagc gttgtccgga attattgggc gtaaagcgcg cgcaggcggc cgtgcaagtc   540
catcttaaaa gcgtggggct taaccccatg aggggatgga aactgcatgg ctggagtgtc   600
ggagggaaa gtggaattcc tagtgtagcg gtgaaatgcg tagagattag gaagaacacc   660
ggtggcgaag gcgactttct agacgacaac tgacgctgag gcgcgaaagc gtggggagca   720
aacaggatta gataccctgg tagtccacgc cgtaaacgat ggatactagg tgtaggaggt   780
atcgacccct tctgtgccgg agttaacgca ataagtatcc cgcctgggaa gtacgatcgc   840
aagattaaaa ctcaaaggaa ttgacggggg cccgcacaag cggtggagta tgtggtttaa   900
ttcgacgcaa cgcgaagaac cttaccaagc cttgacattg atcgcaatct gcagaaatgc   960
ggagttcctc ttcggaggac gagaaaacag gtggtgcacg gctgtcgtca gctcgtgtcg  1020
tgagatgttg ggttaagtcc cgcaacgagc gcaaccccta tcttctgttg ccagcacgta  1080
aaggtgggaa ctcaggagag accgccgcgg acaacgcgga ggaaggcggg gatgacgtca  1140
agtcatcatg ccccttatgg cttgggctac acacgtacta caatgggtgc aaacaaagag  1200
aagcgaagtc gcgagacgga gcggacctca taaacgcact cccagttcag attgcaggct  1260
gcaacccgcc tgcatgaagt aggaatcgct agtaatcgcg ggtcagcata ccgcggtgaa  1320
tacgttcccg ggccttgtac acaccgcccg tcacactatg agagtcagag acacccaaag  1380
ccggtgg                                                              1387
```

<210> SEQ ID NO 141
<211> LENGTH: 1386
<212> TYPE: DNA
<213> ORGANISM: Unknown

```
<220> FEATURE:
<223> OTHER INFORMATION: I36
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(117)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (1200)..(1201)
<223> OTHER INFORMATION: n is a, c, g, or t

<400> SEQUENCE: 141
gagaagcttg cttcttatcn attctagtgg caaacgggtg agtaacgcgt aagcaacctg    60
cccttcagat ggggacaaca gctggaaacg gctgctaata ccgaatacgt tnntnnngcc   120
gcatgacgan atgaagaaag ggaggccttc gggctttcgc tggaggaggg gcttgcgtct   180
gattagctng ttggaggggt aacggcccac caaggcgacg atcagtagcc ggtctgagag   240
gatgaacggc cacattggga ctgagacacg gcccagactc ctacgggagg cagcagtggg   300
gaatcttccg caatggacga aagtctgacg gagcaacgcc gcgtgaacga tgacggcctt   360
cgggttgtaa agttctgtta tatgggacga acaggacatc ggttaatacc cggtgtcttt   420
gacggtaccg taagagaaag ccacggctaa ctacgtgcca gcagccgcgg taatacgtag   480
gtggcaagcg ttgtccggaa ttattgggcg taaagggcgc gcaggcggca tcgcaagtcg   540
gtcttaaaag tgcggggctt aaccccgtga ggggaccgaa actgtgaagc tcgagtgtcg   600
gagaggaaag cggaattcct agtgtagcgg tgaaatgcgt agatattagg aggaacacca   660
gtggcgaaag cggcttctg acgacaact gacgctgagg cgcgaaagcc aggggagcaa   720
acgggattag atacccggt agtcctggcc gtaaacgatg gatactaggt gtaggaggta   780
tcgactcctt ctgtgccgga gttaacgcaa taagtatccc gcctgggag tacggccgca   840 aggctgaaac tcaaaggaat tgacggggc ccgcacaagc ggtggagtat gtggtttaat   900
tcgacgcaac gcgaagaacc ttaccaagcc ttgacattga ttgctacgga aagagatttc   960
cggttcttct tcggaagaca agaaaacagg tggtgcacgg ctgtcgtcag ctcgtgtcgt  1020
gagatgttgg gttaagtccc gcaacgagcg caacccctat cttctgttgc cagcacctcg  1080 ggtgggact cagaagagac tgccgcagac aatgcgagg aaggcgggga tgacgtcaag  1140
tcatcatgcc ccttatggct tgggctacac acgtactaca atggctctta atagagggan  1200
ncgaaggagc gatccggagc aaacccaaa aacagagtcc cagttcggat tgcaggctgc   1260
aactcgcctg catgaagcag gaatcgctag taatcgcagg tcagcatact gcggtgaata  1320
cgttcccggg ccttgtacac accgcccgtc acaccacgaa agtcattcac acccgaagcc  1380
ggtgag                                                              1386

<210> SEQ ID NO 142
```

<211> LENGTH: 1364
<212> TYPE: DNA
<213> ORGANISM: Unknown
<220> FEATURE:
<223> OTHER INFORMATION: I37
<220> FEATURE:
<221> NAME/KEY: misc_feature
<222> LOCATION: (939)..(940)
<223> OTHER INFORMATION: n is a, c, g, or t

<400> SEQUENCE: 142

```
cggcagcgcg gggagcttgc tccctggcgg cgagtggcgc acgggtgagt aatacatcgg      60
aacgtgtctt ctagtggggg ataactgccc gaaagggcag ctaataccgc atgagacctg     120
agggtgaaag cggggatcg caagacctcg cgctggaaga gcggccgatg tccgattagc      180
tagttggtga ggtaaaggct caccaaggcg acgatcggta gctggtctga gaggacgacc     240
agccacactg ggactgagac acggcccaga ctcctacggg aggcagcagt ggggaatttt     300
ggacaatggg gcaaccctg atccagccat gccgcgtgca ggatgaaggt cttcggattg      360
taaactgctt ttgtcaggga cgaaaaggga tgcgataaca ccgtattccg ctgacggtac     420
ctgaagaata agcaccggct aactacgtgc cagcagccgc ggtaatacgt agggtgcaag     480
cgttaatcgg aattactggg cgtaaagcgt gcgcaggcgg ttctgtaaga tagatgtgaa     540
atccccgggc tcaacctggg aattgcatat atgactgcag gacttgagtt tgtcagagga     600
gggtggaatt ccacgtgtag cagtgaaatg cgtagatatg tggaagaaca ccgatggcga     660
aggcagccct ctgggacatg actgacgctc atgcacgaaa gcgtggggag caaacaggat     720
tagatacct ggtagtccac gccctaaacg atgtctacta gttgttgggg acgatagtcc      780
ttggtaacgc agctaacgcg tgaagtagac cgcctgggga gtacggtcgc aagattaaaa     840
ctcaaaggaa ttgacgggga cccgcacaag cggtggatga tgtggattaa ttcgatgcaa     900
cgcgaaaaac cttacctagc cttgacatgc caggaaggnn tgagagatca ggccgtgccc     960
gcaagggaat ctggacacag gtgctgcatg gctgtcgtca gctcgtgtcg tgagatgttg    1020
ggttaagtcc cgcaacgagc gcaacccttg tcattagttg ctacgaaagg gcactctaat    1080
gagactgccg gtgacaaacc ggaggaaggt ggggatgacg tcaagtcctc atggccctta    1140
tggctagggc ctcacacgtc atacaatggt cggaacagag ggaagcgaag ccgcgaggtg    1200
aagccaatcc cagaaaaccg atcgtagtcc ggattgcagt ctgcaactcg actgcatgaa    1260
gtcggaatcg ctagtaatcg cggatcagca tgccgcggtg aatacgttcc cgggtcttgt    1320
acacaccgcc cgtcacacca tgggagtggg gttcaccaga agac                     1364
```

<210> SEQ ID NO 143
<211> LENGTH: 1343
<212> TYPE: DNA
<213> ORGANISM: Unknown
<220> FEATURE:
<223> OTHER INFORMATION: I38

<400> SEQUENCE: 143

```
ggaaacggat tagcggcgga cgggtgagta acacgtgggt aacctgcctc atagagggga      60
atagcctccc gaaagggaga ttaataccgc ataacattgc agtttcgcat gaaacagcaa     120
ttaaaggagc aatccgctat gagatggacc cgcggcgcat tagctagttg gtaaggtaat     180
ggcttaccaa ggcgacgatg cgtagccgac ctgagagggt gatcggccac attgggactg     240
agacacggcc cagactccta cgggaggcag cagtgggaa tattgcacaa tggggaaac      300
cctgatgcag caacgccgcg tgagtgatga cggtcttcgg attgtaaagc tctgtctttg    360
```

```
gggacgataa tgacggtacc caaggaggaa gccacggcta actacgtgcc agcagccgcg    420
gtaatacgta ggtggcgagc gttgtccgga tttactgggc gtaaagggag cgtaggcgga    480
tttttaagtg ggatgtgaaa tacccgggct caacctgggt gctgcattcc aaactgggaa    540
tctagagtgc aggaggggag agtggaattc ctagtgtagc ggtgaaatgc gtagagatta    600
ggaagaacac cagtggcgaa ggcgactctc tggactgtaa ctgacgctga ggctcgaaag    660
cgtggggagc gaacaggatt agataccctg gtagtccacg ccgtaaacga tgaatactag    720
gtgtaggggt ttcaacacct ctgtgccgcc gctaacgcat taagtattcc gcctggggag    780
tacggtcgca agattaaaac tcaaaggaat tgacggggc ccgcacaagt agcggagcat    840
gtggtttaat tcgaagcaac gcgaagaacc ttacctagac ttgacatcct ctgcattacc    900
cttaatcggg gaagttcctt cgggaacaga gtgacaggtg gtgcatggtt gtcgtcagct    960
cgtgtcgtga tgttgggt taagtcccgc aacgagcgca accctattg ttagttgcta    1020 ccattaagtt gagcactcta gcgagactgc ctgggttaac caggaggaag gtggggatga    1080
cgtcaaatca tcatgcccct tatgtctagg gctacacacg tgctacaatg gcaagtacag    1140
agagatgcaa taccgcgagg tggagctaaa cttcaaaact tgtctcagtt cggattgtag    1200
gctgaaactc gcctacatga agctggagtt actagtaatc gcgaatcagc atgtcgcggt    1260
gaatacgttc ccgggccttg tacacaccgc ccgtcacacc atgagagttg caatacccca    1320
aagttcgtga gctaacgcgt aag                                              1343

<210> SEQ ID NO 144
<211> LENGTH: 1318
<212> TYPE: DNA
<213> ORGANISM: Unknown
<220> FEATURE:
<223> OTHER INFORMATION: I39

<400> SEQUENCE: 144
cttagtggcg gacgggtgag taacgcgtga gtaacctgcc tttcagaggg gaataacatt     60
ctgaaaagaa tgctaatacc gcatgagatc gtagtatcgc atggtacagc gaccaaagga    120
gcaatccgct gaaagatgga ctcgcgtccg attagctagt tggtgagata aaggcccacc    180
aaggcgacga tcggtagccg gactgagagg ttgaacggcc acattgggac tgagacacgg    240
cccagactcc tacgggaggc agcagtgggg gatattgcac aatgggggaa accctgatgc    300
agcaacgccg cgtgaaggaa gaaggtcttc ggattgtaaa cttctgtcct cagggaagat    360
aatgacggta cctgaggagg aagctccggc taactacgtg ccagcagccg cggtaatacg    420
tagggagcaa gcgttgtccg gatttactgg gtgtaaaggg tgcgtaggcg gatctgcaag    480
tcagtagtga aatcccaggg cttaaccctg gaactgctat tgaaactgtg ggtcttgagt    540
gaggtagagg caggcggaat tcccggtgta gcggtgaaat gcgtagagat cgggaggaac    600
accagtggcg aaggcggcct gctgggcctt aactgacgct gaggcacgaa agcatgggta    660
gcaaacagga ttagataccc tggtagtcca tgccgtaaac gatgattact aggtgtgggt    720
ggtctgaccc catccgtgcc ggagttaaca caataagtaa tccacctggg gagtacggcc    780
gcaaggttga aactcaaagg aattgacggg ggcccgcaca agcagtggag tatgtggttt    840
aattcgaagc aacgcgaaga accttaccag gtcttgacat cctgctaacg aggtagagat    900
acgttaggtg cccttcgggg aaagcagaga caggtggtgc atggttgtcg tcagctcgtg    960
tcgtgagatg ttgggttaag tcccgcaacg agcgcaaccc ctgctattag ttgctacgca   1020
```

```
agagcactct aataggactg ccgttgacaa aacggaggaa ggtggggacg acgtcaaatc    1080
atcatgcccc ttatgacctg ggctacacac gtactacaat ggccgtcaac agagagaagc    1140
aaagccgcga ggtggagcaa aactctaaaa acggtcccag ttcggatcgt aggctgcaac    1200
ccgcctacgt gaagttggaa ttgctagtaa tcgcggatca tcatgccgcg gtgaatacgt    1260
tcccgggcct tgtacacacc gcccgtcaca ccatgggagc cggtaatacc cgaagtca     1318
```

```
<210> SEQ ID NO 145
<211> LENGTH: 1360
<212> TYPE: DNA
<213> ORGANISM: Unknown
<220> FEATURE:
<223> OTHER INFORMATION: I40

<400> SEQUENCE: 145
```

```
tcatgacaga ggattcgtcc aatggagtga gttacttagt ggcggacggg tgagtaacgc      60
gtgagtaacc tgccttggag tggggaataa caggtggaaa catctgctaa taccgcatga     120
tgcagttggg tcgcatggct ctgactgcca aagatttatc gctctgagat ggactcgcgt     180
ctgattagct ggttggcggg gtaacggccc accaaggcga cgatcagtag ccggactgag     240
aggttggccg gccacattgg gactgagaca cggcccagac tcctacggga ggcagcagtg     300
gggaatattg gcaatgggc gcaagcctga cccagcaacg ccgcgtgaag gaagaaggct     360
ttcgggttgt aaacttcttt tctcagggac gaagcaagtg acggtacctg aggaataagc     420
cacggctaac tacgtgccag cagccgcggt aatacgtagg tggcgagcgt tatccggatt     480
tactgggtgt aaagggcgtg taggcgggac tgcaagtcag atgtgaaaac catgggctca     540
acctgtggcc tgcatttgaa actgtagttc ttgagtactg gagaggcaga cggaattcct     600
agtgtagcgg tgaaatgcgt agatattagg aggaacacca gtggcgaagg cggtctgctg     660
gacagcaact gacgctgagg cgcgaaagcg tggggagcaa acaggattag ataccctggt     720
agtccacgct gtaaacgatg gatactaggt gtgggggtc tgacccccct cgtgccgcag     780
ttaacacaat aagtatccca cctggggagt acgatcgcaa ggttgaaact caaaggaatt     840
gacgggggcc cgcacaagcg gtggagtatg tggtttaatt cgaagcaacg cgaagaacct     900
taccagggct tgacatcccg gtgaccggtg tagagataca ccttcttctt cggaagcgcc     960
ggtgacaggt ggtgcatggt tgtcgtcagc tcgtgtcgtg agatgttggg ttaagtcccg    1020
caacgagcgc aaccccttatt gttagttgct acgcaagagc actctagcga gactgccgtt    1080
gacaaaacgg aggaaggtgg ggacgacgtc aaatcatcat gccccttatg tcctgggcca    1140
cacacgtact acaatggtgg tcaacagagg gaagcaagac cgcgaggtgg agcaaaccc    1200 taaaagccat cccagttcgg attgcaggct gcaactcgcc tgtatgaagt tggaatcgct    1260
agtaatcgcg gatcagcatg ccgcggtgaa tacgttcccg ggccttgtac acaccgcccg    1320
tcacaccatg agagtcggga acacccgaag tccgtagcct                           1360
```

```
<210> SEQ ID NO 146
<211> LENGTH: 1370
<212> TYPE: DNA
<213> ORGANISM: Unknown
<220> FEATURE:
<223> OTHER INFORMATION: I41

<400> SEQUENCE: 146
```

```
gtgctcatga cggagttttc ggacaacgga ttgggttact tagtggcgga cgggtgagta      60
acgcgtgagg aacctgcctc ggagtgggga ataacacacc gaaaggtgtg ctaataccgc     120
```

```
ataatgcagt tgggtcgcat gactctgact gccaaagatt tatcgctctg agatggcctc      180
gcgtctgatt agctagttgg cggggtaacg gcccaccaag gcgacgatca gtagccggac      240
tgagaggttg accggccaca ttgggactga gacacggccc agactcctac gggaggcagc      300
agtggggaat attgggcaat gggcgcaagc ctgacccagc aacgccgcgt gaaggaagaa      360
ggctttcggg ttgtaaactt cttttgtcag gacgaaaca aatgacggta cctgacgaat       420
aagccacggc taactacgtg ccagcagccg cggtaatacg taggtggcaa gcgttatccg      480
gatttactgg gtgtaaaggg cgtgtaggcg ggactgcaag tcaggtgtga aaaccagggg      540
ctcaacctct ggcctgcatt tgaaactgta gttcttgagt gctggagagg caatcggaat      600
tccgtgtgta gcggtgaaat gcgtagatat acggaggaac accagtggcg aaggcggatt      660
gctggacagt aactgacgct gaggcgcgaa agcgtgggga gcaaacagga ttagataccc      720
tggtagtcca cgccgtaaac gatggatact aggtgtgggg ggactgaccc cctccgtgcc      780
gcagttaaca caataagtat cccacctggg gagtacgatc gcaaggttga aactcaaagg      840
aattgacggg ggcccgcaca agcggtggag tatgtggttt aattcgaagc aacgcgaaga      900
accttaccag ggcttgacat cctactaacg aagcagagat gcattaggtg cccttcgggg      960
aaagtagaga caggtggtgc atggttgtcg tcagctcgtg tcgtgagatg ttgggttaag     1020
tcccgcaacg agcgcaaccc ctattgttag ttgctacgca agagcactct agcgagactg     1080
ccgttgacaa aacggaggaa ggtggggacg acgtcaaatc atcatgcccc ttatgtcctg     1140
ggccacacac gtactacaat ggtggttaac agaggggagc aataccgcga ggtggagcaa     1200
atccctaaaa gccatcccag ttcggattgc aggctgaaac ccgcctgtat gaagttggaa     1260
tcgctagtaa tcgcggatca gcatgccgcg gtgaatacgt tcccgggcct tgtacacacc     1320
gcccgtcaca ccatgagagt cgggaacacc cgaagtccgt agcctaaccg                1370
```

<210> SEQ ID NO 147
<211> LENGTH: 1341
<212> TYPE: DNA
<213> ORGANISM: Unknown
<220> FEATURE:
<223> OTHER INFORMATION: I42
<220> FEATURE:
<221> NAME/KEY: misc_feature
<222> LOCATION: (120)..(121)
<223> OTHER INFORMATION: n is a, c, g, or t
<400> SEQUENCE: 147

```
ttgcaccttc aagttagtgg cggacgggtg agtaacgcgt gagcaacctg cctcaaagag       60
ggggataacg tctggaaacg gacgctaata ccgcatgacg tattcgatag gcatctattn      120
nataccaaag gagcaatccg ctttgagatg ggctcgcgtc tgattagctg gttggtgggg      180
taaaggccta ccaaggcgac gatcagtagc cggactgaga ggttgaacgg ccacattggg      240
actgagacac ggcccagact cctacggag gcagcagtgg gggatattgc acaatggggg      300
aaaccctgat gcagcaacgc cgcgtgaagg aagacggttt tcggattgta aacttctgtt      360
cttagtgacg ataatgacgg tagctaagga gaaagctccg gctaactacg tgccagcagc      420
cgcggtaata cgtagggagc gagcgttgtc cggaattact gggtgtaaag ggagcgtagg      480
cgggagatca agtcagatgt gaaaactatg gctcaaccc ataacctgca tttgaaactg       540
gttttcttga gtgaagtaga ggcaggcgga attccgagtg tagcggtgaa atgcgtagat      600
attcggagga acaccagtgg cgaaggcggc ctgctgggct tttactgacg ctgaggctcg      660
```

-continued

```
aaagcatggg gagcaaacag gattagatac cctggtagtc catgccgtaa acgatgatta    720
ctaggtgtgg ggtggctgac ccattccgtg ccggagttaa cacaataagt aatccacctg    780
gggagtacgg ccgcaaggtt gaaactcaaa ggaattgacg ggggcccgca caagcagtgg    840
agtatgtggt ttaattcgaa gcaacgcgaa gaaccttacc aggtcttgac atccgactaa    900
cgaagtagag atacattagg tgcccttcgg ggaaagtcga dacaggtggt gcatggttgt    960
cgtcagctcg tgtcgtgaga tgttgggtta agtcccgcaa cgagcgcaac ccttgtcatt   1020
agttgctacg caagagcact ctaatgagac tgccgttgac aaaacggagg aaggtgggga   1080
cgacgtcaaa tcatcatgcc ccttatgacc tgggctacac acgtactaca atggccgtta   1140
acagagggaa gcaatactgt gaagtggagc aaaccctaa aaacggtccc agttcagatt   1200
gcaggctgca acccgcctgc atgaagtcgg aattgctagt aatcgcggat cagcatgccg   1260
cggtgaatac gttcccgggc cttgtacaca ccgcccgtca ccatgggaa gccggtaata   1320 cccgaagtcg gtagtctaac c                                            1341
```

<210> SEQ ID NO 148
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 148

```
gcgaccagac ctacatgcgt                                                 20
```

<210> SEQ ID NO 149
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 149

```
agtcgaaaga gcccgcgtc                                                  19
```

<210> SEQ ID NO 150
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 150

```
agcactagcg gctgtggtat                                                 20
```

<210> SEQ ID NO 151
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 151

```
acttactcgg gcccttgatt                                                 20
```

<210> SEQ ID NO 152
<211> LENGTH: 20
<212> TYPE: DNA
<213> ORGANISM: Artificial Sequence
<220> FEATURE:
<223> OTHER INFORMATION: Artificially synthesized primer sequence

```
<400> SEQUENCE: 152
cttcgccttc atcagcttca                                                        20

<210> SEQ ID NO 153
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 153
tcatcattaa cgcgggtcag                                                        20

<210> SEQ ID NO 154
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 154
ggtgaatacg ttcccgg                                                           17

<210> SEQ ID NO 155
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 155
tacggctacc ttgttacgac tt                                                     22

<210> SEQ ID NO 156
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 156
agrgtttgat ymtggctcag                                                        20

<210> SEQ ID NO 157
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 157
ggytaccttg ttacgactt                                                         19
```